United States Patent
Fan et al.

(10) Patent No.: US 8,150,627 B2
(45) Date of Patent: *Apr. 3, 2012

(54) METHODS AND COMPOSITIONS FOR DIAGNOSING LUNG CANCER WITH SPECIFIC DNA METHYLATION PATTERNS

(75) Inventors: Jian-Bing Fan, San Diego, CA (US); Marina Bibikova, San Diego, CA (US)

(73) Assignee: Illumina, Inc., San Diego, CA (US)

( * ) Notice: Subject to any disclaimer, the term of this patent is extended or adjusted under 35 U.S.C. 154(b) by 1425 days.

This patent is subject to a terminal disclaimer.

(21) Appl. No.: 11/259,546

(22) Filed: Oct. 25, 2005

(65) Prior Publication Data

US 2007/0231797 A1    Oct. 4, 2007

Related U.S. Application Data

(63) Continuation-in-part of application No. 10/973,783, filed on Oct. 25, 2004, which is a continuation-in-part of application No. 10/845,667, filed on May 14, 2004, now abandoned.

(60) Provisional application No. 60/471,488, filed on May 15, 2003.

(51) Int. Cl.
   G01N 33/48    (2006.01)
   C12Q 1/00    (2006.01)

(52) U.S. Cl. .............................. 702/19; 435/4

(58) Field of Classification Search .................. None
   See application file for complete search history.

(56) References Cited

U.S. PATENT DOCUMENTS 5,786,146 A    7/1998  Herman et al.
5,856,101 A    1/1999  Hubbell et al.
(Continued)

FOREIGN PATENT DOCUMENTS

WO    WO 98/40726    9/1998
(Continued)

OTHER PUBLICATIONS

Grunau et al., "DNA Methylation Database "Meth DB": a User Guide," *J. Nutr.* 132:2435S-2439S (2002).
(Continued)

*Primary Examiner* — Marjorie Moran
*Assistant Examiner* — Larry D Riggs, II
(74) *Attorney, Agent, or Firm* — Lisa de Berg

(57) ABSTRACT

The present invention provides a method for identification of differentially methylated genomic CpG dinucleotide sequences within genomic target sequences that are associated with cancer in an individual by obtaining a biological sample comprising genomic DNA from the individual measuring the level or pattern of methylated genomic CpG dinucleotide sequences for two or more of the genomic targets in the sample, and comparing the level of methylated genomic CpG dinucleotide sequences in the sample to a reference level of methylated genomic CpG dinucleotide sequences, wherein a difference in the level or pattern of methylation of the genomic CpG dinucleotide sequences in the sample compared to the reference level identifies differentially methylated genomic CpG dinucleotide sequences associated with cancer. As disclosed herein, the methods of the invention have numerous diagnostic and prognostic applications. The methods of the invention can be combined with a miniaturized array platform that allows for a high level of assay multiplexing and scalable automation for sample handling and data processing. Also provided by the invention are genomic targets and corresponding nucleic acid probes that are useful in the methods of the invention as they enable detection of differentially methylated genomic CpG dinucleotide sequences associated with adenocarcinomas of the lung.

6 Claims, 43 Drawing Sheets
(29 of 43 Drawing Sheet(s) Filed in Color)

U.S. PATENT DOCUMENTS

| | | | |
|---|---|---|---|
| 5,981,733 | A | 11/1999 | Gamble et al. |
| 6,001,309 | A | 12/1999 | Gamble et al. |
| 6,017,704 | A | 1/2000 | Herman et al. |
| 6,023,540 | A | 2/2000 | Walt et al. |
| 6,110,426 | A | 8/2000 | Shalon et al. |
| 6,200,737 | B1 | 3/2001 | Walt et al. |
| 6,232,072 | B1 | 5/2001 | Fisher |
| 6,251,594 | B1 | 6/2001 | Gonzalgo et al. |
| 6,265,171 | B1 | 7/2001 | Herman et al. |
| 6,280,949 | B1 | 8/2001 | Lizardi |
| 6,327,410 | B1 | 12/2001 | Walt et al. |
| 6,329,150 | B1 | 12/2001 | Lizardi et al. |
| 6,331,393 | B1 | 12/2001 | Laird et al. |
| 6,379,895 | B1 | 4/2002 | Fodor et al. |
| 6,429,027 | B1 | 8/2002 | Chee et al. |
| 6,667,394 | B2 | 12/2003 | Pease et al. |
| 2002/0102578 | A1 | 8/2002 | Dickinson |
| 2003/0170684 | A1 | 9/2003 | Fan |
| 2004/0137473 | A1 | 7/2004 | Wigler et al. |
| 2004/0259100 | A1 | 12/2004 | Gunderson et al. |
| 2005/0026183 | A1 | 2/2005 | Fan et al. |
| 2005/0164246 | A1 | 7/2005 | Fan et al. |
| 2007/0128592 | A1 | 6/2007 | Burger et al. |

FOREIGN PATENT DOCUMENTS

| | | |
|---|---|---|
| WO | WO 98/50782 | 12/1998 |
| WO | WO 99/18434 | 4/1999 |
| WO | WO 02/086163 | 10/2002 |
| WO | WO 03/052135 | 12/2002 |
| WO | WO 03/048732 | 6/2003 |
| WO | WO 2004/051224 | 6/2004 |

OTHER PUBLICATIONS

Tsujiuch et al., "Hypomethylation of CpG Sites and c-myc Gene Overexpression in Hepatocellular Carcinomas, but Not Hyperplastic Nodules, Induced by a Choline-deficient $_L$-Amino Acid-defined Diet in Rats," *Jpn. J. Cancer Res.* 90:909-913 (1999).
U.S. Appl. No. 10/309,803, filed Sep. 11, 2003, Fan.
U.S. Appl. No. 10/973,783, filed Jul. 28, 2005, Fan.
U.S. Appl. No. 10/845,667, filed Feb. 3, 2005, Fan.
U.S. Appl. No. 60/471,488, Fan.
Adorjan et al., "Tumour class prediction and discovery by microarray-based DNA methylation analysis," *Nucleic Acids Res.* 30(5):e21 (2002).
Akama et al., "Restriction landmark genomic scanning (RLGS-M)-based genome-wide scanning of mouse liver tumors for alterations in DNA methylation status," *Cancer Res.* 57(15):3294-3299 (1997).
Aldred et al., "Caveolin-1 and caveolin-2,together with three bone morphogenetic protein-related genes, may encode novel tumor suppressors down-regulated in sporadic follicular thyroid carcinogenesis," *Cancer Res* 63, 2864-71 (2003).
Anderson and Brown, "Variability of X chromosome inactivation: effect on levels of TIMP1 RNA and role of DNA methylation," *Hum. Genet.* 110(3):271-278 (2002).
Antequera and Bird, "Number of CpG islands and genes in human and mouse," *Proc. Natl. Acad. Sci. USA* 90(24):11995-11999 (1993).
Balmain et al., "The genetics and genomics of cancer," *Nat. Genet.* 33 Suppl.:238-244 (2003).
Battacharjee et al., "Classification of human lung carcinomas by mRNA expression profiling reveals distinct adenocarcinoma subclasses," *Proc. Nat. Acad. Sci. USA* 98(24):13790-13795 (2001).
Baylin and Herman, "DNA hypermethylation in tumorigenesis: epigenetics joins genetics," *Trends Genet.* 16(4):168-174 (2000).
Beck et al., "From genomics to epigenomics: a loftier view of life," *Nat. Biotechnol.* 17(12):1144 (1999).
Bestor, "Gene silencing. Methylation meets acetylation," *Nature* 393(6683):311-312 (1998).
Bhattacharjee, et al., "Classification of human lung carcinomas by mRNA expression profiling reveals distinct adenocarcinoma subclasses," *Proc Natl Acad Sci U S A* 98(24):13790-5 (2001).
Bird, "CpG-rich islands and the function of DNA methylation," *Nature* 321:209-213(1986).
Bird, "The essentials of DNA methylation," *Cell* 70:5-8(1992).
Cedar, "DNA methylation and gene activity," *Cell* 53:3-4 (1988).
Chen et al., "A microsphere-based assay for multiplexed single nucleotide polymorphism analysis using single base chain extension," *Genome Res.* 10(4):549-557 (2000).
Chen et al., "Gene expression patterns in human liver cancers," *Mol. Biol. Cell* 13(6):1929-1939 (2002).
Chen et al., "Methylation target array for rapid analysis of CpG island hypermethylation in multiple tissue genomes," *Am J Pathol* 163:37-45 (2003).
Chen, et al., "Heterozygous disruption of Hic1 predisposes mice to a gender-dependent spectrum of malignant tumors," *Nat Genet.* 33(2):197-202 (2003).
Costello et al., "Aberrant CpG-island methylation has non-random and tumour-type-specific patterns," *Nat Genet.* 24(2):132-138 (2000).
Cross et al., "Purification of CpG islands using a methylated DNA binding column," *Nat. Genet.* 6(3):236-244 (1994).
Cui, et al., "Loss of IGF2 imprinting: a potential marker of colorectal cancer risk," *Science* 299(5613):1753-1755 (2003).
Dahl et al., "DNA methylation analysis techniques," *Biogerontology* 4(4):233-250 (2003).
Dai et al., "Global Methylation Profiling of Lung Cancer identifies Novel Methylated Genes," *Neoplasia* 3(4):314-323 (2001).
Davuluri et al., "Computational identification of promoters and first exons in the human genome," *Nat. Genet.* 29(4):412-417 (2001).
Dennis, "Epigenetics and disease: Altered states," *Nature* 421:686-688 (2003).
Dhanasekaran et al., "Delineation of prognostic biomarkers in prostate cancer," *Nature* 412(6849):822-826 (2001).
Eads et al., "CpG island hypermethylation in human colorectal tumors is not associated with DNA methyltransferase overexpression," *Cancer Res.* 59(10):2302-2306 (1999).
Eisen et al., "Cluster analysis and display of genome-wide expression patterns," *Proc. Natl. Acad. Sci. USA* 95(25):14863-14868 (1998).
Esteller, "CpG island hypermethylation and tumor suppressor genes: a booming present, a brighter future," *Oncogene* 21(35): 5427-40 (2002).
Ewing and Green, "Analysis of expressed sequence tags indicates 35,000 human genes," *Nat. Genet.* 25(2):232-234 (2000).
Fackler et al., "DNA methylation of RASSF1A, HIN-1, RAR-beta, Cyclin D2 and Twist in in situ and invasive lobular breast carcinoma," *Int J Cancer* 107:970-5 (2003).
Fan et al., "Parallel genotyping of human SNPs using generic high-density oligonucleotide tag arrays," *Genome Res.* 10(6):853-860 (2000).
Fan et al., "A versatile assay for high-throughput gene expression profiling on universal array matrices," *Genome Res.* 14:878-885 (2004).
Feil et al., "Methylation analysis on individual chromosomes: improved protocol for bisulphite genomic sequencing," *Nucleic Acids Res.* 22(4):695-696 (1994).
Feinberg and Vogelstein, "Hypomethylation distinguishes genes of some human cancers from their normal counterparts," *Nature* 301(5895):89-92 (1983).
Ferguson et al., "High frequency of hypermethylation at the 14-3-3 σ locus leads to gene silencing in breast cancer," *PNAS* 97(11):6049-6054 (2000).
Frommer et al., "A genomic sequencing protocol that yields a positive display of 5-methylcytosine residues in individual DNA strands," *Proc Natl Acad Sci USA* 89(5):1827-1831 (1992).
Fujii et al., "Methylation of the HIC-1 candidate tumor suppressor gene in human breast cancer," *Oncogene* 16(16):2159-2164 (1998).
Gardiner-Garden et al., "CpG islands in vertebrate genomes," *J Mol. Biol.* 196:261-282 (1987).
Golub et al., "Molecular classification of cancer: class discovery and class prediction by gene expression monitoring," *Science* 286(5439):531-537 (1999).
Gonzalgo et al., "Identification and characterization of differentially methylated regions of genomic DNA by methylation-sensitive arbitrarily primed PCR," *Cancer Res.* 57(4):594-599 (1997).

Gonzalgo et al., "Rapid quantitation of methylation differences at specific sites using methylation-sensitive single nucleotide primer extension (Ms-SNuPE)," *Nucleic Acids Res.* 25(12):2529-2531 (1997).

Hanada et al., "bcl-2 gene hypomethylation and high-level expression in B-cell chronic lymphocytic leukemia," *Blood.* 82(6):1820-1828 (1993).

Heid et al., "Real time quantitative PCR," *Genome Res.* 6(10):986-994 (1996).

Herman et al., "Inactivation of the CDKN2/p16/MTS1 gene is frequently associated with aberrant DNA methylation in all common human cancers," *Cancer Res.* 55(20):4525-4530 (1995).

Herman et al., "Methylation-specific PCR: a novel PCR assay for methylation status of CpG islands," *Proc Natl. Acad. Sci. USA* 93(18):9821-9826 (1996).

Hibi et al., "CDH13 promoter region is specifically methylated in poorly differentiated colorectal cancer," *Br J Cancer* 90, 1030-3 (2004).

Hibi et al., "Methylation pattern of CDH13 gene in digestive tract cancers," *Br J Cancer* 91:1139-1142 (2004).

Huang et al., "Methylation profiling of CpG islands in human breast cancer cells," *Hum Mol Genet.* 8(3):459-470 (1999).

Iannone et al., "Multiplexed single nucleotide polymorphism genotyping by oligonucleotide ligation and flow cytometry," *Cytometry* 39(2):131-140 (2000).

Issa et al., "Methylation of the oestrogen receptor CpG island links ageing and neoplasia in human colon," *Nat Genet.* 7(4):536-540 (1994).

Ivanova et al., "Methylation and silencing of the retinoic acid receptor 2 gene in cervical cancer," *BMC Cancer* 2:4 (2002).

Jones and Laird, "Cancer epigenetics comes of age," *Nat. Genet.* 21(2):163-167 (1999).

Jones and Takai, "The role of DNA methylation in mammalian epigenetics," *Science* 293(5532):1068-1070 (2001).

Kanai et al., "DNA hypermethylation at the D17S5 locus and reduced HIC-1 mRNA expression are associated with hepatocarcinogenesis," *Hepatology* 29(3):703-709 (1999).

Kawai et al., "Comparison of DNA methylation patterns among mouse cell lines by restriction landmark genomic scanning," *Mol Cell Biol.* 14(11):7421-7427 (1994).

Kerr and Churchill, "Bootstrapping cluster analysis: assessing the reliability of conclusions from microarray experiments," *Proc. Natl. Acad. Sci. USA* 98(160):8961-8965 (2001).

Khan et al., "Classification and diagnostic prediction of cancers using gene expression profiling and artificial neural networks," *Nat. Med.* 7(6):673-679 (2001).

Klimasauskas et al., "HhaI methyltransferase flips its target base out of the DNA helix," *Cell* 76:357-369(1994).

Kumar, "Rett and ICF syndromes: methylation moves into medicine," *J. Biosci.* 25(3):213-214 (2000).

Kuppuswamy et al., "Single nucleotide primer extension to detect genetic diseases: experimental application to hemophilia B (factor IX) and cystic fibrosis," *Proc. Natl. Acad. Sci USA* 88:1143-1147 (1991).

Laird et al., "DNA methylation and cancer," *Human Mol. Genet.* 3:1487-1495(1994).

Laird, "The power and the promise of DNA methylation markers," *Nat. Rev. Cancer* Apr. 2003;3(4):253-66 (2003).

Li et al, "Targeted mutation of the DNA methyltransferase gene results in embryonic lethality," *Cell* 69:915-926 (1992).

Li et al., "Causal relationship between the loss of RUNX3 expression and gastric cancer," *Cell* 109(1):113-124 (2002).

Liu et al., "Epigenetic regulation of human telomerase reverse transcriptase promoter activity during cellular differentiation," *Genes Chromosomes Cancer* 41:26-37 (2004).

Michael et al., "Randomly ordered addressable high-density optical sensor arrays," *Anal. Chem.* 70(7):1242-1248 (1998).

Ogama et al., "Prevalent hyper-methylation of the CDH13 gene promoter in malignant B cell lymphomas," *Int J Oncol* 25, 685-91 (2004).

Oliphant, et al., "BeadArray technology: enabling an accurate, cost-effective approach to high-throughput genotyping," *Biotechniques* Jun. 2002;Suppl:56-58, 60-61 (2002).

Otterson et al., "CDKN2 gene silencing in lung cancer by DNA hypermethylation and kinetics of p16INK4 protein induction by 5-aza 2'deoxycytidine," *Oncogene* 11(6):1211-1216 (1995).

Pollack et al., "Microarray analysis reveals a major direct role of DNA copy number alteration in the transcriptional program of human breast tumors," *Proc. Natl. Acad. Sci. USA* 99(20):12963-12968 (2002).

Praz et al., "The Eukaryotic Promoter Database, EPD: new entry types and links to gene expression data," *Nucleic Acids Res.* 30(1):322-324 (2002).

Ramaswamy et al., "A molecular signature of metastasis in primary solid tumors," *Nat. Genet.* 33(1):49-54 (2003).

Ramaswamy et al., "Multiclass cancer diagnosis using tumor gene expression signatures," *Proc Natl. Acad. Sci. USA* 98(26):15149-15154 (2001).

Razin et al., "CpG methylation, chromatin structure and gene silencing-a three-way connection," *Embo J.* 17(17):4905-4908 (1998).

Rein et al., "Identifying 5-methylcytosine and related modifications in DNA genomes," *Nucleic Acids Res.* 26(10):2255-2264 (1998).

Roth et al., "Bringing out the best features of expression data," *Genome Res.* 11(11):1801-1802 (2001).

Russo et al., "Comparative studiy of the influence of pregnancy and hormonal treatment on mammary carcinogenesis," *Br. J. Cancer* 64(3):481-484 (1991).

Sano et al., "Random monoallelic expression of three genes clustered within 60 kb of mouse t complex genomic DNA," *Genome Res.* 11(11):1833-1841 (2001).

Schorderet et al., "Analysis of CpG suppression in methylated and nonmethylated species," *Proc. Natl. Acad. Sci. USA* 89:957-961(1992).

Shipp et al., "Diffuse large B-cell lymphoma outcome prediction by gene expression profiling and supervised machine learning," *Nat. Med.* 8(1):68-74 (2002).

Singer-Sam et al., "A quantitative HpaII-PCR assay to measure methylation of DNA from a small number of cells," *Nucleic Acids Res.* 18(3):687 (1990).

Sivaraman et al., "Hormone-induced refractoriness to mammary carcinogenesis in Wistar-Furth rats," *Carcinogenesis* 19(9):1573-1581 (1998).

Smiraglia et al., "A new tool for the rapid cloning of amplified and and hypermethylated human DNA sequences from restriction landmark genome scanning gels," *Genomics.* 58(3):254-262 (1999).

Strichman-Almashanu et al., "A genome-wide screen for normally methylated human CpG islands that can identify novel imprinted genes," *Genome Res.* 12(4):543-554 (2002).

Taylor et al., "The diagnostic significance of Myf-3 hypermethylation in malignant lymphoproliferative disorders," *Leukemia.* 15(4):583-589 (2001).

Toyota et al., "Identification of differentially methylated sequences in colorectal cancer by methylated CpG island amplification," *Cancer Res.* 59(10):2307-2312 (1999).

Tsou et al., "DNA methylation analysis: a powerful new tool for lung cancer diagnosis," *Oncogene* 21(35):5450-5461 (2002).

Umbricht et al., "Hypermethylation of 14-3-3 σ (statifin) is an early event in breast cancer," *Oncogene* 20:3348-3353 (2001).

Venter, et al., "The sequence of the human genome," *Science* 291(5507):1304-1351 (2001).

Walt, "Techview: molecular biology. Bead-based fiber optic arrays," *Science* 287(5452):451-452 (2000).

Welsh et al., "Analysis of gene expression profiles in normal and neoplastic ovarian tissue samples identifies candidates molecular markers of epithelial ovarian cancer," *Proc. Natl. Acad. Sci. USA* (2001) 98(3):1176-1181 (2001).

Widschewendter et al., "DNA methylation and breast carcinogenesis," *Oncogene*, 21(35):5462-5482 (2002).

Wong, et al., "New markers for cancer detection," *Curr Oncol Rep.* 4(6): 471-477 (2002).

Yan et al., "Role of DNA methylation and histone acetylation in steroid receptor expression in breast cancer," *J. Mammary Gland Biol. Neoplasia* 6(2):183-192 (2001).

Yeakley et al., "Profiling alternative splicing on fiber-optic arrays," *Nat. Biotechnol.* 20(4):353-358 (2002).

Zhong, et al., "A survey of FRAXE allele sizes in three populations," *Am. J. Med. Genet.* 64(2):415-419 (1996).

Gerry, et al., "Universal DNA Microarray Method for Multiplex Detection of Low Abundance Point Mutations," *J Mol Biol.* 292:251-262 (1999).

Grunau, et al., "MethDB-a public database for DNA methylation data", *Nucleic Acids Res.* 29(1):270-274 (2001).

Grunau, et al., "DNA Methylation Database "MethDB": a User Guide," *J Nutr* 132:2435S-2439S (2002).

Lander, "Initial sequencing and analysis of the human genome," *Nature* 409(6822):860-921 (2001).

Lockart et al., "Genomics, gene expression and DNA arrays," *Nature* 405(6788):827-836 (2000).

Peroue, et al., "Molecular portraits of human breast tumours," *Nature* 406(6797):747-752 (2000).

Sasaki, Allen and Surani, "DNA methylation and genomic imprinting in mammals," in DNA Methylation: Molecular Biology and biological Significance (Birkhauser Verlag Basel/Switzerland), J.P. Jost & H. P. Saluz, eds. 1993. p. 469-486.

Bibikova et al. (Apr. 2005). DNA methylation profiling in lung cancer using universal bead arrays. Poster presented at the AACR Meeting, Anaheim, CA.

FIG. 1
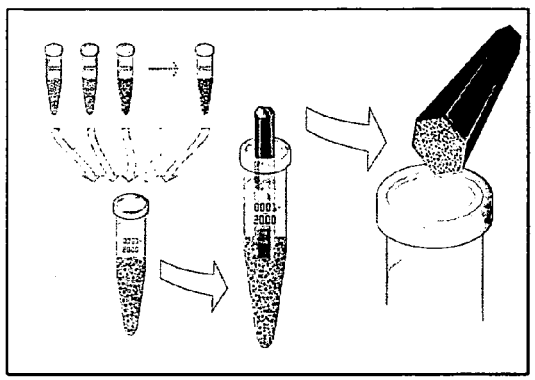
FIG. 1 A
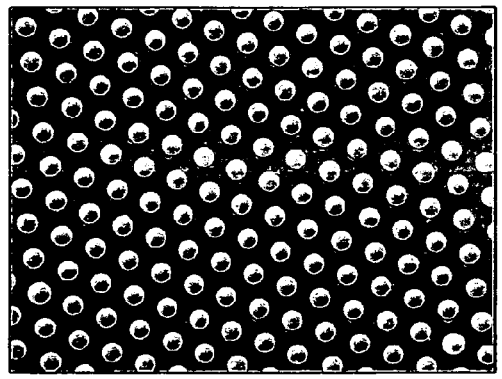
FIG. 1B

FIG. 2
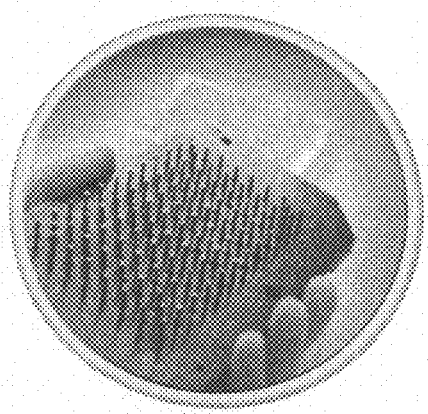
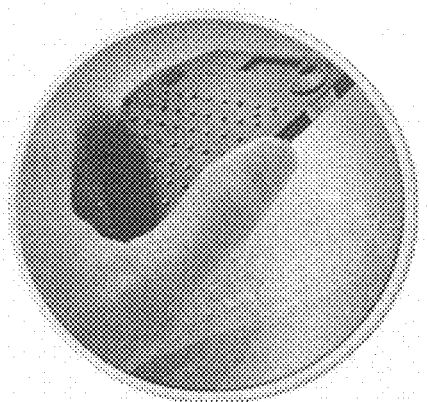
FIG. 2A  FIG. 2B

Supplementary Figure 31. Methylation measurement with internal controls. Methylated, unmethylated and semi-methylated (generated by pre-mixing the methylated and unmethylated at 1:1 ratio) plasmid DNAs were spiked into human genomic DNA at 1:1 molar ratio, and 96 assays were run in parallel. Green, yellow and red colors represent low, medium and high methylation levels, respectively

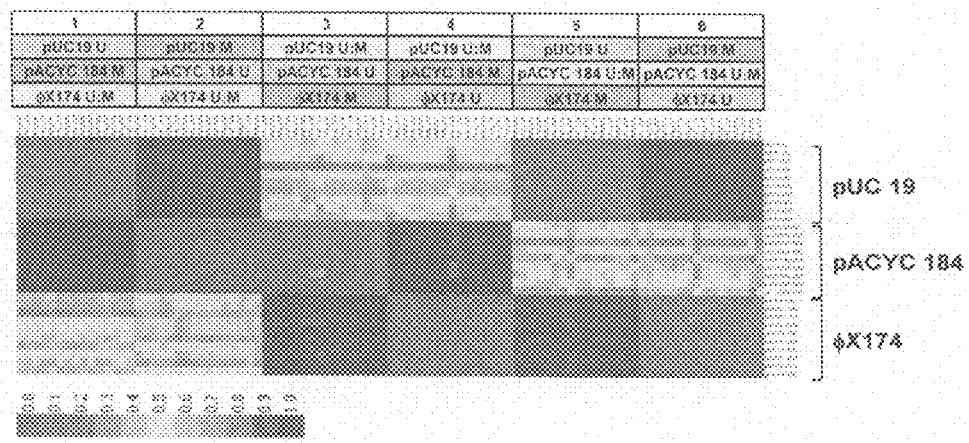

FIG. 31

(A) Target ID (B) Contig (C) PromoterStart-PromoterEnd (D) CpG position relative to TSS
(E) Orientation (F) Strand (G) Start (H)End (I)Length (J) CpG-Position
(K) Target sequence (L) ASO_C (Probe Sequence) (M) ASO_T (Probe Sequence) (N) LSO_C
(Probe Sequence) (O) LSO_T (Probe Sequence)

1(A) ADCYAP1-1103 (B)gi:37545150 (C) 893887-895416 (D) -399 (E) +
(F) Forward (G) 1078 (H) 1127 (I) 50 (J) 26
(K) GATGCCTCTCGGGTGGTGACTCCAG[CG]CAGGAACTTGAAGAAGCGCTTTG
(L) AAACGCTTCTTCAAATTCCTACG (M) CAAAACACTTCTTCAAATTCCTACA
(N) TAAAATCACCACCCGAAAAACAT (O) TAAAATCACCACCCAAAAACATC 2A) APBA2-1397 (B) gi:37540936 (C) 2910-4439 (D) -105 (E) +
(F) Reverse (G) 1373 (H) 1418 (I) 46 (J)25
(K )TCCCATATGAGCGTGTGGCCCAT[CG]TTGCCATCCACACCTGCCCCT
(L)CCATATAAACGTATAACCCATCG (M)TCCCATATAAACATATAACCCATCA
(N)TACCATCCACACCTACCCCT (O)TACCATCCACACCTACCCCT 3(A) ASCL2-1038 (B)gi:37541814 (C) 1055809-1057338 (D) -464 (E) -
(F) Reverse (G)1015 (H) 1064 (I) 50 (J) 24
(K)GCGCCCTGCGCGATTGGCCAAA[CG]GGTGGCCCACGATTGGCTGAGACCCT
(L)CCTACGCGATTAACCAAACG (M)ACACCCTACACAATTAACCAAACA
(N)ATAACCCACGATTAACTAAAACCC (O)ATAACCCACAATTAACTAAAACCCT 4(A) ASCL2-1048 (B)gi:37541814 (C) 1055809-1057338 (D) -454 (E) -
(F) Forward (G) 1025 (H) 1071 (I) 47 (J) 24
(K)CGATTGGCCAAACGGGTGGCCCA[CG]ATTGGCTGAGACCCTGGCCCCC
(L)AAACCAAAATCTCAACCAATCG (M)AAAAACCAAAATCTCAACCAATCA
(N)AAACCACCCGTTTAACCAATC (O)AAACCACCCATTTAACCAATCA 5(A) ASCL2-1339 (B)gi:37541814 (C) 1055809-1057338 (D) -163 (E) -
(F) Forward (G) 1314 (H) 1364 (I) 51 (J) 26
(K) CTAAGCACCTGCCGGGAGCAGGGGG[CG]CACCGGGAACTCGCAGATTTCGCC
(L) GAAATCTACGAATTCCCGATACG (M) AACAAAATCTACAAATTCCCAATACA
(N ) CCCCTACTCCCGACAAATACTTAA (O) CCCCTACTCCCAACAAATACTTAA

FIG. 32

6(A) ASCL2-856 (B)gi:37541814    (C) 1055809-1057338    (D) -646    (E) -    (F) Forward    (G) 830
(H) 880    (I) 51    (J) 27
(K) AGTAGATTAACGCACAGGTGGGGGCG[CG]CTCGGGACATAGCTGCGCTAGGG
(L) TAACGCAACTATATCCCGAACG    (M) CCCTAACACAACTATATCCCAAACA
(N) GCCCCCACCTATACGTTAATCTAC    (O) ACCCCCACCTATACATTAATCTACT 7(A)CCND2-604 (B)gi:29805200    (C) 4235699-4237228    (D) -898    (E) +    (F) Reverse
(G) 579    (H) 630    (I) 52    (J) 26
(K )CTGCATCGGTGTGGCCACGCTCAG[CG]CAGACACCTCGGGCGGCTTGTCAGCA
(L) ATCGATATAACCACGCTCAACG    (M)CTACATCAATATAACCACACTCAACA
(N) AAACACCTCGAACGACTTATCAAC    (O) AAACACCTCAAACAACTTATCAACA 8(A)CD2-1433    (B)gi:37549274    (C) 1211187-1212716    (D) -69    (E) +    (F) Forward
(G) 1405    (H) 1456    (I) 52    (J) 29
(K) TGTAAAGAGAGGCACGTGGTTAAGCTCT[CG]GGGTGTGGACTCCACCAGTCTC
(L)AACTAATAAAATCCACACCCCG    (M)AAAACTAATAAAATCCACACCCCA
(N)AAACTTAACCACGTACCTCTCTTTAC    (O)AAACTTAACCACATACCTCTCTTTACA 9(A)CDH13-1358    (B)gi:37541871    (C) 9370923-9372452    (D) -144    (E) +
(F)Reverse    (G) 1334    (H) 1384    (I) 51    (J) 25
(K)AAGCAAATGGGATGCCACCTCCG[CG]GGGCTCGCTCCTCGCGAGGTGCTCAC
(L)AAATAAAATACCACCTCCGCG    (M)AAACAAATAAAATACCACCTCCACA
(N)AACTCGCTCCTCGCGAAATAC    (O)AACTCACTCCTCACAAAATACTCAC 10(A)CFTR-1051    (B)gi:37538784    (C) 42295207-42296736    (D) -451    (E) +
(F)Forward    (G) 1028    (H) 1070    (I) 43    (J) 24
(K)AGGAGGAGGAGGAAGGCAGGCTC[CG]GGGAAGCTGGTGGCAGCG
(L)GCTACCACCAACTTCCCCG    (M)CACTACCACCAACTTCCCCA
(N)AACCTACCTTCCTCCTCCTCCT    (O)AACCTACCTTCCTCCTCCTCCT 11(A)CFTR-1191    (B)gi:37538784    (C) 42295207-42296736    (D) -311    (E) +
(F)Forward    (G) 1164    (H) 1214    (I) 51    (J) 28
(K)CGTTGCCAACTGGACCTAAAGAGAGGC[CG]CGACTGTCGCCCACCTGCGGGA
(L)GCAAATAAACGACAATCGCG    (M)TCCCACAAATAAACAACAATCACA
(N)CCTCTCTTTAAATCCAATTAACAACG    (O)CCTCTCTTTAAATCCAATTAACAACA

FIG. 32 (CON'T)

12(A) DBC1-1053    (B)gi:37540590    (C) 23789407-23790936    (D) -449    (E) -
(F) Reverse    (G) 1030    (H) 1077    (I) 48    (J) 24
(K)AAACCCACACTCGATGGATCCA[CG]CGGCCGTGGAAACACCTGCCGCCC
(L)CCACACTCGATAAATCCACG    (M)AAACCCACACTCAATAAATCCACA
(N)GACCGTAAAAACACCTACCGC    (O)AACCATAAAAACACCTACCACCC 13(A) DIO3-1355    (B)gi:29736559    (C) 81946229-81947758    (D) -147    (E) +
(F) Reverse    (G)1332    (H) 1378    (I) 47    (J) 24
(K)GCTGGAGGACCTCCCCAGCGGA[CG]CCCAGGTCCCTGGTCGGGCTCCC
(L)AAAACCTCCCCAACGAACG    (M)ACTAAAAAACCTCCCCAACAAACA
(N)CCAAATCCCTAATCGAACTCC    (O)CCAAATCCCTAATCAAACTCCC 14(A) DLC1-1012    (B)gi:37552654    (C)1183380-1184909    (D) -490    (E) -
(F) Forward    (G) 986    (H) 1035    (I) 50    (J) 27
(K)TGTGATCAGAGAGATCTGGAAGAAAT[CG]TTCTATTAACTGGATGCTTGGG
(L)CCCAAACATCCAATTAATAAAACG    (M)CCCAAACATCCAATTAATAAAACA
(N)TTTCTTCCAAATCTCTCTAATCACA    (O)TTTCTTCCAAATCTCTCTAATCACA 15(A) DLK1-1119    (B)gi:29736559    (C)81111794-81113323    (D) -383    (E) +
(F) Forward    (G) 1094    (H) 1143    (I) 50    (J) 26
(K)ATTGCACGTGTGCCCGGGACTTCAG[CG]ATAAGTGTTTCGGTGTTCCTGCG
(L)CAAAAACACCGAAACACTTATCG    (M)CACAAAAACACCAAAACACTTATCA
(N)TAAAATCCCGAACACACGTACAAT    (O)TAAAATCCCAAACACACATACAAT 16(A) DLK1-1185    (B)gi:29736559    (C)81111794-81113323    (D) -317    (E) +
(F)Reverse    (G) 1161    (H) 1212    (I) 52    (J) 25
(K)CGGGGAGGTCTGCGGCCCAGGTT[CG]ATTCCTGCGACTTGTCCTAGGCAGGCC
(L)AAAAATCTACGACCCAAATTCG    (M)CAAAAAAATCTACAACCCAAATTCA
(N)TTCCTACGACTTATCCTAAACAAACC    (O)TTCCTACAACTTATCCTAAACAAACC 17(A) DLK1-1226    (B)gi:29736559    (C)81111794-81113323    (D) -276(E) +    (F)Forward
(G) 1198    (H) 1250    (I) 53    (J) 29
(K)TGTCCTAGGCAGGCCTGTATGTGCGCGG[CG]GCCGCGTGCTGTACAGTGTGAGG
(L)ACACTATACAACACGCGACCG    (M)CCTCACACTATACAACACACAACCA
(N)CGCGCACATACAAACCTACCTA    (O)CACACACATACAAACCTACCTAAAACA

FIG. 32 (CON'T)

18(A) DLK1-1287 (B)gi:29736559 (C)81111794-81113323 (D) -215 (E) +
(F)Reverse (G) 1262 (H) 1315 (I) 54 (J) 26
(K)AAACGCTCGCGGGATACCTGTGCC[CG]TCTAGCCAAGAGTGCACCCGTGTGCGCG
(L)CTCGCGAAATACCTATACCCG (M)AAACACTCACAAAATACCTATACCCA
(N)CTAACCAAAAATACACCCGTATACG (O)CTAACCAAAAATACACCCATATACACA 19(A)GABRB3-1408 (B)gi:29802188 (C)3453697-3455226 (D) -94 (E) -
(F) Forward (G) 1379 (H) 1430 (I) 52 (J) 30
(K)GGTCCAATTGTATAAATGAAAAATAGGGC[CG]CCACGGCAGGGGCTGGAAGAC
(L)TTCCAACCCCTACCGTAACG (M)ATCTTCCAACCCCTACCATAACA
(N)CCCTATTTTTCATTTATACAATTAAACC (O)CCCTATTTTTCATTTATACAATTAAACC 20(A)GALR1-1270 (B)gi:29823169 (C)2626888-2628417 (D) -232 (E) +
(F) Forward (G) 1245 (H) 1292 (I) 48 (J) 26
(K)TATTCCTGGGAGAGAGGCGTTCTCA[CG]GACAGCCACCCTGGGGAGGAG
(L)CTCCTCCCCAAAATAACTATCCG (M)CTCCTCCCCAAAATAACTATCCA
(N)AAAAACGCCTCTCTCCCAAAA (O)AAAAACACCTCTCTCCCAAAAATA 21(A) GDF10-1224 (B)gi:37550940 (C)263043-264572 (D) -278 (E) -
(F)Reverse (G) 1197 (H) 1250 (I) 54 (J) 28
(K)CTCACATTTTGGACATACGCTGACTC[CG]AGGCAACTGGGCGCACACATATCCCC
(L)CATTTTAAACATACGCTAACTCCG (M)CTCACATTTTAAACATACACTAACTCCA
(N)AACAACTAAACGCACACATATCCC (O)AACAACTAAACACACACATATCCCC 22(A) HOXA11-558 (B)gi:37538470 (C)26518409-26519938 (D) -944 (E) -
(F) Forward (G) 532 (H) 583 (I) 52 (J) 27
(K)CCAGAAGACCAGGCAGATGGGTGGAC[CG]GTGAGCAGCAGGGCAGCCCCTGTG
(L)CAAAAACTACCCTACTACTCACCG (M)CACAAAAACTACCCTACTACTCACCA
(N)TCCACCCATCTACCTAATCTTCTAA (O)TCCACCCATCTACCTAATCTTCTAA 23(A) HOXA11-802 (B) gi:37538470 (C) 26518409-26519938 (D) -700 (E) -
(F) Forward (G) 777 (H) 826 (I) 50 (J) 26
(K)GGTTTAGGGACGGAAGGCACTAAAG[CG]CTTCGGAAGTGACCATGAATGAG
(L)CATTCATAATCACTTCCGAAACG (M)CTCATTCATAATCACTTCCAAAACA
(N)TTTAATACCTTCCGTCCCTAAACC (O)TTTAATACCTTCCATCCCTAAACC

FIG. 32 (CON'T)

24(A) HOXA5-1094     (B) gi:37538470     (C) 26476866-26478395     (D) -408     (E) -
(F) Reverse     (G) 1071     (H) 1121     (I) 51     (J) 24
(K)AATCCTCTGCATCCTCGCCGGG[CG]CGCGATCGGCAGCTGACGGCCTAACAA
(L)TCTACATCCTCGCCGAACG     (M)AATCCTCTACATCCTCACCAAACA
(N)GCGATCGACAACTAACGACCTAA     (O)ACAATCAACAACTAACAACCTAACAA 25(A) HOXA5-1247     (B)gi:37538470     (C)26476866-26478395     (D) -255     (E) -
(F) Reverse     (G) 1224     (H) 1275     (I) 52     (J) 24
(K)GGGCGATGAGCCCTGCCTCCAG[CG]GGTGGCGCTCGAGTCCGGCTGAACGGCG
(L)CGATAAACCCTACCTCCAACG     (M)AAACAATAAACCCTACCTCCAACA
(N)ATAACGCTCGAATCCGACTAAAC     (O)ATAACACTCAAATCCAACTAAACAACA 26(A) HOXA5-75     (B) gi:37538470     (C) 26476866-26478395     (D) -1427     (E) -
(F) Forward     (G) 47     (H) 99     (I) 53     (J) 29
(K)AGCCGCCTCCCAGAACAGGAAGGAAGCT[CG]AGGAACAAAGGGGGCCCCAACAG
(L)ATTAAAACCCCCTTTATTCCTCG     (M)CTATTAAAACCCCCTTTATTCCTCA
(N)ACTTCCTTCCTATTCTAAAAAACGA     (O)ACTTCCTTCCTATTCTAAAAAACAACT 27(A) HS3ST2-311     (B) gi:37541485     (C) 14136693-14138222     (D) -1191     (E) +
(F)Forward     (G) 285     (H) 334     (I) 50     (J) 27
(K)TCCCCGGGGAGCAGTCTACCGCTAGG[CG]GCGGCTGCTAAGAGAGGAACCC
(L)CCTCTCTTAACAACCGCCG     (M)AAATTCCTCTCTTAACAACCACCA
(N)CTAACGATAAACTACTCCCCGAAA     (O)CTAACAATAAACTACTCCCCAAAAA 28(A) HTR1B-1278     (B) gi:29740881     (C) 15993262-15994791     (D) -224     (E) -
(F)Forward     (G)1251     (H)1302     (I) 52     (J) 28
(K)TGTGGAGAGGAACAACCACAGACGCGG[CG]GCTTAGCTAGGCGCTCTGGAAGT
(L)CCAAAACGCCTAACTAAACCG     (M)ACTTCCAAAACACCTAACTAAACCA
(N)CGCGTCTATAATTATTCCTCTCCA     (O)CACATCTATAATTATTCCTCTCCACA 29(A) HTR1B-315     (B) gi:29740881     (C) 15993262-15994791     (D) -1187     (E) -
(F) Forward     (G) 290     (H) 341     (I) 52     (J) 26
(K)GGACATGGGTCTCACTGGAGGTCAG[CG]CAGCAAGCTCTGATGTCCGTAGAGG
(L)CCTCTACGAACATCAAAACTTACTACG     (M)CCTCTACAAACATCAAAACTTACTACA
(N)TAACCTCCAATAAAACCCATATCC     (O)TAACCTCCAATAAAACCCATATCC

FIG. 32 (CON'T)

30(A) HTR2A-1387 (B)gi:37546841 (C)28478147-28479676 (D) -115 (E) -
(F)Reverse (G)1359 (H)1414 (I) 56 (J) 29
(K)AGTGGAGAGCACTGACTGCCACACTTG[CG]AGGCTGTCCTGAGGCACTGAAAGCCCC
(L)AAAAAACACTAACTACCACACTTACG (M)AATAAAAAACACTAACTACCACACTTACA
(N)AACTATCCTAAAACACTAAAAACCCC (O)AACTATCCTAAAACACTAAAAACCCC 31(A) IGF2-112 (B) gi:37541814 (C) 923913-925442 (D) -1390 (E) - (F)Forward
(G) 86 (H) 136 (I) 51 (J) 27
(K)TGGGCCGCAAAGGCGAGCTACTTAGA[CG]CACCCCGGTGAGCTCGGCCATGC
(L)ATAACCGAACTCACCGAAATACG (M)ACATAACCAAACTCACCAAAATACA
(N)CTAAATAACTCGCCTTTACGACCC (O)CTAAATAACTCACCTTTACAACCCA 32(A) IGF2AS-1145 (B) gi:37541814 (C) 924187-925716 (D) -357 (E) +
(F) Reverse (G) 1122 (H) 1171 (I) 50 (J) 24
(K)CATGGCCGAGCTCACCGGGGTG[CG]TCTAAGTAGCTCGCCTTTGCGGCCCA
(L)ATAACCGAACTCACCGAAATACG (M)CATAACCAAACTCACCAAAATACA
(N)CTAAATAACTCGCCTTTACGACC (O)CTAAATAACTCACCTTTACAACCCA 33(A) NEFL-1341 (B) gi:37552400 (C) 3188285-3189814 (D) -161 (E) -
(F)Reverse (G) 1317 (H) 1366 (I) 50 (J) 25
(K)CCCACTGGCCGGCGTGCCGTGAT[CG]ATCGCAGGCTGCGTCAGGAGCCTCC
(L)ACTAACCGACGTACCGTAATCG (M)CCCACTAACCAACATACCATAATCA
(N)TCGCAAACTACGTCAAAAACCT (O)TCACAAACTACATCAAAAACCTCC 34(A) NEFL-1367 (B) gi:37552400 (C) 3188285-3189814 (D) -135 (E) -
(F)Forward (G) 1340 (H) 1391 (I) 52 (J) 28
(K)CGATCGCAGGCTGCGTCAGGAGCCTCC[CG]GCGTATAAATAGGGGTGGCAGAA
(L)CTACCACCCCTATTTATACGCCG (M)TTCTACCACCCCTATTTATACACCA
(N)AAAACTCCTAACGCAACCTACGAT (O)AAAACTCCTAACACAACCTACAATCA 35(A) NEFL-524 (B) gi:37552400 (C) 3188285-3189814 (D) -978 (E) - (F) Reverse
(G) 499 (H) 550 (I) 52 (J) 26
(K)AGCTTGAAGCTCCCGGCTGCGGAG[CG]CGCGGCTGCCTCAGCAAGTCAGTCTC
(L)TTAAAACTCCCGACTACGAAACG (M)AACTTAAAACTCCCAACTACAAAACA
(N)GCGACTACCTCAACAAATCAATCT (O)ACAACTACCTCAACAAATCAATCTC

FIG. 32 (CON'T)

36(A) NEFL-600 (B) gi:37552400 (C) 3188285-3189814 (D) -902 (E) - (F) Reverse
(G) 579 (H) 628 (I) 50 (J) 22
(K) ACCACCCACACACTGCAACA[CG]TTAAAGCCATCTGCGGCTTCATTCTCAG
(L) CACCCACACACTACAACACG (M) ACCACCCACACACTACAACACA
(N) TAAAACCATCTACGACTTCATTCTCA (O) TAAAACCATCTACAACTTCATTCTCAA 37(A) NPY-1009 (B) gi:37538470 (C) 23615917-23617446 (D) -493 (E) + (F) Reverse
(G) 987 (H) 1035 (I) 49 (J) 23
(K) CCAGTTGCCTCACTCCAACAG[CG]CGCAGTTGTGCCCGGCGAGGATGCCG
(L) CAATTACCTCACTCCAACAACG (M) CCAATTACCTCACTCCAACAACA
(N) GCAATTATACCCGACGAAAATAC (O) ACAATTATACCCAACAAAAATACCA 38(A) NPY-793 (B) gi:37538470 (C) 23615917-23617446 (D) -709 (E) + (F) Reverse
(G) 769 (H) 821 (I) 53 (J) 25
(K) TTTGAGTCGCCACACTCATGTCT[CG]ACCGAGCCTGGCTCGCTGCGTCTGAGCG
(L) TAAATCGCCACACTCATATCTCG (M) TTTAAATCACCACACTCATATCTCA
(N) CCGAACCTAACTCGCTACGTCTAA (O) CCAAACCTAACTCACTACATCTAAACA 39(A) NPY-931 (B) gi:37538470 (C) 23615917-23617446 (D) -571 (E) + (F) Reverse
(G) 907 (H) 956 (I) 50 (J) 25
(K) GCGCAGCTTTGGGACCCTCTAGC[CG]GAGACTTCCGGCAGCTGCCTCCGAC
(L) GCAACTTTAAAACCCTCTAACCG (M) ACACAACTTTAAAACCCTCTAACCA
(N) AAACTTCCGACAACTACCTCCG (O) AAACTTCCAACAACTACCTCCAAC 40(A) OPCML-967 (B) gi:37540935 (C) 36356795-36358324 (D) -535 (E) -
(F) Reverse (G) 942 (H) 992 (I) 51 (J) 26
(K) GGACGACCCTGGCTGCGCCGGCTG[CG]CGTCCCCGCCTTGGAACTTTTTGCC
(L) ACCCTAACTACGCCGACTACG (M) AAACAACCCTAACTACACCAACTACA
(N) GTCCCCGCCTTAAAACTTTTTA (O) ATCCCCACCTTAAAACTTTTTACC 41(A) PAX6-1337 (B) gi:37541814 (C) 30596676-30598205 (D) -165 (E) -
(F) Reverse (G) 1313 (H) 1365 (I) 53 (J) 25
(K) AGGGAGCATCCAATCGGCTGGCG[CG]AGGCCCCGGCGCTGCTTTGCATAAAGCA
(L) AACATCCAATCGACTAACGCG (M) AAAAAACATCCAATCAACTAACACA
(N) AACCCCGACGCTACTTTACATAAA (O) AACCCCAACACTACTTTACATAAAACA

FIG. 32 (CON'T)

42(A) PENK-1293 (B) gi:37556103 (C) 9201109-9202638 (D) -209 (E) -
(F)Reverse (G) 1270 (H) 1319 (I) 50 (J) 24
(K)CCCTGGTCTGCGGCGTTCTCTC[CG]GAATCTTGCCCTGGGCCGCGGACGCC
(L)CCTAATCTACGACGTTCTCTCCG (M)CCCTAATCTACAACATTCTCTCCA
(N)AATCTTACCCTAAACCGCGAA (O)AATCTTACCCTAAACCACAAACACC 43(A) PENK-1480 (B) gi:37556103 (C) 9201109-9202638 (D) -22 (E) -
(F) Reverse (G) 1454 (H) 1507 (I) 54 (J) 27
(K)AGCATTCCTGCGGGCTTTTGCTCGA[CG]ATCCCCTGCTGAGGCTGTCGCGGCGAG
(L)ATTCCTACGAACTTTTACTCGACG (M)AACATTCCTACAAACTTTTACTCAACA
(N)TCCCCTACTAAAACTATCGCGA (O)TCCCCTACTAAAACTATCACAACAAA 44(A) POMC-1303 (B) gi:37547123 (C) 4207356-4208885 (D) -199 (E) -
(F) Reverse (G) 1280 (H) 1328 (I) 49 (J) 24
(K)GGCGAGCGGCCAGGTGCGCCTT[CG]GCAGGACAGTGCTAATTCCAGCCCC
(L)AACGACCAAATACGCCTTCG (M)AACAAACAACCAAATACACCTTCA
(N0CAAAACAATACTAATTCCAACCCC (O)CAAAACAATACTAATTCCAACCCC 45(A) PTPN6-1214 (B) gi:29805200 (C) 6908501-6910030 (D) -288 (E) +
(F) Reverse (G) 1191 (H) 1239 (I) 49 (J) 24
(K)TTTCCTTAGGCCCTTTGGTTTC[CG]CCTACGGAGAGGTTTCCCCCATTGG
(L)TTCCTTAAACCCTTTAATTTCCG (M)TTTCCTTAAACCCTTTAATTTCCA
(N)CTACGAAAAAATTTCCCCCATTA (O)CTACAAAAAAATTTCCCCCATTAA 46(A) PTPRO-1206 (B) gi:37543832 (C) 8232961-8234490 (D) -296 (E) +
(F) Forward (G) 1182 (H) 1227 (I) 46 (J) 25
(K)CAGAGATTGAGGGAGGGGTTGAGG[CG]GAGTCTGCAATGGGGGCTGT
(L)AACCCCCATTACAAACTCCG (M)ACAACCCCCATTACAAACTCCA
(N)CTCAACCCCTCCCTCAATCTCTA (O)CTCAACCCCTCCCTCAATCTCTA 47(A) RET-1149 (B) gi:37550981 (C) 974325-975854 (D) -353 (E) + (F) Forward
(G) 1123 (H) 1172 (I) 50 (J) 27
(K)GGCAAAAGGCAGGGACTGCAAGCGGG[CG]CGCACCGGGTAGGAAGAGCGGC
(L)TCTTCCTACCCGATACGCG (M)ACCACTCTTCCTACCCAATACACA
(N)CCGCTTACAATCCCTACCTTTTAC (O)CCACTTACAATCCCTACCTTTTACC

FIG. 32 (CON'T)

48(A) RUNX3-368　　　(B) gi:37549544　(C) 892564-894093　　　(D) -1134　　　(E) -
(F) Forward　　　(G) 339　(H) 393　(I) 55　(J) 30
(K)ACAGGCCGCCACAACGAAGAACGACGCCG[CG]AGGCCTGCAAGATCCTGAAACTTG
(L)AATTTCAAAATCTTACAAACCTCG　(M)CAAATTTCAAAATCTTACAAACCTCA
(N)GACGTCGTTCTTCGTTATAACG　(O)AACATCATTCTTCATTATAACAACCTAT 49(A) SEZ6L-1046　　　(B) gi:29807292　(C) 5954705-5956234　　(D) -456　　　(E) +
(F) Forward　　　(G) 1021　(H) 1071　(I) 51　(J) 26
(K)CCTGGCCAGGCAGAGCTGCTGGGAG[CG]TCAGCAGGGAGAGAAAACGCTCGG
(L)GAACGTTTTCTCTCCCTACTAACG　(M)CCAAACATTTTCTCTCCCTACTAACA
(N)TCCCAACAACTCTACCTAACCAAA　(O)TCCCAACAACTCTACCTAACCAAA 50(A) TERT-900　(B) gi:29796148　(C) 1277868-1279397　　(D) -602　　　(E) -　　(F) Forward
(G) 875　(H) 924　(I) 50　(J) 26
(K)CAGGGAGGCACTCCGGGAGGTCCCG[CG]TGCCCGTCCAGGGAGCAATGCGT
(L)GCATTACTCCCTAAACGAACACG　(M)ACACATTACTCCCTAAACAAACACA
(N)GAAACCTCCCGAAATACCTCC　　(O)AAAACCTCCCAAAATACCTCCCTA 51(A) TNF-1343　(B) gi:29804415　(C) 22396426-22397955　(D) -159　　　(E) +　　(F) Forward
(G) 1318　(H) 1369　(I) 52　(J) 26
(K)CCCGCCCCCGCGATGGAGAAGAAAC[CG]AGACAGAAGGTGCAGGGCCCACTAC
(L)ATAAACCCTACACCTTCTATCTCG　(M)ATAATAAACCCTACACCTTCTATCTCA
(N)TTTCTTCTCCATCGCGAAA　(O)TTTCTTCTCCATCACAAAAACAAA 52(A) TNF-1371　(B) gi:29804415　(C) 22396426-22397955　(D) -131　　　(E) +　　(F) Reverse
(G) 1347　(H) 1398　(I) 52　(J) 25
(K)ACAGAAGGTGCAGGGCCCACTAC[CG]CTTCCTCCAGATGAGCTCATGGGTTTC
(L)CAAAAAATACAAAACCCACTACCG　(M)ACAAAAAATACAAAACCCACTACCA
(N)TTCCTCCAAATAAACTCATAAATTTC　(O)TTCCTCCAAATAAACTCATAAATTTC 53(A) TP73-358　(B) gi:29791384　(C) 874404-875933　　(D) -1144　　(E) +　　(F)Forward
(G) 333　(H) 381　(I) 49　(J) 26
(K)GGGGGTCACCATGGGCAGAGGACAT[CG]GTTCGGAGCCAGATCACGGGCC
(L)CCGTAATCTAACTCCGAACCG　(M)AACCCATAATCTAACTCCAAACCA
(N)TATCCTCTACCCATAATAACCCCC　(O)TATCCTCTACCCATAATAACCCCC

FIG. 32 (CON'T)

54(A) TWIST1-1348 (B) gi:37538470 (C) 18452648-18454177 (D) -154 (E) -
(F) Reverse (G) 1323 (H) 1374 (I) 52 (J) 26
(K)CGGGGTGTGCGTCCAGCCGTTGGG[CG]CTTTCTTTTTGGACCTCGGGGCCATC
(L)AAATATACGTCCAACCGTTAAACG (M)CAAAATATACATCCAACCATTAAACA
(N)TTTCTTTTTAAACCTCGAAACCAT (O)TTTCTTTTTAAACCTCAAAACCATC 55(A) TWIST1-524 (B) gi:37538470 (C) 18452648-18454177 (D) -978 (E) -
(F) Forward (G) 501 (H) 547 (I) 47 (J) 24
(K)GTAGTCCTTTGGATGTTGGGGAG[CG]TCAGACTGGGTCGTTGTAGAGG
(L)CTCTACAACGACCCAATCTAACG (M)CCTCTACAACAACCCAATCTAACA
(N)TCCCCAACATCCAAAAACTAC (O)TCCCCAACATCCAAAAACTAC

FIG. 32 (CON'T)

SEQUENCE LISTING

```
<160> NUMBER OF SEQ ID NOS: 1829

<210> SEQ ID NO 1
<211> LENGTH: 47
<212> TYPE: DNA
<213> ORGANISM: Homo sapiens

<400> SEQUENCE: 1
ggatgctcct cagctctggg gacgcggtgc agaagtgtga gggcgcc        47

<210> SEQ ID NO 2
<211> LENGTH: 48
<212> TYPE: DNA
<213> ORGANISM: Homo sapiens

<400> SEQUENCE: 2
cttccgactt tgtcacacac ctgcgccgcc agactggggt cgggcccc       48

<210> SEQ ID NO 3
<211> LENGTH: 52
<212> TYPE: DNA
<213> ORGANISM: Homo sapiens

<400> SEQUENCE: 3
cccggcttcc aggcagtaat gggcgggtcc ctgcgcggga gcgtggcggg cg  52

<210> SEQ ID NO 4
<211> LENGTH: 50
<212> TYPE: DNA
<213> ORGANISM: Homo sapiens

<400> SEQUENCE: 4
aatctgaaga aagctgaggg gaggcggcag atgttctgat ctactaggga     50

<210> SEQ ID NO 5
<211> LENGTH: 45
<212> TYPE: DNA
<213> ORGANISM: Homo sapiens

<400> SEQUENCE: 5
aactcctgag tggtgtggga gggcggtgag gggcagctga aagtc          45

<210> SEQ ID NO 6
<211> LENGTH: 50
<212> TYPE: DNA
<213> ORGANISM: Homo sapiens
```

-continued

<400> SEQUENCE: 6
tggtctagga aacatgattg gcagctacga gagagctagg ggctggacgt           50

<210> SEQ ID NO 7
<211> LENGTH: 49
<212> TYPE: DNA
<213> ORGANISM: Homo sapiens

<400> SEQUENCE: 7
ccgaggagcc cagcgctagt ggcggcggcc aggagagacc cgggtgtca            49

<210> SEQ ID NO 8
<211> LENGTH: 47
<212> TYPE: DNA
<213> ORGANISM: Homo sapiens

<400> SEQUENCE: 8
gacagcaggg agtccggggg aaacgcaggc gtcgggcaca gagtcgg              47

<210> SEQ ID NO 9
<211> LENGTH: 48
<212> TYPE: DNA
<213> ORGANISM: Homo sapiens

<400> SEQUENCE: 9
ggccctggcg ccggacctgc ttcggccctg cgtgggcggc ctcgccgg             48

<210> SEQ ID NO 10
<211> LENGTH: 48
<212> TYPE: DNA
<213> ORGANISM: Homo sapiens

<400> SEQUENCE: 10
tcggaagcgc tcgggcaaag actgcgaaga agaaaagaca tctggcgg             48

<210> SEQ ID NO 11
<211> LENGTH: 50
<212> TYPE: DNA
<213> ORGANISM: Homo sapiens

<400> SEQUENCE: 11
agtctgtccc gacgtgactt cctcgaccct ctaaagacgt acagaccaga           50

<210> SEQ ID NO 12
<211> LENGTH: 49
<212> TYPE: DNA
<213> ORGANISM: Homo sapiens

<400> SEQUENCE: 12
gcgccggcct ggcagggcag ctcggaggtg ggtgggccgc ccgccagc             49

<210> SEQ ID NO 13
<211> LENGTH: 46
<212> TYPE: DNA
<213> ORGANISM: Homo sapiens

<400> SEQUENCE: 13
aaaccttctt gccttcaagc ctcggctcca acaccagtcc ggcaga              46

<210> SEQ ID NO 14
<211> LENGTH: 50
<212> TYPE: DNA
<213> ORGANISM: Homo sapiens

```
<400> SEQUENCE: 14
ggaagtgaga acaagtgtg tgataaacgg tggagaatgg gagcactctc          50

<210> SEQ ID NO 15
<211> LENGTH: 42
<212> TYPE: DNA
<213> ORGANISM: Homo sapiens

<400> SEQUENCE: 15
gcgggaggag acgaggaggg cgttccctgg ggagtggcag tg                 42

<210> SEQ ID NO 16
<211> LENGTH: 48
<212> TYPE: DNA
<213> ORGANISM: Homo sapiens

<400> SEQUENCE: 16
aagccggcgg aaatacccca gcgcgtgggc ggagcagcgg cccgcaga           48

<210> SEQ ID NO 17
<211> LENGTH: 49
<212> TYPE: DNA
<213> ORGANISM: Homo sapiens

<400> SEQUENCE: 17
ggcggtggcg cccacggaac agccgcgtct aattggctga gcgcggagc          49

<210> SEQ ID NO 18
<211> LENGTH: 49
<212> TYPE: DNA
<213> ORGANISM: Homo sapiens

<400> SEQUENCE: 18
ccagttccca gcgtggcaac acgggactgg gctgcagctc acccagccg          49

<210> SEQ ID NO 19
<211> LENGTH: 47
<212> TYPE: DNA
<213> ORGANISM: Homo sapiens

<400> SEQUENCE: 19
gactcacccc tcctttctgc cgctccttcc tttccttgcc ctgcttt            47

<210> SEQ ID NO 20
<211> LENGTH: 47
<212> TYPE: DNA
<213> ORGANISM: Homo sapiens

<400> SEQUENCE: 20
gcccgcgtcc gagttcctgg acgagagccg agcctcgctt agaccgc            47

<210> SEQ ID NO 21
<211> LENGTH: 46
<212> TYPE: DNA
<213> ORGANISM: Homo sapiens

<400> SEQUENCE: 21
tccagcccgc gaggtttagg acggatccag gcagaccgca ggctcc             46

<210> SEQ ID NO 22
<211> LENGTH: 50
<212> TYPE: DNA
<213> ORGANISM: Homo sapiens
```

-continued

```
<400> SEQUENCE: 22
agcagtgcag ccagcattcc tggcggctcc ctggcccagt ctctggcgca          50

<210> SEQ ID NO 23
<211> LENGTH: 50
<212> TYPE: DNA
<213> ORGANISM: Homo sapiens

<400> SEQUENCE: 23
ggctgaagga acagaaatcc tctgctccgc ctactgggga ttaggagctg          50

<210> SEQ ID NO 24
<211> LENGTH: 48
<212> TYPE: DNA
<213> ORGANISM: Homo sapiens

<400> SEQUENCE: 24
agcatctttg ggcaggcttc cccgccctcg tgacgcgtcg gcccgggc            48

<210> SEQ ID NO 25
<211> LENGTH: 48
<212> TYPE: DNA
<213> ORGANISM: Homo sapiens

<400> SEQUENCE: 25
agagcaggca acctccctct cgccctagcc cagctctgga acaggcag            48

<210> SEQ ID NO 26
<211> LENGTH: 48
<212> TYPE: DNA
<213> ORGANISM: Homo sapiens

<400> SEQUENCE: 26
acctttgatt tctcccaaac ccggcagccc gagactgttg caaaccgg            48

<210> SEQ ID NO 27
<211> LENGTH: 48
<212> TYPE: DNA
<213> ORGANISM: Homo sapiens

<400> SEQUENCE: 27
caagggtctc tgctgactcc cccggctcgg tccacaagct ctccactt            48

<210> SEQ ID NO 28
<211> LENGTH: 47
<212> TYPE: DNA
<213> ORGANISM: Homo sapiens

<400> SEQUENCE: 28
cagcaacacc tctcacgcat gcgcattgta gtcttcccac ctcccac             47

<210> SEQ ID NO 29
<211> LENGTH: 48
<212> TYPE: DNA
<213> ORGANISM: Homo sapiens

<400> SEQUENCE: 29
gacagaacag cgaagcagtg cccggcaagc ggagcgcagc acccattg            48

<210> SEQ ID NO 30
<211> LENGTH: 49
<212> TYPE: DNA
<213> ORGANISM: Homo sapiens
```

```
<400> SEQUENCE: 30
cgccggaagc ctagccgctg ctcggggggg acctgcgggc tcaggcccg                49

<210> SEQ ID NO 31
<211> LENGTH: 49
<212> TYPE: DNA
<213> ORGANISM: Homo sapiens

<400> SEQUENCE: 31
tgcccaggcc gcagggctga tgcccccgct cagctgaggg aaggggaag                49

<210> SEQ ID NO 32
<211> LENGTH: 47
<212> TYPE: DNA
<213> ORGANISM: Homo sapiens

<400> SEQUENCE: 32
ctcctgctcc ttctcctggt ccgggcgggc cggcctgggc tcccact                  47

<210> SEQ ID NO 33
<211> LENGTH: 49
<212> TYPE: DNA
<213> ORGANISM: Homo sapiens

<400> SEQUENCE: 33
aactggggca acttctcccg aggcgggagg cgctggttcc tcggctccc                49

<210> SEQ ID NO 34
<211> LENGTH: 52
<212> TYPE: DNA
<213> ORGANISM: Homo sapiens

<400> SEQUENCE: 34
gttagtatct acggcaccag gtcggcgaga atcctgactc tgcaccctcc tc            52

<210> SEQ ID NO 35
<211> LENGTH: 52
<212> TYPE: DNA
<213> ORGANISM: Homo sapiens

<400> SEQUENCE: 35
ctccatttcc tttgcttcct ccggcaggcg gattacttgc ccttacttgt ca            52

<210> SEQ ID NO 36
<211> LENGTH: 50
<212> TYPE: DNA
<213> ORGANISM: Homo sapiens

<400> SEQUENCE: 36
ccccgccgcc tgcagagggc gcagcaggtc ttgcacctct tctgcatctc               50

<210> SEQ ID NO 37
<211> LENGTH: 51
<212> TYPE: DNA
<213> ORGANISM: Homo sapiens

<400> SEQUENCE: 37
tttcgtattc tgagaggctg ctgcttagcg gtagcccctt ggtttccgtg g             51

<210> SEQ ID NO 38
<211> LENGTH: 51
<212> TYPE: DNA
<213> ORGANISM: Homo sapiens
```

```
<400> SEQUENCE: 38
tgggtggcca atccagagcc ccgagagacg cttggctctt tctgtccctc c      51

<210> SEQ ID NO 39
<211> LENGTH: 51
<212> TYPE: DNA
<213> ORGANISM: Homo sapiens

<400> SEQUENCE: 39
ctcaggtaga attcttcctc ttccgtctct ttcctttac gtcatccggg g       51

<210> SEQ ID NO 40
<211> LENGTH: 52
<212> TYPE: DNA
<213> ORGANISM: Homo sapiens

<400> SEQUENCE: 40
agactcgagt cagtgacact gctcaacgca cccatctcag ctttcatcat ca     52

<210> SEQ ID NO 41
<211> LENGTH: 49
<212> TYPE: DNA
<213> ORGANISM: Homo sapiens

<400> SEQUENCE: 41
agggtattcc ccttgcaggg accgtccctg catttccctc tacactgag          49

<210> SEQ ID NO 42
<211> LENGTH: 52
<212> TYPE: DNA
<213> ORGANISM: Homo sapiens

<400> SEQUENCE: 42
aagggagccg gatgaggtga tacacgctgg cgacacaata gcaggttgct ct     52

<210> SEQ ID NO 43
<211> LENGTH: 48
<212> TYPE: DNA
<213> ORGANISM: Homo sapiens

<400> SEQUENCE: 43
cggctctgcg taggtgcgcg gacccgggct cctgggttcc atccccgc           48

<210> SEQ ID NO 44
<211> LENGTH: 50
<212> TYPE: DNA
<213> ORGANISM: Homo sapiens

<400> SEQUENCE: 44
gtcggccaga cctgcatccc gcgtagcatc cctgccctct ctgtgcagcg         50

<210> SEQ ID NO 45
<211> LENGTH: 50
<212> TYPE: DNA
<213> ORGANISM: Homo sapiens

<400> SEQUENCE: 45
ccgcggagag cctggaggcg gggcgcccct ctctgagtcc gcggggtcgc         50

<210> SEQ ID NO 46
<211> LENGTH: 49
<212> TYPE: DNA
<213> ORGANISM: Homo sapiens
```

```
<400> SEQUENCE: 46
cccgtgcgct tcctgggtgg ggccgggggc ggcttcaaaa cccctgcc          49

<210> SEQ ID NO 47
<211> LENGTH: 48
<212> TYPE: DNA
<213> ORGANISM: Homo sapiens

<400> SEQUENCE: 47
ctctttctct ggtgacccac accgcccgca aagccacagc gcatctgg           48

<210> SEQ ID NO 48
<211> LENGTH: 45
<212> TYPE: DNA
<213> ORGANISM: Homo sapiens

<400> SEQUENCE: 48
cccagcctga ctctccttcc gttctgggtc cccctcctct ggtcg              45

<210> SEQ ID NO 49
<211> LENGTH: 52
<212> TYPE: DNA
<213> ORGANISM: Homo sapiens

<400> SEQUENCE: 49
tctcttgaat cttgacaatc cccgaacact gctccccgct ttatttgttt ag      52

<210> SEQ ID NO 50
<211> LENGTH: 50
<212> TYPE: DNA
<213> ORGANISM: Homo sapiens

<400> SEQUENCE: 50
tccctgggtg cctcctgcgc aagcgcagtt gtcctcctgc gccgacctcg         50

<210> SEQ ID NO 51
<211> LENGTH: 51
<212> TYPE: DNA
<213> ORGANISM: Homo sapiens

<400> SEQUENCE: 51
gaaaggaaga gggtgattgg ttagcggaac gtcttacgtg actgattatt g       51

<210> SEQ ID NO 52
<211> LENGTH: 48
<212> TYPE: DNA
<213> ORGANISM: Homo sapiens

<400> SEQUENCE: 52
acacaccaac ctctaacgat accgggtaat tttcctcctt cttccctc           48

<210> SEQ ID NO 53
<211> LENGTH: 50
<212> TYPE: DNA
<213> ORGANISM: Homo sapiens

<400> SEQUENCE: 53
aactcagggc cgtggttttc aaacgttttt cgccttacgg tcacccttag         50

<210> SEQ ID NO 54
<211> LENGTH: 50
<212> TYPE: DNA
<213> ORGANISM: Homo sapiens
```

<400> SEQUENCE: 54
tagagctagc ctctcctgcc ctcgcccacg ctgcgccagc acttgtttct         50

<210> SEQ ID NO 55
<211> LENGTH: 52
<212> TYPE: DNA
<213> ORGANISM: Homo sapiens

<400> SEQUENCE: 55
tcctagagca aatggcacaa tgccacgagg cccgatctat ccctatgacg ga      52

<210> SEQ ID NO 56
<211> LENGTH: 52
<212> TYPE: DNA
<213> ORGANISM: Homo sapiens

<400> SEQUENCE: 56
ccggtggggg cgggacccga ctcgcaaact gttgcatttg ctctccacct cc      52

<210> SEQ ID NO 57
<211> LENGTH: 49
<212> TYPE: DNA
<213> ORGANISM: Homo sapiens

<400> SEQUENCE: 57
tcccgccagg aaacatccgg gtgcccggat gtgacgccac tgacttgcg          49

<210> SEQ ID NO 58
<211> LENGTH: 40
<212> TYPE: DNA
<213> ORGANISM: Homo sapiens

<400> SEQUENCE: 58
ctcaaccctg atgcccatcc gcccagccat tccaccctca                    40

<210> SEQ ID NO 59
<211> LENGTH: 44
<212> TYPE: DNA
<213> ORGANISM: Homo sapiens

<400> SEQUENCE: 59
ccactccaat gctcactccc gtgacccaac ccctcttca ttgt                44

<210> SEQ ID NO 60
<211> LENGTH: 48
<212> TYPE: DNA
<213> ORGANISM: Homo sapiens

<400> SEQUENCE: 60
gacggacagg gcaggcaggg tccgggacga tggccgcaca gtcccggc           48

<210> SEQ ID NO 61
<211> LENGTH: 50
<212> TYPE: DNA
<213> ORGANISM: Homo sapiens

<400> SEQUENCE: 61
gagaccttgg ctggcgcgag gccacgccca ccagacatgc agttccagct         50

<210> SEQ ID NO 62
<211> LENGTH: 50
<212> TYPE: DNA
<213> ORGANISM: Homo sapiens

<400> SEQUENCE: 62
gggcgactag gacagggaca gaacccgttg aacccaggag tgagatccgg    50

<210> SEQ ID NO 63
<211> LENGTH: 50
<212> TYPE: DNA
<213> ORGANISM: Homo sapiens

<400> SEQUENCE: 63
tcccgctccg gagagaagtc tgagtccgcc aggctctgca ggcccgcgga    50

<210> SEQ ID NO 64
<211> LENGTH: 52
<212> TYPE: DNA
<213> ORGANISM: Homo sapiens

<400> SEQUENCE: 64
cggaagctcg gtaatgataa gcacgccggc cactttgcag ggcgtcaccg cc    52

<210> SEQ ID NO 65
<211> LENGTH: 47
<212> TYPE: DNA
<213> ORGANISM: Homo sapiens

<400> SEQUENCE: 65
cccaataggg ccggcttgac ccgcgaacag gcgagggttc ccggggg    47

<210> SEQ ID NO 66
<211> LENGTH: 49
<212> TYPE: DNA
<213> ORGANISM: Homo sapiens

<400> SEQUENCE: 66
gggaagctgt agcccccagt gggcagcggt ggagagagct caaggaagg    49

<210> SEQ ID NO 67
<211> LENGTH: 46
<212> TYPE: DNA
<213> ORGANISM: Homo sapiens

<400> SEQUENCE: 67
ggtagcaacc atcctgcctc ccgctggagc ggcgtctcct ccccgg    46

<210> SEQ ID NO 68
<211> LENGTH: 48
<212> TYPE: DNA
<213> ORGANISM: Homo sapiens

<400> SEQUENCE: 68
ccggccggcc gtgggggtgg ggcgatagtg acatcacccc ggagtcgg    48

<210> SEQ ID NO 69
<211> LENGTH: 50
<212> TYPE: DNA
<213> ORGANISM: Homo sapiens

<400> SEQUENCE: 69
cctctcccct gccctgtgaa gcgggtgtgc aagctccggg atcgcagcgg    50

<210> SEQ ID NO 70
<211> LENGTH: 47
<212> TYPE: DNA
<213> ORGANISM: Homo sapiens

```
<400> SEQUENCE: 70
cggccagctg cgcggcgact ccggggactc cagggcgccc ctctgcg         47

<210> SEQ ID NO 71
<211> LENGTH: 50
<212> TYPE: DNA
<213> ORGANISM: Homo sapiens

<400> SEQUENCE: 71
gctgtgaggt gtgaggaact tacctgcgtc tccatggaag gtgccctccg      50

<210> SEQ ID NO 72
<211> LENGTH: 49
<212> TYPE: DNA
<213> ORGANISM: Homo sapiens

<400> SEQUENCE: 72
ctctgacacg acgactgggc agtgccggtg acgcttatgg cactgcggc       49

<210> SEQ ID NO 73
<211> LENGTH: 54
<212> TYPE: DNA
<213> ORGANISM: Homo sapiens

<400> SEQUENCE: 73
gggctgcgag ttgcacagtc caattcgctg ttgttagggc tcagtttcc caaa  54

<210> SEQ ID NO 74
<211> LENGTH: 49
<212> TYPE: DNA
<213> ORGANISM: Homo sapiens

<400> SEQUENCE: 74
aaggagcagt ggaaaggggt gacgagttcc tggctggcca ccaatcatc       49

<210> SEQ ID NO 75
<211> LENGTH: 49
<212> TYPE: DNA
<213> ORGANISM: Homo sapiens

<400> SEQUENCE: 75
aacttgtggc atttctaaca ggatgaagcg gaagagaaag ggaaagaga       49

<210> SEQ ID NO 76
<211> LENGTH: 49
<212> TYPE: DNA
<213> ORGANISM: Homo sapiens

<400> SEQUENCE: 76
ggggcgaggg ttcaaaacca ggccggactg agaggtgaaa ttcaccatg       49

<210> SEQ ID NO 77
<211> LENGTH: 49
<212> TYPE: DNA
<213> ORGANISM: Homo sapiens

<400> SEQUENCE: 77
caggttctgg aagcatgagg gtgacgcaac ccaggggcaa aggacccct       49

<210> SEQ ID NO 78
<211> LENGTH: 46
<212> TYPE: DNA
<213> ORGANISM: Homo sapiens
```

```
<400> SEQUENCE: 78
cagggcaggg caggattagg aaggcgctga gcccaggctg gtgcgg                    46

<210> SEQ ID NO 79
<211> LENGTH: 49
<212> TYPE: DNA
<213> ORGANISM: Homo sapiens

<400> SEQUENCE: 79
gatagaggag agactccgta gcggggcggg gcctcagctc cagctgggc                 49

<210> SEQ ID NO 80
<211> LENGTH: 47
<212> TYPE: DNA
<213> ORGANISM: Homo sapiens

<400> SEQUENCE: 80
gccgcctcct gatagaggcc ccgacttagg acacaaaccg ctcccac                   47

<210> SEQ ID NO 81
<211> LENGTH: 50
<212> TYPE: DNA
<213> ORGANISM: Homo sapiens

<400> SEQUENCE: 81
ttgcctctct ccaaatctct cacgacctga tttctacagc cgctctaccc                50

<210> SEQ ID NO 82
<211> LENGTH: 52
<212> TYPE: DNA
<213> ORGANISM: Homo sapiens

<400> SEQUENCE: 82
ctttctgcgt gtctctcagc ctctttcggt ccctctttca cggtctcact cc             52

<210> SEQ ID NO 83
<211> LENGTH: 50
<212> TYPE: DNA
<213> ORGANISM: Homo sapiens

<400> SEQUENCE: 83
ggaatatcag agcctctacg acccgtttgt ctcgggctcg cccacttcaa                50

<210> SEQ ID NO 84
<211> LENGTH: 47
<212> TYPE: DNA
<213> ORGANISM: Homo sapiens

<400> SEQUENCE: 84
cgaacccagt ggaatcagaa ccgtgcaggt cccataaccc acctaga                   47

<210> SEQ ID NO 85
<211> LENGTH: 48
<212> TYPE: DNA
<213> ORGANISM: Homo sapiens

<400> SEQUENCE: 85
accctcagcc aatcagcggt acgggggggcg gtgcctccgg ggctcacc                 48

<210> SEQ ID NO 86
<211> LENGTH: 50
<212> TYPE: DNA
<213> ORGANISM: Homo sapiens
```

```
-continued

<400> SEQUENCE: 86
ctgtgctgct ggcttagaga aggcgcggtc gaccagacgg ttcccaaagg            50

<210> SEQ ID NO 87
<211> LENGTH: 47
<212> TYPE: DNA
<213> ORGANISM: Homo sapiens

<400> SEQUENCE: 87
ggctccgttc tgtgccacac ccgtggctcc tgcgtttccc cctggcg               47

<210> SEQ ID NO 88
<211> LENGTH: 53
<212> TYPE: DNA
<213> ORGANISM: Homo sapiens

<400> SEQUENCE: 88
cgtgtgacgt tacgcacagg aaaccggtcg ggctgtgcag agaatgaagt aag        53

<210> SEQ ID NO 89
<211> LENGTH: 46
<212> TYPE: DNA
<213> ORGANISM: Homo sapiens

<400> SEQUENCE: 89
cgggaggcgg ccgtagccag cgccgccgcg caggaccagg aggagg                46

<210> SEQ ID NO 90
<211> LENGTH: 49
<212> TYPE: DNA
<213> ORGANISM: Homo sapiens

<400> SEQUENCE: 90
ccgtcagcgc tcggagcggg ctgcgcggcg ggagctccgg gaggcggcc             49

<210> SEQ ID NO 91
<211> LENGTH: 48
<212> TYPE: DNA
<213> ORGANISM: Homo sapiens

<400> SEQUENCE: 91
gcccagctcc gggctcatgg gcgcggtcag cagggcgggc cagggcgg              48

<210> SEQ ID NO 92
<211> LENGTH: 47
<212> TYPE: DNA
<213> ORGANISM: Homo sapiens

<400> SEQUENCE: 92
gggctcctct acacctgccg ccgcctgggc cgattccgcg ggcctcg               47

<210> SEQ ID NO 93
<211> LENGTH: 47
<212> TYPE: DNA
<213> ORGANISM: Homo sapiens

<400> SEQUENCE: 93
ggaccgatgc ggtccatgtc ccgggcagcc ccaccttctc tgcctgc               47

<210> SEQ ID NO 94
<211> LENGTH: 49
<212> TYPE: DNA
<213> ORGANISM: Homo sapiens
```

-continued

<400> SEQUENCE: 94
gggaatgcaa gatctcggga cctctcgctg gcctgcaagc tttggtctc                49

<210> SEQ ID NO 95
<211> LENGTH: 50
<212> TYPE: DNA
<213> ORGANISM: Homo sapiens

<400> SEQUENCE: 95
ggcggaggaa taattgagga actcacggaa ctatcaactg gggacaaacc               50

<210> SEQ ID NO 96
<211> LENGTH: 48
<212> TYPE: DNA
<213> ORGANISM: Homo sapiens

<400> SEQUENCE: 96 ccctttatg ctccgtctc cgcggggcag ctcgtccgag tggccaga                   48

<210> SEQ ID NO 97
<211> LENGTH: 49
<212> TYPE: DNA
<213> ORGANISM: Homo sapiens

<400> SEQUENCE: 97
ggcttgtacc ggccgaaggg ccatccgggt caggcgcaca gggcagcgg                49

<210> SEQ ID NO 98
<211> LENGTH: 49
<212> TYPE: DNA
<213> ORGANISM: Homo sapiens

<400> SEQUENCE: 98
ggccggcgtg ccggcgtcca gcgaggatgc gcagactgcc tcaggcccg                49

<210> SEQ ID NO 99
<211> LENGTH: 49
<212> TYPE: DNA
<213> ORGANISM: Homo sapiens

<400> SEQUENCE: 99
gaccactcgg gcacgtggca ggtcgcttgc acgcccgcgg actatccct                49

<210> SEQ ID NO 100
<211> LENGTH: 50
<212> TYPE: DNA
<213> ORGANISM: Homo sapiens

<400> SEQUENCE: 100
gaagttgctt actgattggt ggattccgtt tggcgccaac taggaaaggg               50

<210> SEQ ID NO 101
<211> LENGTH: 48
<212> TYPE: DNA
<213> ORGANISM: Homo sapiens

<400> SEQUENCE: 101
gaggccgagc caaggctgga tccggccaga cctccacagg tcttcctt                 48

<210> SEQ ID NO 102
<211> LENGTH: 47
<212> TYPE: DNA
<213> ORGANISM: Homo sapiens

```
<400> SEQUENCE: 102
ctccagagtt gggccctggt ggtcgagtcc agtcctgggg gtcattg          47

<210> SEQ ID NO 103
<211> LENGTH: 51
<212> TYPE: DNA
<213> ORGANISM: Homo sapiens

<400> SEQUENCE: 103
gggcccagcc ctgggcatct gaacaccggc acacttggat ctgcctctgt t     51

<210> SEQ ID NO 104
<211> LENGTH: 52
<212> TYPE: DNA
<213> ORGANISM: Homo sapiens

<400> SEQUENCE: 104
cagccctggg catctgaaca ccggcacact tggatctgcc tctgttgcct cc    52

<210> SEQ ID NO 105
<211> LENGTH: 39
<212> TYPE: DNA
<213> ORGANISM: Homo sapiens

<400> SEQUENCE: 105
ggggctgtag gggtcaggac acgggctgga gtggaatga                   39

<210> SEQ ID NO 106
<211> LENGTH: 55
<212> TYPE: DNA
<213> ORGANISM: Homo sapiens

<400> SEQUENCE: 106
tctgggaagt ctccctctta tctcgcagaa tgcctgtccc tggataaaga tcatt 55

<210> SEQ ID NO 107
<211> LENGTH: 43
<212> TYPE: DNA
<213> ORGANISM: Homo sapiens

<400> SEQUENCE: 107
ttctcagcgg gccagaagga aggacggtag ggtggaaggg ctg              43

<210> SEQ ID NO 108
<211> LENGTH: 54
<212> TYPE: DNA
<213> ORGANISM: Homo sapiens

<400> SEQUENCE: 108
cacaagtcct agaataccag aacggagacg tgctttcttg gaccttaaac gaaa  54

<210> SEQ ID NO 109
<211> LENGTH: 50
<212> TYPE: DNA
<213> ORGANISM: Homo sapiens

<400> SEQUENCE: 109
caaggctgca gtgagccaag ctcgcgccac tgcactccag cccgggcgac       50

<210> SEQ ID NO 110
<211> LENGTH: 52
<212> TYPE: DNA
<213> ORGANISM: Homo sapiens
```

```
<400> SEQUENCE: 110
cccgtgtgag atgcgccacc ctcgaacctt gttacgacgt cggcacattg cg              52

<210> SEQ ID NO 111
<211> LENGTH: 47
<212> TYPE: DNA
<213> ORGANISM: Homo sapiens

<400> SEQUENCE: 111
ggggaattaa gacccaatgg gcaatccgtg actattaggg gatggga                    47

<210> SEQ ID NO 112
<211> LENGTH: 51
<212> TYPE: DNA
<213> ORGANISM: Homo sapiens

<400> SEQUENCE: 112
catagcagta gcagacatct cttgtaccgt gccttacacc tcagcccatt t               51

<210> SEQ ID NO 113
<211> LENGTH: 52
<212> TYPE: DNA
<213> ORGANISM: Homo sapiens

<400> SEQUENCE: 113
agactgtggc ccagcccaac tgcggctgtg tgtagagcaa ccccatttct ca              52

<210> SEQ ID NO 114
<211> LENGTH: 51
<212> TYPE: DNA
<213> ORGANISM: Homo sapiens

<400> SEQUENCE: 114
gagcactgga ccatgaagtc tcagcgtgtg ctcacagcct ctcacacagg a               51

<210> SEQ ID NO 115
<211> LENGTH: 52
<212> TYPE: DNA
<213> ORGANISM: Homo sapiens

<400> SEQUENCE: 115
gggcagttgg tgttaaagtg agaaaggcgg tatctgcgca gactgcaggg tc              52

<210> SEQ ID NO 116
<211> LENGTH: 51
<212> TYPE: DNA
<213> ORGANISM: Homo sapiens

<400> SEQUENCE: 116
cgcagggtgg gactgctctg cctacgaaca gcactgtgtg cgaacacagg g               51

<210> SEQ ID NO 117
<211> LENGTH: 55
<212> TYPE: DNA
<213> ORGANISM: Homo sapiens

<400> SEQUENCE: 117
ctggccggcc tgacgactct caacgggtta gacgcgggct acgatgacct tcacg           55

<210> SEQ ID NO 118
<211> LENGTH: 45
<212> TYPE: DNA
<213> ORGANISM: Homo sapiens
```

```
<400> SEQUENCE: 118
tggaggtctc tgctggctat ctggcgtgtg tgtgtgtgtg gtgtg             45

<210> SEQ ID NO 119
<211> LENGTH: 52
<212> TYPE: DNA
<213> ORGANISM: Homo sapiens

<400> SEQUENCE: 119
caaaaccgat tatctttata accgcggcgc ctagcacagc gcctggtgcc ct     52

<210> SEQ ID NO 120
<211> LENGTH: 52
<212> TYPE: DNA
<213> ORGANISM: Homo sapiens

<400> SEQUENCE: 120
ggagcacatc agaagggctg gcttgtgcgc gctcttgctc tctgtgtatg tg     52

<210> SEQ ID NO 121
<211> LENGTH: 47
<212> TYPE: DNA
<213> ORGANISM: Homo sapiens

<400> SEQUENCE: 121
tcctcacccc aagtgaaggc tcgagacttc ctgccccacc cagtggg           47

<210> SEQ ID NO 122
<211> LENGTH: 47
<212> TYPE: DNA
<213> ORGANISM: Homo sapiens

<400> SEQUENCE: 122
cctgcaccca ggtttccatt gcgcggctct cctcagctcc ttcccgc           47

<210> SEQ ID NO 123
<211> LENGTH: 46
<212> TYPE: DNA
<213> ORGANISM: Homo sapiens

<400> SEQUENCE: 123
agatcacggt ccagcctctg ccggagcccc agtctccgca gtggag            46

<210> SEQ ID NO 124
<211> LENGTH: 49
<212> TYPE: DNA
<213> ORGANISM: Homo sapiens

<400> SEQUENCE: 124
ctggaacatc gcgggcacag ggcagcgttg gtcactgctc ctgggtact         49

<210> SEQ ID NO 125
<211> LENGTH: 49
<212> TYPE: DNA
<213> ORGANISM: Homo sapiens

<400> SEQUENCE: 125
gggggtcccg gagccccca gccccgcagg ccactgcctc gccgcccga          49

<210> SEQ ID NO 126
<211> LENGTH: 54
<212> TYPE: DNA
<213> ORGANISM: Homo sapiens
```

```
<400> SEQUENCE: 126
tcttcatcag aacatctatg agtcgtcgtc tctgcagtcc atttgtttgc ccgc          54

<210> SEQ ID NO 127
<211> LENGTH: 47
<212> TYPE: DNA
<213> ORGANISM: Homo sapiens

<400> SEQUENCE: 127
actccaaggc tgcccaagcc tacggaccca gccacattgg cgaaccg                 47

<210> SEQ ID NO 128
<211> LENGTH: 48
<212> TYPE: DNA
<213> ORGANISM: Homo sapiens

<400> SEQUENCE: 128
actccgcggt ccctgaactt ccggtgctgg cggactcctc gctccagg                48

<210> SEQ ID NO 129
<211> LENGTH: 49
<212> TYPE: DNA
<213> ORGANISM: Homo sapiens

<400> SEQUENCE: 129
ggggtgcctc cggccccatg ctcgcgggca agcagggata agctgtgcc               49

<210> SEQ ID NO 130
<211> LENGTH: 53
<212> TYPE: DNA
<213> ORGANISM: Homo sapiens

<400> SEQUENCE: 130
ggccatccgg caaagacccg agtaaggaac gcagggtcac tgcctgggcc aac          53

<210> SEQ ID NO 131
<211> LENGTH: 47
<212> TYPE: DNA
<213> ORGANISM: Homo sapiens

<400> SEQUENCE: 131
tttctctcag accacttgtc ccgaccaatc tgaccttcca aacacat                 47

<210> SEQ ID NO 132
<211> LENGTH: 47
<212> TYPE: DNA
<213> ORGANISM: Homo sapiens

<400> SEQUENCE: 132
cgcagagcca gagactcctg ccgagttaga ccttctctcg tcgcccc                 47

<210> SEQ ID NO 133
<211> LENGTH: 50
<212> TYPE: DNA
<213> ORGANISM: Homo sapiens

<400> SEQUENCE: 133
gcgcggtccc tttggatgct cgtgcgcata gacacaacac cctacacgcc              50

<210> SEQ ID NO 134
<211> LENGTH: 50
<212> TYPE: DNA
<213> ORGANISM: Homo sapiens
```

<400> SEQUENCE: 134
ccccagaaac actcaggtac tcgcgacaca cacagtacag tcacgcttaa    50

<210> SEQ ID NO 135
<211> LENGTH: 45
<212> TYPE: DNA
<213> ORGANISM: Homo sapiens

<400> SEQUENCE: 135
gcagacacaa acggacccac acgggcaact cccgagacaa aaccc    45

<210> SEQ ID NO 136
<211> LENGTH: 47
<212> TYPE: DNA
<213> ORGANISM: Homo sapiens

<400> SEQUENCE: 136
ggacacaaag ggaaggcgag gaggcgagca agaggctggg cctgcct    47

<210> SEQ ID NO 137
<211> LENGTH: 51
<212> TYPE: DNA
<213> ORGANISM: Homo sapiens

<400> SEQUENCE: 137
cgggcgggcc ggggtctttg tgacgcggtg gcaacggcca cggacacaaa g    51

<210> SEQ ID NO 138
<211> LENGTH: 50
<212> TYPE: DNA
<213> ORGANISM: Homo sapiens

<400> SEQUENCE: 138
gacaagtcac ctttacctct tccgtgactc agtttcttcc acctaaaaac    50

<210> SEQ ID NO 139
<211> LENGTH: 48
<212> TYPE: DNA
<213> ORGANISM: Homo sapiens

<400> SEQUENCE: 139
tgcagccccc ggtcggaagc tgggcgatga gccctgcctc cagcgggt    48

<210> SEQ ID NO 140
<211> LENGTH: 52
<212> TYPE: DNA
<213> ORGANISM: Homo sapiens

<400> SEQUENCE: 140
gggcgatgag ccctgcctcc agcgggtggc gctcgagtcc ggctgaacgg cg    52

<210> SEQ ID NO 141
<211> LENGTH: 50
<212> TYPE: DNA
<213> ORGANISM: Homo sapiens

<400> SEQUENCE: 141
atcctctgca tcctcgccgg gcgcgcgatc ggcagctgac ggcctaacaa    50

<210> SEQ ID NO 142
<211> LENGTH: 53
<212> TYPE: DNA
<213> ORGANISM: Homo sapiens

```
<400> SEQUENCE: 142
ggcgcggcct gtgcccttta taaggtgcgc gctgtgtcca gcgagcatcg gcc          53

<210> SEQ ID NO 143
<211> LENGTH: 54
<212> TYPE: DNA
<213> ORGANISM: Homo sapiens

<400> SEQUENCE: 143
cgcggcctgt gcctttata aggtgcgcgc tgtgtccagc gagcatcggc cacc          54

<210> SEQ ID NO 144
<211> LENGTH: 52
<212> TYPE: DNA
<213> ORGANISM: Homo sapiens

<400> SEQUENCE: 144
tctgcttctt agcgctagcc tcaatgacga cctaagctgc acttttcccc ct           52

<210> SEQ ID NO 145
<211> LENGTH: 50
<212> TYPE: DNA
<213> ORGANISM: Homo sapiens

<400> SEQUENCE: 145
cctggagacg ccttgaagta actgcacgaa atttgaggat ggccaggcag              50

<210> SEQ ID NO 146
<211> LENGTH: 46
<212> TYPE: DNA
<213> ORGANISM: Homo sapiens

<400> SEQUENCE: 146
gtttttgaat ggtttgggag gacgaattgt tagaccccga ggaagg                  46

<210> SEQ ID NO 147
<211> LENGTH: 47
<212> TYPE: DNA
<213> ORGANISM: Homo sapiens

<400> SEQUENCE: 147
ccactccgga tggggctgcc accgcggcca ggacagtctc ctccgac                 47

<210> SEQ ID NO 148
<211> LENGTH: 46
<212> TYPE: DNA
<213> ORGANISM: Homo sapiens

<400> SEQUENCE: 148
ggcctttgga actccaaggg gttcgtctac ctgaccattg ggtggg                  46

<210> SEQ ID NO 149
<211> LENGTH: 51
<212> TYPE: DNA
<213> ORGANISM: Homo sapiens

<400> SEQUENCE: 149
gaagctagag taagctgagg aggtgggcgg aaaccatggc aaccatgggt g            51

<210> SEQ ID NO 150
<211> LENGTH: 47
<212> TYPE: DNA
<213> ORGANISM: Homo sapiens
```

```
<400> SEQUENCE: 150
accacaccca gcctagtgcc acgcaccgca agcgctccat aaacgca                47

<210> SEQ ID NO 151
<211> LENGTH: 53
<212> TYPE: DNA
<213> ORGANISM: Homo sapiens

<400> SEQUENCE: 151
cgcaggcagt gggcgcggac tctgcggttc gcttgactga cggcgcagcc tcc         53

<210> SEQ ID NO 152
<211> LENGTH: 48
<212> TYPE: DNA
<213> ORGANISM: Homo sapiens

<400> SEQUENCE: 152
ttgtgagggc ctttaaatat cctgtactcg tgggccatgt tgggccct               48

<210> SEQ ID NO 153
<211> LENGTH: 48
<212> TYPE: DNA
<213> ORGANISM: Homo sapiens

<400> SEQUENCE: 153
tcaggcactg gaatgagagg agttaacggg gaaggacagg gttatttc               48

<210> SEQ ID NO 154
<211> LENGTH: 46
<212> TYPE: DNA
<213> ORGANISM: Homo sapiens

<400> SEQUENCE: 154
cccatggaca cccaggtgtc cggggtgccc ccacaactct gggcct                 46

<210> SEQ ID NO 155
<211> LENGTH: 51
<212> TYPE: DNA
<213> ORGANISM: Homo sapiens

<400> SEQUENCE: 155
tggctctgat tggctttctg gccgtcagga acatgtccca acatgttgag c           51

<210> SEQ ID NO 156
<211> LENGTH: 50
<212> TYPE: DNA
<213> ORGANISM: Homo sapiens

<400> SEQUENCE: 156
cccacattac ttgagggctc gggcgtgcgc aaagctccgg gttcagtttc             50

<210> SEQ ID NO 157
<211> LENGTH: 52
<212> TYPE: DNA
<213> ORGANISM: Homo sapiens

<400> SEQUENCE: 157
acaatcaaat agccacacgg cacgaagacg catgcgtggc gacaacaaca ac          52

<210> SEQ ID NO 158
<211> LENGTH: 48
<212> TYPE: DNA
<213> ORGANISM: Homo sapiens
```

```
<400> SEQUENCE: 158
cagcctggcc ctttaagtct tccgcgatcc catttcggag tttcctct            48

<210> SEQ ID NO 159
<211> LENGTH: 51
<212> TYPE: DNA
<213> ORGANISM: Homo sapiens

<400> SEQUENCE: 159
tcttttcttt agccctgccc ccgaattgtc agacggcggg cgtctgcctc t          51

<210> SEQ ID NO 160
<211> LENGTH: 49
<212> TYPE: DNA
<213> ORGANISM: Homo sapiens

<400> SEQUENCE: 160
ggctggcagc ttgcaaaggg gaagcggact ccagcactgc acgggcagg            49

<210> SEQ ID NO 161
<211> LENGTH: 52
<212> TYPE: DNA
<213> ORGANISM: Homo sapiens

<400> SEQUENCE: 161
ggcctggcct tatctccggc tgcacgttgc ctgttggtga ctaataacac aa         52

<210> SEQ ID NO 162
<211> LENGTH: 49
<212> TYPE: DNA
<213> ORGANISM: Homo sapiens

<400> SEQUENCE: 162
aagttcaatc aagggactgg gatttcggaa tgaataatga agggagatg            49

<210> SEQ ID NO 163
<211> LENGTH: 50
<212> TYPE: DNA
<213> ORGANISM: Homo sapiens

<400> SEQUENCE: 163
tccttcttcc tggatactca taacgcggcc ccatttctca ctcccattgg           50

<210> SEQ ID NO 164
<211> LENGTH: 41
<212> TYPE: DNA
<213> ORGANISM: Homo sapiens

<400> SEQUENCE: 164
ggggcaggct gggggccccc gctgcctgct gggtcaggct g                    41

<210> SEQ ID NO 165
<211> LENGTH: 47
<212> TYPE: DNA
<213> ORGANISM: Homo sapiens

<400> SEQUENCE: 165
aactctacaa atcccgggat ctcggggtgc agatcacctc tcccaga              47

<210> SEQ ID NO 166
<211> LENGTH: 45
<212> TYPE: DNA
<213> ORGANISM: Homo sapiens
```

```
<400> SEQUENCE: 166
tctgaagctg ggtggggtcc gcccttacac agctgggctt tgtgt            45

<210> SEQ ID NO 167
<211> LENGTH: 50
<212> TYPE: DNA
<213> ORGANISM: Homo sapiens

<400> SEQUENCE: 167
gctgaggcag gagaatcgct tgaacccggg aggcagaggt tgcagtgagc       50

<210> SEQ ID NO 168
<211> LENGTH: 48
<212> TYPE: DNA
<213> ORGANISM: Homo sapiens

<400> SEQUENCE: 168
gagggccaat cggaagggca agcttcgaga tgctgcgtga tcacgtgg         48

<210> SEQ ID NO 169
<211> LENGTH: 52
<212> TYPE: DNA
<213> ORGANISM: Homo sapiens

<400> SEQUENCE: 169
gggcggatca cctgagtcag gagttcgaga ccagcctggc caacatggtg aa    52

<210> SEQ ID NO 170
<211> LENGTH: 48
<212> TYPE: DNA
<213> ORGANISM: Homo sapiens

<400> SEQUENCE: 170
ggtgaaggag gtttggactc aatgcgggtc aaaggttagg gtcaaaag         48

<210> SEQ ID NO 171
<211> LENGTH: 46
<212> TYPE: DNA
<213> ORGANISM: Homo sapiens

<400> SEQUENCE: 171
gggatctgga gggggtagca ctacggggaa aggtcaaaag tcaggg           46

<210> SEQ ID NO 172
<211> LENGTH: 52
<212> TYPE: DNA
<213> ORGANISM: Homo sapiens

<400> SEQUENCE: 172
tggcagcccg gaagtgcggc aagtagtcgc tgcgaagtaa gccccgcccc gg    52

<210> SEQ ID NO 173
<211> LENGTH: 46
<212> TYPE: DNA
<213> ORGANISM: Homo sapiens

<400> SEQUENCE: 173
ataggttttg aggggcatgg ggacggggtt cagcctccag ggtcct           46

<210> SEQ ID NO 174
<211> LENGTH: 52
<212> TYPE: DNA
<213> ORGANISM: Homo sapiens
```

```
<400> SEQUENCE: 174 cccgccccg cgatggagaa gaaaccgaga cagaaggtgc agggcccact ac              52

<210> SEQ ID NO 175
<211> LENGTH: 51
<212> TYPE: DNA
<213> ORGANISM: Homo sapiens

<400> SEQUENCE: 175
cagaaggtgc agggcccact accgcttcct ccagatgagc tcatgggttt c             51

<210> SEQ ID NO 176
<211> LENGTH: 48
<212> TYPE: DNA
<213> ORGANISM: Homo sapiens

<400> SEQUENCE: 176
gtctctggac agagtttccg ggggcggatg ggtaattttc aggctgtg                 48

<210> SEQ ID NO 177
<211> LENGTH: 49
<212> TYPE: DNA
<213> ORGANISM: Homo sapiens

<400> SEQUENCE: 177
tccccttcat tgcggcgggc tgcgggccag gcttcactga gcgtccgca                49

<210> SEQ ID NO 178
<211> LENGTH: 49
<212> TYPE: DNA
<213> ORGANISM: Homo sapiens

<400> SEQUENCE: 178
gaacggctct caggccctgt ccgcacgtaa cctcactttc ctgctccct                49

<210> SEQ ID NO 179
<211> LENGTH: 48
<212> TYPE: DNA
<213> ORGANISM: Homo sapiens

<400> SEQUENCE: 179
catctctact cccaccgcat tcgaccctgc ccggactcac tgcttacc                 48

<210> SEQ ID NO 180
<211> LENGTH: 48
<212> TYPE: DNA
<213> ORGANISM: Homo sapiens

<400> SEQUENCE: 180
tcagtcatgt ttccaaagtc ccgcggtttc ccctagtctc ttcattca                 48

<210> SEQ ID NO 181
<211> LENGTH: 51
<212> TYPE: DNA
<213> ORGANISM: Homo sapiens

<400> SEQUENCE: 181
gtttgctgaa ggcttggaag tgcagcgcag aagacagagg gtgactagga a             51

<210> SEQ ID NO 182
<211> LENGTH: 49
<212> TYPE: DNA
<213> ORGANISM: Homo sapiens
```

```
<400> SEQUENCE: 182
tgtgtgtgtg tatgtgtgtg tctggcgcct ggccagggtg atttcccat            49

<210> SEQ ID NO 183
<211> LENGTH: 56
<212> TYPE: DNA
<213> ORGANISM: Homo sapiens

<400> SEQUENCE: 183
gagcatctct ggttggaatc ataatgcttc ggcctgaagt gaccaggcca ctcact    56

<210> SEQ ID NO 184
<211> LENGTH: 49
<212> TYPE: DNA
<213> ORGANISM: Homo sapiens

<400> SEQUENCE: 184
cgggaggcca caagagcagg gccaacgtta gaaaggccgc aaggggaga             49

<210> SEQ ID NO 185
<211> LENGTH: 51
<212> TYPE: DNA
<213> ORGANISM: Homo sapiens

<400> SEQUENCE: 185
tggcgtaagc tacagctgaa ggaagaacgt gagcacgagg cactgaggtg a          51

<210> SEQ ID NO 186
<211> LENGTH: 53
<212> TYPE: DNA
<213> ORGANISM: Homo sapiens

<400> SEQUENCE: 186
ccgccacata ccgctcgtag tattcgtgct cagcctcgta gtggcgcctg acg        53

<210> SEQ ID NO 187
<211> LENGTH: 52
<212> TYPE: DNA
<213> ORGANISM: Homo sapiens

<400> SEQUENCE: 187
ccacaggaaa tgcacaggtg agaaactgac gttaagggggg actgagtgtc aa        52

<210> SEQ ID NO 188
<211> LENGTH: 46
<212> TYPE: DNA
<213> ORGANISM: Homo sapiens

<400> SEQUENCE: 188
agggcagatt caaacccaac acggtcctcc cctgctgccc ctcggc                46

<210> SEQ ID NO 189
<211> LENGTH: 47
<212> TYPE: DNA
<213> ORGANISM: Homo sapiens

<400> SEQUENCE: 189
cggtcggccc ggtgaggcgc agcgcccag actggcgcat ccgcggc                47

<210> SEQ ID NO 190
<211> LENGTH: 49
<212> TYPE: DNA
<213> ORGANISM: Homo sapiens
```

```
<400> SEQUENCE: 190
ggcgagcggc caggtgcgcc ttcggcagga cagtgctaat tccagcccc          49

<210> SEQ ID NO 191
<211> LENGTH: 48
<212> TYPE: DNA
<213> ORGANISM: Homo sapiens

<400> SEQUENCE: 191
cacacggggg tgctaagcct cccgcccgtt ctaagcggag acccaacg            48

<210> SEQ ID NO 192
<211> LENGTH: 48
<212> TYPE: DNA
<213> ORGANISM: Homo sapiens

<400> SEQUENCE: 192
cgcacgcagg taacttcacc ctcgcctcaa cgacctcaga ggctgccc            48

<210> SEQ ID NO 193
<211> LENGTH: 57
<212> TYPE: DNA
<213> ORGANISM: Homo sapiens

<400> SEQUENCE: 193
gaggtcgctg ccactcctac agagccccca cgccccgccc agctataagg ggccatg    57

<210> SEQ ID NO 194
<211> LENGTH: 43
<212> TYPE: DNA
<213> ORGANISM: Homo sapiens

<400> SEQUENCE: 194
actcctacag agccccacg ccccgcccag ctataagggg cca                  43

<210> SEQ ID NO 195
<211> LENGTH: 49
<212> TYPE: DNA
<213> ORGANISM: Homo sapiens

<400> SEQUENCE: 195
acggtagccg ccttcctatt tccgcccggc gggcagcgct gcggggcga           49

<210> SEQ ID NO 196
<211> LENGTH: 47
<212> TYPE: DNA
<213> ORGANISM: Homo sapiens

<400> SEQUENCE: 196
cgccgcctag agcctggaag ccgccactgc ggcccaggac aatccgg             47

<210> SEQ ID NO 197
<211> LENGTH: 48
<212> TYPE: DNA
<213> ORGANISM: Homo sapiens

<400> SEQUENCE: 197
ccaagtcttg gcaagcggcc ggcgaaactc acaggtccct ttcctggc            48

<210> SEQ ID NO 198
<211> LENGTH: 49
<212> TYPE: DNA
<213> ORGANISM: Homo sapiens
```

```
<400> SEQUENCE: 198
ctcctctcct cagcgctggt ccgggaaagg caagctccgg gcgggagcg          49

<210> SEQ ID NO 199
<211> LENGTH: 46
<212> TYPE: DNA
<213> ORGANISM: Homo sapiens

<400> SEQUENCE: 199
gggaatagag attgctgggg accgcagggg ccaggttgtc attccc            46

<210> SEQ ID NO 200
<211> LENGTH: 40
<212> TYPE: DNA
<213> ORGANISM: Homo sapiens

<400> SEQUENCE: 200
cccgaagcct ggctccctcg ccacgcccac ttcctgcccc                   40

<210> SEQ ID NO 201
<211> LENGTH: 45
<212> TYPE: DNA
<213> ORGANISM: Homo sapiens

<400> SEQUENCE: 201
caccaatcag cgccgacctc gccttcgcag gcctaaccaa tcagt             45

<210> SEQ ID NO 202
<211> LENGTH: 49
<212> TYPE: DNA
<213> ORGANISM: Homo sapiens

<400> SEQUENCE: 202
cgcgctcagt tacttagcaa cctcggcgct aagccacccc aggtggagc         49

<210> SEQ ID NO 203
<211> LENGTH: 47
<212> TYPE: DNA
<213> ORGANISM: Homo sapiens

<400> SEQUENCE: 203
ggagaatcgc ttgaacccgg gaggcggagg ttgcgatgag ccgagat           47

<210> SEQ ID NO 204
<211> LENGTH: 49
<212> TYPE: DNA
<213> ORGANISM: Homo sapiens

<400> SEQUENCE: 204
ggcagcctag ggaatttatc ccggactccg ggggaggggg cagagtcac         49

<210> SEQ ID NO 205
<211> LENGTH: 51
<212> TYPE: DNA
<213> ORGANISM: Homo sapiens

<400> SEQUENCE: 205
gattctccga ggaaaagtgt gagaacggct gcaggcaacc caggcgtccc g      51

<210> SEQ ID NO 206
<211> LENGTH: 48
<212> TYPE: DNA
<213> ORGANISM: Homo sapiens
```

```
<400> SEQUENCE: 206
aggagggacg cacccaggcc tgcgcgaaga gagggagaaa gtgaagct        48

<210> SEQ ID NO 207
<211> LENGTH: 51
<212> TYPE: DNA
<213> ORGANISM: Homo sapiens

<400> SEQUENCE: 207
gtggcccaag cgcccgaatg aaggctcggg gccaaagtca tgtgtctgac t    51

<210> SEQ ID NO 208
<211> LENGTH: 48
<212> TYPE: DNA
<213> ORGANISM: Homo sapiens

<400> SEQUENCE: 208
ctgtggaggg agaggaagca gctgcggaaa gccaataaga gtggggaa        48

<210> SEQ ID NO 209
<211> LENGTH: 50
<212> TYPE: DNA
<213> ORGANISM: Homo sapiens

<400> SEQUENCE: 209
tcccgccaac tctatggtcg agcgtttcag ggatcggcca atcgtaatcc      50

<210> SEQ ID NO 210
<211> LENGTH: 50
<212> TYPE: DNA
<213> ORGANISM: Homo sapiens

<400> SEQUENCE: 210
ctcgggaagc caatttgctc gcgaacgaag gaagtgagtc agagaacccg      50

<210> SEQ ID NO 211
<211> LENGTH: 53
<212> TYPE: DNA
<213> ORGANISM: Homo sapiens

<400> SEQUENCE: 211
gggtggagag aagaaagcaa gcagctaacc ggaaaggtct gaaaaagcta gcg  53

<210> SEQ ID NO 212
<211> LENGTH: 51
<212> TYPE: DNA
<213> ORGANISM: Homo sapiens

<400> SEQUENCE: 212
cgcaacgtgt gagcgccacc tctcgggaag ccaatttgct cgcgaacgaa g    51

<210> SEQ ID NO 213
<211> LENGTH: 49
<212> TYPE: DNA
<213> ORGANISM: Homo sapiens

<400> SEQUENCE: 213
ctcccgggtc agctctggca ctcgccagct gagcccagcg ccagtctag       49

<210> SEQ ID NO 214
<211> LENGTH: 46
<212> TYPE: DNA
<213> ORGANISM: Homo sapiens
```

```
<400> SEQUENCE: 214
gggcgcccta acttccaact ccgggagcaa tccaaacccg gaggcc                46

<210> SEQ ID NO 215
<211> LENGTH: 49
<212> TYPE: DNA
<213> ORGANISM: Homo sapiens

<400> SEQUENCE: 215
ttttcattaa tgaaaccggc cggcgcgggc gcatgcgcgg caggccgcc             49

<210> SEQ ID NO 216
<211> LENGTH: 46
<212> TYPE: DNA
<213> ORGANISM: Homo sapiens

<400> SEQUENCE: 216
ttcaggaggg tgagggcagg agcgtgggtg gagtcagcag gtcccc                46

<210> SEQ ID NO 217
<211> LENGTH: 50
<212> TYPE: DNA
<213> ORGANISM: Homo sapiens

<400> SEQUENCE: 217
caacccagcc tctgtcggag gcgaattctc agagtgaggg ttccctgtca            50

<210> SEQ ID NO 218
<211> LENGTH: 50
<212> TYPE: DNA
<213> ORGANISM: Homo sapiens

<400> SEQUENCE: 218
ttccctgtga cgtgaccttg ggggacgtca ttgccctttc tgtccccacc            50

<210> SEQ ID NO 219
<211> LENGTH: 53
<212> TYPE: DNA
<213> ORGANISM: Homo sapiens

<400> SEQUENCE: 219
ggtttcacta tgttggccag gctggtctcg aactcctgac ctcgtgatcc gcc        53

<210> SEQ ID NO 220
<211> LENGTH: 49
<212> TYPE: DNA
<213> ORGANISM: Homo sapiens

<400> SEQUENCE: 220
cggtggctca gctcacagcc tctcgctaga ctccagacac ccacctgcc             49

<210> SEQ ID NO 221
<211> LENGTH: 46
<212> TYPE: DNA
<213> ORGANISM: Homo sapiens

<400> SEQUENCE: 221
atccttgacc tgcctcgacc tccggaccct ccggacctcc agctgc                46

<210> SEQ ID NO 222
<211> LENGTH: 51
<212> TYPE: DNA
<213> ORGANISM: Homo sapiens
```

```
<400> SEQUENCE: 222
agccagcctg gggactggag ggtggcggct gcatctgctc atttcctccc a        51

<210> SEQ ID NO 223
<211> LENGTH: 54
<212> TYPE: DNA
<213> ORGANISM: Homo sapiens

<400> SEQUENCE: 223
ggagtcttgc tgtgtctccc aggccggagt gcaatggcat gacctctgcc tccc     54

<210> SEQ ID NO 224
<211> LENGTH: 49
<212> TYPE: DNA
<213> ORGANISM: Homo sapiens

<400> SEQUENCE: 224
tggagtcttg ctgtgtctcc caggccggag tgcaatggca tgacctctg            49

<210> SEQ ID NO 225
<211> LENGTH: 46
<212> TYPE: DNA
<213> ORGANISM: Homo sapiens

<400> SEQUENCE: 225
gccattgccg gcggtccacc ggttgccaca ctctgaccaa tcagga               46

<210> SEQ ID NO 226
<211> LENGTH: 50
<212> TYPE: DNA
<213> ORGANISM: Homo sapiens

<400> SEQUENCE: 226
agttaaacca gccttctttc ccgcctgccg ggttcatttg aaaaccgaaa           50

<210> SEQ ID NO 227
<211> LENGTH: 47
<212> TYPE: DNA
<213> ORGANISM: Homo sapiens

<400> SEQUENCE: 227
ctcatccact ccgtctctcc gtttcccttt cttcacggtg cttgaca              47

<210> SEQ ID NO 228
<211> LENGTH: 47
<212> TYPE: DNA
<213> ORGANISM: Homo sapiens

<400> SEQUENCE: 228
agcttggaaa ttccggagct gaagcggcca gcgagggagg atgaccc              47

<210> SEQ ID NO 229
<211> LENGTH: 47
<212> TYPE: DNA
<213> ORGANISM: Homo sapiens

<400> SEQUENCE: 229
tccccggacg tggtgagacc gcgcttcgtc actcccacgg ttagcgg              47

<210> SEQ ID NO 230
<211> LENGTH: 50
<212> TYPE: DNA
<213> ORGANISM: Homo sapiens
```

```
<400> SEQUENCE: 230
cctggctctg ctctggccgc ttctcgagaa atgcccgtgt cagctaggtg              50

<210> SEQ ID NO 231
<211> LENGTH: 47
<212> TYPE: DNA
<213> ORGANISM: Homo sapiens

<400> SEQUENCE: 231
ccagtctcta gtatccacct ctcgccatca accaggcatt ccgggag                 47

<210> SEQ ID NO 232
<211> LENGTH: 47
<212> TYPE: DNA
<213> ORGANISM: Homo sapiens

<400> SEQUENCE: 232
gggccagctc aggacaggcg ctcggggac gcgtgtcctc accccac                  47

<210> SEQ ID NO 233
<211> LENGTH: 48
<212> TYPE: DNA
<213> ORGANISM: Homo sapiens

<400> SEQUENCE: 233
gtggaggaga gtcagcgagg gcccgagggg caggtacttt aacgaatg                48

<210> SEQ ID NO 234
<211> LENGTH: 50
<212> TYPE: DNA
<213> ORGANISM: Homo sapiens

<400> SEQUENCE: 234
gccttttcag ttgctcacag tccgtcagtc cttgagccaa tcggcgtgga              50

<210> SEQ ID NO 235
<211> LENGTH: 49
<212> TYPE: DNA
<213> ORGANISM: Homo sapiens

<400> SEQUENCE: 235
agcgctttgg ccaatcagcg agcggcggga cattgggctc ctcctcctc               49

<210> SEQ ID NO 236
<211> LENGTH: 53
<212> TYPE: DNA
<213> ORGANISM: Homo sapiens

<400> SEQUENCE: 236
ccatttctat acaagccctg cttccgctga gcagcatggc gtgcgacacc gcc          53

<210> SEQ ID NO 237
<211> LENGTH: 49
<212> TYPE: DNA
<213> ORGANISM: Homo sapiens

<400> SEQUENCE: 237
cgggggttcg gcctcagtca ggcgctcagc tccgtttcgg tttcacttc               49

<210> SEQ ID NO 238
<211> LENGTH: 51
<212> TYPE: DNA
<213> ORGANISM: Homo sapiens
```

<400> SEQUENCE: 238
cagaaatggg cgttctggcc ctcgcgaggc agtgcgacct gtcaccgccc t    51

<210> SEQ ID NO 239
<211> LENGTH: 48
<212> TYPE: DNA
<213> ORGANISM: Homo sapiens

<400> SEQUENCE: 239
acctcccgct cagtcagact gcgctacttt gaaccggacc aaaccaaa    48

<210> SEQ ID NO 240
<211> LENGTH: 50
<212> TYPE: DNA
<213> ORGANISM: Homo sapiens

<400> SEQUENCE: 240
tccactgcga tattgctcca aatccgagga aattcaaact cccgggcgcg    50

<210> SEQ ID NO 241
<211> LENGTH: 47
<212> TYPE: DNA
<213> ORGANISM: Homo sapiens

<400> SEQUENCE: 241
agcaggggct cccttgggcc ccgacttctt ccggctcttc acctcag    47

<210> SEQ ID NO 242
<211> LENGTH: 51
<212> TYPE: DNA
<213> ORGANISM: Homo sapiens

<400> SEQUENCE: 242
cccgagtccg gcattggtgg gaacgcggcg cgtccctgag gcttagccac g    51

<210> SEQ ID NO 243
<211> LENGTH: 45
<212> TYPE: DNA
<213> ORGANISM: Homo sapiens

<400> SEQUENCE: 243
gctgaaagaa ggcctgtggc gaagcggagg gggacctaag tcagg    45

<210> SEQ ID NO 244
<211> LENGTH: 55
<212> TYPE: DNA
<213> ORGANISM: Homo sapiens

<400> SEQUENCE: 244
ccagagcgcc ctgtgtagag cggctgcgag cgggcagctg ggctcggctg ccggg    55

<210> SEQ ID NO 245
<211> LENGTH: 50
<212> TYPE: DNA
<213> ORGANISM: Homo sapiens

<400> SEQUENCE: 245
ccagagccag tcagagcgga cggctgctgg gaagccaatc agcgcgctcg    50

<210> SEQ ID NO 246
<211> LENGTH: 52
<212> TYPE: DNA
<213> ORGANISM: Homo sapiens

```
<400> SEQUENCE: 246
aaatacaagg gcaggaggat taggatccgt tttgaagaag ccaaagttgg ag        52

<210> SEQ ID NO 247
<211> LENGTH: 56
<212> TYPE: DNA
<213> ORGANISM: Homo sapiens

<400> SEQUENCE: 247
gggaggagag ctaactgccc agccagcttg cgtcaccgct tcagagcgga gaagag    56

<210> SEQ ID NO 248
<211> LENGTH: 52
<212> TYPE: DNA
<213> ORGANISM: Homo sapiens

<400> SEQUENCE: 248
agaaggttgt tttctccaca tttcggggtt ctggacgttt cccggctgcg gg        52

<210> SEQ ID NO 249
<211> LENGTH: 48
<212> TYPE: DNA
<213> ORGANISM: Homo sapiens

<400> SEQUENCE: 249
tttacatcat tttgccaatt tcgcgtactg caaccggcgg gccacgcc              48

<210> SEQ ID NO 250
<211> LENGTH: 44
<212> TYPE: DNA
<213> ORGANISM: Homo sapiens

<400> SEQUENCE: 250
cagtcattcc cggccactcg cgacccgagg ctgccgcagg gggc                  44

<210> SEQ ID NO 251
<211> LENGTH: 48
<212> TYPE: DNA
<213> ORGANISM: Homo sapiens

<400> SEQUENCE: 251
ccccagcacc gctgtggtgt gccgggatcc tgagcctagg cctcccga              48

<210> SEQ ID NO 252
<211> LENGTH: 46
<212> TYPE: DNA
<213> ORGANISM: Homo sapiens

<400> SEQUENCE: 252
gagaccccat tttctgtcga ggcgggccga gtcttccctt atcccc                46

<210> SEQ ID NO 253
<211> LENGTH: 48
<212> TYPE: DNA
<213> ORGANISM: Homo sapiens

<400> SEQUENCE: 253
aaggaggcca gaggctgcaa ggagcggggt cgtgaccgct tacacccc              48

<210> SEQ ID NO 254
<211> LENGTH: 50
<212> TYPE: DNA
<213> ORGANISM: Homo sapiens
```

```
<400> SEQUENCE: 254
tttctgcgct tcctgaagt tcccgccctc ttggagccta cctgcccctc              50

<210> SEQ ID NO 255
<211> LENGTH: 51
<212> TYPE: DNA
<213> ORGANISM: Homo sapiens

<400> SEQUENCE: 255
cgcccggctt ataactggtg caactcccgg ccacccaact gagggacgtt c           51

<210> SEQ ID NO 256
<211> LENGTH: 45
<212> TYPE: DNA
<213> ORGANISM: Homo sapiens

<400> SEQUENCE: 256
cgaacaggcg ggcagagggc cccgcgggag ggtccagaag agagg                  45

<210> SEQ ID NO 257
<211> LENGTH: 48
<212> TYPE: DNA
<213> ORGANISM: Homo sapiens

<400> SEQUENCE: 257
gggtccgaga agtggccgga aggcgcaggg tcggggccag agcccctc               48

<210> SEQ ID NO 258
<211> LENGTH: 52
<212> TYPE: DNA
<213> ORGANISM: Homo sapiens

<400> SEQUENCE: 258
cgggcgccga acagagcgag ctgcggccgt ggcagctgca cggctcctgg cc          52

<210> SEQ ID NO 259
<211> LENGTH: 48
<212> TYPE: DNA
<213> ORGANISM: Homo sapiens

<400> SEQUENCE: 259
gagaatcgct tcagcccggg aggtcgaggc tgtagtgagc cgagatcg               48

<210> SEQ ID NO 260
<211> LENGTH: 52
<212> TYPE: DNA
<213> ORGANISM: Homo sapiens

<400> SEQUENCE: 260
cgagatcgcg ctactgcact cctgggcgac agagcgagac cctgtctcca aa          52

<210> SEQ ID NO 261
<211> LENGTH: 46
<212> TYPE: DNA
<213> ORGANISM: Homo sapiens

<400> SEQUENCE: 261
aaagacaggg agctgggatg gtgcgggttg gtctctaaac cggcgt                 46

<210> SEQ ID NO 262
<211> LENGTH: 50
<212> TYPE: DNA
<213> ORGANISM: Homo sapiens
```

-continued

```
<400> SEQUENCE: 262
cgcgcggtgc ggagcctgcg ggccgggcgg ggctctgcgg cggcgcctcc            50

<210> SEQ ID NO 263
<211> LENGTH: 51
<212> TYPE: DNA
<213> ORGANISM: Homo sapiens

<400> SEQUENCE: 263
cccgcggtga catcagccga tgcgaagggc ggggccgcgg ctataagagc g           51

<210> SEQ ID NO 264
<211> LENGTH: 49
<212> TYPE: DNA
<213> ORGANISM: Homo sapiens

<400> SEQUENCE: 264
atgcctctcg ggtggtgact ccagcgcagg aacttgaaga agcgctttg              49

<210> SEQ ID NO 265
<211> LENGTH: 53
<212> TYPE: DNA
<213> ORGANISM: Homo sapiens

<400> SEQUENCE: 265
ggtaagggag ggaaaatctt accaaagcga ccggctcact cgactgctga ttc         53

<210> SEQ ID NO 266
<211> LENGTH: 50
<212> TYPE: DNA
<213> ORGANISM: Homo sapiens

<400> SEQUENCE: 266
tcctgctgct cccgctggtt cctgcggctt ctgctcagac accaacgcca             50

<210> SEQ ID NO 267
<211> LENGTH: 50
<212> TYPE: DNA
<213> ORGANISM: Homo sapiens

<400> SEQUENCE: 267
cctgaagaat caatcaagtt ttccgtgaag tcaagtccaa gtaacatccc             50

<210> SEQ ID NO 268
<211> LENGTH: 52
<212> TYPE: DNA
<213> ORGANISM: Homo sapiens

<400> SEQUENCE: 268
tctcctcctg cggctccata gctgcggctc ccgccacttt actaggaact cc          52

<210> SEQ ID NO 269
<211> LENGTH: 49
<212> TYPE: DNA
<213> ORGANISM: Homo sapiens

<400> SEQUENCE: 269
ggctctggca ttgcaagcct cgcttcgttg ccacttccca gctcttccc              49

<210> SEQ ID NO 270
<211> LENGTH: 50
<212> TYPE: DNA
<213> ORGANISM: Homo sapiens
```

<400> SEQUENCE: 270
ctcccagtgt tgggatgcag ggcgcggaag cagttcagat gtggaagccg      50

<210> SEQ ID NO 271
<211> LENGTH: 54
<212> TYPE: DNA
<213> ORGANISM: Homo sapiens

<400> SEQUENCE: 271
cgggtcccag gagcccgcag gcatccccgg gagcggcaga agcagcagca ggaa      54

<210> SEQ ID NO 272
<211> LENGTH: 44
<212> TYPE: DNA
<213> ORGANISM: Homo sapiens

<400> SEQUENCE: 272
acgctcagcg gccgtgccca cgcggcggcg cccatgtcgg cccg      44

<210> SEQ ID NO 273
<211> LENGTH: 47
<212> TYPE: DNA
<213> ORGANISM: Homo sapiens

<400> SEQUENCE: 273
ggcttagacc tcaagcaagt cacgtaacct ctcccagcct cagtttt      47

<210> SEQ ID NO 274
<211> LENGTH: 53
<212> TYPE: DNA
<213> ORGANISM: Homo sapiens

<400> SEQUENCE: 274
aaagcagaga agcgagagcg gccactagtt cggcaggaaa tttgttggaa gat      53

<210> SEQ ID NO 275
<211> LENGTH: 56
<212> TYPE: DNA
<213> ORGANISM: Homo sapiens

<400> SEQUENCE: 275
caatgcattc cttttcgtca gagtcgaggg caaactcgct gaaatctggg tgaccc      56

<210> SEQ ID NO 276
<211> LENGTH: 52
<212> TYPE: DNA
<213> ORGANISM: Homo sapiens

<400> SEQUENCE: 276
ggattggttc cacaggcctt ttaaaaagcg gacttaaaag ttgctggcaa tg      52

<210> SEQ ID NO 277
<211> LENGTH: 47
<212> TYPE: DNA
<213> ORGANISM: Homo sapiens

<400> SEQUENCE: 277
gggacagact ccgcctggca ccgggaccat cctccgcctc aactttg      47

<210> SEQ ID NO 278
<211> LENGTH: 49
<212> TYPE: DNA
<213> ORGANISM: Homo sapiens

```
<400> SEQUENCE: 278
gtgccagacg cctgtgcctt ggccgtccta cagccctgct gcccctgcc           49

<210> SEQ ID NO 279
<211> LENGTH: 49
<212> TYPE: DNA
<213> ORGANISM: Homo sapiens

<400> SEQUENCE: 279
ctggagtgtg gcctctgtgc cagacgcctg tgccttggcc gtcctacag           49

<210> SEQ ID NO 280
<211> LENGTH: 49
<212> TYPE: DNA
<213> ORGANISM: Homo sapiens

<400> SEQUENCE: 280
cctagaggaa gtttagtcct tgggacgctt ggcctgccag tctctgaaa           49

<210> SEQ ID NO 281
<211> LENGTH: 38
<212> TYPE: DNA
<213> ORGANISM: Homo sapiens

<400> SEQUENCE: 281
gatggtggtg gtggtagtgc acgttgggtt gaggggac                       38

<210> SEQ ID NO 282
<211> LENGTH: 53
<212> TYPE: DNA
<213> ORGANISM: Homo sapiens

<400> SEQUENCE: 282
tctgagacag gaactgcgaa atgctcacga gattaggaca cgcgccaagg cgg      53

<210> SEQ ID NO 283
<211> LENGTH: 54
<212> TYPE: DNA
<213> ORGANISM: Homo sapiens

<400> SEQUENCE: 283
caagggtccg cattgaacca ggtgcgaatg ttctctctca ttctgcgccg ttcc     54

<210> SEQ ID NO 284
<211> LENGTH: 51
<212> TYPE: DNA
<213> ORGANISM: Homo sapiens

<400> SEQUENCE: 284
cgggagccga ggcttaagtc ctcggggtcc tgtactcgat gccgtttctc c        51

<210> SEQ ID NO 285
<211> LENGTH: 44
<212> TYPE: DNA
<213> ORGANISM: Homo sapiens

<400> SEQUENCE: 285
agacataggg tttggtgtgg ctgtgcgggg ttcccgggcc ttgc                44

<210> SEQ ID NO 286
<211> LENGTH: 52
<212> TYPE: DNA
<213> ORGANISM: Homo sapiens
```

-continued

```
<400> SEQUENCE: 286
gctggcctgt cggcctctga tgcactcgaa cttccagccc ttggagcaga ca      52

<210> SEQ ID NO 287
<211> LENGTH: 48
<212> TYPE: DNA
<213> ORGANISM: Homo sapiens

<400> SEQUENCE: 287
tcagggaagc tgctctttgg gatcgctcca aatcgagttg tgcctgga            48

<210> SEQ ID NO 288
<211> LENGTH: 47
<212> TYPE: DNA
<213> ORGANISM: Homo sapiens

<400> SEQUENCE: 288
ggcccctgga tccgtctttc gcgtttattt taagcccagt cttccct             47

<210> SEQ ID NO 289
<211> LENGTH: 50
<212> TYPE: DNA
<213> ORGANISM: Homo sapiens

<400> SEQUENCE: 289
ccccattcta tctgccctat ctcggttaca gtgtagtcct ccccagggtc          50

<210> SEQ ID NO 290
<211> LENGTH: 48
<212> TYPE: DNA
<213> ORGANISM: Homo sapiens

<400> SEQUENCE: 290
cctggaaggc gcctggaccc acgccaggtt tcccagttta attcctca            48

<210> SEQ ID NO 291
<211> LENGTH: 52
<212> TYPE: DNA
<213> ORGANISM: Homo sapiens

<400> SEQUENCE: 291
gcgggcggaa gtgacgtttt cccgcggttg gacgcggcgc tcagttgccg gg       52

<210> SEQ ID NO 292
<211> LENGTH: 49
<212> TYPE: DNA
<213> ORGANISM: Homo sapiens

<400> SEQUENCE: 292
tcgcagccag ggcaggctgc ggcgccgaca cacaggagcc ggctgcggg           49

<210> SEQ ID NO 293
<211> LENGTH: 51
<212> TYPE: DNA
<213> ORGANISM: Homo sapiens

<400> SEQUENCE: 293
tcatcttgca atcacatagc catcgcatgc cattgcaggg gcaacccagc a        51

<210> SEQ ID NO 294
<211> LENGTH: 53
<212> TYPE: DNA
<213> ORGANISM: Homo sapiens
```

<400> SEQUENCE: 294
catacgctga ctccgaggca actgggcgca cacatatccc ctctctggtc ctc            53

<210> SEQ ID NO 295
<211> LENGTH: 47
<212> TYPE: DNA
<213> ORGANISM: Homo sapiens

<400> SEQUENCE: 295
cagggttcaa gggcatgggg ctcccgcagc tgtggctggg gcagagc                   47

<210> SEQ ID NO 296
<211> LENGTH: 47
<212> TYPE: DNA
<213> ORGANISM: Homo sapiens

<400> SEQUENCE: 296
gcccaacaga cttttccttt tcgggcctca gtcttctcgt cagcaag                   47

<210> SEQ ID NO 297
<211> LENGTH: 49
<212> TYPE: DNA
<213> ORGANISM: Homo sapiens

<400> SEQUENCE: 297
cacgcgattg gtatcctgcc ctccgcccca gccaatgagc ggcgagggt                 49

<210> SEQ ID NO 298
<211> LENGTH: 44
<212> TYPE: DNA
<213> ORGANISM: Homo sapiens

<400> SEQUENCE: 298
tccccgatgc agaccacagc gccctcacgg gctgccctca ggcc                      44

<210> SEQ ID NO 299
<211> LENGTH: 50
<212> TYPE: DNA
<213> ORGANISM: Homo sapiens

<400> SEQUENCE: 299
aaagggagag aagttggtgc tcaacgtgag ccaggagcag cgtcccggct                50

<210> SEQ ID NO 300
<211> LENGTH: 47
<212> TYPE: DNA
<213> ORGANISM: Homo sapiens

<400> SEQUENCE: 300
cgtgagccag gagcagcgtc ccggctcctc ccctgctcat tttaaaa                   47

<210> SEQ ID NO 301
<211> LENGTH: 47
<212> TYPE: DNA
<213> ORGANISM: Homo sapiens

<400> SEQUENCE: 301
gagcgggcgc aggcggaaca ccgttttcca agctaagccg ccgcaaa                   47

<210> SEQ ID NO 302
<211> LENGTH: 56
<212> TYPE: DNA
<213> ORGANISM: Homo sapiens -continued

```
<400> SEQUENCE: 302
ggctggggca cacaaaacca ggtgctaccg tcaacgacta ggcccatagg gtactg        56

<210> SEQ ID NO 303
<211> LENGTH: 49
<212> TYPE: DNA
<213> ORGANISM: Homo sapiens

<400> SEQUENCE: 303
aagggagaaa gaagccagac ggagctcgga gatgtggagg gcagacgca               49

<210> SEQ ID NO 304
<211> LENGTH: 52
<212> TYPE: DNA
<213> ORGANISM: Homo sapiens

<400> SEQUENCE: 304
cccaaaacgc tcggtaggcg gtggtgcgca gctttcaatg catccgccgc ca           52

<210> SEQ ID NO 305
<211> LENGTH: 47
<212> TYPE: DNA
<213> ORGANISM: Homo sapiens

<400> SEQUENCE: 305
ctcctgaacc tttatgggct ctgtcgaggc tgaagcagcc aggggct                 47

<210> SEQ ID NO 306
<211> LENGTH: 41
<212> TYPE: DNA
<213> ORGANISM: Homo sapiens

<400> SEQUENCE: 306
gcaggtcttg ggccctggtc ccgcccctg ctcctcccca c                        41

<210> SEQ ID NO 307
<211> LENGTH: 41
<212> TYPE: DNA
<213> ORGANISM: Homo sapiens

<400> SEQUENCE: 307
gaggggctgg aggaggaaac ggggaggccc acacagaagg g                       41

<210> SEQ ID NO 308
<211> LENGTH: 42
<212> TYPE: DNA
<213> ORGANISM: Homo sapiens

<400> SEQUENCE: 308
gggcaactgt ccccacccgt ccctggcacg gctctgccca gt                      42

<210> SEQ ID NO 309
<211> LENGTH: 46
<212> TYPE: DNA
<213> ORGANISM: Homo sapiens

<400> SEQUENCE: 309
tccttgctgc cacacattta gccgccctcc ccatgccagc ttgggg                  46

<210> SEQ ID NO 310
<211> LENGTH: 51
<212> TYPE: DNA
<213> ORGANISM: Homo sapiens
```

```
<400> SEQUENCE: 310
gttgggtgcc ctcatttcag atgatttcga gggtgcttga caagatctga a              51

<210> SEQ ID NO 311
<211> LENGTH: 48
<212> TYPE: DNA
<213> ORGANISM: Homo sapiens

<400> SEQUENCE: 311
ggggaccctg gcacagattt ggctcgacct ggacataggc tgggcctg                  48

<210> SEQ ID NO 312
<211> LENGTH: 50
<212> TYPE: DNA
<213> ORGANISM: Homo sapiens

<400> SEQUENCE: 312
ggcagtgctg ggaacgcccc tctcggaaat taactcctca gggcacccgc                50

<210> SEQ ID NO 313
<211> LENGTH: 48
<212> TYPE: DNA
<213> ORGANISM: Homo sapiens

<400> SEQUENCE: 313
gacctggagg cagccctggg tctccggatc aggccagcgg ccaaaggg                  48

<210> SEQ ID NO 314
<211> LENGTH: 48
<212> TYPE: DNA
<213> ORGANISM: Homo sapiens

<400> SEQUENCE: 314
ccgcccggag cagctgcgct gtcggggcca ggccgggctc ccagtgga                  48

<210> SEQ ID NO 315
<211> LENGTH: 47
<212> TYPE: DNA
<213> ORGANISM: Homo sapiens

<400> SEQUENCE: 315
gggttacccc acagcctagg ccgattcgac ctctctccgc tggggcc                   47

<210> SEQ ID NO 316
<211> LENGTH: 47
<212> TYPE: DNA
<213> ORGANISM: Homo sapiens

<400> SEQUENCE: 316
ggccgcgcag atcccgctta tcgggcccat ctcccgttac ataaggc                   47

<210> SEQ ID NO 317
<211> LENGTH: 47
<212> TYPE: DNA
<213> ORGANISM: Homo sapiens

<400> SEQUENCE: 317
gagccgctgg cccgggtgtc cagccggccc ttgccctgcc tggcgct                   47

<210> SEQ ID NO 318
<211> LENGTH: 50
<212> TYPE: DNA
<213> ORGANISM: Homo sapiens
```

```
<400> SEQUENCE: 318
cacgcagcgc attgcaggca ggtgcgagcc acatgcgcca agtgcccgga        50

<210> SEQ ID NO 319
<211> LENGTH: 51
<212> TYPE: DNA
<213> ORGANISM: Homo sapiens

<400> SEQUENCE: 319
atcctggggt ttatttgctg agggcgcttc ccataaaagc gagagagtgt g      51

<210> SEQ ID NO 320
<211> LENGTH: 49
<212> TYPE: DNA
<213> ORGANISM: Homo sapiens

<400> SEQUENCE: 320
gtgaacaaat agctgagggg cggccgggcc agaacggctt gtgtaactt         49

<210> SEQ ID NO 321
<211> LENGTH: 54
<212> TYPE: DNA
<213> ORGANISM: Homo sapiens

<400> SEQUENCE: 321
aggcgaggag ctgtccgcct tgcacgtttc caatcgcatt acgtgaacaa atag   54

<210> SEQ ID NO 322
<211> LENGTH: 52
<212> TYPE: DNA
<213> ORGANISM: Homo sapiens

<400> SEQUENCE: 322
ttgtgaatat cagtggcagg tttccagaac gcaggtgggg ataagagtga gt     52

<210> SEQ ID NO 323
<211> LENGTH: 48
<212> TYPE: DNA
<213> ORGANISM: Homo sapiens

<400> SEQUENCE: 323
cggtttcatg gcagcccagg gtccagcggc atccaggatg ctggtggg          48

<210> SEQ ID NO 324
<211> LENGTH: 50
<212> TYPE: DNA
<213> ORGANISM: Homo sapiens

<400> SEQUENCE: 324
agctgcacag cccaggccgc gggaggttgg ctgctctcac ctaacaggcc        50

<210> SEQ ID NO 325
<211> LENGTH: 42
<212> TYPE: DNA
<213> ORGANISM: Homo sapiens

<400> SEQUENCE: 325
acctcagatc ctccaaccgg tttcatggca gcccagggtc ca                42

<210> SEQ ID NO 326
<211> LENGTH: 49
<212> TYPE: DNA
<213> ORGANISM: Homo sapiens
```

```
<400> SEQUENCE: 326
agtgcctggc tcacggtcag tgctcacgtt tgggcagctg cacttgggc        49

<210> SEQ ID NO 327
<211> LENGTH: 54
<212> TYPE: DNA
<213> ORGANISM: Homo sapiens

<400> SEQUENCE: 327
ccaggccggc tcgggtctac ctgcgccagc gctgtacctg ggcgaccttg gctt    54

<210> SEQ ID NO 328
<211> LENGTH: 48
<212> TYPE: DNA
<213> ORGANISM: Homo sapiens

<400> SEQUENCE: 328
gggctctggc ggcccatcct ggcggagact tcggctagca ggccccgc            48

<210> SEQ ID NO 329
<211> LENGTH: 48
<212> TYPE: DNA
<213> ORGANISM: Homo sapiens

<400> SEQUENCE: 329
ctggctttgt cttctgggat aagacgggga atccagagg atgtaagc              48

<210> SEQ ID NO 330
<211> LENGTH: 48
<212> TYPE: DNA
<213> ORGANISM: Homo sapiens

<400> SEQUENCE: 330
ggcagcttga tccccctagc ccgcttccag ccctcacctg gctttgtc             48

<210> SEQ ID NO 331
<211> LENGTH: 52
<212> TYPE: DNA
<213> ORGANISM: Homo sapiens

<400> SEQUENCE: 331
ggtgtgacgg ccggtcctac tctccggcct gttcagatca gctccttctg gg       52

<210> SEQ ID NO 332
<211> LENGTH: 47
<212> TYPE: DNA
<213> ORGANISM: Homo sapiens

<400> SEQUENCE: 332
tcctggggac ccttgaccct ccgacacaaa caagcgctcc aggagtc              47

<210> SEQ ID NO 333
<211> LENGTH: 52
<212> TYPE: DNA
<213> ORGANISM: Homo sapiens

<400> SEQUENCE: 333
cccttagctt acggagaccc tggggcgagg gaaataggag agaacagcag tc        52

<210> SEQ ID NO 334
<211> LENGTH: 48
<212> TYPE: DNA
<213> ORGANISM: Homo sapiens
```

<400> SEQUENCE: 334
tgttaatggg tgagagggat tttgcgctct ccggggagaa agccccac 48

<210> SEQ ID NO 335
<211> LENGTH: 48
<212> TYPE: DNA
<213> ORGANISM: Homo sapiens

<400> SEQUENCE: 335
ggccctccag ggtcgcggcc tcttcgggca gcccaagtgg aggaactt 48

<210> SEQ ID NO 336
<211> LENGTH: 47
<212> TYPE: DNA
<213> ORGANISM: Homo sapiens

<400> SEQUENCE: 336
gggctcaggg ccctccaggg tcgcggcctc ttcgggcagc ccaagtg 47

<210> SEQ ID NO 337
<211> LENGTH: 49
<212> TYPE: DNA
<213> ORGANISM: Homo sapiens

<400> SEQUENCE: 337
ccagctgggc gaccaggaca gggacggagg ctgctgagcc cagttagag 49

<210> SEQ ID NO 338
<211> LENGTH: 50
<212> TYPE: DNA
<213> ORGANISM: Homo sapiens

<400> SEQUENCE: 338
gagaccttgg ctggcgcgag gccacgccca ccagacatgc agttccagct 50

<210> SEQ ID NO 339
<211> LENGTH: 50
<212> TYPE: DNA
<213> ORGANISM: Homo sapiens

<400> SEQUENCE: 339
gggcgactag gacagggaca gaacccgttg aacccaggag tgagatccgg 50

<210> SEQ ID NO 340
<211> LENGTH: 48
<212> TYPE: DNA
<213> ORGANISM: Homo sapiens

<400> SEQUENCE: 340 gggggggcctc tgcccggggg ccgggctctc tggggccgcc gtcgcgcc 48

<210> SEQ ID NO 341
<211> LENGTH: 48
<212> TYPE: DNA
<213> ORGANISM: Homo sapiens

<400> SEQUENCE: 341
ggggtacggg ctgcttcacc cccgcgtgga cctcccccct cagctgggg 48

<210> SEQ ID NO 342
<211> LENGTH: 49
<212> TYPE: DNA
<213> ORGANISM: Homo sapiens

```
<400> SEQUENCE: 342
ctgggagcca gagcgccagg cagcgtcgca ggagcaggtt ctgggctgg            49

<210> SEQ ID NO 343
<211> LENGTH: 53
<212> TYPE: DNA
<213> ORGANISM: Homo sapiens

<400> SEQUENCE: 343
tgaaacaggc acaccaggga attggagcgg aggagggtaa ctcaaactca gag       53

<210> SEQ ID NO 344
<211> LENGTH: 49
<212> TYPE: DNA
<213> ORGANISM: Homo sapiens

<400> SEQUENCE: 344
ggcccctctg gttatctctt tgccgtgcca acacagtctc tgcgcccac             49

<210> SEQ ID NO 345
<211> LENGTH: 49
<212> TYPE: DNA
<213> ORGANISM: Homo sapiens

<400> SEQUENCE: 345
gcagcctgtc caagtcacaa agcggggcct cgggccttga cagttcgcg             49

<210> SEQ ID NO 346
<211> LENGTH: 48
<212> TYPE: DNA
<213> ORGANISM: Homo sapiens

<400> SEQUENCE: 346
aaggggatga gtgcagggaa ccccgacccc acccgggaga cctgcaag              48

<210> SEQ ID NO 347
<211> LENGTH: 39
<212> TYPE: DNA
<213> ORGANISM: Homo sapiens

<400> SEQUENCE: 347
gcagacactc ccctcccgcc cccactgaac ccttgaccc                        39

<210> SEQ ID NO 348
<211> LENGTH: 44
<212> TYPE: DNA
<213> ORGANISM: Homo sapiens

<400> SEQUENCE: 348
cgaaacctca gtctgggagc cacggagggc tctcccctct cccc                  44

<210> SEQ ID NO 349
<211> LENGTH: 45
<212> TYPE: DNA
<213> ORGANISM: Homo sapiens

<400> SEQUENCE: 349
gccccctccc agatgatcga ggggtccagg ctccttacct ctagt                 45

<210> SEQ ID NO 350
<211> LENGTH: 56
<212> TYPE: DNA
<213> ORGANISM: Homo sapiens
```

```
<400> SEQUENCE: 350
catattatat cctgccattt gatgcccggt gaacattcta tacctgcttc ccagaa          56

<210> SEQ ID NO 351
<211> LENGTH: 54
<212> TYPE: DNA
<213> ORGANISM: Homo sapiens

<400> SEQUENCE: 351
gaaaagtgga atcagctggc attgcccagc gtgatttgtg aggctgagcc ccaa            54

<210> SEQ ID NO 352
<211> LENGTH: 49
<212> TYPE: DNA
<213> ORGANISM: Homo sapiens

<400> SEQUENCE: 352
acgagggagc gttaggaagg aatccgtctt gtaaagccat tggtcctgg                  49

<210> SEQ ID NO 353
<211> LENGTH: 51
<212> TYPE: DNA
<213> ORGANISM: Homo sapiens

<400> SEQUENCE: 353
aagcaaatgg gatgccacct ccgcggggct cgctcctcgc gaggtgctca c               51

<210> SEQ ID NO 354
<211> LENGTH: 53
<212> TYPE: DNA
<213> ORGANISM: Homo sapiens

<400> SEQUENCE: 354
ggttcgggga accgcggagg tttcggggtt ctagaaatcc gaggttctaa gcc             53

<210> SEQ ID NO 355
<211> LENGTH: 50
<212> TYPE: DNA
<213> ORGANISM: Homo sapiens

<400> SEQUENCE: 355
ggaggtttcg gggttctaga aatccgaggt tctaagccta ggtgctccaa                 50

<210> SEQ ID NO 356
<211> LENGTH: 50
<212> TYPE: DNA
<213> ORGANISM: Homo sapiens

<400> SEQUENCE: 356
gtgagagcca gcccaggttt ccggtctgta cccgctggtg caagcccaga                 50

<210> SEQ ID NO 357
<211> LENGTH: 49
<212> TYPE: DNA
<213> ORGANISM: Homo sapiens

<400> SEQUENCE: 357
caccacatac acactacaca ccgggacaca cacacaaaag gcctatgca                  49

<210> SEQ ID NO 358
<211> LENGTH: 48
<212> TYPE: DNA
<213> ORGANISM: Homo sapiens
```

<400> SEQUENCE: 358
cacacacaca aaccacatgc acgtgcatgc acgcacactc agacacac                48

<210> SEQ ID NO 359
<211> LENGTH: 41
<212> TYPE: DNA
<213> ORGANISM: Homo sapiens

<400> SEQUENCE: 359
tgagctcagg gctcaagggg gacggggctg gtgcctgttt t                       41

<210> SEQ ID NO 360
<211> LENGTH: 50
<212> TYPE: DNA
<213> ORGANISM: Homo sapiens

<400> SEQUENCE: 360
ttcaccttcc ggtcctgcgt gggccgagag gattgccgta cgcatgtctg              50

<210> SEQ ID NO 361
<211> LENGTH: 49
<212> TYPE: DNA
<213> ORGANISM: Homo sapiens

<400> SEQUENCE: 361
caaactcctg ggctcaagca atccgctcac gtcaacctcc ccaaatgct               49

<210> SEQ ID NO 362
<211> LENGTH: 47
<212> TYPE: DNA
<213> ORGANISM: Homo sapiens

<400> SEQUENCE: 362
agcggtactc gaaggccggg gccgagatgc caccttccgc aggccgc                 47

<210> SEQ ID NO 363
<211> LENGTH: 46
<212> TYPE: DNA
<213> ORGANISM: Homo sapiens

<400> SEQUENCE: 363
gggtgctgtg agactgggct gcgacccagg tccagcaggg agtgtg                  46

<210> SEQ ID NO 364
<211> LENGTH: 49
<212> TYPE: DNA
<213> ORGANISM: Homo sapiens

<400> SEQUENCE: 364
tgagccaagg ccgcgagcag gcttctcgca tcctgtgagc tgaggttgg               49

<210> SEQ ID NO 365
<211> LENGTH: 48
<212> TYPE: DNA
<213> ORGANISM: Homo sapiens

<400> SEQUENCE: 365
gtgacatcac ggcccaggtg accgcggccc agccaatgag ccaaggcc                48

<210> SEQ ID NO 366
<211> LENGTH: 49
<212> TYPE: DNA
<213> ORGANISM: Homo sapiens

```
<400> SEQUENCE: 366
tggtggacaa tggcagggag tcagccgcag cccaggggcg aggtggcat              49

<210> SEQ ID NO 367
<211> LENGTH: 51
<212> TYPE: DNA
<213> ORGANISM: Homo sapiens

<400> SEQUENCE: 367
cccagctcgg agtgggcaag gagcacggtt tagctcagcc ggctggcacc g           51

<210> SEQ ID NO 368
<211> LENGTH: 48
<212> TYPE: DNA
<213> ORGANISM: Homo sapiens

<400> SEQUENCE: 368
cgacgggtga ccagacggac gccgggacca gcccaagttc agggctga              48

<210> SEQ ID NO 369
<211> LENGTH: 50
<212> TYPE: DNA
<213> ORGANISM: Homo sapiens

<400> SEQUENCE: 369
ggcagggacc agggagccag gaactgcgcc gccccgccc ctgccctggc              50

<210> SEQ ID NO 370
<211> LENGTH: 48
<212> TYPE: DNA
<213> ORGANISM: Homo sapiens

<400> SEQUENCE: 370
ggcgaggacc gggtataaga agcctcgtgg ccttgcccgg gcagccgc               48

<210> SEQ ID NO 371
<211> LENGTH: 51
<212> TYPE: DNA
<213> ORGANISM: Homo sapiens

<400> SEQUENCE: 371
cgcgtggggt cagaccgcaa agcgaaggtg cgggccgggg tgggcctcgc g           51

<210> SEQ ID NO 372
<211> LENGTH: 48
<212> TYPE: DNA
<213> ORGANISM: Homo sapiens

<400> SEQUENCE: 372
tggggctcat ggctgagcca ggtcgcagga cagacaagtt ggcctgga               48

<210> SEQ ID NO 373
<211> LENGTH: 51
<212> TYPE: DNA
<213> ORGANISM: Homo sapiens

<400> SEQUENCE: 373
ttacagacct ggagttcctc tttcgcaggt tctgtgctcc cctcaagggt c           51

<210> SEQ ID NO 374
<211> LENGTH: 49
<212> TYPE: DNA
<213> ORGANISM: Homo sapiens
```

```
<400> SEQUENCE: 374
agacagaaac tgcagctctc ccgtgacctt ccaggtgctg ccctgactc          49

<210> SEQ ID NO 375
<211> LENGTH: 48
<212> TYPE: DNA
<213> ORGANISM: Homo sapiens

<400> SEQUENCE: 375
ccgagagaca gggtctcgct ctgtcgccca ggcctggagt gcattggc           48

<210> SEQ ID NO 376
<211> LENGTH: 54
<212> TYPE: DNA
<213> ORGANISM: Homo sapiens

<400> SEQUENCE: 376
cgctaggatt acaggcgtgg gccaccgcgc ctgaccagtc ttctcttctt gcag    54

<210> SEQ ID NO 377
<211> LENGTH: 45
<212> TYPE: DNA
<213> ORGANISM: Homo sapiens

<400> SEQUENCE: 377
gctcagaccc tctggcctca agcgatcctc cagcctgggc ctccc             45

<210> SEQ ID NO 378
<211> LENGTH: 20
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 378
gccctcacac ttctacaccg                                         20

<210> SEQ ID NO 379
<211> LENGTH: 22
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 379
ccgactttat cacacaccta cg                                      22

<210> SEQ ID NO 380
<211> LENGTH: 23
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 380
cgacttccaa acaataataa acg                                     23

<210> SEQ ID NO 381
<211> LENGTH: 25
<212> TYPE: DNA
<213> ORGANISM: Artificial Sequence
<220> FEATURE:
<223> OTHER INFORMATION: Description of Artificial Sequence: Synthetic
```

```
                                probe

<400> SEQUENCE: 381
ccctaataaa tcaaaacatc taccg                                             25

<210> SEQ ID NO 382
<211> LENGTH: 21
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 382
actttcaact acccctcacc g                                                 21

<210> SEQ ID NO 383
<211> LENGTH: 21
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 383
gtccaacccc taactctctc g                                                 21

<210> SEQ ID NO 384
<211> LENGTH: 20
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 384
acccgaatct ctcctaaccg                                                   20

<210> SEQ ID NO 385
<211> LENGTH: 21
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 385
actctatacc cgacgcctac g                                                 21

<210> SEQ ID NO 386
<211> LENGTH: 20
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 386
ctaacgccga acctacttcg                                                   20

<210> SEQ ID NO 387
<211> LENGTH: 23
<212> TYPE: DNA
<213> ORGANISM: Artificial Sequence
<220> FEATURE:
<223> OTHER INFORMATION: Description of Artificial Sequence: Synthetic
      probe
```

```
<400> SEQUENCE: 387
cgccaaatat cttttcttct tcg                                             23

<210> SEQ ID NO 388
<211> LENGTH: 21
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 388
tatcccgacg taacttcctc g                                               21

<210> SEQ ID NO 389
<211> LENGTH: 21
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 389
ccgacctaac aaaacaactc g                                               21

<210> SEQ ID NO 390
<211> LENGTH: 23
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 390
aaccttctta ccttcaaacc tcg                                             23

<210> SEQ ID NO 391
<211> LENGTH: 21
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 391
aaatactccc attctccacc g                                               21

<210> SEQ ID NO 392
<211> LENGTH: 21
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 392
actaccactc cccaaaaaac g                                               21

<210> SEQ ID NO 393
<211> LENGTH: 19
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 393
```

```
cgacgaaaat accccaacg                                          19
```

<210> SEQ ID NO 394
<211> LENGTH: 19
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 394

```
gcgctcaacc aattaaacg                                          19
```

<210> SEQ ID NO 395
<211> LENGTH: 21
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 395

```
aattcccaac gtaacaacac g                                       21
```

<210> SEQ ID NO 396
<211> LENGTH: 21
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 396

```
actcacccct cctttctacc g                                       21
```

<210> SEQ ID NO 397
<211> LENGTH: 19
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 397

```
gcgtccgaat tcctaaacg                                          19
```

<210> SEQ ID NO 398
<211> LENGTH: 20
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 398

```
aacccgcgaa atttaaaacg                                         20
```

<210> SEQ ID NO 399
<211> LENGTH: 23
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 399

```
caatacaacc aacattccta acg                                     23
```

```
<210> SEQ ID NO 400
<211> LENGTH: 23
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 400
caactcctaa tccccaataa acg                                              23

<210> SEQ ID NO 401
<211> LENGTH: 22
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 401
catctttaaa caaacttccc cg                                               22

<210> SEQ ID NO 402
<211> LENGTH: 21
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 402
aaacaaacaa cctccctctc g                                                21

<210> SEQ ID NO 403
<211> LENGTH: 21
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 403
ctttaatttc tcccaaaccc g                                                21

<210> SEQ ID NO 404
<211> LENGTH: 23
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 404
aaaaatctct actaactccc ccg                                              23

<210> SEQ ID NO 405
<211> LENGTH: 22
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 405
aacaacacct ctcacgcata cg                                               22

<210> SEQ ID NO 406
```

```
<211> LENGTH: 22
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 406
caaaacaacg aaacaatacc cg                                              22

<210> SEQ ID NO 407
<211> LENGTH: 21
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 407
cgaaaaccta accgctactc g                                               21

<210> SEQ ID NO 408
<211> LENGTH: 20
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 408
ccccttccct caactaaacg                                                 20

<210> SEQ ID NO 409
<211> LENGTH: 23
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 409
ctcctactcc ttctcctaat ccg                                             23

<210> SEQ ID NO 410
<211> LENGTH: 22
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 410
taaaacaact tctcccgaaa cg                                              22

<210> SEQ ID NO 411
<211> LENGTH: 22
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 411
tatctacgac accaaatcga cg                                              22

<210> SEQ ID NO 412
<211> LENGTH: 21
<212> TYPE: DNA
```

```
<213> ORGANISM: Artificial Sequence
<220> FEATURE:
<223> OTHER INFORMATION: Description of Artificial Sequence: Synthetic
      probe

<400> SEQUENCE: 412
ccatttcctt tacttcctcc g                                           21

<210> SEQ ID NO 413
<211> LENGTH: 18
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 413
cgccgcctac aaaaaacg                                               18

<210> SEQ ID NO 414
<211> LENGTH: 22
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 414
cacgaaaacc aaaaaactac cg                                          22

<210> SEQ ID NO 415
<211> LENGTH: 21
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 415
aataaccaat ccaaaacccc g                                           21

<210> SEQ ID NO 416
<211> LENGTH: 23
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 416
caaataaaat tcttcctctt ccg                                         23

<210> SEQ ID NO 417
<211> LENGTH: 25
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 417
ctcgaatcaa taacactact caacg                                       25

<210> SEQ ID NO 418
<211> LENGTH: 23
<212> TYPE: DNA
<213> ORGANISM: Artificial Sequence
<220> FEATURE:
```

<223> OTHER INFORMATION: Description of Artificial Sequence: Synthetic
      probe

<400> SEQUENCE: 418
aaatattccc cttacaaaaa ccg                                              23

<210> SEQ ID NO 419
<211> LENGTH: 24
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 419
caacctacta ttatatcgcc aacg                                             24

<210> SEQ ID NO 420
<211> LENGTH: 20
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 420
tacgtaaata cgcgaacccg                                                  20

<210> SEQ ID NO 421
<211> LENGTH: 17
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 421
caaacctaca tcccgcg                                                     17

<210> SEQ ID NO 422
<211> LENGTH: 22
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 422
cgaaaaacct aaaaacgaaa cg                                               22

<210> SEQ ID NO 423
<211> LENGTH: 23
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 423
cgtacgcttc ctaaataaaa ccg                                              23

<210> SEQ ID NO 424
<211> LENGTH: 23
<212> TYPE: DNA
<213> ORGANISM: Artificial Sequence
<220> FEATURE:
<223> OTHER INFORMATION: Description of Artificial Sequence: Synthetic
      probe

```
<400> SEQUENCE: 424
tctttctcta ataacccaca ccg                                                  23

<210> SEQ ID NO 425
<211> LENGTH: 20
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 425
ccaacctaac tctccttccg                                                      20

<210> SEQ ID NO 426
<211> LENGTH: 22
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 426
tcttaaatct taacaatccc cg                                                   22

<210> SEQ ID NO 427
<211> LENGTH: 23
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 427
cctaaatacc tcctacgcaa acg                                                  23

<210> SEQ ID NO 428
<211> LENGTH: 22
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 428
atcaatcacg taaaacgttc cg                                                   22

<210> SEQ ID NO 429
<211> LENGTH: 22
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 429
acaccaacct ctaacgatac cg                                                   22

<210> SEQ ID NO 430
<211> LENGTH: 23
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 430
```
ctcaaaaccg taattttcaa acg                                          23

<210> SEQ ID NO 431
<211> LENGTH: 23
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 431
aaaactaacc tctcctaccc tcg                                          23

<210> SEQ ID NO 432
<211> LENGTH: 26
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 432
cctaaaacaa ataacacaat accacg                                       26

<210> SEQ ID NO 433
<211> LENGTH: 21
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 433
ataaaaacga aacccgactc g                                            21

<210> SEQ ID NO 434
<211> LENGTH: 22
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 434
caaatcaata acgtcacatc cg                                           22

<210> SEQ ID NO 435
<211> LENGTH: 21
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 435
ctcaacccta atacccatcc g                                            21

<210> SEQ ID NO 436
<211> LENGTH: 21
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 436
ccactccaat actcactccc g                                            21

<210> SEQ ID NO 437
<211> LENGTH: 22
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 437
cgaacaaaac aaacaaaatc cg                                              22

<210> SEQ ID NO 438
<211> LENGTH: 21
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 438
cttaactaac gcgaaaccac g                                               21

<210> SEQ ID NO 439
<211> LENGTH: 23
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 439
gaatctcact cctaaattca acg                                             23

<210> SEQ ID NO 440
<211> LENGTH: 21
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 440
gcgaacctac aaaacctaac g                                               21

<210> SEQ ID NO 441
<211> LENGTH: 23
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 441
actcgataat aataaacacg ccg                                             23

<210> SEQ ID NO 442
<211> LENGTH: 22
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 442
ccaataaaac cgacttaacc cg                                              22

```
<210> SEQ ID NO 443
<211> LENGTH: 22
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 443
cttccttaaa ctctctccac cg                                          22

<210> SEQ ID NO 444
<211> LENGTH: 22
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 444
ataacaacca tcctacctcc cg                                          22

<210> SEQ ID NO 445
<211> LENGTH: 22
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 445
gaccgaccgt aaaaataaaa cg                                          22

<210> SEQ ID NO 446
<211> LENGTH: 23
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 446
cctctcccct accctataaa acg                                         23

<210> SEQ ID NO 447
<211> LENGTH: 18
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 447
aactacgcga cgactccg                                               18

<210> SEQ ID NO 448
<211> LENGTH: 23
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 448
gaaaaacacc ttccataaaa acg                                         23

<210> SEQ ID NO 449
<211> LENGTH: 21
```

```
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 449
gcaataccat aaacgtcacc g                                           21

<210> SEQ ID NO 450
<211> LENGTH: 22
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 450
acgaattaca caatccaatt cg                                          22

<210> SEQ ID NO 451
<211> LENGTH: 24
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 451
aattaataac caaccaaaaa ctcg                                        24

<210> SEQ ID NO 452
<211> LENGTH: 21
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 452
tctctttccc tttctcttcc g                                           21

<210> SEQ ID NO 453
<211> LENGTH: 23
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 453
aataaatttc acctctcaat ccg                                         23

<210> SEQ ID NO 454
<211> LENGTH: 24
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 454
aaaatccttt acccctaaat tacg                                        24

<210> SEQ ID NO 455
<211> LENGTH: 20
<212> TYPE: DNA
<213> ORGANISM: Artificial Sequence
```

```
<220> FEATURE:
<223> OTHER INFORMATION: Description of Artificial Sequence: Synthetic
      probe

<400> SEQUENCE: 455
gcaccaacct aaactcaacg                                                 20

<210> SEQ ID NO 456
<211> LENGTH: 22
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 456
cccaactaaa actaaaaccc cg                                              22

<210> SEQ ID NO 457
<211> LENGTH: 20
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 457
gcctcctaat aaaaacccccg                                                20

<210> SEQ ID NO 458
<211> LENGTH: 23
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 458
tacctctctc caaatctctc acg                                             23

<210> SEQ ID NO 459
<211> LENGTH: 23
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 459
tacgtatctc tcaacctctt tcg                                             23

<210> SEQ ID NO 460
<211> LENGTH: 23
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 460
aatatcaaaa cctctacgac ccg                                             23

<210> SEQ ID NO 461
<211> LENGTH: 22
<212> TYPE: DNA
<213> ORGANISM: Artificial Sequence
<220> FEATURE:
<223> OTHER INFORMATION: Description of Artificial Sequence: Synthetic
```

```
        probe

<400> SEQUENCE: 461
gaacccaata aaatcaaaac cg                                               22

<210> SEQ ID NO 462
<211> LENGTH: 21
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 462
cctcaaccaa tcaacgatac g                                                21

<210> SEQ ID NO 463
<211> LENGTH: 22
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 463
ttaaaaaccg tctaatcgac cg                                               22

<210> SEQ ID NO 464
<211> LENGTH: 20
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 464
tccgttctat accacacccg                                                  20

<210> SEQ ID NO 465
<211> LENGTH: 23
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 465
tacttcattc tctacacaac ccg                                              23

<210> SEQ ID NO 466
<211> LENGTH: 20
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 466
cctcctaatc ctacgcgacg                                                  20

<210> SEQ ID NO 467
<211> LENGTH: 20
<212> TYPE: DNA
<213> ORGANISM: Artificial Sequence
<220> FEATURE:
<223> OTHER INFORMATION: Description of Artificial Sequence: Synthetic
      probe
```

```
<400> SEQUENCE: 467
aacgctcgaa acgaactacg                                               20

<210> SEQ ID NO 468
<211> LENGTH: 21
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 468
ccaactccga actcataaac g                                             21

<210> SEQ ID NO 469
<211> LENGTH: 21
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 469
actcctctac acctaccgcc g                                             21

<210> SEQ ID NO 470
<211> LENGTH: 21
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 470
accgatacga tccatatccc g                                             21

<210> SEQ ID NO 471
<211> LENGTH: 23
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 471
aaaccaaaac ttacaaacca acg                                           23

<210> SEQ ID NO 472
<211> LENGTH: 23
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 472
tttatcccca attaataatt ccg                                           23

<210> SEQ ID NO 473
<211> LENGTH: 20
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 473
```

```
tttataactc cgtctccgcg                                                    20
```

<210> SEQ ID NO 474
<211> LENGTH: 21
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 474

```
ctaccctata cgcctaaccc g                                                  21
```

<210> SEQ ID NO 475
<211> LENGTH: 18
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 475

```
acgtaccgac gtccaacg                                                      18
```

<210> SEQ ID NO 476
<211> LENGTH: 22
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 476

```
cactcgaaca cgtaacaaat cg                                                 22
```

<210> SEQ ID NO 477
<211> LENGTH: 22
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 477

```
ctttcctaat taacgccaaa cg                                                 22
```

<210> SEQ ID NO 478
<211> LENGTH: 22
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 478

```
aaccgaacca aaactaaatc cg                                                 22
```

<210> SEQ ID NO 479
<211> LENGTH: 23
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 479

```
aataacccccc aaaactaaac tcg                                               23
```

```
<210> SEQ ID NO 480
<211> LENGTH: 23
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 480
caaaaacaaa tccaaatata ccg                                              23

<210> SEQ ID NO 481
<211> LENGTH: 23
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 481
caaccctaaa catctaaaca ccg                                              23

<210> SEQ ID NO 482
<211> LENGTH: 18
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 482
tcattccact ccaacccg                                                    18

<210> SEQ ID NO 483
<211> LENGTH: 24
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 483
ctaaaaaatc tccctcttat ctcg                                             24

<210> SEQ ID NO 484
<211> LENGTH: 18
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 484
aacccttcca ccctaccg                                                    18

<210> SEQ ID NO 485
<211> LENGTH: 24
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 485
cacaaatcct aaaataccaa aacg                                             24

<210> SEQ ID NO 486
```

```
<211> LENGTH: 23
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 486
aactacaata aaccaaactc gcg                                           23

<210> SEQ ID NO 487
<211> LENGTH: 21
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 487
gtataaaata cgccaccctc g                                             21

<210> SEQ ID NO 488
<211> LENGTH: 20
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 488
cccatcccct aataatcacg                                               20

<210> SEQ ID NO 489
<211> LENGTH: 26
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 489
aacaataaca aacatctctt ataccg                                        26

<210> SEQ ID NO 490
<211> LENGTH: 22
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 490
actataaccc aacccaacta cg                                            22

<210> SEQ ID NO 491
<211> LENGTH: 25
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 491
aacactaaac cataaaatct caacg                                         25

<210> SEQ ID NO 492
<211> LENGTH: 22
<212> TYPE: DNA
```

```
<213> ORGANISM: Artificial Sequence
<220> FEATURE:
<223> OTHER INFORMATION: Description of Artificial Sequence: Synthetic
      probe

<400> SEQUENCE: 492
cctacaatct acgcaaatac cg                                              22

<210> SEQ ID NO 493
<211> LENGTH: 26
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 493
cctatattcg cacacaatac tattcg                                          26

<210> SEQ ID NO 494
<211> LENGTH: 22
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 494
accgacctaa cgactctcaa cg                                              22

<210> SEQ ID NO 495
<211> LENGTH: 20
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 495
acaccacaca cacacacacg                                                 20

<210> SEQ ID NO 496
<211> LENGTH: 23
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 496
aaccgattat ctttataacc gcg                                             23

<210> SEQ ID NO 497
<211> LENGTH: 19
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 497
cacaaaaaac aaaaacgcg                                                  19

<210> SEQ ID NO 498
<211> LENGTH: 22
<212> TYPE: DNA
<213> ORGANISM: Artificial Sequence
<220> FEATURE:
```

```
<223> OTHER INFORMATION: Description of Artificial Sequence: Synthetic
      probe

<400> SEQUENCE: 498 cctcaccccaa ataaaaact cg                                              22

<210> SEQ ID NO 499
<211> LENGTH: 22
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 499
ctacacccaa atttccatta cg                                              22

<210> SEQ ID NO 500
<211> LENGTH: 22
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 500
aatcacgatc caacctctac cg                                              22

<210> SEQ ID NO 501
<211> LENGTH: 23
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 501
atacccaaaa acaataacca acg                                             23

<210> SEQ ID NO 502
<211> LENGTH: 23
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 502
gaacgacgaa acaataacct acg                                             23

<210> SEQ ID NO 503
<211> LENGTH: 25
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 503
tcatcaaaac atctataaat cgtcg                                           25

<210> SEQ ID NO 504
<211> LENGTH: 22
<212> TYPE: DNA
<213> ORGANISM: Artificial Sequence
<220> FEATURE:
<223> OTHER INFORMATION: Description of Artificial Sequence: Synthetic
      probe
```

```
<400> SEQUENCE: 504
tccaaaacta cccaaaccta cg                                              22

<210> SEQ ID NO 505
<211> LENGTH: 18
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 505
gcgatcccta aacttccg                                                   18

<210> SEQ ID NO 506
<211> LENGTH: 23
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 506
cacaacttat ccctacttac ccg                                             23

<210> SEQ ID NO 507
<211> LENGTH: 23
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 507
ttaacccaaa caataaccct acg                                             23

<210> SEQ ID NO 508
<211> LENGTH: 22
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 508
ttctctcaaa ccacttatcc cg                                              22

<210> SEQ ID NO 509
<211> LENGTH: 22
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 509
gcaaaaccaa aaactcctac cg                                              22

<210> SEQ ID NO 510
<211> LENGTH: 23
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 510
```
cgatcccttt aaatactcgt acg                                            23

<210> SEQ ID NO 511
<211> LENGTH: 22
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 511
cccaaaaaca ctcaaatact cg                                             22

<210> SEQ ID NO 512
<211> LENGTH: 19
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 512
acacaaacga acccacacg                                                 19

<210> SEQ ID NO 513
<211> LENGTH: 22
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 513
aacaaaccca acctcttact cg                                             22

<210> SEQ ID NO 514
<211> LENGTH: 22
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 514
gaaccgaaat ctttataacg cg                                             22

<210> SEQ ID NO 515
<211> LENGTH: 22
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 515
caaatcacct ttacctcttc cg                                             22

<210> SEQ ID NO 516
<211> LENGTH: 22
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 516
ccgctaaaaa caaaactcat cg                                             22

<210> SEQ ID NO 517
<211> LENGTH: 21
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 517
cgataaaccc tacctccaac g                                              21

<210> SEQ ID NO 518
<211> LENGTH: 18
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 518
ctacatcctc gccgaacg                                                  18

<210> SEQ ID NO 519
<211> LENGTH: 21
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 519
atactcgcta aacacaacgc g                                              21

<210> SEQ ID NO 520
<211> LENGTH: 26
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 520
gacctatacc ctttataaaa tacgcg                                         26

<210> SEQ ID NO 521
<211> LENGTH: 23
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 521
tcttaacgct aacctcaata acg                                            23

<210> SEQ ID NO 522
<211> LENGTH: 23
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 522
tacctaacca tcctcaaatt tcg                                            23

<210> SEQ ID NO 523
<211> LENGTH: 23
<212> TYPE: DNA
<213> ORGANISM: Artificial Sequence
<220> FEATURE:
<223> OTHER INFORMATION: Description of Artificial Sequence: Synthetic
    probe

<400> SEQUENCE: 523
cttcctcgaa atctaacaat tcg                                              23

<210> SEQ ID NO 524
<211> LENGTH: 22
<212> TYPE: DNA
<213> ORGANISM: Artificial Sequence
<220> FEATURE:
<223> OTHER INFORMATION: Description of Artificial Sequence: Synthetic
    probe

<400> SEQUENCE: 524
actccgaata aaactaccac cg                                               22

<210> SEQ ID NO 525
<211> LENGTH: 23
<212> TYPE: DNA
<213> ORGANISM: Artificial Sequence
<220> FEATURE:
<223> OTHER INFORMATION: Description of Artificial Sequence: Synthetic
    probe

<400> SEQUENCE: 525
cccacccaat aatcaaataa acg                                              23

<210> SEQ ID NO 526
<211> LENGTH: 23
<212> TYPE: DNA
<213> ORGANISM: Artificial Sequence
<220> FEATURE:
<223> OTHER INFORMATION: Description of Artificial Sequence: Synthetic
    probe

<400> SEQUENCE: 526
acccataatt accataattt ccg                                              23

<210> SEQ ID NO 527
<211> LENGTH: 21
<212> TYPE: DNA
<213> ORGANISM: Artificial Sequence
<220> FEATURE:
<223> OTHER INFORMATION: Description of Artificial Sequence: Synthetic
    probe

<400> SEQUENCE: 527
cacacccaac ctaataccac g                                                21

<210> SEQ ID NO 528
<211> LENGTH: 23
<212> TYPE: DNA
<213> ORGANISM: Artificial Sequence
<220> FEATURE:
<223> OTHER INFORMATION: Description of Artificial Sequence: Synthetic
    probe

<400> SEQUENCE: 528
aaacaataaa cgcgaactct acg                                              23

<210> SEQ ID NO 529
<211> LENGTH: 19

```
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 529
aaacccaaca taacccacg                                                   19

<210> SEQ ID NO 530
<211> LENGTH: 17
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 530
aaccctatcc ttccccg                                                     17

<210> SEQ ID NO 531
<211> LENGTH: 21
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 531
ccataaacac ccaaatatcc g                                                21

<210> SEQ ID NO 532
<211> LENGTH: 27
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 532
tcaacatatt aaaacatatt cctaacg                                          27

<210> SEQ ID NO 533
<211> LENGTH: 24
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 533
ccacattact taaaaactcg aacg                                             24

<210> SEQ ID NO 534
<211> LENGTH: 22
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 534
aatcaaataa ccacacgaca cg                                               22

<210> SEQ ID NO 535
<211> LENGTH: 23
<212> TYPE: DNA
<213> ORGANISM: Artificial Sequence
```

```
<220> FEATURE:
<223> OTHER INFORMATION: Description of Artificial Sequence: Synthetic
      probe

<400> SEQUENCE: 535
aacctaaccc tttaaatctt ccg                                            23

<210> SEQ ID NO 536
<211> LENGTH: 22
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 536
cttttcttta accctacccc cg                                             22

<210> SEQ ID NO 537
<211> LENGTH: 23
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 537
tacccgtaca atactaaaat ccg                                            23

<210> SEQ ID NO 538
<211> LENGTH: 24
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 538
attattaatc accaacaaac aacg                                           24

<210> SEQ ID NO 539
<211> LENGTH: 22
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 539
tctcccttca ttattcattc cg                                             22

<210> SEQ ID NO 540
<211> LENGTH: 23
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 540
tcttcctaaa tactcataac gcg                                            23

<210> SEQ ID NO 541
<211> LENGTH: 21
<212> TYPE: DNA
<213> ORGANISM: Artificial Sequence
<220> FEATURE:
<223> OTHER INFORMATION: Description of Artificial Sequence: Synthetic
``` probe

<400> SEQUENCE: 541
aacctaaccc aacaaacaac g    21

<210> SEQ ID NO 542
<211> LENGTH: 21
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 542
tctacaaatc ccgaaatctc g    21

<210> SEQ ID NO 543
<211> LENGTH: 25
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 543
cacaaaaccc aactatataa aaacg    25

<210> SEQ ID NO 544
<211> LENGTH: 22
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 544
tcactacaac ctctacctcc cg    22

<210> SEQ ID NO 545
<211> LENGTH: 21
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 545
acgtaatcac gcaacatctc g    21

<210> SEQ ID NO 546
<211> LENGTH: 26
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 546
tcaccatatt aaccaaacta atctcg    26

<210> SEQ ID NO 547
<211> LENGTH: 23
<212> TYPE: DNA
<213> ORGANISM: Artificial Sequence
<220> FEATURE:
<223> OTHER INFORMATION: Description of Artificial Sequence: Synthetic
      probe

```
<400> SEQUENCE: 547 ttttaacccct aacctttaac ccg                                        23

<210> SEQ ID NO 548
<211> LENGTH: 22
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 548
cctaactttt aacctttccc cg                                          22

<210> SEQ ID NO 549
<211> LENGTH: 22
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 549
aaacgaaact tacttcgcaa cg                                          22

<210> SEQ ID NO 550
<211> LENGTH: 22
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 550
aaaccctaaa aactaaaccc cg                                          22

<210> SEQ ID NO 551
<211> LENGTH: 25
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 551
aataaaccct acaccttcta tctcg                                       25

<210> SEQ ID NO 552
<211> LENGTH: 23
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 552
aaaaaataca aacccacta ccg                                          23

<210> SEQ ID NO 553
<211> LENGTH: 23
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 553
```
acaacctaaa aattacccat ccg                                          23

<210> SEQ ID NO 554
<211> LENGTH: 22
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 554
cccttcatta cgacgaacta cg                                           22

<210> SEQ ID NO 555
<211> LENGTH: 22
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 555
aacgactctc aaaccctatc cg                                           22

<210> SEQ ID NO 556
<211> LENGTH: 18
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 556
ctactcccac cgcattcg                                                18

<210> SEQ ID NO 557
<211> LENGTH: 22
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 557
caatcatatt tccaaaatcc cg                                           22

<210> SEQ ID NO 558
<211> LENGTH: 25
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 558
tcctaatcac cctctatctt ctacg                                        25

<210> SEQ ID NO 559
<211> LENGTH: 22
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 559
aaaaaatcac cctaaccaaa cg                                           22

<210> SEQ ID NO 560
<211> LENGTH: 24
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 560
aaataaccta atcacttcaa accg                                           24

<210> SEQ ID NO 561
<211> LENGTH: 21
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 561
ccccttacga cctttctaac g                                              21

<210> SEQ ID NO 562
<211> LENGTH: 23
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 562
cacctcaata cctcgtactc acg                                            23

<210> SEQ ID NO 563
<211> LENGTH: 22
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 563
cacataccgc tcgtaatatt cg                                             22

<210> SEQ ID NO 564
<211> LENGTH: 22
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 564
taacactcaa tcccccttaa cg                                             22

<210> SEQ ID NO 565
<211> LENGTH: 22
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 565
aaacaaattc aaacccaaca cg                                             22

<210> SEQ ID NO 566

```
<211> LENGTH: 18
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 566
acccgataaa acgcaacg                                                       18

<210> SEQ ID NO 567
<211> LENGTH: 20
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 567
aacgaccaaa tacgccttcg                                                     20

<210> SEQ ID NO 568
<211> LENGTH: 22
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 568
cacgaaaata ctaaacctcc cg                                                  22

<210> SEQ ID NO 569
<211> LENGTH: 21
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 569
acgcaaataa cttcaccctc g                                                   21

<210> SEQ ID NO 570
<211> LENGTH: 22
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 570 cccttataa ctaaacgaaa cg                                                   22

<210> SEQ ID NO 571
<211> LENGTH: 18
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 571
tcctacaaaa cccccacg                                                       18

<210> SEQ ID NO 572
<211> LENGTH: 21
<212> TYPE: DNA
```

<213> ORGANISM: Artificial Sequence
<220> FEATURE:
<223> OTHER INFORMATION: Description of Artificial Sequence: Synthetic
     probe

<400> SEQUENCE: 572
ataaccgcct tcctatttcc g                                              21

<210> SEQ ID NO 573
<211> LENGTH: 21
<212> TYPE: DNA
<213> ORGANISM: Artificial Sequence
<220> FEATURE:
<223> OTHER INFORMATION: Description of Artificial Sequence: Synthetic
     probe

<400> SEQUENCE: 573
ccgcctaaaa cctaaaaacc g                                              21

<210> SEQ ID NO 574
<211> LENGTH: 22
<212> TYPE: DNA
<213> ORGANISM: Artificial Sequence
<220> FEATURE:
<223> OTHER INFORMATION: Description of Artificial Sequence: Synthetic
     probe

<400> SEQUENCE: 574
aaatcttaac aaacgaccga cg                                             22

<210> SEQ ID NO 575
<211> LENGTH: 20
<212> TYPE: DNA
<213> ORGANISM: Artificial Sequence
<220> FEATURE:
<223> OTHER INFORMATION: Description of Artificial Sequence: Synthetic
     probe

<400> SEQUENCE: 575
ctctcctcaa cgctaatccg                                                20

<210> SEQ ID NO 576
<211> LENGTH: 23
<212> TYPE: DNA
<213> ORGANISM: Artificial Sequence
<220> FEATURE:
<223> OTHER INFORMATION: Description of Artificial Sequence: Synthetic
     probe

<400> SEQUENCE: 576
aaaataacaa cctaacccct acg                                            23

<210> SEQ ID NO 577
<211> LENGTH: 19
<212> TYPE: DNA
<213> ORGANISM: Artificial Sequence
<220> FEATURE:
<223> OTHER INFORMATION: Description of Artificial Sequence: Synthetic
     probe

<400> SEQUENCE: 577
ccgaaaccta actccctcg                                                 19

<210> SEQ ID NO 578
<211> LENGTH: 17
<212> TYPE: DNA
<213> ORGANISM: Artificial Sequence
<220> FEATURE:

```
<223> OTHER INFORMATION: Description of Artificial Sequence: Synthetic
      probe

<400> SEQUENCE: 578
aatcaacgcc gacctcg                                                        17

<210> SEQ ID NO 579
<211> LENGTH: 23
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 579
cgctcaatta cttaacaacc tcg                                                 23

<210> SEQ ID NO 580
<211> LENGTH: 18
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 580
gactcatcgc aacctccg                                                       18

<210> SEQ ID NO 581
<211> LENGTH: 17
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 581
ctctaccccc tccccccg                                                       17

<210> SEQ ID NO 582
<211> LENGTH: 23
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 582
aacgcctaaa ttacctacaa ccg                                                 23

<210> SEQ ID NO 583
<211> LENGTH: 23
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 583
acttcacttt ctccctctct tcg                                                 23

<210> SEQ ID NO 584
<211> LENGTH: 23
<212> TYPE: DNA
<213> ORGANISM: Artificial Sequence
<220> FEATURE:
<223> OTHER INFORMATION: Description of Artificial Sequence: Synthetic
      probe
```

```
<400> SEQUENCE: 584
tcaaacacat aactttaacc ccg                                    23

<210> SEQ ID NO 585
<211> LENGTH: 23
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 585
tccccactct tattaacttt ccg                                    23

<210> SEQ ID NO 586
<211> LENGTH: 21
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 586
cgccaactct ataatcgaac g                                      21

<210> SEQ ID NO 587
<211> LENGTH: 24
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 587
gaattctcta actcacttcc ttcg                                   24

<210> SEQ ID NO 588
<211> LENGTH: 23
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 588
gctaactttt tcaaaccttt ccg                                    23

<210> SEQ ID NO 589
<211> LENGTH: 22
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 589
aacgtataaa cgccacctct cg                                     22

<210> SEQ ID NO 590
<211> LENGTH: 22
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 590
```

```
cccgaatcaa ctctaacact cg                                              22
```

<210> SEQ ID NO 591
<211> LENGTH: 19
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 591

```
gccctaactt ccaactccg                                                  19
```

<210> SEQ ID NO 592
<211> LENGTH: 22
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 592

```
tcattaataa aaccgaccga cg                                              22
```

<210> SEQ ID NO 593
<211> LENGTH: 22
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 593

```
aaacctacta actccaccca cg                                              22
```

<210> SEQ ID NO 594
<211> LENGTH: 22
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 594

```
aacccaacct ctatcgaaaa cg                                              22
```

<210> SEQ ID NO 595
<211> LENGTH: 26
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 595

```
tccctataac gtaaccttaa aaaacg                                          26
```

<210> SEQ ID NO 596
<211> LENGTH: 22
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 596

```
gaatcacgaa atcaaaaatt cg                                              22
```

<210> SEQ ID NO 597
<211> LENGTH: 23
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 597
ataactcaac tcacaacctc tcg                                         23

<210> SEQ ID NO 598
<211> LENGTH: 21
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 598
cttaacctac ctcgacctcc g                                           21

<210> SEQ ID NO 599
<211> LENGTH: 26
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 599
accaacctaa aaactaaaaa ataacg                                      26

<210> SEQ ID NO 600
<211> LENGTH: 25
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 600
aaatcttact atatctccca aaccg                                       25

<210> SEQ ID NO 601
<211> LENGTH: 24
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 601
caaaaatcat accattacac tccg                                        24

<210> SEQ ID NO 602
<211> LENGTH: 18
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 602
attaccgacg atccaccg                                               18

```
<210> SEQ ID NO 603
<211> LENGTH: 22
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 603
attaaaccaa ccttctttcc cg                                              22

<210> SEQ ID NO 604
<211> LENGTH: 19
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 604
catccactcc gtctctccg                                                  19

<210> SEQ ID NO 605
<211> LENGTH: 18
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 605
atcctccctc gctaaccg                                                   18

<210> SEQ ID NO 606
<211> LENGTH: 19
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 606
cgaacgtaat aaaaccgcg                                                  19

<210> SEQ ID NO 607
<211> LENGTH: 24
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 607
cctaactaac acgaacattt ctcg                                            24

<210> SEQ ID NO 608
<211> LENGTH: 24
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 608
ccaatctcta atatccacct ctcg                                            24

<210> SEQ ID NO 609
<211> LENGTH: 20
```

```
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 609
caactcaaaa caaacgctcg                                              20

<210> SEQ ID NO 610
<211> LENGTH: 23
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 610
ttcgttaaaa tacctacccc tcg                                          23

<210> SEQ ID NO 611
<211> LENGTH: 23
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 611 cctttcaat tactcacaat ccg                                           23

<210> SEQ ID NO 612
<211> LENGTH: 21
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 612
gctttaacca atcaacgaac g                                            21

<210> SEQ ID NO 613
<211> LENGTH: 25
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 613
catttctata caaccctac ttccg                                         25

<210> SEQ ID NO 614
<211> LENGTH: 22
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 614
aaaattcgac ctcaatcaaa cg                                           22

<210> SEQ ID NO 615
<211> LENGTH: 22
<212> TYPE: DNA
<213> ORGANISM: Artificial Sequence
```

<220> FEATURE:
<223> OTHER INFORMATION: Description of Artificial Sequence: Synthetic
      probe

<400> SEQUENCE: 615
aataaacgtt ctaccctcg cg                                           22

<210> SEQ ID NO 616
<211> LENGTH: 20
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 616
tcccgctcaa tcaaactacg                                             20

<210> SEQ ID NO 617
<211> LENGTH: 24
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 617
cactacgata ttactccaaa tccg                                        24

<210> SEQ ID NO 618
<211> LENGTH: 22
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 618
acaaaaactc ccttaaaccc cg                                          22

<210> SEQ ID NO 619
<211> LENGTH: 23
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 619
cgaatccgac attaataaaa acg                                         23

<210> SEQ ID NO 620
<211> LENGTH: 21
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 620
cctaacttaa atcccctcc g                                            21

<210> SEQ ID NO 621
<211> LENGTH: 23
<212> TYPE: DNA
<213> ORGANISM: Artificial Sequence
<220> FEATURE:
<223> OTHER INFORMATION: Description of Artificial Sequence: Synthetic

```
                                     probe

<400> SEQUENCE: 621
acgccctata taaaacgact acg                                            23

<210> SEQ ID NO 622
<211> LENGTH: 21
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 622
caaaaccaat caaaacgaac g                                              21

<210> SEQ ID NO 623
<211> LENGTH: 23
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 623
ccaactttaa cttcttcaaa acg                                            23

<210> SEQ ID NO 624
<211> LENGTH: 22
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 624
tctccgctct aaaacgataa cg                                             22

<210> SEQ ID NO 625
<211> LENGTH: 24
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 625
aaaaattatt ttctccacat ttcg                                           24

<210> SEQ ID NO 626
<211> LENGTH: 22
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 626
acatcatttt accaatttcg cg                                             22

<210> SEQ ID NO 627
<211> LENGTH: 19
<212> TYPE: DNA
<213> ORGANISM: Artificial Sequence
<220> FEATURE:
<223> OTHER INFORMATION: Description of Artificial Sequence: Synthetic
      probe
```

```
<400> SEQUENCE: 627
aatcattccc gaccactcg                                                    19

<210> SEQ ID NO 628
<211> LENGTH: 22
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 628
ccaacaccgc tataatatac cg                                                22

<210> SEQ ID NO 629
<211> LENGTH: 22
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 629
aaccccattt tctatcgaaa cg                                                22

<210> SEQ ID NO 630
<211> LENGTH: 22
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 630
aatataaacg atcacgaccc cg                                                22

<210> SEQ ID NO 631
<211> LENGTH: 21
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 631
tacgctttcc taaaattccc g                                                 21

<210> SEQ ID NO 632
<211> LENGTH: 23
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 632
aacgtccctc aattaaataa ccg                                               23

<210> SEQ ID NO 633
<211> LENGTH: 21
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 633
```

```
cctctcttct aaaccctccc g                                              21

<210> SEQ ID NO 634
<211> LENGTH: 21
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 634
ccgaaaaata accgaaaaac g                                              21

<210> SEQ ID NO 635
<211> LENGTH: 20
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 635
gccgaacaaa acgaactacg                                                20

<210> SEQ ID NO 636
<211> LENGTH: 23
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 636
gatctcgact cactacaacc tcg                                            23

<210> SEQ ID NO 637
<211> LENGTH: 22
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 637
cgcgctacta cactcctaaa cg                                             22

<210> SEQ ID NO 638
<211> LENGTH: 20
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 638
ccgatttaaa aaccaacccg                                                20

<210> SEQ ID NO 639
<211> LENGTH: 21
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 639
cgatacgaaa cctacgaacc g                                              21
```

-continued

<210> SEQ ID NO 640
<211> LENGTH: 21
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 640
gcgataacat caaccgatac g                                             21

<210> SEQ ID NO 641
<211> LENGTH: 22
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 641
aacgcttctt caaattccta cg                                            22

<210> SEQ ID NO 642
<211> LENGTH: 22
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 642
caacaatcga ataaaccgat cg                                            22

<210> SEQ ID NO 643
<211> LENGTH: 23
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 643
tactactccc gctaattcct acg                                           23

<210> SEQ ID NO 644
<211> LENGTH: 22
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 644
aaaaaatcaa tcaaattttc cg                                            22

<210> SEQ ID NO 645
<211> LENGTH: 23
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 645
cctcctacga ctccataact acg                                           23

<210> SEQ ID NO 646

```
<211> LENGTH: 23
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 646
ctaacattac aaacctcgct tcg                                              23

<210> SEQ ID NO 647
<211> LENGTH: 23
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 647
cttccacatc taaactactt ccg                                              23

<210> SEQ ID NO 648
<211> LENGTH: 23
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 648
tactactact tctaccgctc ccg                                              23

<210> SEQ ID NO 649
<211> LENGTH: 18
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 649
tcaacgaccg tacccacg                                                    18

<210> SEQ ID NO 650
<211> LENGTH: 23
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 650
acttaaacct caaacaaatc acg                                              23

<210> SEQ ID NO 651
<211> LENGTH: 20
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 651
ttccaacaaa tttcctaccg                                                  20

<210> SEQ ID NO 652
<211> LENGTH: 22
<212> TYPE: DNA
```

```
<213> ORGANISM: Artificial Sequence
<220> FEATURE:
<223> OTHER INFORMATION: Description of Artificial Sequence: Synthetic
      probe

<400> SEQUENCE: 652
acattccttt tcgtcaaaat cg                                              22

<210> SEQ ID NO 653
<211> LENGTH: 24
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 653
cattaccaac aacttttaaa tccg                                            24

<210> SEQ ID NO 654
<211> LENGTH: 20
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 654
acaaactccg cctaacaccg                                                 20

<210> SEQ ID NO 655
<211> LENGTH: 22
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 655
ccaaacgcct ataccttaac cg                                              22

<210> SEQ ID NO 656
<211> LENGTH: 22
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 656
taaaacgacc aaaacacaaa cg                                              22

<210> SEQ ID NO 657
<211> LENGTH: 22
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 657
tcaaaaacta acaaaccaaa cg                                              22

<210> SEQ ID NO 658
<211> LENGTH: 17
<212> TYPE: DNA
<213> ORGANISM: Artificial Sequence
<220> FEATURE:
```

<223> OTHER INFORMATION: Description of Artificial Sequence: Synthetic
      probe

<400> SEQUENCE: 658
atcccctcaa cccaacg                                                        17

<210> SEQ ID NO 659
<211> LENGTH: 23
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 659
ccttaacgcg tatcctaatc tcg                                                 23

<210> SEQ ID NO 660
<211> LENGTH: 22
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 660
aatccgcatt aaaccaaata cg                                                  22

<210> SEQ ID NO 661
<211> LENGTH: 23
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 661
gaaaaccgaa acttaaatcc tcg                                                 23

<210> SEQ ID NO 662
<211> LENGTH: 17
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 662
aaaacccgaa aaccccg                                                        17

<210> SEQ ID NO 663
<211> LENGTH: 23
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 663
cctatcgacc tctaatacac tcg                                                 23

<210> SEQ ID NO 664
<211> LENGTH: 23
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 664
caaacacaac tcgatttaaa acg                23

<210> SEQ ID NO 665
<211> LENGTH: 19
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 665
cctaaatccg tctttcgcg                19

<210> SEQ ID NO 666
<211> LENGTH: 23
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 666
cccattctat ctaccctatc tcg                23

<210> SEQ ID NO 667
<211> LENGTH: 21
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 667
taaaaaacgc ctaaacccac g                21

<210> SEQ ID NO 668
<211> LENGTH: 21
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 668
aacgaaaata acgttttccc g                21

<210> SEQ ID NO 669
<211> LENGTH: 22
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 669
gcaaccaaaa caaactacga cg                22

<210> SEQ ID NO 670
<211> LENGTH: 25
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 670
tcatcttaca atcacataac catcg                                    25

<210> SEQ ID NO 671
<211> LENGTH: 23
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 671
gctaactccg aaacaactaa acg                                      23

<210> SEQ ID NO 672
<211> LENGTH: 22
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 672
ctctacccca accacaacta cg                                       22

<210> SEQ ID NO 673
<211> LENGTH: 22
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 673
cccaacaaac ttttcctttt cg                                       22

<210> SEQ ID NO 674
<211> LENGTH: 22
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 674
gcgattaata tcctaccctc cg                                       22

<210> SEQ ID NO 675
<211> LENGTH: 19
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 675
cccgatacaa accacaacg                                           19

<210> SEQ ID NO 676
<211> LENGTH: 22
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 676
gaaacgctac tcctaactca cg                                       22

```
<210> SEQ ID NO 677
<211> LENGTH: 22
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 677
gtaaaccaaa aacaacgtcc cg                                            22

<210> SEQ ID NO 678
<211> LENGTH: 18
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 678
aacgcaaacg aaacaccg                                                 18

<210> SEQ ID NO 679
<211> LENGTH: 24
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 679
accctataaa cctaatcgtt aacg                                          24

<210> SEQ ID NO 680
<211> LENGTH: 20
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 680
gtctaccctc cacatctccg                                               20

<210> SEQ ID NO 681
<211> LENGTH: 23
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 681
aacgctcgat aaacgataat acg                                           23

<210> SEQ ID NO 682
<211> LENGTH: 22
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 682
acccctaact acttcaacct cg                                            22
```

<210> SEQ ID NO 683
<211> LENGTH: 22
<212> TYPE: DNA
<213> ORGANISM: Artificial Sequence
<220> FEATURE:
<223> OTHER INFORMATION: Description of Artificial Sequence: Synthetic probe

<400> SEQUENCE: 683
caaatcttaa accctaatcc cg     22

<210> SEQ ID NO 684
<211> LENGTH: 22
<212> TYPE: DNA
<213> ORGANISM: Artificial Sequence
<220> FEATURE:
<223> OTHER INFORMATION: Description of Artificial Sequence: Synthetic probe

<400> SEQUENCE: 684
cccttctata taaacctccc cg     22

<210> SEQ ID NO 685
<211> LENGTH: 19
<212> TYPE: DNA
<213> ORGANISM: Artificial Sequence
<220> FEATURE:
<223> OTHER INFORMATION: Description of Artificial Sequence: Synthetic probe

<400> SEQUENCE: 685
aaacaactat ccccacccg     19

<210> SEQ ID NO 686
<211> LENGTH: 23
<212> TYPE: DNA
<213> ORGANISM: Artificial Sequence
<220> FEATURE:
<223> OTHER INFORMATION: Description of Artificial Sequence: Synthetic probe

<400> SEQUENCE: 686
ccttactacc acacatttaa ccg     23

<210> SEQ ID NO 687
<211> LENGTH: 23
<212> TYPE: DNA
<213> ORGANISM: Artificial Sequence
<220> FEATURE:
<223> OTHER INFORMATION: Description of Artificial Sequence: Synthetic probe

<400> SEQUENCE: 687
tcaaatctta tcaaacaccc tcg     23

<210> SEQ ID NO 688
<211> LENGTH: 23
<212> TYPE: DNA
<213> ORGANISM: Artificial Sequence
<220> FEATURE:
<223> OTHER INFORMATION: Description of Artificial Sequence: Synthetic probe

<400> SEQUENCE: 688
aaacccaacc tatatccaaa tcg     23

<210> SEQ ID NO 689
<211> LENGTH: 22

```
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 689
aatactaaaa acgcccctct cg                                              22

<210> SEQ ID NO 690
<211> LENGTH: 22
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 690
ctttaaccgc taacctaatc cg                                              22

<210> SEQ ID NO 691
<211> LENGTH: 21
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 691
cccgaaacaa ctacgctatc g                                               21

<210> SEQ ID NO 692
<211> LENGTH: 22
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 692
aattacccca caacctaaac cg                                              22

<210> SEQ ID NO 693
<211> LENGTH: 18
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 693
cgcaaatccc gcttatcg                                                   18

<210> SEQ ID NO 694
<211> LENGTH: 20
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 694
gccaaacaaa acaaaaaccg                                                 20

<210> SEQ ID NO 695
<211> LENGTH: 23
<212> TYPE: DNA
<213> ORGANISM: Artificial Sequence
```

```
<220> FEATURE:
<223> OTHER INFORMATION: Description of Artificial Sequence: Synthetic
      probe

<400> SEQUENCE: 695
gcaacgcatt acaaacaaat acg                                              23

<210> SEQ ID NO 696
<211> LENGTH: 25
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 696
cactctctcg cttttataaa aaacg                                            25

<210> SEQ ID NO 697
<211> LENGTH: 23
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 697
attacacaaa ccgttctaac ccg                                              23

<210> SEQ ID NO 698
<211> LENGTH: 22
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 698
gaaaaactat ccgccttaca cg                                               22

<210> SEQ ID NO 699
<211> LENGTH: 21
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 699
tcactcttat ccccacctac g                                                21

<210> SEQ ID NO 700
<211> LENGTH: 21
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 700
ccaccaacat cctaaatacc g                                                21

<210> SEQ ID NO 701
<211> LENGTH: 17
<212> TYPE: DNA
<213> ORGANISM: Artificial Sequence
<220> FEATURE:
<223> OTHER INFORMATION: Description of Artificial Sequence: Synthetic
```

```
                              probe

<400> SEQUENCE: 701
acacaaccca aaccgcg                                                    17

<210> SEQ ID NO 702
<211> LENGTH: 19
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 702
acctcaaatc ctccaaccg                                                  19

<210> SEQ ID NO 703
<211> LENGTH: 22
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 703
cccaaataca actacccaaa cg                                              22

<210> SEQ ID NO 704
<211> LENGTH: 22
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 704
aaccgactcg aatctaccta cg                                              22

<210> SEQ ID NO 705
<211> LENGTH: 22
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 705
actctaacga cccatcctaa cg                                              22

<210> SEQ ID NO 706
<211> LENGTH: 23
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 706
cttacatcct ctaaatttcc ccg                                             23

<210> SEQ ID NO 707
<211> LENGTH: 22
<212> TYPE: DNA
<213> ORGANISM: Artificial Sequence
<220> FEATURE:
<223> OTHER INFORMATION: Description of Artificial Sequence: Synthetic
      probe
```

```
<400> SEQUENCE: 707
acaacttaat cccctaacc cg                                              22

<210> SEQ ID NO 708
<211> LENGTH: 23
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 708
ataacgaccg atcctactct ccg                                            23

<210> SEQ ID NO 709
<211> LENGTH: 21
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 709
ctaaaaaccc ttaaccctcc g                                              21

<210> SEQ ID NO 710
<211> LENGTH: 23
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 710
actattctct cctatttccc tcg                                            23

<210> SEQ ID NO 711
<211> LENGTH: 23
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 711
taaaactttc tccccgaaaa acg                                            23

<210> SEQ ID NO 712
<211> LENGTH: 23
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 712
aattcctcca cttaaactac ccg                                            23

<210> SEQ ID NO 713
<211> LENGTH: 22
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 713
```
aactcaaaac cctccaaaat cg                                          22

<210> SEQ ID NO 714
<211> LENGTH: 23
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 714
ctaactaaac tcaacaacct ccg                                         23

<210> SEQ ID NO 715
<211> LENGTH: 21
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 715
cttaactaac gcgaaaccac g                                           21

<210> SEQ ID NO 716
<211> LENGTH: 23
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 716
gaatctcact cctaaattca acg                                         23

<210> SEQ ID NO 717
<211> LENGTH: 21
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 717
aaaacctcta cccgaaaacc g                                           21

<210> SEQ ID NO 718
<211> LENGTH: 22
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 718
aatacgaact acttcacccc cg                                          22

<210> SEQ ID NO 719
<211> LENGTH: 22
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 719
caacccaaaa cctactccta cg                                          22

```
<210> SEQ ID NO 720
<211> LENGTH: 22
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 720
aaatttaaat taccctcctc cg                                              22

<210> SEQ ID NO 721
<211> LENGTH: 23
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 721
cccctctaat tatctcttta ccg                                             23

<210> SEQ ID NO 722
<211> LENGTH: 23
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 722
caacctatcc aaatcacaaa acg                                             23

<210> SEQ ID NO 723
<211> LENGTH: 21
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 723
caaatctccc gaataaaatc g                                               21

<210> SEQ ID NO 724
<211> LENGTH: 17
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 724
caaacactcc cctcccg                                                    17

<210> SEQ ID NO 725
<211> LENGTH: 22
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 725
aaacctcaat ctaaaaacca cg                                              22

<210> SEQ ID NO 726
```

```
<211> LENGTH: 18
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 726
cccctcccca aataatcg                                                       18

<210> SEQ ID NO 727
<211> LENGTH: 28
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 727
catattatat cctaccattt aatacccg                                            28

<210> SEQ ID NO 728
<211> LENGTH: 22
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 728
aaactcaacc tcacaaatca cg                                                  22

<210> SEQ ID NO 729
<211> LENGTH: 25
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 729
ccaaaaccaa taactttaca aaacg                                               25

<210> SEQ ID NO 730
<211> LENGTH: 21
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 730
aaataaaata ccacctccgc g                                                   21

<210> SEQ ID NO 731
<211> LENGTH: 19
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 731
aaaaaccgcg aaaatttcg                                                      19

<210> SEQ ID NO 732
<211> LENGTH: 24
<212> TYPE: DNA
```

```
<213> ORGANISM: Artificial Sequence
<220> FEATURE:
<223> OTHER INFORMATION: Description of Artificial Sequence: Synthetic
      probe

<400> SEQUENCE: 732
aaaacaccta aacttaaaac ctcg                                              24

<210> SEQ ID NO 733
<211> LENGTH: 19
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 733
aaaccaaccc aaatttccg                                                    19

<210> SEQ ID NO 734
<211> LENGTH: 22
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 734
accacataca cactacacac cg                                                22

<210> SEQ ID NO 735
<211> LENGTH: 22
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 735
acacacacaa accacataca cg                                                22

<210> SEQ ID NO 736
<211> LENGTH: 18
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 736
aaacaaacac caaccccg                                                     18

<210> SEQ ID NO 737
<211> LENGTH: 23
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 737
acatacgtac gacaatcctc tcg                                               23

<210> SEQ ID NO 738
<211> LENGTH: 23
<212> TYPE: DNA
<213> ORGANISM: Artificial Sequence
<220> FEATURE:
```

-continued

<223> OTHER INFORMATION: Description of Artificial Sequence: Synthetic
      probe

<400> SEQUENCE: 738
aactcctaaa ctcaaacaat ccg                                           23

<210> SEQ ID NO 739
<211> LENGTH: 21
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 739
gatactcgaa aaccgaaacc g                                             21

<210> SEQ ID NO 740
<211> LENGTH: 25
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 740
cacactccct actaaaccta aatcg                                         25

<210> SEQ ID NO 741
<211> LENGTH: 23
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 741
ccaacctcaa ctcacaaaat acg                                           23

<210> SEQ ID NO 742
<211> LENGTH: 23
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 742
taacatcacg acccaaataa ccg                                           23

<210> SEQ ID NO 743
<211> LENGTH: 19
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 743
acctcgcccc taaactacg                                                19

<210> SEQ ID NO 744
<211> LENGTH: 23
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 744
taccaaccga ctaaactaaa ccg                                              23

<210> SEQ ID NO 745
<211> LENGTH: 19
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 745
aataaccaaa cgaacgccg                                                   19

<210> SEQ ID NO 746
<211> LENGTH: 22
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 746
caaaacaaaa acgaaaacga cg                                               22

<210> SEQ ID NO 747
<211> LENGTH: 20
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 747
actacccgaa caaaaccacg                                                  20

<210> SEQ ID NO 748
<211> LENGTH: 21
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 748
gtaaaatcaa accgcaaaac g                                                21

<210> SEQ ID NO 749
<211> LENGTH: 24
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 749
ccaaaccaac ttatctatcc tacg                                             24

<210> SEQ ID NO 750
<211> LENGTH: 22
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 750

-continued caaacctaaa attcctctttt cg   22

<210> SEQ ID NO 751
<211> LENGTH: 22
<212> TYPE: DNA
<213> ORGANISM: Artificial Sequence
<220> FEATURE:
<223> OTHER INFORMATION: Description of Artificial Sequence: Synthetic probe

<400> SEQUENCE: 751
aacaaaaact acaactctcc cg   22

<210> SEQ ID NO 752
<211> LENGTH: 23
<212> TYPE: DNA
<213> ORGANISM: Artificial Sequence
<220> FEATURE:
<223> OTHER INFORMATION: Description of Artificial Sequence: Synthetic probe

<400> SEQUENCE: 752
ccaatacact ccaaacctaa acg   23

<210> SEQ ID NO 753
<211> LENGTH: 23
<212> TYPE: DNA
<213> ORGANISM: Artificial Sequence
<220> FEATURE:
<223> OTHER INFORMATION: Description of Artificial Sequence: Synthetic probe

<400> SEQUENCE: 753
aaaattacaa acgtaaacca ccg   23

<210> SEQ ID NO 754
<211> LENGTH: 22
<212> TYPE: DNA
<213> ORGANISM: Artificial Sequence
<220> FEATURE:
<223> OTHER INFORMATION: Description of Artificial Sequence: Synthetic probe

<400> SEQUENCE: 754
tcaaaccctc taacctcaaa cg   22

<210> SEQ ID NO 755
<211> LENGTH: 23
<212> TYPE: DNA
<213> ORGANISM: Artificial Sequence
<220> FEATURE:
<223> OTHER INFORMATION: Description of Artificial Sequence: Synthetic probe

<400> SEQUENCE: 755
gtccccaaaa ctaaaaaaca tcc   23

<210> SEQ ID NO 756
<211> LENGTH: 20
<212> TYPE: DNA
<213> ORGANISM: Artificial Sequence
<220> FEATURE:
<223> OTHER INFORMATION: Description of Artificial Sequence: Synthetic probe

<400> SEQUENCE: 756
cgccaaacta aaatcgaacc   20

<210> SEQ ID NO 757
<211> LENGTH: 21
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 757
atccctacgc gaaaacgtaa c                                              21

<210> SEQ ID NO 758
<211> LENGTH: 23
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 758
ctcccctcaa ctttcttcaa att                                            23

<210> SEQ ID NO 759
<211> LENGTH: 22
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 759
cctcccacac cactcaaaaa tt                                             22

<210> SEQ ID NO 760
<211> LENGTH: 26
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 760
aactaccaat catatttcct aaacca                                         26

<210> SEQ ID NO 761
<211> LENGTH: 21
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 761
cgccactaac gctaaactcc t                                              21

<210> SEQ ID NO 762
<211> LENGTH: 21
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 762
ttcccccgaa ctccctacta t                                              21

```
<210> SEQ ID NO 763
<211> LENGTH: 20
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 763
ccctacgtaa acgacctcgc                                             20

<210> SEQ ID NO 764
<211> LENGTH: 21
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 764
aatctttacc cgaacgcttc c                                           21

<210> SEQ ID NO 765
<211> LENGTH: 23
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 765
ccctctaaaa acgtacaaac caa                                         23

<210> SEQ ID NO 766
<211> LENGTH: 19
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 766
aaataaataa accgcgccg                                              19

<210> SEQ ID NO 767
<211> LENGTH: 19
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 767
ctccaacacc aatccgaca                                              19

<210> SEQ ID NO 768
<211> LENGTH: 26
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 768
ttatcacaca cttatttctc acttcc                                      26

<210> SEQ ID NO 769
<211> LENGTH: 17
```

```
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 769
cctcctcgtc tcctccc                                                        17

<210> SEQ ID NO 770
<211> LENGTH: 20
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 770
gtaaacgaaa caacgacccg                                                     20

<210> SEQ ID NO 771
<211> LENGTH: 21
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 771
gactattccg taaacgccac c                                                   21

<210> SEQ ID NO 772
<211> LENGTH: 24
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 772
aactaaacta caactcaccc aacc                                                24

<210> SEQ ID NO 773
<211> LENGTH: 24
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 773
tccttccttt ccttacccta cttt                                                24

<210> SEQ ID NO 774
<211> LENGTH: 21
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 774
aaaccgaacc tcgcttaaac c                                                   21

<210> SEQ ID NO 775
<211> LENGTH: 20
<212> TYPE: DNA
<213> ORGANISM: Artificial Sequence
```

```
<220> FEATURE:
<223> OTHER INFORMATION: Description of Artificial Sequence: Synthetic
      probe

<400> SEQUENCE: 775
atccaaacaa accgcaaact                                                 20

<210> SEQ ID NO 776
<211> LENGTH: 22
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 776
ctccctaacc caatctctaa cg                                              22

<210> SEQ ID NO 777
<211> LENGTH: 26
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 777
aacaaaaaat ttctattcct tcaacc                                          26

<210> SEQ ID NO 778
<211> LENGTH: 17
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 778
cctcgtaacg cgtcgac                                                    17

<210> SEQ ID NO 779
<211> LENGTH: 25
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 779
cctaacccaa ctctaaaaca aacaa                                           25

<210> SEQ ID NO 780
<211> LENGTH: 23
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 780
caacccgaaa ctattacaaa ccg                                             23

<210> SEQ ID NO 781
<211> LENGTH: 22
<212> TYPE: DNA
<213> ORGANISM: Artificial Sequence
<220> FEATURE:
<223> OTHER INFORMATION: Description of Artificial Sequence: Synthetic
``` probe

<400> SEQUENCE: 781
ctcgatccac aaactctcca ct                                            22

<210> SEQ ID NO 782
<211> LENGTH: 23
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 782
attataatct tcccacctcc cac                                           23

<210> SEQ ID NO 783
<211> LENGTH: 18
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 783
caaacgaaac gcaacacc                                                 18

<210> SEQ ID NO 784
<211> LENGTH: 23
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 784
aaaaaaccta cgaactcaaa ccc                                           23

<210> SEQ ID NO 785
<211> LENGTH: 23
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 785
aaacatcaac cctacgacct aaa                                           23

<210> SEQ ID NO 786
<211> LENGTH: 20
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 786
acgaaccgac ctaaactccc                                               20

<210> SEQ ID NO 787
<211> LENGTH: 22
<212> TYPE: DNA
<213> ORGANISM: Artificial Sequence
<220> FEATURE:
<223> OTHER INFORMATION: Description of Artificial Sequence: Synthetic
      probe

```
<400> SEQUENCE: 787
aaaacgctaa ttcctcgact cc                                              22

<210> SEQ ID NO 788
<211> LENGTH: 24
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 788
aaatcctaac tctacaccct cctc                                            24

<210> SEQ ID NO 789
<211> LENGTH: 28
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 789
caaacgaatt acttaccctt acttatca                                        28

<210> SEQ ID NO 790
<211> LENGTH: 28
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 790
aacaaatctt acacctcttc tacatctc                                        28

<210> SEQ ID NO 791
<211> LENGTH: 24
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 791
taaacaacaa cctctcaaaa tacg                                            24

<210> SEQ ID NO 792
<211> LENGTH: 24
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 792
aaaacgctta actctttcta tccc                                            24

<210> SEQ ID NO 793
<211> LENGTH: 22
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 793
```
ctctttcctt ttacgtcatc cg                                              22

<210> SEQ ID NO 794
<211> LENGTH: 23
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 794
acccatctca actttcatca tca                                             23

<210> SEQ ID NO 795
<211> LENGTH: 24
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 795
ccctacattt ccctctacac taaa                                            24

<210> SEQ ID NO 796
<211> LENGTH: 23
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 796
atatcacctc atccgactcc ctt                                             23

<210> SEQ ID NO 797
<211> LENGTH: 20
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 797
actcctaaat tccatccccg                                                 20

<210> SEQ ID NO 798
<211> LENGTH: 24
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 798
aacatcccta ccctctctat acaa                                            24

<210> SEQ ID NO 799
<211> LENGTH: 21
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 799
ccttctctaa atccgcgaaa t                                               21

<210> SEQ ID NO 800
<211> LENGTH: 22
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 800
aaacgacttc aaaaccccct ac                                              22

<210> SEQ ID NO 801
<211> LENGTH: 17
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 801
ccgcaaaacc acaacgc                                                    17

<210> SEQ ID NO 802
<211> LENGTH: 23
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 802
tctaaatccc cctcctctaa tcg                                             23

<210> SEQ ID NO 803
<211> LENGTH: 24
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 803
acactactcc ccgctttatt tatt                                            24

<210> SEQ ID NO 804
<211> LENGTH: 22
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 804
aattatcctc ctacgccgac ct                                              22

<210> SEQ ID NO 805
<211> LENGTH: 23
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 805
taaccaatca ccctcttcct ttc                                             23

<210> SEQ ID NO 806

```
<211> LENGTH: 23
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 806
ataattttcc tccttcttcc ctc                                              23

<210> SEQ ID NO 807
<211> LENGTH: 19
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 807
ttttcgcctt acgatcacc                                                   19

<210> SEQ ID NO 808
<211> LENGTH: 21
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 808
ccacgctacg ccaacactta t                                                21

<210> SEQ ID NO 809
<211> LENGTH: 23
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 809
aacccgatct atccctataa cga                                              23

<210> SEQ ID NO 810
<211> LENGTH: 27
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 810
aaactattac atttactctc cacctcc                                          27

<210> SEQ ID NO 811
<211> LENGTH: 23
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 811
acacccgaat atttcctaac gaa                                              23

<210> SEQ ID NO 812
<211> LENGTH: 18
<212> TYPE: DNA
```

```
<213> ORGANISM: Artificial Sequence
<220> FEATURE:
<223> OTHER INFORMATION: Description of Artificial Sequence: Synthetic
      probe

<400> SEQUENCE: 812
ccaaccattc caccctca                                                     18

<210> SEQ ID NO 813
<211> LENGTH: 22
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 813
aacccaaccc cctcttcatt at                                                22

<210> SEQ ID NO 814
<211> LENGTH: 19
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 814
aacgataacc gcacaatcc                                                    19

<210> SEQ ID NO 815
<211> LENGTH: 23
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 815
ccaccaaaca tacaattcca act                                               23

<210> SEQ ID NO 816
<211> LENGTH: 23
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 816
attctatccc tatcctaatc gcc                                               23

<210> SEQ ID NO 817
<211> LENGTH: 22
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 817
actcaaactt ctctccgaaa cg                                                22

<210> SEQ ID NO 818
<211> LENGTH: 21
<212> TYPE: DNA
<213> ORGANISM: Artificial Sequence
<220> FEATURE:
```

```
<223> OTHER INFORMATION: Description of Artificial Sequence: Synthetic
      probe

<400> SEQUENCE: 818
ccactttaca aaacgtcacc g                                                    21

<210> SEQ ID NO 819
<211> LENGTH: 20
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 819
gaacaaacga aaattcccga                                                      20

<210> SEQ ID NO 820
<211> LENGTH: 25
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 820
tacccactaa aaactacaac ttccc                                                25

<210> SEQ ID NO 821
<211> LENGTH: 20
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 821
taaaacgacg tctcctcccc                                                      20

<210> SEQ ID NO 822
<211> LENGTH: 22
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 822
taataacatc accccgaaat cg                                                   22

<210> SEQ ID NO 823
<211> LENGTH: 23
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 823
atatacaaac tccgaaatcg caa                                                  23

<210> SEQ ID NO 824
<211> LENGTH: 22
<212> TYPE: DNA
<213> ORGANISM: Artificial Sequence
<220> FEATURE:
<223> OTHER INFORMATION: Description of Artificial Sequence: Synthetic
      probe
```

<400> SEQUENCE: 824
aaactccaaa acgccctct ac                                                  22

<210> SEQ ID NO 825
<211> LENGTH: 25
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 825
aaataaattc ctcacacctc acaac                                              25

<210> SEQ ID NO 826
<211> LENGTH: 23
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 826
cactacccaa tcgtcgtatc aaa                                                23

<210> SEQ ID NO 827
<211> LENGTH: 26
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 827
tattattaaa acctcaattt cccaaa                                             26

<210> SEQ ID NO 828
<211> LENGTH: 21
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 828 caccccttc cactactcct t                                                   21

<210> SEQ ID NO 829
<211> LENGTH: 27
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 829
ttcatcctat taaaaatacc acaaatt                                            27

<210> SEQ ID NO 830
<211> LENGTH: 21
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 830

```
cctaatttta aaccctcgcc c                                              21

<210> SEQ ID NO 831
<211> LENGTH: 23
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 831
caccctcata cttccaaaac cta                                            23

<210> SEQ ID NO 832
<211> LENGTH: 23
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 832
cttcctaatc ctaccctacc cta                                            23

<210> SEQ ID NO 833
<211> LENGTH: 20
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 833
cccgctacga aatctctcct                                                20

<210> SEQ ID NO 834
<211> LENGTH: 21
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 834
cttaaaacac aaaccgctcc c                                              21

<210> SEQ ID NO 835
<211> LENGTH: 24
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 835
cctaatttct acaaccgctc tacc                                           24

<210> SEQ ID NO 836
<211> LENGTH: 22
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 836
tccctctttc acgatctcac tc                                             22
```

<210> SEQ ID NO 837
<211> LENGTH: 21
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 837
ttatctcgaa ctcgcccact t                                          21

<210> SEQ ID NO 838
<211> LENGTH: 23
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 838
acaaatccca taacccacct aaa                                        23

<210> SEQ ID NO 839
<211> LENGTH: 23
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 839
aaaacgatac ctccgaaact cac                                        23

<210> SEQ ID NO 840
<211> LENGTH: 23
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 840
gccttctcta aaccaacaac aca                                        23

<210> SEQ ID NO 841
<211> LENGTH: 22
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 841
aactcctacg tttcccccta ac                                         22

<210> SEQ ID NO 842
<211> LENGTH: 23
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 842
ccgatttcct atacgtaacg tca                                        23

<210> SEQ ID NO 843
<211> LENGTH: 19
<212> TYPE: DNA
<213> ORGANISM: Artificial Sequence
<220> FEATURE:
<223> OTHER INFORMATION: Description of Artificial Sequence: Synthetic probe

<400> SEQUENCE: 843
cgctaactac gaccgcctc                                                    19

<210> SEQ ID NO 844
<211> LENGTH: 22
<212> TYPE: DNA
<213> ORGANISM: Artificial Sequence
<220> FEATURE:
<223> OTHER INFORMATION: Description of Artificial Sequence: Synthetic probe

<400> SEQUENCE: 844
gacgaaaact ccgaaaaacg ac                                                22

<210> SEQ ID NO 845
<211> LENGTH: 23
<212> TYPE: DNA
<213> ORGANISM: Artificial Sequence
<220> FEATURE:
<223> OTHER INFORMATION: Description of Artificial Sequence: Synthetic probe

<400> SEQUENCE: 845
gatcaacaaa acgaaccaaa acg                                               23

<210> SEQ ID NO 846
<211> LENGTH: 19
<212> TYPE: DNA
<213> ORGANISM: Artificial Sequence
<220> FEATURE:
<223> OTHER INFORMATION: Description of Artificial Sequence: Synthetic probe

<400> SEQUENCE: 846
ctaaaccgat tccgcgaac                                                    19

<210> SEQ ID NO 847
<211> LENGTH: 23
<212> TYPE: DNA
<213> ORGANISM: Artificial Sequence
<220> FEATURE:
<223> OTHER INFORMATION: Description of Artificial Sequence: Synthetic probe

<400> SEQUENCE: 847
acaaccccac cttctctacc tac                                               23

<210> SEQ ID NO 848
<211> LENGTH: 23
<212> TYPE: DNA
<213> ORGANISM: Artificial Sequence
<220> FEATURE:
<223> OTHER INFORMATION: Description of Artificial Sequence: Synthetic probe

<400> SEQUENCE: 848
aaaatcccga aatcttacat tcc                                               23

<210> SEQ ID NO 849
<211> LENGTH: 23

```
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 849
aaattcctca attattcctc cgc                                             23

<210> SEQ ID NO 850
<211> LENGTH: 22
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 850
aacaactcgt ccgaataacc aa                                              22

<210> SEQ ID NO 851
<211> LENGTH: 23
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 851
ataacccttc gaccgataca aac                                             23

<210> SEQ ID NO 852
<211> LENGTH: 23
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 852
aaatacgcaa actacctcaa acc                                             23

<210> SEQ ID NO 853
<211> LENGTH: 19
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 853
ttacacgccc gcgaactat                                                  19

<210> SEQ ID NO 854
<211> LENGTH: 25
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 854
aatccaccaa tcaataaaca acttc                                           25

<210> SEQ ID NO 855
<211> LENGTH: 23
<212> TYPE: DNA
<213> ORGANISM: Artificial Sequence
```

```
<220> FEATURE:
<223> OTHER INFORMATION: Description of Artificial Sequence: Synthetic
      probe

<400> SEQUENCE: 855
ccaaacctcc acaaatcttc ctt                                                 23

<210> SEQ ID NO 856
<211> LENGTH: 22
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 856
ccaccaaaac ccaactctaa aa                                                  22

<210> SEQ ID NO 857
<211> LENGTH: 25
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 857
tattcaaata cccaaaacta aaccc                                               25

<210> SEQ ID NO 858
<211> LENGTH: 28
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 858
cacacttaaa tctacctcta ttacctcc                                            28

<210> SEQ ID NO 859
<211> LENGTH: 20
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 859
atcctaaccc ctacaacccc                                                     20

<210> SEQ ID NO 860
<211> LENGTH: 29
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 860
aaaataccta tccctaaata aaaatcatt                                           29

<210> SEQ ID NO 861
<211> LENGTH: 21
<212> TYPE: DNA
<213> ORGANISM: Artificial Sequence
<220> FEATURE:
<223> OTHER INFORMATION: Description of Artificial Sequence: Synthetic
```

```
    probe

<400> SEQUENCE: 861
ccttccttct aacccgctaa a                                          21

<210> SEQ ID NO 862
<211> LENGTH: 26
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 862
aaacgtactt tcttaaacct taaacg                                     26

<210> SEQ ID NO 863
<211> LENGTH: 20
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 863
cactacactc caacccgaac                                            20

<210> SEQ ID NO 864
<211> LENGTH: 23
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 864
accttattac gacgtcgaca cat                                        23

<210> SEQ ID NO 865
<211> LENGTH: 25
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 865
attacccatt aaatcttaat tcccc                                      25

<210> SEQ ID NO 866
<211> LENGTH: 21
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 866
accttacacc tcaacccatt t                                          21

<210> SEQ ID NO 867
<211> LENGTH: 27
<212> TYPE: DNA
<213> ORGANISM: Artificial Sequence
<220> FEATURE:
<223> OTHER INFORMATION: Description of Artificial Sequence: Synthetic
      probe
```

```
<400> SEQUENCE: 867
ctatatataa aacaaccccca tttctca                                      27

<210> SEQ ID NO 868
<211> LENGTH: 24
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 868
atactcacaa cctctcacac aaaa                                          24

<210> SEQ ID NO 869
<211> LENGTH: 26
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 869
ctttctcact ttaacaccaa ctaccc                                        26

<210> SEQ ID NO 870
<211> LENGTH: 22
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 870
aaacaaaaca atcccaccct ac                                            22

<210> SEQ ID NO 871
<211> LENGTH: 23
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 871
attaaacgcg aactacgata acc                                           23

<210> SEQ ID NO 872
<211> LENGTH: 23
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 872
caaataacca acaaaaacct cca                                           23

<210> SEQ ID NO 873
<211> LENGTH: 22
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 873
```
cgcctaacac aacgcctaat ac                                              22

<210> SEQ ID NO 874
<211> LENGTH: 26
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 874
acaaaccaac ccttctaata tactcc                                          26

<210> SEQ ID NO 875
<211> LENGTH: 23
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 875
aacttcctac cccacccaat aaa                                             23

<210> SEQ ID NO 876
<211> LENGTH: 21
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 876
gactctcctc aactccttcc c                                               21

<210> SEQ ID NO 877
<211> LENGTH: 21
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 877
aaccccaatc tccgcaataa a                                               21

<210> SEQ ID NO 878
<211> LENGTH: 22
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 878
taccctatac ccgcgatatt cc                                              22

<210> SEQ ID NO 879
<211> LENGTH: 22
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 879
aactaaaaaa ctccgaaacc cc                                              22

-continued

<210> SEQ ID NO 880
<211> LENGTH: 24
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 880
ctctacaatc catttattta cccg                                          24

<210> SEQ ID NO 881
<211> LENGTH: 21
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 881
acccaaccac attaacgaac c                                             21

<210> SEQ ID NO 882
<211> LENGTH: 23
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 882
tactaacgaa ctcctcgctc caa                                           23

<210> SEQ ID NO 883
<211> LENGTH: 22
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 883
gaacataaaa ccgaaaacac cc                                            22

<210> SEQ ID NO 884
<211> LENGTH: 23
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 884
tccttactcg aatctttacc gaa                                           23

<210> SEQ ID NO 885
<211> LENGTH: 23
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 885
ccaatctaac cttccaaaca cat                                           23

<210> SEQ ID NO 886

```
<211> LENGTH: 21
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 886
attaaacctt ctctcgtcgc c                                            21

<210> SEQ ID NO 887
<211> LENGTH: 22
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 887
ataaacacaa caccctacac gc                                           22

<210> SEQ ID NO 888
<211> LENGTH: 23
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 888
gacacacaca atacaatcac gct                                          23

<210> SEQ ID NO 889
<211> LENGTH: 20
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 889
acaactcccg aaacaaaacc                                              20

<210> SEQ ID NO 890
<211> LENGTH: 22
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 890
ctcctcgcct tccctttata tc                                           22

<210> SEQ ID NO 891
<211> LENGTH: 21
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 891
taacaacgac cacgaacaca a                                            21

<210> SEQ ID NO 892
<211> LENGTH: 25
<212> TYPE: DNA
```

```
<213> ORGANISM: Artificial Sequence
<220> FEATURE:
<223> OTHER INFORMATION: Description of Artificial Sequence: Synthetic
      probe

<400> SEQUENCE: 892
aactcaattt cttccaccta aaaac                                              25

<210> SEQ ID NO 893
<211> LENGTH: 22
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 893
ccaacttccg accgaaaact ac                                                 22

<210> SEQ ID NO 894
<211> LENGTH: 23
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 894
ataacgctcg aatccgacta aac                                                23

<210> SEQ ID NO 895
<211> LENGTH: 23
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 895
gcgatcgaca actaacgacc taa                                                23

<210> SEQ ID NO 896
<211> LENGTH: 23
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 896
accttataaa aaacacaaac cgc                                                23

<210> SEQ ID NO 897
<211> LENGTH: 22
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 897
tatatccaac gaacatcgac ca                                                 22

<210> SEQ ID NO 898
<211> LENGTH: 22
<212> TYPE: DNA
<213> ORGANISM: Artificial Sequence
<220> FEATURE:
```

<223> OTHER INFORMATION: Description of Artificial Sequence: Synthetic
      probe

<400> SEQUENCE: 898
cctaaactac acttttcccc ct                                              22

<210> SEQ ID NO 899
<211> LENGTH: 24
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 899
acaattactt caaaacgtct ccaa                                            24

<210> SEQ ID NO 900
<211> LENGTH: 21
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 900
cctcccaaac cattcaaaaa c                                               21

<210> SEQ ID NO 901
<211> LENGTH: 22
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 901
gaccaaaaca atctcctccg ac                                              22

<210> SEQ ID NO 902
<211> LENGTH: 22
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 902 acccctta aa attccaaaaa cc                                             22

<210> SEQ ID NO 903
<211> LENGTH: 26
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 903
ccacctcctc aacttactct aacttc                                          26

<210> SEQ ID NO 904
<211> LENGTH: 18
<212> TYPE: DNA
<213> ORGANISM: Artificial Sequence
<220> FEATURE:
<223> OTHER INFORMATION: Description of Artificial Sequence: Synthetic
      probe

```
<400> SEQUENCE: 904
accgcaaacg ctccataa                                                 18

<210> SEQ ID NO 905
<211> LENGTH: 22
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 905
ttcgcttaac taacgacgca ac                                            22

<210> SEQ ID NO 906
<211> LENGTH: 27
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 906
atacaaaata tttaaaaacc ctcacaa                                       27

<210> SEQ ID NO 907
<211> LENGTH: 25
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 907
taactcctct cattccaata cctaa                                         25

<210> SEQ ID NO 908
<211> LENGTH: 23
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 908 aatacccca caactctaaa cct                                            23

<210> SEQ ID NO 909
<211> LENGTH: 21
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 909
ccaaaaaacc aatcaaaacc a                                             21

<210> SEQ ID NO 910
<211> LENGTH: 21
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 910
```

```
acgcaaaact ccgaattcaa t                                          21

<210> SEQ ID NO 911
<211> LENGTH: 22
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 911
aaacgcatac gtaacgacaa ca                                         22

<210> SEQ ID NO 912
<211> LENGTH: 23
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 912
gatcccattt cgaaatttcc tct                                        23

<210> SEQ ID NO 913
<211> LENGTH: 24
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 913
attatcaaac gacgaacgtc tacc                                       24

<210> SEQ ID NO 914
<211> LENGTH: 23
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 914
ttccccttta caaactacca acc                                        23

<210> SEQ ID NO 915
<211> LENGTH: 23
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 915
acaaccgaaa ataaaaccaa acc                                        23

<210> SEQ ID NO 916
<211> LENGTH: 24
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 916
aatcccaatc ccttaattaa actt                                       24
```

<210> SEQ ID NO 917
<211> LENGTH: 22
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 917
ccccatttct cactcccatt aa                                          22

<210> SEQ ID NO 918
<211> LENGTH: 18
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 918
aaacccccaa cctacccc                                               18

<210> SEQ ID NO 919
<211> LENGTH: 22
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 919
aatacaaatc acctctccca aa                                          22

<210> SEQ ID NO 920
<211> LENGTH: 18
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 920
accccaccca acttcaaa                                               18

<210> SEQ ID NO 921
<211> LENGTH: 23
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 921
attcaaacga ttctcctacc tca                                         23

<210> SEQ ID NO 922
<211> LENGTH: 23
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 922
aacttaccct tccgattaac cct                                         23

-continued

```
<210> SEQ ID NO 923
<211> LENGTH: 23
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 923
actcctaact caaataatcc gcc                                              23

<210> SEQ ID NO 924
<211> LENGTH: 23
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 924
attaaatcca aacctccttc acc                                              23

<210> SEQ ID NO 925
<211> LENGTH: 22
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 925
aatactaccc cctccaaatc cc                                               22

<210> SEQ ID NO 926
<211> LENGTH: 23
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 926
ctacttaccg cacttccgaa cta                                              23

<210> SEQ ID NO 927
<211> LENGTH: 22
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 927
ccccataccc ctcaaaacct at                                               22

<210> SEQ ID NO 928
<211> LENGTH: 19
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 928
tttcttctcc atcgcgaaa                                                   19

<210> SEQ ID NO 929
<211> LENGTH: 26
```

-continued

<212> TYPE: DNA
<213> ORGANISM: Artificial Sequence
<220> FEATURE:
<223> OTHER INFORMATION: Description of Artificial Sequence: Synthetic
      probe

<400> SEQUENCE: 929
ttcctccaaa taaactcata aatttc                                          26

<210> SEQ ID NO 930
<211> LENGTH: 21
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 930
ccccgaaaac tctatccaaa a                                               21

<210> SEQ ID NO 931
<211> LENGTH: 22
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 931
accaaacttc actaaacgtc cg                                              22

<210> SEQ ID NO 932
<211> LENGTH: 23
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 932
acgtaacctc actttcctac tcc                                             23

<210> SEQ ID NO 933
<211> LENGTH: 23
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 933
ccctacccga actcactact tac                                             23

<210> SEQ ID NO 934
<211> LENGTH: 24
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 934
gatttcccct aatctcttca ttca                                            24

<210> SEQ ID NO 935
<211> LENGTH: 24
<212> TYPE: DNA
<213> ORGANISM: Artificial Sequence

```
<220> FEATURE:
<223> OTHER INFORMATION: Description of Artificial Sequence: Synthetic
      probe

<400> SEQUENCE: 935
tacacttcca aaccttcaac aaac                                           24

<210> SEQ ID NO 936
<211> LENGTH: 24
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 936
caaacacaca catacacaca caca                                           24

<210> SEQ ID NO 937
<211> LENGTH: 28
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 937
aacattataa ttccaaccaa aaatactc                                       28

<210> SEQ ID NO 938
<211> LENGTH: 24
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 938
taaccctact cttataacct cccg                                           24

<210> SEQ ID NO 939
<211> LENGTH: 25
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 939
tcttccttca actataactt acgcc                                          25

<210> SEQ ID NO 940
<211> LENGTH: 23
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 940
actcaacctc gtaataacgc cta                                            23

<210> SEQ ID NO 941
<211> LENGTH: 28
<212> TYPE: DNA
<213> ORGANISM: Artificial Sequence
<220> FEATURE:
<223> OTHER INFORMATION: Description of Artificial Sequence: Synthetic
```

-continued probe

<400> SEQUENCE: 941
caatttctca cctatacatt tcctataa                                    28

<210> SEQ ID NO 942
<211> LENGTH: 20
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 942 tcctcccta ctaccctcg                                               20

<210> SEQ ID NO 943
<211> LENGTH: 18
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 943
cccaaactaa cgcatccg                                               18

<210> SEQ ID NO 944
<211> LENGTH: 24
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 944
caaaacaata ctaattccaa cccc                                        24

<210> SEQ ID NO 945
<211> LENGTH: 22
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 945
ccgttctaaa cgaaaaccca ac                                          22

<210> SEQ ID NO 946
<211> LENGTH: 23
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 946
ctcaacgacc tcaaaaacta ccc                                         23

<210> SEQ ID NO 947
<211> LENGTH: 28
<212> TYPE: DNA
<213> ORGANISM: Artificial Sequence
<220> FEATURE:
<223> OTHER INFORMATION: Description of Artificial Sequence: Synthetic
      probe

```
<400> SEQUENCE: 947
aaaaactcta taaaaataac aacgacct                                          28

<210> SEQ ID NO 948
<211> LENGTH: 19
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 948
cccgcccaac tataaaaaa                                                    19

<210> SEQ ID NO 949
<211> LENGTH: 18
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 949
ccgacgaaca acgctacg                                                     18

<210> SEQ ID NO 950
<211> LENGTH: 21
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 950
cactacgacc caaaacaatc c                                                 21

<210> SEQ ID NO 951
<211> LENGTH: 23
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 951
aactcacaaa tccctttcct aac                                               23

<210> SEQ ID NO 952
<211> LENGTH: 22
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 952
aaaaaacaaa ctccgaacga aa                                                22

<210> SEQ ID NO 953
<211> LENGTH: 21
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 953
```

```
tccccaacaa tctctattcc c                                              21
```

<210> SEQ ID NO 954
<211> LENGTH: 18
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 954

```
cacgcccact tcctaccc                                                  18
```

<210> SEQ ID NO 955
<211> LENGTH: 23
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 955

```
cttcgcaaac ctaaccaatc aat                                            23
```

<210> SEQ ID NO 956
<211> LENGTH: 23
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 956

```
cgctaaacca ccccaaataa aac                                            23
```

<210> SEQ ID NO 957
<211> LENGTH: 21
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 957

```
ctcccgaatt caaacgattc t                                              21
```

<210> SEQ ID NO 958
<211> LENGTH: 24
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 958

```
aatccgaaat aaattcccta aact                                           24
```

<210> SEQ ID NO 959
<211> LENGTH: 23
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 959

```
tctcacactt ttcctcgaaa aat                                            23
```

<210> SEQ ID NO 960
<211> LENGTH: 23
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 960
gcaaacctaa atacgtccct cct                                          23

<210> SEQ ID NO 961
<211> LENGTH: 22
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 961
accttcattc gaacgcttaa ac                                           22

<210> SEQ ID NO 962
<211> LENGTH: 23
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 962
aactacttcc tctccctcca caa                                          23

<210> SEQ ID NO 963
<211> LENGTH: 23
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 963
ttcaaaaatc gaccaatcgt aat                                          23

<210> SEQ ID NO 964
<211> LENGTH: 21
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 964
tcgcgaacaa attaacttcc c                                            21

<210> SEQ ID NO 965
<211> LENGTH: 28
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 965
ttaactactt actttcttct ctccaccc                                     28

<210> SEQ ID NO 966

```
<211> LENGTH: 22
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 966
aaaaccaatt tactcgcgaa cg                                              22

<210> SEQ ID NO 967
<211> LENGTH: 23
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 967
caactaaacc caacgccaat cta                                             23

<210> SEQ ID NO 968
<211> LENGTH: 21
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 968
aaacaatcca aacccgaaaa c                                               21

<210> SEQ ID NO 969
<211> LENGTH: 19
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 969
gaacgcatac gcgacaaac                                                  19

<210> SEQ ID NO 970
<211> LENGTH: 21
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 970
tcctaccctc accctcctaa a                                               21

<210> SEQ ID NO 971
<211> LENGTH: 26
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 971
attctcaaaa taaaaattcc ctatca                                          26

<210> SEQ ID NO 972
<211> LENGTH: 22
<212> TYPE: DNA
```

```
<213> ORGANISM: Artificial Sequence
<220> FEATURE:
<223> OTHER INFORMATION: Description of Artificial Sequence: Synthetic
      probe

<400> SEQUENCE: 972
cattaccctt tctatcccca cc                                              22

<210> SEQ ID NO 973
<211> LENGTH: 27
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 973
aaccaaccta accaacataa taaaacc                                         27

<210> SEQ ID NO 974
<211> LENGTH: 23
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 974
taaactccaa acacccacct acc                                             23

<210> SEQ ID NO 975
<211> LENGTH: 21
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 975
accctccgaa cctccaacta c                                               21

<210> SEQ ID NO 976
<211> LENGTH: 23
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 976
ctacatctac tcatttcctc cca                                             23

<210> SEQ ID NO 977
<211> LENGTH: 27
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 977
aatacaataa cataacctct acctccc                                         27

<210> SEQ ID NO 978
<211> LENGTH: 24
<212> TYPE: DNA
<213> ORGANISM: Artificial Sequence
<220> FEATURE:
```

```
<223> OTHER INFORMATION: Description of Artificial Sequence: Synthetic
      probe

<400> SEQUENCE: 978
cctaaaaaac acaacaaaac tcca                                              24

<210> SEQ ID NO 979
<211> LENGTH: 24
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 979
ttaccacact ctaaccaatc aaaa                                              24

<210> SEQ ID NO 980
<211> LENGTH: 23
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 980
ctaccgaatt catttaaaaa ccg                                               23

<210> SEQ ID NO 981
<211> LENGTH: 25
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 981
ttccctttct tcacgatact taaca                                             25

<210> SEQ ID NO 982
<211> LENGTH: 23
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 982
ttcaactccg aaatttccaa act                                               23

<210> SEQ ID NO 983
<211> LENGTH: 21
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 983
ttcgtcactc ccacgattaa c                                                 21

<210> SEQ ID NO 984
<211> LENGTH: 22
<212> TYPE: DNA
<213> ORGANISM: Artificial Sequence
<220> FEATURE:
<223> OTHER INFORMATION: Description of Artificial Sequence: Synthetic
      probe
```

```
<400> SEQUENCE: 984
aaaacgacca aaacaaaacc aa                                              22

<210> SEQ ID NO 985
<211> LENGTH: 21
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 985
catcaaccaa acattccgaa a                                               21

<210> SEQ ID NO 986
<211> LENGTH: 19
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 986
aaaacgcgta tcctcaccc                                                  19

<210> SEQ ID NO 987
<211> LENGTH: 20
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 987
accctcgcta actctcctcc                                                 20

<210> SEQ ID NO 988
<211> LENGTH: 23
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 988
caatccttaa accaatcgac gta                                             23

<210> SEQ ID NO 989
<211> LENGTH: 23
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 989
cgaaacatta aactcctcct cct                                             23

<210> SEQ ID NO 990
<211> LENGTH: 24
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 990
```
taaacaacat aacgtacgac accg                                          24

<210> SEQ ID NO 991
<211> LENGTH: 22
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 991
tcaactccgt ttcgatttca ct                                            22

<210> SEQ ID NO 992
<211> LENGTH: 21
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 992
aacaatacga cctatcaccg c                                             21

<210> SEQ ID NO 993
<211> LENGTH: 23
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 993
tactttaaac cgaaccaaac caa                                           23

<210> SEQ ID NO 994
<211> LENGTH: 21
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 994
aaaaattcaa actcccgaac g                                             21

<210> SEQ ID NO 995
<211> LENGTH: 23
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 995
cttcttccga ctcttcacct caa                                           23

<210> SEQ ID NO 996
<211> LENGTH: 22
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 996
gacgcgtccc taaaacttaa cc                                            22

```
<210> SEQ ID NO 997
<211> LENGTH: 20
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 997
ttcgccacaa accttctttc                                              20

<210> SEQ ID NO 998
<211> LENGTH: 24
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 998
acgaacaact aaactcgact accg                                         24

<210> SEQ ID NO 999
<211> LENGTH: 23
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 999
ctactaaaaa accaatcaac gcg                                          23

<210> SEQ ID NO 1000
<211> LENGTH: 26
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 1000
atcctaatcc tcctaccctt atattt                                       26

<210> SEQ ID NO 1001
<211> LENGTH: 29
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 1001
aaactaacta aacaattaac tctcctccc                                    29

<210> SEQ ID NO 1002
<211> LENGTH: 23
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 1002
aattctaaac gtttcccgac tac                                          23
```

```
<210> SEQ ID NO 1003
<211> LENGTH: 20
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 1003
actacaaccg acgaaccacg                                                  20

<210> SEQ ID NO 1004
<211> LENGTH: 19
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 1004
gacccgaaac taccgcaaa                                                   19

<210> SEQ ID NO 1005
<211> LENGTH: 23
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 1005
aatcctaaac ctaaacctcc cga                                              23

<210> SEQ ID NO 1006
<211> LENGTH: 20
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 1006
accgaatctt cccttatccc                                                  20

<210> SEQ ID NO 1007
<211> LENGTH: 23
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 1007
tccttacaac ctctaacctc ctt                                              23

<210> SEQ ID NO 1008
<211> LENGTH: 24
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 1008
cctcttaaaa cctacctacc cctc                                             24

<210> SEQ ID NO 1009
<211> LENGTH: 26
```

```
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 1009
aaattacacc aattataaac cgaacg                                       26

<210> SEQ ID NO 1010
<211> LENGTH: 21
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 1010
gaaaccctct acccgcctat t                                            21

<210> SEQ ID NO 1011
<211> LENGTH: 20
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 1011
aaaatcgaaa ccaaaacccc                                              20

<210> SEQ ID NO 1012
<211> LENGTH: 24
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 1012
ccgtaacaac tacacgactc ctaa                                         24

<210> SEQ ID NO 1013
<211> LENGTH: 22
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 1013
cctcccgaac taaaacgatt ct                                           22

<210> SEQ ID NO 1014
<211> LENGTH: 22
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 1014
caaaacgaaa ccctatctcc aa                                           22

<210> SEQ ID NO 1015
<211> LENGTH: 22
<212> TYPE: DNA
<213> ORGANISM: Artificial Sequence
```

```
<220> FEATURE:
<223> OTHER INFORMATION: Description of Artificial Sequence: Synthetic
      probe

<400> SEQUENCE: 1015
accatcccaa ctccctatct tt                                                22

<210> SEQ ID NO 1016
<211> LENGTH: 20
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 1016
acgaaactct acgacgacgc                                                   20

<210> SEQ ID NO 1017
<211> LENGTH: 22
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 1017
aaaacgaaac cgcgactata aa                                                22

<210> SEQ ID NO 1018
<211> LENGTH: 23
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 1018
taaaatcacc acccgaaaaa cat                                               23

<210> SEQ ID NO 1019
<211> LENGTH: 26
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 1019
tttaataaaa ttttccctcc cttacc                                            26

<210> SEQ ID NO 1020
<211> LENGTH: 22
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 1020
cttctactca aacaccaacg cc                                                22

<210> SEQ ID NO 1021
<211> LENGTH: 24
<212> TYPE: DNA
<213> ORGANISM: Artificial Sequence
<220> FEATURE:
<223> OTHER INFORMATION: Description of Artificial Sequence: Synthetic
```

-continued probe

<400> SEQUENCE: 1021
aaaatcaaat ccaaataaca tccc  24

<210> SEQ ID NO 1022
<211> LENGTH: 23
<212> TYPE: DNA
<213> ORGANISM: Artificial Sequence
<220> FEATURE:
<223> OTHER INFORMATION: Description of Artificial Sequence: Synthetic
  probe

<400> SEQUENCE: 1022
ctcccgccac tttactaaaa act  23

<210> SEQ ID NO 1023
<211> LENGTH: 21
<212> TYPE: DNA
<213> ORGANISM: Artificial Sequence
<220> FEATURE:
<223> OTHER INFORMATION: Description of Artificial Sequence: Synthetic
  probe

<400> SEQUENCE: 1023
taccacttcc caactcttcc c  21

<210> SEQ ID NO 1024
<211> LENGTH: 22
<212> TYPE: DNA
<213> ORGANISM: Artificial Sequence
<220> FEATURE:
<223> OTHER INFORMATION: Description of Artificial Sequence: Synthetic
  probe

<400> SEQUENCE: 1024
gccctacatc ccaacactaa aa  22

<210> SEQ ID NO 1025
<211> LENGTH: 25
<212> TYPE: DNA
<213> ORGANISM: Artificial Sequence
<220> FEATURE:
<223> OTHER INFORMATION: Description of Artificial Sequence: Synthetic
  probe

<400> SEQUENCE: 1025
aaatacctac gaactcctaa aaccc  25

<210> SEQ ID NO 1026
<211> LENGTH: 18
<212> TYPE: DNA
<213> ORGANISM: Artificial Sequence
<220> FEATURE:
<223> OTHER INFORMATION: Description of Artificial Sequence: Synthetic
  probe

<400> SEQUENCE: 1026
gacgacgccc atatcgac  18

<210> SEQ ID NO 1027
<211> LENGTH: 22
<212> TYPE: DNA
<213> ORGANISM: Artificial Sequence
<220> FEATURE:
<223> OTHER INFORMATION: Description of Artificial Sequence: Synthetic
  probe

```
<400> SEQUENCE: 1027
aacctctccc aacctcaatt tt                                          22

<210> SEQ ID NO 1028
<211> LENGTH: 22
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 1028
actaataacc gctctcgctt ct                                          22

<210> SEQ ID NO 1029
<211> LENGTH: 27
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 1029
aaacaaactc gctaaaatct aaataac                                     27

<210> SEQ ID NO 1030
<211> LENGTH: 27
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 1030
tttttaaaaa acctataaaa ccaatcc                                     27

<210> SEQ ID NO 1031
<211> LENGTH: 17
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 1031
aaccatcctc cgcctca                                                17

<210> SEQ ID NO 1032
<211> LENGTH: 23
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 1032
cctacaaccc tactacccct acc                                         23

<210> SEQ ID NO 1033
<211> LENGTH: 23
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 1033
```
ctaacacaaa aaccacactc caa                                          23

<210> SEQ ID NO 1034
<211> LENGTH: 24
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 1034
cccaaaaact aaacttcctc taaa                                         24

<210> SEQ ID NO 1035
<211> LENGTH: 20
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 1035
acactaccac caccaccatc                                              20

<210> SEQ ID NO 1036
<211> LENGTH: 23
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 1036
aaacatttcg caattcctat ctc                                          23

<210> SEQ ID NO 1037
<211> LENGTH: 23
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 1037
atattctctc tcattctacg ccg                                          23

<210> SEQ ID NO 1038
<211> LENGTH: 25
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 1038
aatcctatac tcgataccgt ttctc                                        25

<210> SEQ ID NO 1039
<211> LENGTH: 24
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 1039
acaaccacac caaaccctat atct                                         24

<210> SEQ ID NO 1040
<211> LENGTH: 23
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 1040
acttccaacc cttaaaacaa aca                                            23

<210> SEQ ID NO 1041
<211> LENGTH: 22
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 1041
tcccaaaaaa caacttccct aa                                             22

<210> SEQ ID NO 1042
<211> LENGTH: 23
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 1042
ttattttaaa cccaatcttc cct                                            23

<210> SEQ ID NO 1043
<211> LENGTH: 25
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 1043
ttacaatata atcctcccca aaatc                                          25

<210> SEQ ID NO 1044
<211> LENGTH: 24
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 1044
caaatttccc aatttaattc ctca                                           24

<210> SEQ ID NO 1045
<211> LENGTH: 23
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 1045
gattaaacgc gacgctcaat tac                                            23

<210> SEQ ID NO 1046

```
<211> LENGTH: 21
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 1046
cgacacacaa aaaccgacta c                                              21

<210> SEQ ID NO 1047
<211> LENGTH: 25
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 1047
ataccattac aaaaacaacc caaca                                          25

<210> SEQ ID NO 1048
<211> LENGTH: 24
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 1048
acacatatcc cctctctaat cctc                                           24

<210> SEQ ID NO 1049
<211> LENGTH: 23
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 1049 aaacccata cccttaaacc cta                                             23

<210> SEQ ID NO 1050
<211> LENGTH: 23
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 1050
acctcaatct tctcgtcaac aaa                                            23

<210> SEQ ID NO 1051
<211> LENGTH: 21
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 1051
cccaaccaat aaacgacgaa a                                              21

<210> SEQ ID NO 1052
<211> LENGTH: 21
<212> TYPE: DNA
```

```
<213> ORGANISM: Artificial Sequence
<220> FEATURE:
<223> OTHER INFORMATION: Description of Artificial Sequence: Synthetic
      probe

<400> SEQUENCE: 1052
cctcacgaac taccctcaaa c                                              21

<210> SEQ ID NO 1053
<211> LENGTH: 23
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 1053
taaacaccaa cttctctccc ttt                                            23

<210> SEQ ID NO 1054
<211> LENGTH: 23
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 1054
ctcctcccct actcatttta aaa                                            23

<210> SEQ ID NO 1055
<211> LENGTH: 19
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 1055
tttccaaact aaaccgccg                                                 19

<210> SEQ ID NO 1056
<211> LENGTH: 27
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 1056
taacacctaa ttttatatac cccaacc                                        27

<210> SEQ ID NO 1057
<211> LENGTH: 23
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 1057
actccgtcta acttctttct ccc                                            23

<210> SEQ ID NO 1058
<211> LENGTH: 20
<212> TYPE: DNA
<213> ORGANISM: Artificial Sequence
<220> FEATURE:
```

-continued

<223> OTHER INFORMATION: Description of Artificial Sequence: Synthetic
      probe

<400> SEQUENCE: 1058
aactttcaat acatccgccg                                                    20

<210> SEQ ID NO 1059
<211> LENGTH: 23
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 1059
caaaacccat aaaaattcaa aaa                                                23

<210> SEQ ID NO 1060
<211> LENGTH: 17
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 1060
cccctactcc tccccac                                                       17

<210> SEQ ID NO 1061
<211> LENGTH: 18
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 1061
ttcctcctcc aacccctc                                                      18

<210> SEQ ID NO 1062
<211> LENGTH: 21
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 1062
ccctaacacg actctaccca a                                                  21

<210> SEQ ID NO 1063
<211> LENGTH: 21
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 1063
cctccccata ccaacttaaa a                                                  21

<210> SEQ ID NO 1064
<211> LENGTH: 26
<212> TYPE: DNA
<213> ORGANISM: Artificial Sequence
<220> FEATURE:
<223> OTHER INFORMATION: Description of Artificial Sequence: Synthetic
      probe -continued

<400> SEQUENCE: 1064
aatcatctaa aataaaaaca cccaac                                              26

<210> SEQ ID NO 1065
<211> LENGTH: 23
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 1065
accaaatcta taccaaaatc ccc                                                 23

<210> SEQ ID NO 1066
<211> LENGTH: 23
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 1066
aaattaactc ctcaaaacac ccg                                                 23

<210> SEQ ID NO 1067
<211> LENGTH: 23
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 1067
aaacccaaaa ctacctccaa atc                                                 23

<210> SEQ ID NO 1068
<211> LENGTH: 22
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 1068
aaccaaaccg aactcccaat aa                                                  22

<210> SEQ ID NO 1069
<211> LENGTH: 20
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 1069
ttcgacctct ctccgctaaa                                                     20

<210> SEQ ID NO 1070
<211> LENGTH: 23
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 1070
acccatctcc cgttacataa aac                           23

<210> SEQ ID NO 1071
<211> LENGTH: 22
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 1071
ctaaacaccc gaaccaacga ct                            22

<210> SEQ ID NO 1072
<211> LENGTH: 20
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 1072
accacatacg ccaaataccc                               20

<210> SEQ ID NO 1073
<211> LENGTH: 23
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 1073
cctcaacaaa taaccccaa aat                            23

<210> SEQ ID NO 1074
<211> LENGTH: 21
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 1074
ccgcccctca actatttatt c                             21

<210> SEQ ID NO 1075
<211> LENGTH: 22
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 1075
ttccaatcgc attacgtaaa ca                            22

<210> SEQ ID NO 1076
<211> LENGTH: 28
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 1076
tctaaaaacc taccactaat attcacaa                      28

<210> SEQ ID NO 1077
<211> LENGTH: 25
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 1077
taaaccctaa actaccataa aaccg                                          25

<210> SEQ ID NO 1078
<211> LENGTH: 28
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 1078
aaaattaact actctcacct aacaaacc                                       28

<210> SEQ ID NO 1079
<211> LENGTH: 22
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 1079
tttcataaca acccaaaatc ca                                             22

<210> SEQ ID NO 1080
<211> LENGTH: 24
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 1080
aaacactaac cgtaaaccaa acac                                           24

<210> SEQ ID NO 1081
<211> LENGTH: 23
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 1081
caacgctata cctaaacgac ctt                                            23

<210> SEQ ID NO 1082
<211> LENGTH: 22
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 1082
aaacttcgac taacaaaccc cg                                             22

<210> SEQ ID NO 1083
<211> LENGTH: 23
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 1083
cttatcccaa aaacaaaac caa                                        23

<210> SEQ ID NO 1084
<211> LENGTH: 24
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 1084
ttccaaccct cacctaactt tatc                                      24

<210> SEQ ID NO 1085
<211> LENGTH: 25
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 1085
cctattcaaa tcaactcctt ctaaa                                     25

<210> SEQ ID NO 1086
<211> LENGTH: 20
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 1086
cacaaacaaa cgctccaaaa                                           20

<210> SEQ ID NO 1087
<211> LENGTH: 23
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 1087
cccaaaatct ccgtaaacta aaa                                       23

<210> SEQ ID NO 1088
<211> LENGTH: 23
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 1088
aaaatccctc tcacccatta aca                                       23

<210> SEQ ID NO 1089
<211> LENGTH: 20

```
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 1089
aaaaaccgcg accctaaaaa                                                    20

<210> SEQ ID NO 1090
<211> LENGTH: 23
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 1090
gacctcttcg aacaacccaa ata                                                23

<210> SEQ ID NO 1091
<211> LENGTH: 23
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 1091
ccctatccta atcgcccaac taa                                                23

<210> SEQ ID NO 1092
<211> LENGTH: 23
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 1092
ccaccaaaca tacaattcca act                                                23

<210> SEQ ID NO 1093
<211> LENGTH: 23
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 1093
attctatccc tatcctaatc gcc                                                23

<210> SEQ ID NO 1094
<211> LENGTH: 20
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 1094
actctctaaa accgccgtcg                                                    20

<210> SEQ ID NO 1095
<211> LENGTH: 23
<212> TYPE: DNA
<213> ORGANISM: Artificial Sequence
```

```
<220> FEATURE:
<223> OTHER INFORMATION: Description of Artificial Sequence: Synthetic
      probe

<400> SEQUENCE: 1095
gtaaacctcc ccctcaacta aaa                                          23

<210> SEQ ID NO 1096
<211> LENGTH: 22
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 1096
cgctacctaa cgctctaact cc                                           22

<210> SEQ ID NO 1097
<211> LENGTH: 26
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 1097
tccaattccc taatatacct atttca                                       26

<210> SEQ ID NO 1098
<211> LENGTH: 21
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 1098
accaacacaa tctctacgcc c                                            21

<210> SEQ ID NO 1099
<211> LENGTH: 22
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 1099
aacctcgaac cttaacaatt cg                                           22

<210> SEQ ID NO 1100
<211> LENGTH: 22
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 1100
aattccctac actcatcccc tt                                           22

<210> SEQ ID NO 1101
<211> LENGTH: 20
<212> TYPE: DNA
<213> ORGANISM: Artificial Sequence
<220> FEATURE:
<223> OTHER INFORMATION: Description of Artificial Sequence: Synthetic
```

```
                                probe

<400> SEQUENCE: 1101
ccccactaaa cccttaaccc                                                    20

<210> SEQ ID NO 1102
<211> LENGTH: 19
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 1102
aaaactctcc cctctcccc                                                     19

<210> SEQ ID NO 1103
<211> LENGTH: 25
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 1103
aaaatccaaa ctccttacct ctaat                                              25

<210> SEQ ID NO 1104
<211> LENGTH: 27
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 1104
taaacattct atacctactt cccaaaa                                            27

<210> SEQ ID NO 1105
<211> LENGTH: 28
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 1105
taaacaatac caactaattc cacttttc                                           28

<210> SEQ ID NO 1106
<211> LENGTH: 21
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 1106
attccttcct aacgctccct c                                                  21

<210> SEQ ID NO 1107
<211> LENGTH: 21
<212> TYPE: DNA
<213> ORGANISM: Artificial Sequence
<220> FEATURE:
<223> OTHER INFORMATION: Description of Artificial Sequence: Synthetic
      probe
```

-continued

```
<400> SEQUENCE: 1107
aactcgctcc tcgcgaaata c                                            21

<210> SEQ ID NO 1108
<211> LENGTH: 27
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 1108
aattctaaaa atccgaaatt ctaaacc                                      27

<210> SEQ ID NO 1109
<211> LENGTH: 22
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 1109
atttctaaaa ccccgaaacc tc                                           22

<210> SEQ ID NO 1110
<211> LENGTH: 23
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 1110
tctatacccg ctaatacaaa ccc                                          23

<210> SEQ ID NO 1111
<211> LENGTH: 25
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 1111
aacacacaca caaaaaacct ataca                                        25

<210> SEQ ID NO 1112
<211> LENGTH: 21
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 1112
acatacacgc acactcaaac a                                            21

<210> SEQ ID NO 1113
<211> LENGTH: 21
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 1113
```

```
cccccttaaa ccctaaactc a                                              21

<210> SEQ ID NO 1114
<211> LENGTH: 18
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 1114
cccacgcaaa accgaaaa                                                  18

<210> SEQ ID NO 1115
<211> LENGTH: 21
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 1115
tcacgtcaac ctcccaaat a                                               21

<210> SEQ ID NO 1116
<211> LENGTH: 20
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 1116
aataccacct tccgcaaacc                                                20

<210> SEQ ID NO 1117
<211> LENGTH: 20
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 1117
aacccaatct cacaacaccc                                                20

<210> SEQ ID NO 1118
<211> LENGTH: 23
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 1118
aaaacctact cgcgacctta act                                            23

<210> SEQ ID NO 1119
<211> LENGTH: 22
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 1119
gacccaacca ataaaccaaa ac                                             22
```

<210> SEQ ID NO 1120
<211> LENGTH: 24
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 1120
ctaactccct accattatcc acca                                          24

<210> SEQ ID NO 1121
<211> LENGTH: 23
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 1121
actccttacc cactccgaac taa                                           23

<210> SEQ ID NO 1122
<211> LENGTH: 23
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 1122
aaccaaccca aattcaaaac taa                                           23

<210> SEQ ID NO 1123
<211> LENGTH: 25
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 1123
aattcctaac tccctaatcc ctacc                                         25

<210> SEQ ID NO 1124
<211> LENGTH: 22
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 1124
aacttcttat acccgatcct cg                                            22

<210> SEQ ID NO 1125
<211> LENGTH: 23
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 1125
aaatacgaac cgaaataaac ctc                                           23

<210> SEQ ID NO 1126

<211> LENGTH: 22
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 1126
cctaactcaa ccataaaccc ca                                              22

<210> SEQ ID NO 1127
<211> LENGTH: 25
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 1127
aaattctata ctcccctcaa aaatc                                           25

<210> SEQ ID NO 1128
<211> LENGTH: 25
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 1128
aaccttccaa atactaccct aactc                                           25

<210> SEQ ID NO 1129
<211> LENGTH: 22
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 1129
caaaacgaaa ccctatctct cg                                              22

<210> SEQ ID NO 1130
<211> LENGTH: 25
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 1130
gcctaaccaa tcttctcttc ttaca                                           25

<210> SEQ ID NO 1131
<211> LENGTH: 20
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 1131
tcctccaacc taaacctccc                                                 20

<210> SEQ ID NO 1132
<211> LENGTH: 23
<212> TYPE: DNA

```
<213> ORGANISM: Artificial Sequence
<220> FEATURE:
<223> OTHER INFORMATION: Description of Artificial Sequence: Synthetic
      probe

<400> SEQUENCE: 1132
aacaccctca cacttctaca cca                                                 23

<210> SEQ ID NO 1133
<211> LENGTH: 25
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 1133
cttccaactt tatcacacac ctaca                                               25

<210> SEQ ID NO 1134
<211> LENGTH: 25
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 1134
cccaacttcc aaacaataat aaaca                                               25

<210> SEQ ID NO 1135
<211> LENGTH: 26
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 1135
tccctaataa atcaaaacat ctacca                                              26

<210> SEQ ID NO 1136
<211> LENGTH: 22
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 1136
aactttcaac taccctcac ca                                                   22

<210> SEQ ID NO 1137
<211> LENGTH: 23
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 1137
acatccaacc cctaactctc tca                                                 23

<210> SEQ ID NO 1138
<211> LENGTH: 24
<212> TYPE: DNA
<213> ORGANISM: Artificial Sequence
<220> FEATURE:
```

```
<223> OTHER INFORMATION: Description of Artificial Sequence: Synthetic
      probe

<400> SEQUENCE: 1138
taacacccaa atctctccta acca                                          24

<210> SEQ ID NO 1139
<211> LENGTH: 24
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 1139
ccaactctat acccaacacc taca                                          24

<210> SEQ ID NO 1140
<211> LENGTH: 24
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 1140
aaccctaaca ccaaacctac ttca                                          24

<210> SEQ ID NO 1141
<211> LENGTH: 24
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 1141
ccaccaaata tcttttcttc ttca                                          24

<210> SEQ ID NO 1142
<211> LENGTH: 25
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 1142
aatctatccc aacataactt cctca                                         25

<210> SEQ ID NO 1143
<211> LENGTH: 24
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 1143
acaccaacct aacaaaacaa ctca                                          24

<210> SEQ ID NO 1144
<211> LENGTH: 24
<212> TYPE: DNA
<213> ORGANISM: Artificial Sequence
<220> FEATURE:
<223> OTHER INFORMATION: Description of Artificial Sequence: Synthetic
      probe
```

```
<400> SEQUENCE: 1144
aaaccttctt accttcaaac ctca                                            24

<210> SEQ ID NO 1145
<211> LENGTH: 23
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 1145
aaaaatactc ccattctcca cca                                             23

<210> SEQ ID NO 1146
<211> LENGTH: 22
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 1146
cactaccact ccccaaaaaa ca                                              22

<210> SEQ ID NO 1147
<211> LENGTH: 23
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 1147
aaaccaacaa aaatacccca aca                                             23

<210> SEQ ID NO 1148
<211> LENGTH: 24
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 1148
actccacact caaccaatta aaca                                            24

<210> SEQ ID NO 1149
<211> LENGTH: 23
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 1149
ccaattccca acataacaac aca                                             23

<210> SEQ ID NO 1150
<211> LENGTH: 22
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 1150
```
aactcacccc tcctttctac ca                                              22

<210> SEQ ID NO 1151
<211> LENGTH: 23
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 1151
acccacatcc aaattcctaa aca                                             23

<210> SEQ ID NO 1152
<211> LENGTH: 23
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 1152
tccaacccac aaaatttaaa aca                                             23

<210> SEQ ID NO 1153
<211> LENGTH: 25
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 1153
aacaatacaa ccaacattcc taaca                                           25

<210> SEQ ID NO 1154
<211> LENGTH: 23
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 1154
caactcctaa tccccaataa aca                                             23

<210> SEQ ID NO 1155
<211> LENGTH: 24
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 1155
aacatcttta aacaaacttc ccca                                            24

<210> SEQ ID NO 1156
<211> LENGTH: 22
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 1156
aaaacaaaca acctccctct ca                                              22

<210> SEQ ID NO 1157
<211> LENGTH: 23
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 1157
acctttaatt tctcccaaac cca                                              23

<210> SEQ ID NO 1158
<211> LENGTH: 24
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 1158
caaaaatctc tactaactcc ccca                                             24

<210> SEQ ID NO 1159
<211> LENGTH: 23
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 1159
caacaacacc tctcacacat aca                                              23

<210> SEQ ID NO 1160
<211> LENGTH: 24
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 1160
aacaaaacaa caaaacaata ccca                                             24

<210> SEQ ID NO 1161
<211> LENGTH: 24
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 1161
caccaaaaac ctaaccacta ctca                                             24

<210> SEQ ID NO 1162
<211> LENGTH: 23
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 1162
cttccccttc cctcaactaa aca                                              23

```
<210> SEQ ID NO 1163
<211> LENGTH: 23
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 1163
ctcctactcc ttctcctaat cca                                               23

<210> SEQ ID NO 1164
<211> LENGTH: 25
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 1164
aactaaaaca acttctccca aaaca                                             25

<210> SEQ ID NO 1165
<211> LENGTH: 27
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 1165
attaatatct acaacaccaa atcaaca                                           27

<210> SEQ ID NO 1166
<211> LENGTH: 23
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 1166
ctccatttcc tttacttcct cca                                               23

<210> SEQ ID NO 1167
<211> LENGTH: 21
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 1167
ccccaccacc tacaaaaaac a                                                 21

<210> SEQ ID NO 1168
<211> LENGTH: 23
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 1168
ccacaaaaac caaaaaacta cca                                               23

<210> SEQ ID NO 1169
<211> LENGTH: 23
```

```
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 1169
taaataacca atccaaaacc cca                                          23

<210> SEQ ID NO 1170
<211> LENGTH: 25
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 1170
ctcaaataaa attcttcctc ttcca                                        25

<210> SEQ ID NO 1171
<211> LENGTH: 28
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 1171
aaactcaaat caataacact actcaaca                                     28

<210> SEQ ID NO 1172
<211> LENGTH: 24
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 1172
aaaatattcc ccttacaaaa acca                                         24

<210> SEQ ID NO 1173
<211> LENGTH: 28
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 1173
aaaacaacct actattatat caccaaca                                     28

<210> SEQ ID NO 1174
<211> LENGTH: 26
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 1174
caactctaca taaatacaca aaccca                                       26

<210> SEQ ID NO 1175
<211> LENGTH: 23
<212> TYPE: DNA
<213> ORGANISM: Artificial Sequence
```

```
<220> FEATURE:
<223> OTHER INFORMATION: Description of Artificial Sequence: Synthetic
      probe

<400> SEQUENCE: 1175
atcaaccaaa cctacatccc aca                                          23

<210> SEQ ID NO 1176
<211> LENGTH: 25
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 1176
ccacaaaaaa cctaaaaaca aaaca                                        25

<210> SEQ ID NO 1177
<211> LENGTH: 25
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 1177
cccatacact tcctaaataa aacca                                        25

<210> SEQ ID NO 1178
<211> LENGTH: 24
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 1178
ctctttctct aataacccac acca                                         24

<210> SEQ ID NO 1179
<211> LENGTH: 21
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 1179
cccaacctaa ctctccttcc a                                            21

<210> SEQ ID NO 1180
<211> LENGTH: 24
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 1180
tctcttaaat cttaacaatc ccca                                         24

<210> SEQ ID NO 1181
<211> LENGTH: 25
<212> TYPE: DNA
<213> ORGANISM: Artificial Sequence
<220> FEATURE:
<223> OTHER INFORMATION: Description of Artificial Sequence: Synthetic
``` probe

<400> SEQUENCE: 1181
tccctaaata cctcctacac aaaca                          25

<210> SEQ ID NO 1182
<211> LENGTH: 27
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 1182
caataatcaa tcacataaaa cattcca                        27

<210> SEQ ID NO 1183
<211> LENGTH: 24
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 1183
acacaccaac ctctaacaat acca                           24

<210> SEQ ID NO 1184
<211> LENGTH: 25
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 1184
aactcaaaac cataattttc aaaca                          25

<210> SEQ ID NO 1185
<211> LENGTH: 24
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 1185
taaaactaac ctctcctacc ctca                           24

<210> SEQ ID NO 1186
<211> LENGTH: 27
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 1186
tcctaaaaca aataacacaa taccaca                        27

<210> SEQ ID NO 1187
<211> LENGTH: 24
<212> TYPE: DNA
<213> ORGANISM: Artificial Sequence
<220> FEATURE:
<223> OTHER INFORMATION: Description of Artificial Sequence: Synthetic
      probe

```
<400> SEQUENCE: 1187
ccaataaaaa caaaacccaa ctca                                          24

<210> SEQ ID NO 1188
<211> LENGTH: 24
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 1188
cacaaatcaa taacatcaca tcca                                          24

<210> SEQ ID NO 1189
<211> LENGTH: 21
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 1189
ctcaacccta atacccatcc a                                             21

<210> SEQ ID NO 1190
<211> LENGTH: 21
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 1190
ccactccaat actcactccc a                                             21

<210> SEQ ID NO 1191
<211> LENGTH: 24
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 1191
aacaaacaaa acaaacaaaa tcca                                          24

<210> SEQ ID NO 1192
<211> LENGTH: 26
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 1192
aaaaccttaa ctaacacaaa accaca                                        26

<210> SEQ ID NO 1193
<211> LENGTH: 25
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 1193
```
ccaaatctca ctcctaaatt caaca                                         25

<210> SEQ ID NO 1194
<211> LENGTH: 24
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 1194
tccacaaacc tacaaaacct aaca                                          24

<210> SEQ ID NO 1195
<211> LENGTH: 28
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 1195
caaaaactca ataataataa acacacca                                      28

<210> SEQ ID NO 1196
<211> LENGTH: 23
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 1196
cccaataaaa ccaacttaac cca                                           23

<210> SEQ ID NO 1197
<211> LENGTH: 23
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 1197
ccttccttaa actctctcca cca                                           23

<210> SEQ ID NO 1198
<211> LENGTH: 23
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 1198
aataacaacc atcctacctc cca                                           23

<210> SEQ ID NO 1199
<211> LENGTH: 24
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 1199
ccaaccaacc ataaaaataa aaca                                          24

<210> SEQ ID NO 1200
<211> LENGTH: 23
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 1200
cctctcccct accctataaa aca                                              23

<210> SEQ ID NO 1201
<211> LENGTH: 23
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 1201
caaccaacta cacaacaact cca                                              23

<210> SEQ ID NO 1202
<211> LENGTH: 24
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 1202
caaaaaacac cttccataaa aaca                                             24

<210> SEQ ID NO 1203
<211> LENGTH: 24
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 1203
accacaatac cataaacatc acca                                             24

<210> SEQ ID NO 1204
<211> LENGTH: 27
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 1204
aaactacaaa ttacacaatc caattca                                          27

<210> SEQ ID NO 1205
<211> LENGTH: 27
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 1205
aataattaat aaccaaccaa aaactca                                          27

<210> SEQ ID NO 1206

```
<211> LENGTH: 21
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 1206
tctctttccc tttctcttcc a                                              21

<210> SEQ ID NO 1207
<211> LENGTH: 26
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 1207
cataataaat ttcacctctc aatcca                                         26

<210> SEQ ID NO 1208
<211> LENGTH: 25
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 1208
aaaaatcctt taccctaaa ttaca                                           25

<210> SEQ ID NO 1209
<211> LENGTH: 22
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 1209
ccacaccaac ctaaactcaa ca                                             22

<210> SEQ ID NO 1210
<211> LENGTH: 23
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 1210
acccaactaa aactaaaacc cca                                            23

<210> SEQ ID NO 1211
<211> LENGTH: 23
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 1211
accacctcct aataaaaacc cca                                            23

<210> SEQ ID NO 1212
<211> LENGTH: 24
<212> TYPE: DNA
```

<213> ORGANISM: Artificial Sequence
<220> FEATURE:
<223> OTHER INFORMATION: Description of Artificial Sequence: Synthetic
      probe

<400> SEQUENCE: 1212
ttacctctct ccaaatctct caca                                              24

<210> SEQ ID NO 1213
<211> LENGTH: 28
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 1213
ctttctacat atctctcaac ctctttca                                          28

<210> SEQ ID NO 1214
<211> LENGTH: 25
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 1214
aaaatatcaa aacctctaca accca                                             25

<210> SEQ ID NO 1215
<211> LENGTH: 23
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 1215
caaacccaat aaaatcaaaa cca                                               23

<210> SEQ ID NO 1216
<211> LENGTH: 23
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 1216
accctcaacc aatcaacaat aca                                               23

<210> SEQ ID NO 1217
<211> LENGTH: 25
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 1217
cctttaaaaa ccatctaatc aacca                                             25

<210> SEQ ID NO 1218
<211> LENGTH: 23
<212> TYPE: DNA
<213> ORGANISM: Artificial Sequence
<220> FEATURE:

<223> OTHER INFORMATION: Description of Artificial Sequence: Synthetic
      probe

<400> SEQUENCE: 1218
aactccattc tataccacac cca                                            23

<210> SEQ ID NO 1219
<211> LENGTH: 25
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 1219
cttacttcat tctctacaca accca                                          25

<210> SEQ ID NO 1220
<211> LENGTH: 23
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 1220
cctcctccta atcctacaca aca                                            23

<210> SEQ ID NO 1221
<211> LENGTH: 25
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 1221
ccatcaacac tcaaaacaaa ctaca                                          25

<210> SEQ ID NO 1222
<211> LENGTH: 23
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 1222
acccaactcc aaactcataa aca                                            23

<210> SEQ ID NO 1223
<211> LENGTH: 23
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 1223
aaactcctct acacctacca cca                                            23

<210> SEQ ID NO 1224
<211> LENGTH: 23
<212> TYPE: DNA
<213> ORGANISM: Artificial Sequence
<220> FEATURE:
<223> OTHER INFORMATION: Description of Artificial Sequence: Synthetic
      probe

```
<400> SEQUENCE: 1224
aaaccaatac aatccatatc cca                                          23

<210> SEQ ID NO 1225
<211> LENGTH: 24
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 1225
aaaaccaaaa cttacaaacc aaca                                         24

<210> SEQ ID NO 1226
<211> LENGTH: 25
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 1226
aatttatccc caattaataa ttcca                                        25

<210> SEQ ID NO 1227
<211> LENGTH: 24
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 1227
cccttttata actccatctc caca                                         24

<210> SEQ ID NO 1228
<211> LENGTH: 24
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 1228
ccactaccct atacacctaa ccca                                         24

<210> SEQ ID NO 1229
<211> LENGTH: 23
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 1229
aaccaacata ccaacatcca aca                                          23

<210> SEQ ID NO 1230
<211> LENGTH: 25
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 1230
```

```
aaccactcaa acacataaca aatca                                       25

<210> SEQ ID NO 1231
<211> LENGTH: 24
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 1231
ccctttccta attaacacca aaca                                        24

<210> SEQ ID NO 1232
<211> LENGTH: 24
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 1232
aaaaccaaac caaaactaaa tcca                                        24

<210> SEQ ID NO 1233
<211> LENGTH: 24
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 1233
caataacccc caaaactaaa ctca                                        24

<210> SEQ ID NO 1234
<211> LENGTH: 25
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 1234
aacaaaaaca aatccaaata tacca                                       25

<210> SEQ ID NO 1235
<211> LENGTH: 23
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 1235
caaccctaaa catctaaaca cca                                         23

<210> SEQ ID NO 1236
<211> LENGTH: 18
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 1236
tcattccact ccaaccca                                               18
```

<210> SEQ ID NO 1237
<211> LENGTH: 25
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 1237
tctaaaaaat ctccctctta tctca                                        25

<210> SEQ ID NO 1238
<211> LENGTH: 19
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 1238
caacccttcc accctacca                                               19

<210> SEQ ID NO 1239
<211> LENGTH: 24
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 1239
cacaaatcct aaaataccaa aaca                                         24

<210> SEQ ID NO 1240
<211> LENGTH: 26
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 1240
caaaactaca ataaaccaaa ctcaca                                       26

<210> SEQ ID NO 1241
<211> LENGTH: 24
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 1241
cccatataaa atacaccacc ctca                                         24

<210> SEQ ID NO 1242
<211> LENGTH: 21
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 1242
tcccatcccc taataatcac a                                            21

```
<210> SEQ ID NO 1243
<211> LENGTH: 29
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 1243
cataacaata acaaacatct cttatacca                                          29

<210> SEQ ID NO 1244
<211> LENGTH: 24
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 1244
aaactataac ccaacccaac taca                                               24

<210> SEQ ID NO 1245
<211> LENGTH: 26
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 1245
aaacactaaa ccataaaatc tcaaca                                             26

<210> SEQ ID NO 1246
<211> LENGTH: 25
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 1246
aaccctacaa tctacacaaa tacca                                              25

<210> SEQ ID NO 1247
<211> LENGTH: 27
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 1247
ccctatattc acacacaata ctattca                                            27

<210> SEQ ID NO 1248
<211> LENGTH: 25
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 1248
ctaaccaacc taacaactct caaca                                              25

<210> SEQ ID NO 1249
<211> LENGTH: 21
```

```
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 1249
cacaccacac acacacacac a                                              21

<210> SEQ ID NO 1250
<211> LENGTH: 26
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 1250
caaaaccaat tatctttata accaca                                         26

<210> SEQ ID NO 1251
<211> LENGTH: 25
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 1251
cacatacaca aaaacaaaa acaca                                           25

<210> SEQ ID NO 1252
<211> LENGTH: 23
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 1252
tcctcacccc aaataaaaac tca                                            23

<210> SEQ ID NO 1253
<211> LENGTH: 23
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 1253
cctacaccca aatttccatt aca                                            23

<210> SEQ ID NO 1254
<211> LENGTH: 23
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 1254
aaatcacaat ccaacctcta cca                                            23

<210> SEQ ID NO 1255
<211> LENGTH: 24
<212> TYPE: DNA
<213> ORGANISM: Artificial Sequence
```

```
<220> FEATURE:
<223> OTHER INFORMATION: Description of Artificial Sequence: Synthetic
      probe

<400> SEQUENCE: 1255
aatacccaaa aacaataacc aaca                                              24

<210> SEQ ID NO 1256
<211> LENGTH: 25
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 1256
tcaaacaaca aaacaataac ctaca                                             25

<210> SEQ ID NO 1257
<211> LENGTH: 28
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 1257
tcttcatcaa aacatctata aatcatca                                          28

<210> SEQ ID NO 1258
<211> LENGTH: 24
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 1258
actccaaaac tacccaaacc taca                                              24

<210> SEQ ID NO 1259
<211> LENGTH: 23
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 1259
actccacaat ccctaaactt cca                                               23

<210> SEQ ID NO 1260
<211> LENGTH: 25
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 1260
aacacaactt atccctactt accca                                             25

<210> SEQ ID NO 1261
<211> LENGTH: 24
<212> TYPE: DNA
<213> ORGANISM: Artificial Sequence
<220> FEATURE:
<223> OTHER INFORMATION: Description of Artificial Sequence: Synthetic
```

```
                                   probe

<400> SEQUENCE: 1261
attaacccaa acaataaccc taca                                           24

<210> SEQ ID NO 1262
<211> LENGTH: 23
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 1262
tttctctcaa accacttatc cca                                            23

<210> SEQ ID NO 1263
<211> LENGTH: 23
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 1263
cacaaaacca aaaactccta cca                                            23

<210> SEQ ID NO 1264
<211> LENGTH: 26
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 1264
acacaatccc tttaaatact cataca                                         26

<210> SEQ ID NO 1265
<211> LENGTH: 23
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 1265
ccccaaaaac actcaaatac tca                                            23

<210> SEQ ID NO 1266
<211> LENGTH: 23
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 1266
acaaacacaa acaaacccac aca                                            23

<210> SEQ ID NO 1267
<211> LENGTH: 23
<212> TYPE: DNA
<213> ORGANISM: Artificial Sequence
<220> FEATURE:
<223> OTHER INFORMATION: Description of Artificial Sequence: Synthetic
      probe
```

```
<400> SEQUENCE: 1267
aaacaaaccc aacctcttac tca                                             23

<210> SEQ ID NO 1268
<211> LENGTH: 27
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 1268
caaacaaacc aaaatcttta taacaca                                         27

<210> SEQ ID NO 1269
<211> LENGTH: 24
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 1269
aacaaatcac ctttacctct tcca                                            24

<210> SEQ ID NO 1270
<211> LENGTH: 24
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 1270
acccactaaa aacaaaactc atca                                            24

<210> SEQ ID NO 1271
<211> LENGTH: 24
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 1271
aaacaataaa ccctacctcc aaca                                            24

<210> SEQ ID NO 1272
<211> LENGTH: 23
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 1272
atcctctaca tcctcaccaa aca                                             23

<210> SEQ ID NO 1273
<211> LENGTH: 26
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 1273
```
aaccaatact cactaaacac aacaca                                              26

<210> SEQ ID NO 1274
<211> LENGTH: 29
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 1274
cacaacctat accctttata aaatacaca                                           29

<210> SEQ ID NO 1275
<211> LENGTH: 29
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 1275
tctacttctt aacactaacc tcaataaca                                           29

<210> SEQ ID NO 1276
<211> LENGTH: 24
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 1276
ctacctaacc atcctcaaat ttca                                                24

<210> SEQ ID NO 1277
<211> LENGTH: 24
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 1277
ccttcctcaa aatctaacaa ttca                                                24

<210> SEQ ID NO 1278
<211> LENGTH: 24
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 1278
ccactccaaa taaaactacc acca                                                24

<210> SEQ ID NO 1279
<211> LENGTH: 23
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 1279
cccacccaat aatcaaataa aca                                                 23

```
<210> SEQ ID NO 1280
<211> LENGTH: 24
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 1280
cacccataat taccataatt tcca                                          24

<210> SEQ ID NO 1281
<211> LENGTH: 23
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 1281
accacaccca acctaatacc aca                                           23

<210> SEQ ID NO 1282
<211> LENGTH: 26
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 1282
cacaaacaat aaacacaaac tctaca                                        26

<210> SEQ ID NO 1283
<211> LENGTH: 20
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 1283
aaaacccaac ataacccaca                                               20

<210> SEQ ID NO 1284
<211> LENGTH: 22
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 1284
aaaataaccc tatccttccc ca                                            22

<210> SEQ ID NO 1285
<211> LENGTH: 22
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 1285
cccataaaca cccaaatatc ca                                            22

<210> SEQ ID NO 1286
```

<211> LENGTH: 29
<212> TYPE: DNA
<213> ORGANISM: Artificial Sequence
<220> FEATURE:
<223> OTHER INFORMATION: Description of Artificial Sequence: Synthetic probe

<400> SEQUENCE: 1286
actcaacata ttaaaacata ttcctaaca                                          29

<210> SEQ ID NO 1287
<211> LENGTH: 25
<212> TYPE: DNA
<213> ORGANISM: Artificial Sequence
<220> FEATURE:
<223> OTHER INFORMATION: Description of Artificial Sequence: Synthetic probe

<400> SEQUENCE: 1287
cccacattac ttaaaaactc aaaca                                              25

<210> SEQ ID NO 1288
<211> LENGTH: 24
<212> TYPE: DNA
<213> ORGANISM: Artificial Sequence
<220> FEATURE:
<223> OTHER INFORMATION: Description of Artificial Sequence: Synthetic probe

<400> SEQUENCE: 1288
acaatcaaat aaccacacaa caca                                               24

<210> SEQ ID NO 1289
<211> LENGTH: 24
<212> TYPE: DNA
<213> ORGANISM: Artificial Sequence
<220> FEATURE:
<223> OTHER INFORMATION: Description of Artificial Sequence: Synthetic probe

<400> SEQUENCE: 1289
caacctaacc ctttaaatct tcca                                               24

<210> SEQ ID NO 1290
<211> LENGTH: 23
<212> TYPE: DNA
<213> ORGANISM: Artificial Sequence
<220> FEATURE:
<223> OTHER INFORMATION: Description of Artificial Sequence: Synthetic probe

<400> SEQUENCE: 1290 tcttttctt aaccctaccc cca                                                 23

<210> SEQ ID NO 1291
<211> LENGTH: 25
<212> TYPE: DNA
<213> ORGANISM: Artificial Sequence
<220> FEATURE:
<223> OTHER INFORMATION: Description of Artificial Sequence: Synthetic probe

<400> SEQUENCE: 1291
cctacccata caatactaaa atcca                                              25

<210> SEQ ID NO 1292
<211> LENGTH: 28
<212> TYPE: DNA

```
<213> ORGANISM: Artificial Sequence
<220> FEATURE:
<223> OTHER INFORMATION: Description of Artificial Sequence: Synthetic
      probe

<400> SEQUENCE: 1292
ttatattatt aatcaccaac aaacaaca                                          28

<210> SEQ ID NO 1293
<211> LENGTH: 24
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 1293
catctccctt cattattcat tcca                                              24

<210> SEQ ID NO 1294
<211> LENGTH: 27
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 1294
tccttcttcc taaatactca taacaca                                           27

<210> SEQ ID NO 1295
<211> LENGTH: 22
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 1295
caacctaacc caacaaacaa ca                                                22

<210> SEQ ID NO 1296
<211> LENGTH: 24
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 1296
aactctacaa atcccaaaat ctca                                              24

<210> SEQ ID NO 1297
<211> LENGTH: 26
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 1297
acacaaaacc caactatata aaaaca                                            26

<210> SEQ ID NO 1298
<211> LENGTH: 24
<212> TYPE: DNA
<213> ORGANISM: Artificial Sequence
<220> FEATURE:
```

<223> OTHER INFORMATION: Description of Artificial Sequence: Synthetic
      probe

<400> SEQUENCE: 1298
actcactaca acctctacct ccca                                           24

<210> SEQ ID NO 1299
<211> LENGTH: 23
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 1299
ccacataatc acacaacatc tca                                            23

<210> SEQ ID NO 1300
<211> LENGTH: 27
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 1300
ttcaccatat taaccaaact aatctca                                        27

<210> SEQ ID NO 1301
<211> LENGTH: 24
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 1301
cttttaaccc taacctttaa ccca                                           24

<210> SEQ ID NO 1302
<211> LENGTH: 23
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 1302
ccctaacttt taacctttcc cca                                            23

<210> SEQ ID NO 1303
<211> LENGTH: 25
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 1303
ccaaaacaaa acttacttca caaca                                          25

<210> SEQ ID NO 1304
<211> LENGTH: 23
<212> TYPE: DNA
<213> ORGANISM: Artificial Sequence
<220> FEATURE:
<223> OTHER INFORMATION: Description of Artificial Sequence: Synthetic
      probe

```
<400> SEQUENCE: 1304
aaaaccctaa aaactaaacc cca                                            23

<210> SEQ ID NO 1305
<211> LENGTH: 27
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 1305
ataataaacc ctacaccttc tatctca                                        27

<210> SEQ ID NO 1306
<211> LENGTH: 24
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 1306
caaaaaatac aaaacccact acca                                           24

<210> SEQ ID NO 1307
<211> LENGTH: 24
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 1307
cacaacctaa aaattaccca tcca                                           24

<210> SEQ ID NO 1308
<211> LENGTH: 24
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 1308
tccccttcat tacaacaaac taca                                           24

<210> SEQ ID NO 1309
<211> LENGTH: 23
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 1309
aaacaactct caaaccctat cca                                            23

<210> SEQ ID NO 1310
<211> LENGTH: 23
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 1310
```
catctctact cccaccacat tca                                               23

<210> SEQ ID NO 1311
<211> LENGTH: 23
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 1311
tcaatcatat ttccaaaatc cca                                               23

<210> SEQ ID NO 1312
<211> LENGTH: 26
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 1312
ttcctaatca ccctctatct tctaca                                            26

<210> SEQ ID NO 1313
<211> LENGTH: 24
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 1313
ataaaaaatc accctaacca aaca                                              24

<210> SEQ ID NO 1314
<211> LENGTH: 27
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 1314
aataaataac ctaatcactt caaacca                                           27

<210> SEQ ID NO 1315
<211> LENGTH: 24
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 1315
tctcccctta caacctttct aaca                                              24

<210> SEQ ID NO 1316
<211> LENGTH: 24
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 1316
tcacctcaat acctctatct caca                                              24

```
<210> SEQ ID NO 1317
<211> LENGTH: 26
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 1317
ccaccacata ccactcataa tattca                                              26

<210> SEQ ID NO 1318
<211> LENGTH: 23
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 1318
ttaacactca atcccccttaa aca                                                23

<210> SEQ ID NO 1319
<211> LENGTH: 23
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 1319
aaaacaaatt caaacccaac aca                                                 23

<210> SEQ ID NO 1320
<211> LENGTH: 24
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 1320
caatcaaccc aataaaacac aaca                                                24

<210> SEQ ID NO 1321
<211> LENGTH: 24
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 1321
aacaaacaac caaatacacc ttca                                                24

<210> SEQ ID NO 1322
<211> LENGTH: 24
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 1322
cacacaaaaa tactaaacct ccca                                                24
```

<210> SEQ ID NO 1323
<211> LENGTH: 24
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 1323
cacacacaaa taacttcacc ctca                                          24

<210> SEQ ID NO 1324
<211> LENGTH: 27
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 1324
cataacccct tataactaaa caaaaca                                       27

<210> SEQ ID NO 1325
<211> LENGTH: 20
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 1325
actcctacaa aaccccaca                                                20

<210> SEQ ID NO 1326
<211> LENGTH: 24
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 1326
acaataacca ccttcctatt tcca                                          24

<210> SEQ ID NO 1327
<211> LENGTH: 23
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 1327
caccacctaa aacctaaaaa cca                                           23

<210> SEQ ID NO 1328
<211> LENGTH: 24
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 1328
ccaaatctta acaaacaacc aaca                                          24

<210> SEQ ID NO 1329
<211> LENGTH: 23

```
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 1329
ctcctctcct caacactaat cca                                                23

<210> SEQ ID NO 1330
<211> LENGTH: 24
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 1330
aaaaataaca acctaacccc taca                                               24

<210> SEQ ID NO 1331
<211> LENGTH: 20
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 1331
cccaaaacct aactccctca                                                    20

<210> SEQ ID NO 1332
<211> LENGTH: 21
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 1332
caccaatcaa caccaacctc a                                                  21

<210> SEQ ID NO 1333
<211> LENGTH: 25
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 1333
cacactcaat tacttaacaa cctca                                              25

<210> SEQ ID NO 1334
<211> LENGTH: 23
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 1334
atctcaactc atcacaacct cca                                                23

<210> SEQ ID NO 1335
<211> LENGTH: 21
<212> TYPE: DNA
<213> ORGANISM: Artificial Sequence
```

```
<220> FEATURE:
<223> OTHER INFORMATION: Description of Artificial Sequence: Synthetic
      probe

<400> SEQUENCE: 1335
ataactctac ccctccccc a                                              21

<210> SEQ ID NO 1336
<211> LENGTH: 26
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 1336
caaaacacct aaattaccta caacca                                        26

<210> SEQ ID NO 1337
<211> LENGTH: 24
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 1337
aacttcactt tctccctctc ttca                                          24

<210> SEQ ID NO 1338
<211> LENGTH: 25
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 1338
aatcaaacac ataactttaa cccca                                         25

<210> SEQ ID NO 1339
<211> LENGTH: 24
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 1339
ttccccactc ttattaactt tcca                                          24

<210> SEQ ID NO 1340
<211> LENGTH: 24
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 1340
tcccaccaac tctataatca aaca                                          24

<210> SEQ ID NO 1341
<211> LENGTH: 25
<212> TYPE: DNA
<213> ORGANISM: Artificial Sequence
<220> FEATURE:
<223> OTHER INFORMATION: Description of Artificial Sequence: Synthetic
```

```
                                                        probe

<400> SEQUENCE: 1341
caaattctct aactcacttc cttca                                               25

<210> SEQ ID NO 1342
<211> LENGTH: 24
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 1342
cactaacttt ttcaaacctt tcca                                                24

<210> SEQ ID NO 1343
<211> LENGTH: 25
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 1343
cacaacatat aaacaccacc tctca                                               25

<210> SEQ ID NO 1344
<211> LENGTH: 24
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 1344
ctcccaaatc aactctaaca ctca                                                24

<210> SEQ ID NO 1345
<211> LENGTH: 23
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 1345 aaacaccctaa acttccaact cca                                                23

<210> SEQ ID NO 1346
<211> LENGTH: 25
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 1346
ttttcattaa taaaaccaac caaca                                               25

<210> SEQ ID NO 1347
<211> LENGTH: 24
<212> TYPE: DNA
<213> ORGANISM: Artificial Sequence
<220> FEATURE:
<223> OTHER INFORMATION: Description of Artificial Sequence: Synthetic
      probe
```

-continued

```
<400> SEQUENCE: 1347
aaaaacctac taactccacc caca                                             24

<210> SEQ ID NO 1348
<211> LENGTH: 23
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 1348
caacccaacc tctatcaaaa aca                                              23

<210> SEQ ID NO 1349
<211> LENGTH: 27
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 1349
ttccctataa cataacctta aaaaaca                                          27

<210> SEQ ID NO 1350
<211> LENGTH: 25
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 1350
aacaaatcac aaaatcaaaa attca                                            25

<210> SEQ ID NO 1351
<211> LENGTH: 25
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 1351
caataactca actcacaacc tctca                                            25

<210> SEQ ID NO 1352
<211> LENGTH: 24
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 1352
atccttaacc tacctcaacc tcca                                             24

<210> SEQ ID NO 1353
<211> LENGTH: 27
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 1353
```

-continued aaccaaccta aaaactaaaa aataaca    27

<210> SEQ ID NO 1354
<211> LENGTH: 26
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 1354
aaaatcttac tatatctccc aaacca    26

<210> SEQ ID NO 1355
<211> LENGTH: 24
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 1355
caaaaatcat accattacac tcca    24

<210> SEQ ID NO 1356
<211> LENGTH: 21
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 1356
accattacca acaatccacc a    21

<210> SEQ ID NO 1357
<211> LENGTH: 23
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 1357
aattaaacca accttctttc cca    23

<210> SEQ ID NO 1358
<211> LENGTH: 21
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 1358
ctcatccact ccatctctcc a    21

<210> SEQ ID NO 1359
<211> LENGTH: 23
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 1359
aaatcatcct ccctcactaa cca    23

<210> SEQ ID NO 1360
<211> LENGTH: 23
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 1360
tccccaaaca taataaaacc aca                                              23

<210> SEQ ID NO 1361
<211> LENGTH: 26
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 1361
cacctaacta acacaaacat ttctca                                           26

<210> SEQ ID NO 1362
<211> LENGTH: 24
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 1362
ccaatctcta atatccacct ctca                                             24

<210> SEQ ID NO 1363
<211> LENGTH: 24
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 1363
aaaccaactc aaaacaaaca ctca                                             24

<210> SEQ ID NO 1364
<211> LENGTH: 25
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 1364
cattcattaa aatacctacc cctca                                            25

<210> SEQ ID NO 1365
<211> LENGTH: 24
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 1365
accttttcaa ttactcacaa tcca                                             24

<210> SEQ ID NO 1366

```
<211> LENGTH: 24
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 1366
aacactttaa ccaatcaaca aaca                                          24

<210> SEQ ID NO 1367
<211> LENGTH: 26
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 1367
ccatttctat acaaaccta cttcca                                         26

<210> SEQ ID NO 1368
<211> LENGTH: 24
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 1368
caaaaattca acctcaatca aaca                                          24

<210> SEQ ID NO 1369
<211> LENGTH: 26
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 1369
caaaaataaa cattctaacc ctcaca                                        26

<210> SEQ ID NO 1370
<211> LENGTH: 23
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 1370
acctcccact caatcaaact aca                                           23

<210> SEQ ID NO 1371
<211> LENGTH: 26
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 1371
tccactacaa tattactcca aatcca                                        26

<210> SEQ ID NO 1372
<211> LENGTH: 23
<212> TYPE: DNA
```

```
<213> ORGANISM: Artificial Sequence
<220> FEATURE:
<223> OTHER INFORMATION: Description of Artificial Sequence: Synthetic
      probe

<400> SEQUENCE: 1372
aacaaaaact cccttaaacc cca                                           23

<210> SEQ ID NO 1373
<211> LENGTH: 25
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 1373
cccaaatcca acattaataa aaaca                                         25

<210> SEQ ID NO 1374
<211> LENGTH: 21
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 1374
cctaacttaa atccccctcc a                                             21

<210> SEQ ID NO 1375
<211> LENGTH: 28
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 1375
ccaaaacacc ctatataaaa caactaca                                      28

<210> SEQ ID NO 1376
<211> LENGTH: 22
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 1376
ccaaaaccaa tcaaaacaaa ca                                            22

<210> SEQ ID NO 1377
<211> LENGTH: 25
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 1377
ctccaacttt aacttcttca aaaca                                         25

<210> SEQ ID NO 1378
<211> LENGTH: 26
<212> TYPE: DNA
<213> ORGANISM: Artificial Sequence
<220> FEATURE:
```

```
<223> OTHER INFORMATION: Description of Artificial Sequence: Synthetic
      probe

<400> SEQUENCE: 1378
ctcttctcca ctctaaaaca ataaca                                              26

<210> SEQ ID NO 1379
<211> LENGTH: 25
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 1379
aaaaaattat tttctccaca tttca                                               25

<210> SEQ ID NO 1380
<211> LENGTH: 25
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 1380
tttacatcat tttaccaatt tcaca                                               25

<210> SEQ ID NO 1381
<211> LENGTH: 20
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 1381
caatcattcc caaccactca                                                     20

<210> SEQ ID NO 1382
<211> LENGTH: 24
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 1382
ccccaacacc actataatat acca                                                24

<210> SEQ ID NO 1383
<211> LENGTH: 24
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 1383
aaaaccccat tttctatcaa aaca                                                24

<210> SEQ ID NO 1384
<211> LENGTH: 24
<212> TYPE: DNA
<213> ORGANISM: Artificial Sequence
<220> FEATURE:
<223> OTHER INFORMATION: Description of Artificial Sequence: Synthetic
      probe
```

```
<400> SEQUENCE: 1384
aaaatataaa caatcacaac ccca                                          24

<210> SEQ ID NO 1385
<211> LENGTH: 25
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 1385
tttctacact ttcctaaaat tccca                                         25

<210> SEQ ID NO 1386
<211> LENGTH: 24
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 1386
aaacatccct caattaaata acca                                          24

<210> SEQ ID NO 1387
<211> LENGTH: 21
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 1387
cctctcttct aaaccctccc a                                             21

<210> SEQ ID NO 1388
<211> LENGTH: 25
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 1388
aaatccaaaa aataaccaaa aaaca                                         25

<210> SEQ ID NO 1389
<211> LENGTH: 25
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 1389
caaacaccaa acaaaacaaa ctaca                                         25

<210> SEQ ID NO 1390
<211> LENGTH: 24
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 1390
```
caatctcaac tcactacaac ctca                                    24

<210> SEQ ID NO 1391
<211> LENGTH: 28
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 1391
caaaatcaca ctactacact cctaaaca                                28

<210> SEQ ID NO 1392
<211> LENGTH: 23
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 1392
acaccaattt aaaaaccaac cca                                     23

<210> SEQ ID NO 1393
<211> LENGTH: 25
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 1393
cacacaatac aaaacctaca aacca                                   25

<210> SEQ ID NO 1394
<211> LENGTH: 24
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 1394
cccacaataa catcaaccaa taca                                    24

<210> SEQ ID NO 1395
<211> LENGTH: 25
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 1395
caaaacactt cttcaaattc ctaca                                   25

<210> SEQ ID NO 1396
<211> LENGTH: 26
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 1396
aaatcaacaa tcaaataaac caatca                                  26

```
<210> SEQ ID NO 1397
<211> LENGTH: 26
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 1397
tcctactact cccactaatt cctaca                                           26

<210> SEQ ID NO 1398
<211> LENGTH: 25
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 1398
cctaaaaaat caatcaaatt ttcca                                            25

<210> SEQ ID NO 1399
<211> LENGTH: 26
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 1399
tctcctccta caactccata actaca                                           26

<210> SEQ ID NO 1400
<211> LENGTH: 27
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 1400
aactctaaca ttacaaacct cacttca                                          27

<210> SEQ ID NO 1401
<211> LENGTH: 26
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 1401
caacttccac atctaaacta cttcca                                           26

<210> SEQ ID NO 1402
<211> LENGTH: 27
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 1402
ttcctactac tacttctacc actccca                                          27
```

-continued

```
<210> SEQ ID NO 1403
<211> LENGTH: 22
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 1403
acactcaaca accatacccca ca                                              22

<210> SEQ ID NO 1404
<211> LENGTH: 24
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 1404
aacttaaacc tcaaacaaat caca                                             24

<210> SEQ ID NO 1405
<211> LENGTH: 23
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 1405
atcttccaac aaatttccta cca                                              23

<210> SEQ ID NO 1406
<211> LENGTH: 26
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 1406
caatacattc cttttcatca aaatca                                           26

<210> SEQ ID NO 1407
<211> LENGTH: 24
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 1407
cattaccaac aacttttaaa tcca                                             24

<210> SEQ ID NO 1408
<211> LENGTH: 23
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 1408
aaaacaaact ccacctaaca cca                                              23

<210> SEQ ID NO 1409
<211> LENGTH: 25
```

```
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 1409
ataccaaaca cctataccctt aacca                                            25

<210> SEQ ID NO 1410
<211> LENGTH: 25
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 1410
ctataaaaca accaaaacac aaaca                                             25

<210> SEQ ID NO 1411
<211> LENGTH: 24
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 1411
tttcaaaaac taacaaacca aaca                                              24

<210> SEQ ID NO 1412
<211> LENGTH: 17
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 1412
atcccctcaa cccaaca                                                      17

<210> SEQ ID NO 1413
<211> LENGTH: 26
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 1413
ccaccttaac acatatccta atctca                                            26

<210> SEQ ID NO 1414
<211> LENGTH: 26
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 1414
caaaaatcca cattaaacca aataca                                            26

<210> SEQ ID NO 1415
<211> LENGTH: 24
<212> TYPE: DNA
<213> ORGANISM: Artificial Sequence
```

```
<220> FEATURE:
<223> OTHER INFORMATION: Description of Artificial Sequence: Synthetic
      probe

<400> SEQUENCE: 1415
caaaaaccaa aacttaaatc ctca                                              24

<210> SEQ ID NO 1416
<211> LENGTH: 19
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 1416
acaaaaccca aaaccccca                                                    19

<210> SEQ ID NO 1417
<211> LENGTH: 28
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 1417
actaacctat caacctctaa tacactca                                          28

<210> SEQ ID NO 1418
<211> LENGTH: 25
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 1418
tccaaacaca actcaattta aaaca                                             25

<210> SEQ ID NO 1419
<211> LENGTH: 23
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 1419
aacccctaaa tccatctttc aca                                               23

<210> SEQ ID NO 1420
<211> LENGTH: 24
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 1420
ccccattcta tctaccctat ctca                                              24

<210> SEQ ID NO 1421
<211> LENGTH: 23
<212> TYPE: DNA
<213> ORGANISM: Artificial Sequence
<220> FEATURE:
<223> OTHER INFORMATION: Description of Artificial Sequence: Synthetic
```

```
                                      probe

<400> SEQUENCE: 1421
cctaaaaaac acctaaaccc aca                                             23

<210> SEQ ID NO 1422
<211> LENGTH: 24
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 1422
acaaacaaaa ataacatttt ccca                                            24

<210> SEQ ID NO 1423
<211> LENGTH: 24
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 1423
tcacaaccaa aacaaactac aaca                                            24

<210> SEQ ID NO 1424
<211> LENGTH: 25
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 1424
tcatcttaca atcacataac catca                                           25

<210> SEQ ID NO 1425
<211> LENGTH: 28
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 1425
catacactaa ctccaaaaca actaaaca                                        28

<210> SEQ ID NO 1426
<211> LENGTH: 23
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 1426
actctacccc aaccacaact aca                                             23

<210> SEQ ID NO 1427
<211> LENGTH: 23
<212> TYPE: DNA
<213> ORGANISM: Artificial Sequence
<220> FEATURE:
<223> OTHER INFORMATION: Description of Artificial Sequence: Synthetic
      probe
```

-continued

```
<400> SEQUENCE: 1427
acccaacaaa cttttcctttt tca                                           23

<210> SEQ ID NO 1428
<211> LENGTH: 25
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 1428
cacacaatta atatcctacc ctcca                                          25

<210> SEQ ID NO 1429
<211> LENGTH: 21
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 1429
tccccaatac aaaccacaac a                                              21

<210> SEQ ID NO 1430
<211> LENGTH: 26
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 1430
aaccaaaaca ctactcctaa ctcaca                                         26

<210> SEQ ID NO 1431
<211> LENGTH: 23
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 1431
cataaaccaa aaacaacatc cca                                            23

<210> SEQ ID NO 1432
<211> LENGTH: 23
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 1432
aaacaaacac aaacaaaaca cca                                            23

<210> SEQ ID NO 1433
<211> LENGTH: 28
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 1433
```

-continued caataccota taaacctaat cattaaca                                28

<210> SEQ ID NO 1434
<211> LENGTH: 23
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 1434
tacatctacc ctccacatct cca                                     23

<210> SEQ ID NO 1435
<211> LENGTH: 28
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 1435
cccaaaacac tcaataaaca ataataca                                28

<210> SEQ ID NO 1436
<211> LENGTH: 23
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 1436
aacccctaac tacttcaacc tca                                     23

<210> SEQ ID NO 1437
<211> LENGTH: 23
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 1437
acaaatctta aaccctaatc cca                                     23

<210> SEQ ID NO 1438
<211> LENGTH: 22
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 1438
cccttctata taaacctccc ca                                      22

<210> SEQ ID NO 1439
<211> LENGTH: 19
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 1439
aaacaactat ccccaccca                                          19

```
<210> SEQ ID NO 1440
<211> LENGTH: 24
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 1440
tccttactac cacacattta acca                                              24

<210> SEQ ID NO 1441
<211> LENGTH: 24
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 1441
ttcaaatctt atcaaacacc ctca                                              24

<210> SEQ ID NO 1442
<211> LENGTH: 24
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 1442
caaacccaac ctatatccaa atca                                              24

<210> SEQ ID NO 1443
<211> LENGTH: 25
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 1443
aacaatacta aaaacacccc tctca                                             25

<210> SEQ ID NO 1444
<211> LENGTH: 24
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 1444
ccctttaacc actaacctaa tcca                                              24

<210> SEQ ID NO 1445
<211> LENGTH: 24
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 1445
ccacccaaaa caactacact atca                                              24

<210> SEQ ID NO 1446
```

```
<211> LENGTH: 23
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 1446
aaattacccc acaacctaaa cca                                            23

<210> SEQ ID NO 1447
<211> LENGTH: 23
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 1447
aaccacacaa atcccactta tca                                            23

<210> SEQ ID NO 1448
<211> LENGTH: 23
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 1448
aacaccaaac aaaacaaaaa cca                                            23

<210> SEQ ID NO 1449
<211> LENGTH: 26
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 1449
cacacaacac attacaaaca aataca                                         26

<210> SEQ ID NO 1450
<211> LENGTH: 27
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 1450
cacactctct cacttttata aaaaca                                         27

<210> SEQ ID NO 1451
<211> LENGTH: 25
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 1451
aaattacaca aaccattcta accca                                          25

<210> SEQ ID NO 1452
<211> LENGTH: 26
<212> TYPE: DNA
```

```
<213> ORGANISM: Artificial Sequence
<220> FEATURE:
<223> OTHER INFORMATION: Description of Artificial Sequence: Synthetic
      probe

<400> SEQUENCE: 1452
aaacaaaaaa ctatccacct tacaca                                              26

<210> SEQ ID NO 1453
<211> LENGTH: 23
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 1453
actcactctt atccccacct aca                                                 23

<210> SEQ ID NO 1454
<211> LENGTH: 22
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 1454
cccaccaaca tcctaaatac ca                                                  22

<210> SEQ ID NO 1455
<211> LENGTH: 21
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 1455
aactacacaa cccaaaccac a                                                   21

<210> SEQ ID NO 1456
<211> LENGTH: 19
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 1456
acctcaaatc ctccaacca                                                      19

<210> SEQ ID NO 1457
<211> LENGTH: 23
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 1457
acccaaatac aactacccaa aca                                                 23

<210> SEQ ID NO 1458
<211> LENGTH: 25
<212> TYPE: DNA
<213> ORGANISM: Artificial Sequence
<220> FEATURE:
```

<223> OTHER INFORMATION: Description of Artificial Sequence: Synthetic
      probe

<400> SEQUENCE: 1458
ccaaaccaac tcaaatctac ctaca                                      25

<210> SEQ ID NO 1459
<211> LENGTH: 24
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 1459
aaactctaac aacccatcct aaca                                       24

<210> SEQ ID NO 1460
<211> LENGTH: 24
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 1460
acttacatcc tctaaatttc ccca                                       24

<210> SEQ ID NO 1461
<211> LENGTH: 23
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 1461
aacaacttaa tccccctaac cca                                        23

<210> SEQ ID NO 1462
<211> LENGTH: 26
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 1462
aatataacaa ccaatcctac tctcca                                     26

<210> SEQ ID NO 1463
<211> LENGTH: 23
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 1463
tcctaaaaac ccttaaccct cca                                        23

<210> SEQ ID NO 1464
<211> LENGTH: 27
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 1464
aactactatt ctctcctatt tccctca                                                27

<210> SEQ ID NO 1465
<211> LENGTH: 24
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 1465
ataaaacttt ctccccaaaa aaca                                                   24

<210> SEQ ID NO 1466
<211> LENGTH: 24
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 1466
aaattcctcc acttaaacta ccca                                                   24

<210> SEQ ID NO 1467
<211> LENGTH: 23
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 1467
aaactcaaaa ccctccaaaa tca                                                    23

<210> SEQ ID NO 1468
<211> LENGTH: 25
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 1468
ctctaactaa actcaacaac ctcca                                                  25

<210> SEQ ID NO 1469
<211> LENGTH: 26
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 1469
aaaaccttaa ctaacacaaa accaca                                                 26

<210> SEQ ID NO 1470
<211> LENGTH: 25
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 1470
ccaaatctca ctcctaaatt caaca                                             25

<210> SEQ ID NO 1471
<211> LENGTH: 23
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 1471
aaaaaacctc tacccaaaaa cca                                               23

<210> SEQ ID NO 1472
<211> LENGTH: 24
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 1472
aaaatacaaa ctacttcacc ccca                                              24

<210> SEQ ID NO 1473
<211> LENGTH: 23
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 1473
ccaacccaaa acctactcct aca                                               23

<210> SEQ ID NO 1474
<211> LENGTH: 26
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 1474
ctctaaattt aaattaccct cctcca                                            26

<210> SEQ ID NO 1475
<211> LENGTH: 25
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 1475
aacccctcta attatctctt tacca                                             25

<210> SEQ ID NO 1476
<211> LENGTH: 24
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 1476
acaacctatc caaatcacaa aaca                                              24

<210> SEQ ID NO 1477
<211> LENGTH: 25
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 1477
cttacaaatc tcccaaataa aatca                                        25

<210> SEQ ID NO 1478
<211> LENGTH: 18
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 1478
acaaacactc ccctccca                                                18

<210> SEQ ID NO 1479
<211> LENGTH: 24
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 1479
caaaacctca atctaaaaac caca                                         24

<210> SEQ ID NO 1480
<211> LENGTH: 19
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 1480
acccctcccc aaataatca                                               19

<210> SEQ ID NO 1481
<211> LENGTH: 28
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 1481
catattatat cctaccattt aataccca                                     28

<210> SEQ ID NO 1482
<211> LENGTH: 25
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 1482
ttaaaactca acctcacaaa tcaca                                        25

-continued

<210> SEQ ID NO 1483
<211> LENGTH: 25
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 1483
ccaaaaccaa taactttaca aaaca                                           25

<210> SEQ ID NO 1484
<211> LENGTH: 25
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 1484
aaacaaataa aataccacct ccaca                                           25

<210> SEQ ID NO 1485
<211> LENGTH: 25
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 1485
aattcaaaaa accacaaaaa tttca                                           25

<210> SEQ ID NO 1486
<211> LENGTH: 26
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 1486
ttaaaacacc taaacttaaa acctca                                          26

<210> SEQ ID NO 1487
<211> LENGTH: 23
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 1487
ataaaaacca acccaaattt cca                                             23

<210> SEQ ID NO 1488
<211> LENGTH: 23
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 1488
caccacatac acactacaca cca                                             23

<210> SEQ ID NO 1489
<211> LENGTH: 23

```
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 1489
cacacacaca aaccacatac aca                                              23

<210> SEQ ID NO 1490
<211> LENGTH: 19
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 1490
aaaacaaaca ccaacccca                                                   19

<210> SEQ ID NO 1491
<211> LENGTH: 26
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 1491
caaacataca tacaacaatc ctctca                                           26

<210> SEQ ID NO 1492
<211> LENGTH: 25
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 1492
caaactccta aactcaaaca atcca                                            25

<210> SEQ ID NO 1493
<211> LENGTH: 24
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 1493
aacaatactc aaaaccaaa acca                                              24

<210> SEQ ID NO 1494
<211> LENGTH: 25
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 1494
cacactccct actaaaccta aatca                                            25

<210> SEQ ID NO 1495
<211> LENGTH: 23
<212> TYPE: DNA
<213> ORGANISM: Artificial Sequence
```

```
<220> FEATURE:
<223> OTHER INFORMATION: Description of Artificial Sequence: Synthetic
      probe

<400> SEQUENCE: 1495
ccaacctcaa ctcacaaaat aca                                            23

<210> SEQ ID NO 1496
<211> LENGTH: 24
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 1496
ataacatcac aacccaaata acca                                           24

<210> SEQ ID NO 1497
<211> LENGTH: 24
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 1497
ataccacctc accccctaaac taca                                          24

<210> SEQ ID NO 1498
<211> LENGTH: 26
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 1498
caataccaac caactaaact aaacca                                         26

<210> SEQ ID NO 1499
<211> LENGTH: 24
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 1499
caacaaataa ccaaacaaac acca                                           24

<210> SEQ ID NO 1500
<211> LENGTH: 24
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 1500
accaaaacaa aacaaaaaac aaca                                           24

<210> SEQ ID NO 1501
<211> LENGTH: 23
<212> TYPE: DNA
<213> ORGANISM: Artificial Sequence
<220> FEATURE:
<223> OTHER INFORMATION: Description of Artificial Sequence: Synthetic
```

```
      probe

<400> SEQUENCE: 1501
acaactaccc aaacaaaacc aca                                            23

<210> SEQ ID NO 1502
<211> LENGTH: 24
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 1502
cacataaaat caaaccacaa aaca                                           24

<210> SEQ ID NO 1503
<211> LENGTH: 25
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 1503
tccaaaccaa cttatctatc ctaca                                          25

<210> SEQ ID NO 1504
<211> LENGTH: 25
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 1504
ttacaaacct aaaattcctc tttca                                          25

<210> SEQ ID NO 1505
<211> LENGTH: 23
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 1505
aaacaaaaac tacaactctc cca                                            23

<210> SEQ ID NO 1506
<211> LENGTH: 24
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 1506
accaatacac tccaaaccta aaca                                           24

<210> SEQ ID NO 1507
<211> LENGTH: 27
<212> TYPE: DNA
<213> ORGANISM: Artificial Sequence
<220> FEATURE:
<223> OTHER INFORMATION: Description of Artificial Sequence: Synthetic
      probe
```

```
<400> SEQUENCE: 1507
cactaaaatt acaaacataa accacca                                            27

<210> SEQ ID NO 1508
<211> LENGTH: 24
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 1508
actcaaaccc tctaacctca aaca                                               24

<210> SEQ ID NO 1509
<211> LENGTH: 41
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 1509
cccctggagc ggcccctggg cgaggtgtac ctggacagca g                            41

<210> SEQ ID NO 1510
<211> LENGTH: 41
<212> TYPE: DNA
<213> ORGANISM: Artificial Sequence
<220> FEATURE:
<223> OTHER INFORMATION: Description of Artificial Sequence: Synthetic
      probe
<220> FEATURE:
<223> OTHER INFORMATION: Description of Combined DNA/RNA Molecule:
      Synthetic probe

<400> SEQUENCE: 1510
uuuutggagu gguuuutggg cgaggtgtau utggauagua g                            41

<210> SEQ ID NO 1511
<211> LENGTH: 19
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 1511
aaaaacctcr ccaaaaacc                                                     19

<210> SEQ ID NO 1512
<211> LENGTH: 21
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 1512
gctccacata aacctatcat c                                                  21

<210> SEQ ID NO 1513
<211> LENGTH: 21
<212> TYPE: DNA
<213> ORGANISM: Artificial Sequence
<220> FEATURE:
<223> OTHER INFORMATION: Description of Artificial Sequence: Synthetic
      probe
```

-continued

<400> SEQUENCE: 1513
actccacata aacctatcat c   21

<210> SEQ ID NO 1514
<211> LENGTH: 17
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 1514
gtaaaacgac ggccagt   17

<210> SEQ ID NO 1515
<211> LENGTH: 16
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 1515
caggaacagc tatgac   16

<210> SEQ ID NO 1516
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 1516
tggtgatgga ggaggtttag taagt   25

<210> SEQ ID NO 1517
<211> LENGTH: 27
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 1517
aaccaataaa acctactcct cccttaa   27

<210> SEQ ID NO 1518
<211> LENGTH: 26
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 1518
gttttgggtt tggcggattt tgacgc   26

<210> SEQ ID NO 1519
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 1519
cccgcaaata aacgacaatc gcgac					25

<210> SEQ ID NO 1520
<211> LENGTH: 27
<212> TYPE: DNA
<213> ORGANISM: Artificial Sequence
<220> FEATURE:
<223> OTHER INFORMATION: Description of Artificial Sequence: Synthetic primer

<400> SEQUENCE: 1520
ggttttgggt ttggtggatt ttgatgt					27

<210> SEQ ID NO 1521
<211> LENGTH: 28
<212> TYPE: DNA
<213> ORGANISM: Artificial Sequence
<220> FEATURE:
<223> OTHER INFORMATION: Description of Artificial Sequence: Synthetic primer

<400> SEQUENCE: 1521
catcccacaa ataaacaaca atcacaac					28

<210> SEQ ID NO 1522
<211> LENGTH: 26
<212> TYPE: DNA
<213> ORGANISM: Artificial Sequence
<220> FEATURE:
<223> OTHER INFORMATION: Description of Artificial Sequence: Synthetic primer

<400> SEQUENCE: 1522
acgcgatccc tttaaatact cgtacg					26

<210> SEQ ID NO 1523
<211> LENGTH: 24
<212> TYPE: DNA
<213> ORGANISM: Artificial Sequence
<220> FEATURE:
<223> OTHER INFORMATION: Description of Artificial Sequence: Synthetic primer

<400> SEQUENCE: 1523
gaggagagac gggaggtcgt ttcg					24

<210> SEQ ID NO 1524
<211> LENGTH: 30
<212> TYPE: DNA
<213> ORGANISM: Artificial Sequence
<220> FEATURE:
<223> OTHER INFORMATION: Description of Artificial Sequence: Synthetic primer

<400> SEQUENCE: 1524
atatacacaa tccctttaaa tactcataca					30

<210> SEQ ID NO 1525
<211> LENGTH: 25
<212> TYPE: DNA
<213> ORGANISM: Artificial Sequence
<220> FEATURE:
<223> OTHER INFORMATION: Description of Artificial Sequence: Synthetic primer

<400> SEQUENCE: 1525
ggaggagaga tgggaggttg ttttg					25

<210> SEQ ID NO 1526
<211> LENGTH: 27
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 1526
tccgaaaaaa tctacgaccc aaattcg                                       27

<210> SEQ ID NO 1527
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 1527
agacgggtat aggtatttcg cgagc                                         25

<210> SEQ ID NO 1528
<211> LENGTH: 29
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 1528
tctccaaaaa aatctacaac ccaaattca                                     29

<210> SEQ ID NO 1529
<211> LENGTH: 28
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 1529
gttagatggg tataggtatt ttgtgagt                                      28

<210> SEQ ID NO 1530
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 1530
tacggagatt acggcggcgt tattc                                         25

<210> SEQ ID NO 1531
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 1531
aacgcgaaaa acgacgacgc gcga                                          24

```
<210> SEQ ID NO 1532
<211> LENGTH: 28
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 1532
gggtatggag attatggtgg tgttattt                                          28

<210> SEQ ID NO 1533
<211> LENGTH: 29
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 1533
ccaaaaacac aaaaaacaac aacacacaa                                         29

<210> SEQ ID NO 1534
<211> LENGTH: 27
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 1534
ttaaaaccct ctaaccgaaa acttccg                                           27

<210> SEQ ID NO 1535
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 1535
acgattagcg cggtattttc gtcgg                                             25

<210> SEQ ID NO 1536
<211> LENGTH: 29
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 1536
ctttaaaacc ctctaaccaa aaacttcca                                         29

<210> SEQ ID NO 1537
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 1537
tttttatgat tagtgtggta ttttttgttgg                                       30

<210> SEQ ID NO 1538
<211> LENGTH: 29
```

```
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 1538
gtagtttatt tttatttttta gtagattaa                                    29

<210> SEQ ID NO 1539
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 1539
aaaaccaaaa tctcaaccaa tc                                            22

<210> SEQ ID NO 1540
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 1540 atttttttgga aaagtggaat tagtt                                        25

<210> SEQ ID NO 1541
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 1541
ccaaataaat caacaacaac atcac                                         25

<210> SEQ ID NO 1542
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 1542
tagtttttgt gtttttgttt ttgt                                          24

<210> SEQ ID NO 1543
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 1543
ataacttaat tacactctct cattcataat                                    30

<210> SEQ ID NO 1544
<211> LENGTH: 23
<212> TYPE: DNA
<213> ORGANISM: Artificial Sequence
```

```
<220> FEATURE:
<223> OTHER INFORMATION: Description of Artificial Sequence: Synthetic
      primer

<400> SEQUENCE: 1544
gttgtaggga gtttgggttt att                                         23

<210> SEQ ID NO 1545
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 1545
cctaaaaaat cttcatcaca aaatc                                       25

<210> SEQ ID NO 1546
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 1546
gagaaggggt agaagttttt gaaat                                       25

<210> SEQ ID NO 1547
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 1547
atctcctacc aacaaaacta ccaac                                       25

<210> SEQ ID NO 1548
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 1548
ttttgtagtt attgttgttt ttttt                                       25

<210> SEQ ID NO 1549
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 1549
caaatttcaa aatcttacaa acctc                                       25

<210> SEQ ID NO 1550
<211> LENGTH: 25
<212> TYPE: DNA
<213> ORGANISM: Artificial Sequence
<220> FEATURE:
<223> OTHER INFORMATION: Description of Artificial Sequence: Synthetic
```

```
                           primer

<400> SEQUENCE: 1550
tttgagaatt tgtaaagaga aatga                                              25

<210> SEQ ID NO 1551
<211> LENGTH: 26
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 1551
aatataaaaa ccctaaaaac aaatac                                             26

<210> SEQ ID NO 1552
<211> LENGTH: 28
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 1552
agtaaatagt gggtgagtta tgaagatg                                           28

<210> SEQ ID NO 1553
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 1553
tacaccaaac cctaactaaa aaacc                                              25

<210> SEQ ID NO 1554
<211> LENGTH: 41
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 1554
ggggauutug uuggggauuu gctuuauatg gauutgtugt u                            41

<210> SEQ ID NO 1555
<211> LENGTH: 49
<212> TYPE: DNA
<213> ORGANISM: Homo sapiens

<400> SEQUENCE: 1555
gatgcctctc gggtggtgac tccagscagg aacttgaaga agcgctttg                    49

<210> SEQ ID NO 1556
<211> LENGTH: 45
<212> TYPE: DNA
<213> ORGANISM: Homo sapiens

<400> SEQUENCE: 1556
tcccatatga gcgtgtggcc catsttgcca tccacacctg cccct                        45
```

<210> SEQ ID NO 1557
<211> LENGTH: 49
<212> TYPE: DNA
<213> ORGANISM: Homo sapiens

<400> SEQUENCE: 1557
gcgccctgcg cgattggcca aasggtggcc cacgattggc tgagaccct          49

<210> SEQ ID NO 1558
<211> LENGTH: 46
<212> TYPE: DNA
<213> ORGANISM: Homo sapiens

<400> SEQUENCE: 1558
cgattggcca aacgggtggc ccasattggc tgagaccctg gccccc             46

<210> SEQ ID NO 1559
<211> LENGTH: 50
<212> TYPE: DNA
<213> ORGANISM: Homo sapiens

<400> SEQUENCE: 1559
ctaagcacct gccgggagca gggggscacc gggaactcgc agatttcgcc          50

<210> SEQ ID NO 1560
<211> LENGTH: 50
<212> TYPE: DNA
<213> ORGANISM: Homo sapiens

<400> SEQUENCE: 1560
agtagattaa cgcacaggtg ggggcgsctc gggacatagc tgcgctaggg          50

<210> SEQ ID NO 1561
<211> LENGTH: 51
<212> TYPE: DNA
<213> ORGANISM: Homo sapiens

<400> SEQUENCE: 1561
ctgcatcggt gtggccacgc tcagscagac acctcgggcg gcttgtcagc a        51

<210> SEQ ID NO 1562
<211> LENGTH: 51
<212> TYPE: DNA
<213> ORGANISM: Homo sapiens

<400> SEQUENCE: 1562
tgtaaagaga ggcacgtggt taagctctsg ggtgtggact ccaccagtct c        51

<210> SEQ ID NO 1563
<211> LENGTH: 50
<212> TYPE: DNA
<213> ORGANISM: Homo sapiens

<400> SEQUENCE: 1563
aagcaaatgg gatgccacct ccgsgggctc gctcctcgcg aggtgctcac          50

<210> SEQ ID NO 1564
<211> LENGTH: 42
<212> TYPE: DNA
<213> ORGANISM: Homo sapiens

<400> SEQUENCE: 1564
aggaggagga ggaaggcagg ctcsgggaag ctggtggcag cg                  42

<210> SEQ ID NO 1565
<211> LENGTH: 50
<212> TYPE: DNA
<213> ORGANISM: Homo sapiens

<400> SEQUENCE: 1565
cgttgccaac tggacctaaa gagaggcscg actgtcgccc acctgcggga             50

<210> SEQ ID NO 1566
<211> LENGTH: 47
<212> TYPE: DNA
<213> ORGANISM: Homo sapiens

<400> SEQUENCE: 1566
aaacccacac tcgatggatc cascggccgt ggaaacacct gccgccc                47

<210> SEQ ID NO 1567
<211> LENGTH: 46
<212> TYPE: DNA
<213> ORGANISM: Homo sapiens

<400> SEQUENCE: 1567
gctggaggac ctccccagcg gasccccaggt ccctggtcgg gctccc                46

<210> SEQ ID NO 1568
<211> LENGTH: 49
<212> TYPE: DNA
<213> ORGANISM: Homo sapiens

<400> SEQUENCE: 1568
tgtgatcaga gagatctgga agaaatsttc tattaactgg atgcttggg              49

<210> SEQ ID NO 1569
<211> LENGTH: 49
<212> TYPE: DNA
<213> ORGANISM: Homo sapiens

<400> SEQUENCE: 1569
attgcacgtg tgcccgggac ttcagsataa gtgtttcggt gttcctgcg              49

<210> SEQ ID NO 1570
<211> LENGTH: 51
<212> TYPE: DNA
<213> ORGANISM: Homo sapiens

<400> SEQUENCE: 1570
cggggaggtc tgcggcccag gttsattcct gcgacttgtc ctaggcaggc c           51

<210> SEQ ID NO 1571
<211> LENGTH: 52
<212> TYPE: DNA
<213> ORGANISM: Homo sapiens

<400> SEQUENCE: 1571
tgtcctaggc aggcctgtat gtgcgcggsg ccgcgtgctg tacagtgtga gg          52

<210> SEQ ID NO 1572
<211> LENGTH: 53
<212> TYPE: DNA
<213> ORGANISM: Homo sapiens

<400> SEQUENCE: 1572
aaacgctcgc gggatacctg tgccstctag ccaagagtgc accgtgtgc gcg          53

<210> SEQ ID NO 1573
<211> LENGTH: 51
<212> TYPE: DNA
<213> ORGANISM: Homo sapiens

<400> SEQUENCE: 1573
ggtccaattg tataaatgaa aaatagggcs ccacggcagg ggctggaaga c         51

<210> SEQ ID NO 1574
<211> LENGTH: 47
<212> TYPE: DNA
<213> ORGANISM: Homo sapiens

<400> SEQUENCE: 1574
tattcctggg agagaggcgt tctcasgaca gccaccctgg ggaggag               47

<210> SEQ ID NO 1575
<211> LENGTH: 53
<212> TYPE: DNA
<213> ORGANISM: Homo sapiens

<400> SEQUENCE: 1575
ctcacatttt ggacatacgc tgactcsagg caactgggcg cacacatatc ccc        53

<210> SEQ ID NO 1576
<211> LENGTH: 51
<212> TYPE: DNA
<213> ORGANISM: Homo sapiens

<400> SEQUENCE: 1576
ccagaagacc aggcagatgg gtggacsgtg agcagcaggg cagcccctgt g          51

<210> SEQ ID NO 1577
<211> LENGTH: 49
<212> TYPE: DNA
<213> ORGANISM: Homo sapiens

<400> SEQUENCE: 1577
ggtttaggga cggaaggcac taaagscttc ggaagtgacc atgaatgag             49

<210> SEQ ID NO 1578
<211> LENGTH: 50
<212> TYPE: DNA
<213> ORGANISM: Homo sapiens

<400> SEQUENCE: 1578
aatcctctgc atcctcgccg ggscgcgatc ggcagctgac ggcctaacaa            50

<210> SEQ ID NO 1579
<211> LENGTH: 51
<212> TYPE: DNA
<213> ORGANISM: Homo sapiens

<400> SEQUENCE: 1579
gggcgatgag ccctgcctcc agsggtggcg ctcgagtccg gctgaacggc g          51

<210> SEQ ID NO 1580
<211> LENGTH: 52
<212> TYPE: DNA
<213> ORGANISM: Homo sapiens

<400> SEQUENCE: 1580
agccgcctcc cagaacagga aggaagctsa ggaacaaagg gggccccaac ag         52

<210> SEQ ID NO 1581
<211> LENGTH: 49
<212> TYPE: DNA
<213> ORGANISM: Homo sapiens

<400> SEQUENCE: 1581
tccccgggga gcagtctacc gctaggsgcg gctgctaaga gaggaaccc         49

<210> SEQ ID NO 1582
<211> LENGTH: 51
<212> TYPE: DNA
<213> ORGANISM: Homo sapiens

<400> SEQUENCE: 1582
tgtggagagg aacaaccaca gacgcggsgc ttagctaggc gctctggaag t       51

<210> SEQ ID NO 1583
<211> LENGTH: 51
<212> TYPE: DNA
<213> ORGANISM: Homo sapiens

<400> SEQUENCE: 1583
ggacatgggt ctcactggag gtcagscagc aagctctgat gtccgtagag g       51

<210> SEQ ID NO 1584
<211> LENGTH: 55
<212> TYPE: DNA
<213> ORGANISM: Homo sapiens

<400> SEQUENCE: 1584
agtggagagc actgactgcc acacttgsag gctgtcctga ggcactgaaa gcccc    55

<210> SEQ ID NO 1585
<211> LENGTH: 50
<212> TYPE: DNA
<213> ORGANISM: Homo sapiens

<400> SEQUENCE: 1585
tgggccgcaa aggcgagcta cttagascac cccggtgagc tcggccatgc          50

<210> SEQ ID NO 1586
<211> LENGTH: 49
<212> TYPE: DNA
<213> ORGANISM: Homo sapiens

<400> SEQUENCE: 1586
catggccgag ctcaccgggg tgstctaagt agctcgcctt tgcggccca           49

<210> SEQ ID NO 1587
<211> LENGTH: 49
<212> TYPE: DNA
<213> ORGANISM: Homo sapiens

<400> SEQUENCE: 1587
cccactggcc ggcgtgccgt gatsatcgca ggctgcgtca ggagcctcc           49

<210> SEQ ID NO 1588
<211> LENGTH: 51
<212> TYPE: DNA
<213> ORGANISM: Homo sapiens

<400> SEQUENCE: 1588
cgatcgcagg ctgcgtcagg agcctccsgc gtataaatag gggtggcaga a        51

```
<210> SEQ ID NO 1589
<211> LENGTH: 51
<212> TYPE: DNA
<213> ORGANISM: Homo sapiens

<400> SEQUENCE: 1589
agcttgaagc tcccggctgc ggagscgcgg ctgcctcagc aagtcagtct c        51

<210> SEQ ID NO 1590
<211> LENGTH: 49
<212> TYPE: DNA
<213> ORGANISM: Homo sapiens

<400> SEQUENCE: 1590
accacccaca cactgcaaca sttaaagcca tctgcggctt cattctcag             49

<210> SEQ ID NO 1591
<211> LENGTH: 48
<212> TYPE: DNA
<213> ORGANISM: Homo sapiens

<400> SEQUENCE: 1591
ccagttgcct cactccaaca gscgcagttg tgcccggcga ggatgccg               48

<210> SEQ ID NO 1592
<211> LENGTH: 52
<212> TYPE: DNA
<213> ORGANISM: Homo sapiens

<400> SEQUENCE: 1592
tttgagtcgc cacactcatg tctsaccgag cctggctcgc tgcgtctgag cg         52

<210> SEQ ID NO 1593
<211> LENGTH: 49
<212> TYPE: DNA
<213> ORGANISM: Homo sapiens

<400> SEQUENCE: 1593
gcgcagcttt gggaccctct agcsgagact tccggcagct gcctccgac             49

<210> SEQ ID NO 1594
<211> LENGTH: 50
<212> TYPE: DNA
<213> ORGANISM: Homo sapiens

<400> SEQUENCE: 1594
ggacgaccct ggctgcgccg gctgscgtcc ccgccttgga acttttttgcc           50

<210> SEQ ID NO 1595
<211> LENGTH: 52
<212> TYPE: DNA
<213> ORGANISM: Homo sapiens

<400> SEQUENCE: 1595
agggagcatc caatcggctg gcgsaggccc cggcgctgct ttgcataaag ca         52

<210> SEQ ID NO 1596
<211> LENGTH: 49
<212> TYPE: DNA
<213> ORGANISM: Homo sapiens

<400> SEQUENCE: 1596
ccctggtctg cggcgttctc tcsgaatctt gccctgggcc gcggacgcc             49
```

<210> SEQ ID NO 1597
<211> LENGTH: 53
<212> TYPE: DNA
<213> ORGANISM: Homo sapiens

<400> SEQUENCE: 1597
agcattcctg cgggcttttg ctcgasatcc cctgctgagg ctgtcgcggc gag        53

<210> SEQ ID NO 1598
<211> LENGTH: 48
<212> TYPE: DNA
<213> ORGANISM: Homo sapiens

<400> SEQUENCE: 1598
ggcgagcggc caggtgcgcc ttsgcaggac agtgctaatt ccagcccc              48

<210> SEQ ID NO 1599
<211> LENGTH: 48
<212> TYPE: DNA
<213> ORGANISM: Homo sapiens

<400> SEQUENCE: 1599
tttccttagg ccctttggtt tcscctacgg agaggtttcc cccattgg              48

<210> SEQ ID NO 1600
<211> LENGTH: 45
<212> TYPE: DNA
<213> ORGANISM: Homo sapiens

<400> SEQUENCE: 1600
cagagattga gggaggggtt gaggsgagtc tgcaatgggg gctgt                 45

<210> SEQ ID NO 1601
<211> LENGTH: 49
<212> TYPE: DNA
<213> ORGANISM: Homo sapiens

<400> SEQUENCE: 1601
ggcaaaaggc agggactgca agcgggscgc accgggtagg aagagcggc             49

<210> SEQ ID NO 1602
<211> LENGTH: 54
<212> TYPE: DNA
<213> ORGANISM: Homo sapiens

<400> SEQUENCE: 1602
acaggccgcc acaacgaaga acgacgccgs aggcctgcaa gatcctgaaa cttg       54

<210> SEQ ID NO 1603
<211> LENGTH: 50
<212> TYPE: DNA
<213> ORGANISM: Homo sapiens

<400> SEQUENCE: 1603
cctggccagg cagagctgct gggagstcag cagggagaga aaacgctcgg            50

<210> SEQ ID NO 1604
<211> LENGTH: 49
<212> TYPE: DNA
<213> ORGANISM: Homo sapiens

<400> SEQUENCE: 1604
cagggaggca ctccgggagg tcccgstgcc cgtccaggga gcaatgcgt             49

<210> SEQ ID NO 1605
<211> LENGTH: 51
<212> TYPE: DNA
<213> ORGANISM: Homo sapiens

<400> SEQUENCE: 1605
cccgcccccg cgatggagaa gaaacsagac agaaggtgca gggcccacta c    51

<210> SEQ ID NO 1606
<211> LENGTH: 51
<212> TYPE: DNA
<213> ORGANISM: Homo sapiens

<400> SEQUENCE: 1606
acagaaggtg cagggcccac tacscttcct ccagatgagc tcatgggttt c    51

<210> SEQ ID NO 1607
<211> LENGTH: 48
<212> TYPE: DNA
<213> ORGANISM: Homo sapiens

<400> SEQUENCE: 1607
gggggtcacc atgggcagag gacatsgttc ggagccagat cacgggcc    48

<210> SEQ ID NO 1608
<211> LENGTH: 51
<212> TYPE: DNA
<213> ORGANISM: Homo sapiens

<400> SEQUENCE: 1608
cggggtgtgc gtccagccgt tgggsctttc tttttggacc tcggggccat c    51

<210> SEQ ID NO 1609
<211> LENGTH: 46
<212> TYPE: DNA
<213> ORGANISM: Homo sapiens

<400> SEQUENCE: 1609
gtagtccttt ggatgttggg gagstcagac tgggtcgttg tagagg    46

<210> SEQ ID NO 1610
<211> LENGTH: 23
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 1610
aaacgcttct tcaaattcct acg    23

<210> SEQ ID NO 1611
<211> LENGTH: 23
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 1611
ccatataaac gtataaccca tcg    23

<210> SEQ ID NO 1612
<211> LENGTH: 20

```
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 1612
cctacgcgat taaccaaacg                                                    20

<210> SEQ ID NO 1613
<211> LENGTH: 22
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 1613
aaaccaaaat ctcaaccaat cg                                                 22

<210> SEQ ID NO 1614
<211> LENGTH: 23
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 1614
gaaatctacg aattcccgat acg                                                23

<210> SEQ ID NO 1615
<211> LENGTH: 22
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 1615
taacgcaact atatcccgaa cg                                                 22

<210> SEQ ID NO 1616
<211> LENGTH: 22
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 1616
atcgatataa ccacgctcaa cg                                                 22

<210> SEQ ID NO 1617
<211> LENGTH: 22
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 1617
aactaataaa atccacaccc cg                                                 22

<210> SEQ ID NO 1618
<211> LENGTH: 21
<212> TYPE: DNA
<213> ORGANISM: Artificial Sequence
```

```
<220> FEATURE:
<223> OTHER INFORMATION: Description of Artificial Sequence: Synthetic
      probe

<400> SEQUENCE: 1618
aaataaaata ccacctccgc g                                              21

<210> SEQ ID NO 1619
<211> LENGTH: 19
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 1619
gctaccacca acttccccg                                                 19

<210> SEQ ID NO 1620
<211> LENGTH: 20
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 1620
gcaaataaac gacaatcgcg                                                20

<210> SEQ ID NO 1621
<211> LENGTH: 20
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 1621
ccacactcga taaatccacg                                                20

<210> SEQ ID NO 1622
<211> LENGTH: 19
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 1622
aaaacctccc caacgaacg                                                 19

<210> SEQ ID NO 1623
<211> LENGTH: 24
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 1623
cccaaacatc caattaataa aacg                                           24

<210> SEQ ID NO 1624
<211> LENGTH: 23
<212> TYPE: DNA
<213> ORGANISM: Artificial Sequence
<220> FEATURE:
<223> OTHER INFORMATION: Description of Artificial Sequence: Synthetic
``` probe

<400> SEQUENCE: 1624
caaaaacacc gaaacactta tcg                                              23

<210> SEQ ID NO 1625
<211> LENGTH: 22
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 1625
aaaaatctac gacccaaatt cg                                               22

<210> SEQ ID NO 1626
<211> LENGTH: 21
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 1626
acactataca acacgcgacc g                                                21

<210> SEQ ID NO 1627
<211> LENGTH: 21
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 1627
ctcgcgaaat acctataccc g                                                21

<210> SEQ ID NO 1628
<211> LENGTH: 20
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 1628
ttccaacccc taccgtaacg                                                  20

<210> SEQ ID NO 1629
<211> LENGTH: 23
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 1629
ctcctcccca aataactat ccg                                               23

<210> SEQ ID NO 1630
<211> LENGTH: 24
<212> TYPE: DNA
<213> ORGANISM: Artificial Sequence
<220> FEATURE:
<223> OTHER INFORMATION: Description of Artificial Sequence: Synthetic
      probe

```
<400> SEQUENCE: 1630
cattttaaac atacgctaac tccg                                            24

<210> SEQ ID NO 1631
<211> LENGTH: 24
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 1631
caaaaactac cctactactc accg                                            24

<210> SEQ ID NO 1632
<211> LENGTH: 23
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 1632
cattcataat cacttccgaa acg                                             23

<210> SEQ ID NO 1633
<211> LENGTH: 19
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 1633
tctacatcct cgccgaacg                                                  19

<210> SEQ ID NO 1634
<211> LENGTH: 21
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 1634
cgataaaccc tacctccaac g                                               21

<210> SEQ ID NO 1635
<211> LENGTH: 23
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 1635
attaaaaccc cctttattcc tcg                                             23

<210> SEQ ID NO 1636
<211> LENGTH: 19
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 1636
```

```
cctctcttaa caaccgccg                                               19
```

<210> SEQ ID NO 1637
<211> LENGTH: 21
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 1637

```
ccaaaacgcc taactaaacc g                                            21
```

<210> SEQ ID NO 1638
<211> LENGTH: 27
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 1638

```
cctctacgaa catcaaaact tactacg                                      27
```

<210> SEQ ID NO 1639
<211> LENGTH: 26
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 1639

```
aaaaaacact aactaccaca cttacg                                       26
```

<210> SEQ ID NO 1640
<211> LENGTH: 23
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 1640

```
ataaccgaac tcaccgaaat acg                                          23
```

<210> SEQ ID NO 1641
<211> LENGTH: 23
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 1641

```
ataaccgaac tcaccgaaat acg                                          23
```

<210> SEQ ID NO 1642
<211> LENGTH: 22
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 1642

```
actaaccgac gtaccgtaat cg                                           22
```

<210> SEQ ID NO 1643
<211> LENGTH: 23
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 1643
ctaccacccc tatttatacg ccg                                            23

<210> SEQ ID NO 1644
<211> LENGTH: 23
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 1644
ttaaaactcc cgactacgaa acg                                            23

<210> SEQ ID NO 1645
<211> LENGTH: 20
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 1645
cacccacaca ctacaacacg                                                20

<210> SEQ ID NO 1646
<211> LENGTH: 22
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 1646
caattacctc actccaacaa cg                                             22

<210> SEQ ID NO 1647
<211> LENGTH: 23
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 1647
taaatcgcca cactcatatc tcg                                            23

<210> SEQ ID NO 1648
<211> LENGTH: 23
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 1648
gcaactttaa aaccctctaa ccg                                            23

<210> SEQ ID NO 1649

```
<211> LENGTH: 21
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 1649
accctaacta cgccgactac g                                                 21

<210> SEQ ID NO 1650
<211> LENGTH: 21
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 1650
aacatccaat cgactaacgc g                                                 21

<210> SEQ ID NO 1651
<211> LENGTH: 23
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 1651
cctaatctac gacgttctct ccg                                               23

<210> SEQ ID NO 1652
<211> LENGTH: 24
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 1652
attcctacga acttttactc gacg                                              24

<210> SEQ ID NO 1653
<211> LENGTH: 20
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 1653
aacgaccaaa tacgccttcg                                                   20

<210> SEQ ID NO 1654
<211> LENGTH: 23
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 1654
ttccttaaac cctttaattt ccg                                               23

<210> SEQ ID NO 1655
<211> LENGTH: 20
<212> TYPE: DNA
```

```
<213> ORGANISM: Artificial Sequence
<220> FEATURE:
<223> OTHER INFORMATION: Description of Artificial Sequence: Synthetic
      probe

<400> SEQUENCE: 1655
aacccccatt acaaactccg                                                    20

<210> SEQ ID NO 1656
<211> LENGTH: 19
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 1656
tcttcctacc cgatacgcg                                                     19

<210> SEQ ID NO 1657
<211> LENGTH: 24
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 1657
aatttcaaaa tcttacaaac ctcg                                               24

<210> SEQ ID NO 1658
<211> LENGTH: 24
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 1658
gaacgttttc tctccctact aacg                                               24

<210> SEQ ID NO 1659
<211> LENGTH: 23
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 1659
gcattactcc ctaaacgaac acg                                                23

<210> SEQ ID NO 1660
<211> LENGTH: 24
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 1660 ataaaccta caccttctat ctcg                                                24

<210> SEQ ID NO 1661
<211> LENGTH: 24
<212> TYPE: DNA
<213> ORGANISM: Artificial Sequence
<220> FEATURE:
```

<223> OTHER INFORMATION: Description of Artificial Sequence: Synthetic
      probe

<400> SEQUENCE: 1661
caaaaaatac aaaacccact accg                                              24

<210> SEQ ID NO 1662
<211> LENGTH: 21
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 1662
ccgtaatcta actccgaacc g                                                 21

<210> SEQ ID NO 1663
<211> LENGTH: 24
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 1663
aaatatacgt ccaaccgtta aacg                                              24

<210> SEQ ID NO 1664
<211> LENGTH: 23
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 1664
ctctacaacg acccaatcta acg                                               23

<210> SEQ ID NO 1665
<211> LENGTH: 25
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 1665
caaaacactt cttcaaattc ctaca                                             25

<210> SEQ ID NO 1666
<211> LENGTH: 25
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 1666
tcccatataa acatataacc catca                                             25

<210> SEQ ID NO 1667
<211> LENGTH: 24
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 1667
acaccctaca caattaacca aaca                                          24

<210> SEQ ID NO 1668
<211> LENGTH: 24
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 1668
aaaaaccaaa atctcaacca atca                                          24

<210> SEQ ID NO 1669
<211> LENGTH: 26
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 1669
aacaaaatct acaaattccc aataca                                        26

<210> SEQ ID NO 1670
<211> LENGTH: 25
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 1670
ccctaacaca actatatccc aaaca                                         25

<210> SEQ ID NO 1671
<211> LENGTH: 26
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 1671
ctacatcaat ataaccacac tcaaca                                        26

<210> SEQ ID NO 1672
<211> LENGTH: 24
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 1672
aaaactaata aaatccacac ccca                                          24

<210> SEQ ID NO 1673
<211> LENGTH: 25
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 1673
aaacaaataa aataccacct ccaca        25

<210> SEQ ID NO 1674
<211> LENGTH: 20
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 1674
cactaccacc aacttcccca        20

<210> SEQ ID NO 1675
<211> LENGTH: 24
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 1675
tcccacaaat aaacaacaat caca        24

<210> SEQ ID NO 1676
<211> LENGTH: 24
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 1676
aaacccacac tcaataaatc caca        24

<210> SEQ ID NO 1677
<211> LENGTH: 24
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 1677
actaaaaaac ctccccaaca aaca        24

<210> SEQ ID NO 1678
<211> LENGTH: 24
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 1678
cccaaacatc caattaataa aaca        24

<210> SEQ ID NO 1679
<211> LENGTH: 25
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 1679
cacaaaaaca ccaaaacact tatca        25

<210> SEQ ID NO 1680
<211> LENGTH: 25
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 1680
caaaaaaatc tacaacccaa attca                                              25

<210> SEQ ID NO 1681
<211> LENGTH: 25
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 1681
cctcacacta tacaacacac aacca                                              25

<210> SEQ ID NO 1682
<211> LENGTH: 26
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 1682
aaacactcac aaaataccta taccca                                             26

<210> SEQ ID NO 1683
<211> LENGTH: 23
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 1683
atcttccaac ccctaccata aca                                                23

<210> SEQ ID NO 1684
<211> LENGTH: 23
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 1684
ctcctcccca aaataactat cca                                                23

<210> SEQ ID NO 1685
<211> LENGTH: 28
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 1685
ctcacatttt aaacatacac taactcca                                           28

```
<210> SEQ ID NO 1686
<211> LENGTH: 26
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 1686
cacaaaaact accctactac tcacca                                           26

<210> SEQ ID NO 1687
<211> LENGTH: 25
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 1687
ctcattcata atcacttcca aaaca                                            25

<210> SEQ ID NO 1688
<211> LENGTH: 24
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 1688
aatcctctac atcctcacca aaca                                             24

<210> SEQ ID NO 1689
<211> LENGTH: 24
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 1689
aaacaataaa ccctacctcc aaca                                             24

<210> SEQ ID NO 1690
<211> LENGTH: 25
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 1690
ctattaaaac cccctttatt cctca                                            25

<210> SEQ ID NO 1691
<211> LENGTH: 24
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 1691
aaattcctct cttaacaacc acca                                             24

<210> SEQ ID NO 1692
<211> LENGTH: 25
```

-continued

```
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 1692
acttccaaaa cacctaacta aacca                                              25

<210> SEQ ID NO 1693
<211> LENGTH: 27
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 1693
cctctacaaa catcaaaact tactaca                                            27

<210> SEQ ID NO 1694
<211> LENGTH: 29
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 1694
aataaaaaac actaactacc acacttaca                                          29

<210> SEQ ID NO 1695
<211> LENGTH: 25
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 1695
acataaccaa actcaccaaa ataca                                              25

<210> SEQ ID NO 1696
<211> LENGTH: 24
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 1696
cataaccaaa ctcaccaaaa taca                                               24

<210> SEQ ID NO 1697
<211> LENGTH: 25
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 1697
cccactaacc aacataccat aatca                                              25

<210> SEQ ID NO 1698
<211> LENGTH: 25
<212> TYPE: DNA
<213> ORGANISM: Artificial Sequence
```

<220> FEATURE:
<223> OTHER INFORMATION: Description of Artificial Sequence: Synthetic
      probe

<400> SEQUENCE: 1698
ttctaccacc cctatttata cacca                                       25

<210> SEQ ID NO 1699
<211> LENGTH: 26
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 1699
aacttaaaac tcccaactac aaaaca                                      26

<210> SEQ ID NO 1700
<211> LENGTH: 22
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 1700
accacccaca cactacaaca ca                                          22

<210> SEQ ID NO 1701
<211> LENGTH: 23
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 1701
ccaattacct cactccaaca aca                                         23

<210> SEQ ID NO 1702
<211> LENGTH: 25
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 1702
tttaaatcac cacactcata tctca                                       25

<210> SEQ ID NO 1703
<211> LENGTH: 25
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 1703
acacaacttt aaaccctct aacca                                        25

<210> SEQ ID NO 1704
<211> LENGTH: 26
<212> TYPE: DNA
<213> ORGANISM: Artificial Sequence
<220> FEATURE:
<223> OTHER INFORMATION: Description of Artificial Sequence: Synthetic -continued probe

<400> SEQUENCE: 1704
aaacaaccct aactacacca actaca                                          26

<210> SEQ ID NO 1705
<211> LENGTH: 25
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 1705
aaaaaacatc caatcaacta acaca                                           25

<210> SEQ ID NO 1706
<211> LENGTH: 24
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 1706
ccctaatcta caacattctc tcca                                            24

<210> SEQ ID NO 1707
<211> LENGTH: 27
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 1707
aacattccta caaacttta ctcaaca                                          27

<210> SEQ ID NO 1708
<211> LENGTH: 24
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 1708
aacaaacaac caaatacacc ttca                                            24

<210> SEQ ID NO 1709
<211> LENGTH: 24
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 1709
tttccttaaa ccctttaatt tcca                                            24

<210> SEQ ID NO 1710
<211> LENGTH: 22
<212> TYPE: DNA
<213> ORGANISM: Artificial Sequence
<220> FEATURE:
<223> OTHER INFORMATION: Description of Artificial Sequence: Synthetic
      probe

```
<400> SEQUENCE: 1710
acaaccccca ttacaaactc ca                                              22

<210> SEQ ID NO 1711
<211> LENGTH: 24
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 1711
accactcttc ctacccaata caca                                            24

<210> SEQ ID NO 1712
<211> LENGTH: 26
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 1712
caaatttcaa aatcttacaa acctca                                          26

<210> SEQ ID NO 1713
<211> LENGTH: 26
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 1713
ccaaacattt tctctcccta ctaaca                                          26

<210> SEQ ID NO 1714
<211> LENGTH: 25
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 1714
acacattact ccctaaacaa acaca                                           25

<210> SEQ ID NO 1715
<211> LENGTH: 27
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 1715
ataataaacc ctacaccttc tatctca                                         27

<210> SEQ ID NO 1716
<211> LENGTH: 25
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 1716
```
acaaaaaata caaaacccac tacca                                        25

<210> SEQ ID NO 1717
<211> LENGTH: 24
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 1717
aacccataat ctaactccaa acca                                         24

<210> SEQ ID NO 1718
<211> LENGTH: 26
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 1718
caaaatatac atccaaccat taaaca                                       26

<210> SEQ ID NO 1719
<211> LENGTH: 24
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 1719
cctctacaac aacccaatct aaca                                         24

<210> SEQ ID NO 1720
<211> LENGTH: 23
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 1720
taaaatcacc acccgaaaaa cat                                          23

<210> SEQ ID NO 1721
<211> LENGTH: 20
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 1721
taccatccac acctacccct                                              20

<210> SEQ ID NO 1722
<211> LENGTH: 24
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 1722
ataacccacg attaactaaa accc                                         24

-continued

<210> SEQ ID NO 1723
<211> LENGTH: 21
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 1723
aaaccacccg tttaaccaat c                                              21

<210> SEQ ID NO 1724
<211> LENGTH: 24
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 1724
cccctactcc cgacaaatac ttaa                                           24

<210> SEQ ID NO 1725
<211> LENGTH: 24
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 1725
gcccccacct atacgttaat ctac                                           24

<210> SEQ ID NO 1726
<211> LENGTH: 24
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 1726
aaacacctcg aacgacttat caac                                           24

<210> SEQ ID NO 1727
<211> LENGTH: 26
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 1727
aaacttaacc acgtacctct ctttac                                         26

<210> SEQ ID NO 1728
<211> LENGTH: 21
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 1728
aactcgctcc tcgcgaaata c                                              21

<210> SEQ ID NO 1729

```
<211> LENGTH: 22
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 1729
aacctacctt cctcctcctc ct                                                  22

<210> SEQ ID NO 1730
<211> LENGTH: 26
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 1730
cctctcttta aatccaatta acaacg                                              26

<210> SEQ ID NO 1731
<211> LENGTH: 21
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 1731
gaccgtaaaa acacctaccg c                                                   21

<210> SEQ ID NO 1732
<211> LENGTH: 21
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 1732
ccaaatccct aatcgaactc c                                                   21

<210> SEQ ID NO 1733
<211> LENGTH: 25
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 1733
tttcttccaa atctctctaa tcaca                                               25

<210> SEQ ID NO 1734
<211> LENGTH: 24
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 1734
taaaatcccg aacacacgta caat                                                24

<210> SEQ ID NO 1735
<211> LENGTH: 26
<212> TYPE: DNA
```

<213> ORGANISM: Artificial Sequence
<220> FEATURE:
<223> OTHER INFORMATION: Description of Artificial Sequence: Synthetic
      probe

<400> SEQUENCE: 1735
ttcctacgac ttatcctaaa caaacc                                              26

<210> SEQ ID NO 1736
<211> LENGTH: 22
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 1736
cgcgcacata caaacctacc ta                                                  22

<210> SEQ ID NO 1737
<211> LENGTH: 25
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 1737
ctaaccaaaa atacacccgt atacg                                               25

<210> SEQ ID NO 1738
<211> LENGTH: 28
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 1738
ccctattttt catttataca attaaacc                                            28

<210> SEQ ID NO 1739
<211> LENGTH: 21
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 1739
aaaaacgcct ctctcccaaa a                                                   21

<210> SEQ ID NO 1740
<211> LENGTH: 24
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 1740
aacaactaaa cgcacacata tccc                                                24

<210> SEQ ID NO 1741
<211> LENGTH: 25
<212> TYPE: DNA
<213> ORGANISM: Artificial Sequence
<220> FEATURE:

<223> OTHER INFORMATION: Description of Artificial Sequence: Synthetic
      probe

<400> SEQUENCE: 1741
tccacccatc tacctaatct tctaa                                                25

<210> SEQ ID NO 1742
<211> LENGTH: 24
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 1742
tttaatacct tccgtcccta aacc                                                 24

<210> SEQ ID NO 1743
<211> LENGTH: 23
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 1743
gcgatcgaca actaacgacc taa                                                  23

<210> SEQ ID NO 1744
<211> LENGTH: 23
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 1744
ataacgctcg aatccgacta aac                                                  23

<210> SEQ ID NO 1745
<211> LENGTH: 25
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 1745
acttccttcc tattctaaaa aacga                                                25

<210> SEQ ID NO 1746
<211> LENGTH: 24
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 1746
ctaacgataa actactcccc gaaa                                                 24

<210> SEQ ID NO 1747
<211> LENGTH: 24
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 1747
cgcgtctata attattcctc tcca                                          24

<210> SEQ ID NO 1748
<211> LENGTH: 24
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 1748
taacctccaa taaaacccat atcc                                          24

<210> SEQ ID NO 1749
<211> LENGTH: 26
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 1749
aactatccta aaacactaaa aacccc                                        26

<210> SEQ ID NO 1750
<211> LENGTH: 24
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 1750
ctaaataact cgcctttacg accc                                          24

<210> SEQ ID NO 1751
<211> LENGTH: 23
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 1751
ctaaataact cgcctttacg acc                                           23

<210> SEQ ID NO 1752
<211> LENGTH: 22
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 1752
tcgcaaacta cgtcaaaaac ct                                            22

<210> SEQ ID NO 1753
<211> LENGTH: 24
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 1753

```
aaaactccta acgcaaccta cgat                                          24

<210> SEQ ID NO 1754
<211> LENGTH: 24
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 1754
gcgactacct caacaaatca atct                                          24

<210> SEQ ID NO 1755
<211> LENGTH: 26
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 1755
taaaaccatc tacgacttca ttctca                                        26

<210> SEQ ID NO 1756
<211> LENGTH: 23
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 1756
gcaattatac ccgacgaaaa tac                                           23

<210> SEQ ID NO 1757
<211> LENGTH: 24
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 1757
ccgaacctaa ctcgctacgt ctaa                                          24

<210> SEQ ID NO 1758
<211> LENGTH: 22
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 1758
aaacttccga caactacctc cg                                            22

<210> SEQ ID NO 1759
<211> LENGTH: 22
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 1759
gtccccgcct taaaactttt ta                                            22
```

<210> SEQ ID NO 1760
<211> LENGTH: 24
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 1760
aaccccgacg ctactttaca taaa                                          24

<210> SEQ ID NO 1761
<211> LENGTH: 21
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 1761
aatcttaccc taaaccgcga a                                             21

<210> SEQ ID NO 1762
<211> LENGTH: 22
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 1762
tcccctacta aaactatcgc ga                                            22

<210> SEQ ID NO 1763
<211> LENGTH: 24
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 1763
caaaacaata ctaattccaa cccc                                          24

<210> SEQ ID NO 1764
<211> LENGTH: 23
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 1764
ctacgaaaaa atttcccca tta                                            23

<210> SEQ ID NO 1765
<211> LENGTH: 23
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 1765
ctcaacccct ccctcaatct cta                                           23

```
<210> SEQ ID NO 1766
<211> LENGTH: 24
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 1766
ccgcttacaa tccctacctt ttac                                              24

<210> SEQ ID NO 1767
<211> LENGTH: 22
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 1767
gacgtcgttc ttcgttataa cg                                                22

<210> SEQ ID NO 1768
<211> LENGTH: 24
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 1768
tcccaacaac tctacctaac caaa                                              24

<210> SEQ ID NO 1769
<211> LENGTH: 21
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 1769
gaaacctccc gaaatacctc c                                                 21

<210> SEQ ID NO 1770
<211> LENGTH: 19
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 1770
tttcttctcc atcgcgaaa                                                    19

<210> SEQ ID NO 1771
<211> LENGTH: 26
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 1771
ttcctccaaa taaactcata aatttc                                            26

<210> SEQ ID NO 1772
<211> LENGTH: 24
```

```
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 1772
tatcctctac ccataataac cccc                                          24

<210> SEQ ID NO 1773
<211> LENGTH: 24
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 1773
tttcttttta aacctcgaaa ccat                                          24

<210> SEQ ID NO 1774
<211> LENGTH: 22
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 1774
tccccaacat ccaaaaaact ac                                            22

<210> SEQ ID NO 1775
<211> LENGTH: 24
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 1775
taaaatcacc acccaaaaaa catc                                          24

<210> SEQ ID NO 1776
<211> LENGTH: 20
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 1776
taccatccac acctacccct                                               20

<210> SEQ ID NO 1777
<211> LENGTH: 25
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 1777
ataacccaca attaactaaa accct                                         25

<210> SEQ ID NO 1778
<211> LENGTH: 22
<212> TYPE: DNA
<213> ORGANISM: Artificial Sequence
```

```
<220> FEATURE:
<223> OTHER INFORMATION: Description of Artificial Sequence: Synthetic
      probe

<400> SEQUENCE: 1778
aaaccaccca tttaaccaat ca                                              22

<210> SEQ ID NO 1779
<211> LENGTH: 24
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 1779
cccctactcc caacaaatac ttaa                                            24

<210> SEQ ID NO 1780
<211> LENGTH: 25
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 1780
acccccacct atacattaat ctact                                           25

<210> SEQ ID NO 1781
<211> LENGTH: 25
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 1781
aaacacctca aacaacttat caaca                                           25

<210> SEQ ID NO 1782
<211> LENGTH: 27
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 1782
aaacttaacc acatacctct ctttaca                                         27

<210> SEQ ID NO 1783
<211> LENGTH: 25
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 1783
aactcactcc tcacaaaata ctcac                                           25

<210> SEQ ID NO 1784
<211> LENGTH: 22
<212> TYPE: DNA
<213> ORGANISM: Artificial Sequence
<220> FEATURE:
<223> OTHER INFORMATION: Description of Artificial Sequence: Synthetic
```

-continued

```
        probe

<400> SEQUENCE: 1784
aacctacctt cctcctcctc ct                                              22

<210> SEQ ID NO 1785
<211> LENGTH: 26
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 1785
cctctcttta aatccaatta acaaca                                          26

<210> SEQ ID NO 1786
<211> LENGTH: 23
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 1786
aaccataaaa acacctacca ccc                                             23

<210> SEQ ID NO 1787
<211> LENGTH: 22
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 1787
ccaaatccct aatcaaactc cc                                              22

<210> SEQ ID NO 1788
<211> LENGTH: 25
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 1788
tttcttccaa atctctctaa tcaca                                           25

<210> SEQ ID NO 1789
<211> LENGTH: 24
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 1789
taaaatccca aacacacata caat                                            24

<210> SEQ ID NO 1790
<211> LENGTH: 26
<212> TYPE: DNA
<213> ORGANISM: Artificial Sequence
<220> FEATURE:
<223> OTHER INFORMATION: Description of Artificial Sequence: Synthetic
      probe
```

-continued

```
<400> SEQUENCE: 1790
ttcctacaac ttatcctaaa caaacc                                          26

<210> SEQ ID NO 1791
<211> LENGTH: 27
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 1791
cacacacata caaacctacc taaaaca                                         27

<210> SEQ ID NO 1792
<211> LENGTH: 27
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 1792
ctaaccaaaa atacacccat atacaca                                         27

<210> SEQ ID NO 1793
<211> LENGTH: 28
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 1793
ccctattttt catttataca attaaacc                                        28

<210> SEQ ID NO 1794
<211> LENGTH: 24
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 1794
aaaaacacct ctctcccaaa aata                                            24

<210> SEQ ID NO 1795
<211> LENGTH: 25
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 1795
aacaactaaa cacacacata tcccc                                           25

<210> SEQ ID NO 1796
<211> LENGTH: 25
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 1796
```

```
tccacccatc tacctaatct tctaa                                      25
```

<210> SEQ ID NO 1797
<211> LENGTH: 24
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 1797

```
tttaatacct tccatcccta aacc                                       24
```

<210> SEQ ID NO 1798
<211> LENGTH: 26
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 1798

```
acaatcaaca actaacaacc taacaa                                     26
```

<210> SEQ ID NO 1799
<211> LENGTH: 27
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 1799

```
ataacactca aatccaacta aacaaca                                    27
```

<210> SEQ ID NO 1800
<211> LENGTH: 27
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 1800

```
acttccttcc tattctaaaa aacaact                                    27
```

<210> SEQ ID NO 1801
<211> LENGTH: 25
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 1801

```
ctaacaataa actactcccc aaaaa                                      25
```

<210> SEQ ID NO 1802
<211> LENGTH: 26
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 1802

```
cacatctata attattcctc tccaca                                     26
```

<210> SEQ ID NO 1803
<211> LENGTH: 24
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 1803
taacctccaa taaaacccat atcc                                            24

<210> SEQ ID NO 1804
<211> LENGTH: 26
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 1804
aactatccta aaacactaaa aacccc                                          26

<210> SEQ ID NO 1805
<211> LENGTH: 25
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 1805
ctaaataact cacctttaca accca                                           25

<210> SEQ ID NO 1806
<211> LENGTH: 25
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 1806
ctaaataact cacctttaca accca                                           25

<210> SEQ ID NO 1807
<211> LENGTH: 24
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 1807
tcacaaacta catcaaaaac ctcc                                            24

<210> SEQ ID NO 1808
<211> LENGTH: 26
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 1808
aaaactccta acacaaccta caatca                                          26

<210> SEQ ID NO 1809

```
<211> LENGTH: 25
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 1809
acaactacct caacaaatca atctc                                           25

<210> SEQ ID NO 1810
<211> LENGTH: 27
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 1810
taaaaccatc tacaacttca ttctcaa                                         27

<210> SEQ ID NO 1811
<211> LENGTH: 25
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 1811
acaattatac ccaacaaaaa tacca                                           25

<210> SEQ ID NO 1812
<211> LENGTH: 27
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 1812
ccaaacctaa ctcactacat ctaaaca                                         27

<210> SEQ ID NO 1813
<211> LENGTH: 24
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 1813
aaacttccaa caactacctc caac                                            24

<210> SEQ ID NO 1814
<211> LENGTH: 24
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 1814
atccccacct taaaactttt tacc                                            24

<210> SEQ ID NO 1815
<211> LENGTH: 27
<212> TYPE: DNA
```

```
<213> ORGANISM: Artificial Sequence
<220> FEATURE:
<223> OTHER INFORMATION: Description of Artificial Sequence: Synthetic
      probe

<400> SEQUENCE: 1815
aaccccaaca ctactttaca taaaaca                                            27

<210> SEQ ID NO 1816
<211> LENGTH: 25
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 1816
aatcttaccc taaaccacaa acacc                                              25

<210> SEQ ID NO 1817
<211> LENGTH: 26
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 1817
tcccctacta aaactatcac aacaaa                                             26

<210> SEQ ID NO 1818
<211> LENGTH: 24
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 1818
caaaacaata ctaattccaa cccc                                               24

<210> SEQ ID NO 1819
<211> LENGTH: 24
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 1819
ctacaaaaaa atttccccca ttaa                                               24

<210> SEQ ID NO 1820
<211> LENGTH: 23
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 1820
ctcaacccct ccctcaatct cta                                                23

<210> SEQ ID NO 1821
<211> LENGTH: 25
<212> TYPE: DNA
<213> ORGANISM: Artificial Sequence
<220> FEATURE:
```

-continued

<223> OTHER INFORMATION: Description of Artificial Sequence: Synthetic
      probe

<400> SEQUENCE: 1821
ccacttacaa tccctacctt ttacc                                          25

<210> SEQ ID NO 1822
<211> LENGTH: 28
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 1822
aacatcattc ttcattataa caacctat                                       28

<210> SEQ ID NO 1823
<211> LENGTH: 24
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 1823
tcccaacaac tctacctaac caaa                                           24

<210> SEQ ID NO 1824
<211> LENGTH: 24
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 1824
aaaacctccc aaaataccct ccta                                           24

<210> SEQ ID NO 1825
<211> LENGTH: 24
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 1825
tttcttctcc atcacaaaaa caaa                                           24

<210> SEQ ID NO 1826
<211> LENGTH: 26
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 1826
ttcctccaaa taaactcata aatttc                                         26

<210> SEQ ID NO 1827
<211> LENGTH: 24
<212> TYPE: DNA
<213> ORGANISM: Artificial Sequence
<220> FEATURE:
<223> OTHER INFORMATION: Description of Artificial Sequence: Synthetic
      probe

```
<400> SEQUENCE: 1827
tatcctctac ccataataac cccc                                      24

<210> SEQ ID NO 1828
<211> LENGTH: 25
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 1828
tttcttttta aacctcaaaa ccatc                                     25

<210> SEQ ID NO 1829
<211> LENGTH: 22
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 1829
tccccaacat ccaaaaaact ac                                        22
```

METHODS AND COMPOSITIONS FOR DIAGNOSING LUNG CANCER WITH SPECIFIC DNA METHYLATION PATTERNS

This application is a continuation-in-part of U.S. Ser. No. 10/973,783, filed Oct. 25, 2004, which is a continuation-in-part of U.S. Ser. No. 10/845,667, filed May 14, 2004 now abandoned, which is based on, and claims the benefit of, U.S. Provisional Application No. 60/471,488, filed May 15, 2003, entitled METHODS AND COMPOSITIONS FOR DIAGNOSING CANCER, each of which is incorporated herein by reference.

This invention was made with government support under grant numbers 1 R43 CA097851-01, 2 R44 CA097851-02 and R37-NL-34788 awarded by the National Institutes of Health. The United States Government has certain rights in this invention.

FIELD OF THE INVENTION

The present invention relates to conditions characterized by differentially methylated genomic CpG dinucleotide sequences and, in particular, to diagnostic and prognostic methods that exploit the presence of such genomic DNA sequences that exhibit altered CpG methylation patterns.

BACKGROUND OF THE INVENTION

Methylation of DNA is widespread and plays a critical role in the regulation of gene expression in development, differentiation and diseases such as multiple sclerosis, diabetes, schizophrenia, aging, and cancers. Methylation in particular gene regions, for example in their promoters, can inhibit the expression of these genes. Recent work has shown that the gene silencing effect of methylated regions is accomplished through the interaction of methylcytosine binding proteins with other structural components of chromatin which, in turn, makes the DNA inaccessible to transcription factors through histone deacetylation and chromatin structure changes. Differentially methylated CpG islands have long been-thought to function as genomic imprinting control regions (ICRs).

Deregulation of imprinting has been implicated in several developmental disorders. Identification of the ICRs in a large number of human genes and their regulation patterns during development can shed light on genomic imprinting as well as other fundamental epigenetic control mechanisms. Moreover, rapid advances in genomics, both in terms of technology, for example, high-throughput low-cost capillary sequencers and microarray technologies, as well as in terms of availability of information, for example, information gained by virtue of whole genome sequencing, bioinformatics tools and databases, have paved the way for new opportunities in epigenetic studies. For example, it is known that random autosomal inactivation is one of the mechanisms that mammals use to achieve gene dosage control, in addition to random X-chromosome inactivation in females and genomic imprinting. However, genes belonging to this category are just now emerging, with only a few identified so far. Technologies are needed that can provide a systematic survey for identification of genes regulated by this kind of random monoallelic expression control, and determination of when and how such genes are regulated through a wide screening of samples from different tissues or different disease stages.

Changes in DNA methylation have been recognized as one of the most common molecular alternations in human neoplasia. Hypermethylation of CpG islands located in the promoter regions of tumor suppressor genes are now firmly established as the most frequent mechanisms for gene inactivation in cancers. In contrast, a global hypomethylation of genomic DNA and loss of IGF imprinting are observed in tumor cells; and a correlation between hypomethylation and increased gene expression has been reported for many oncogenes. In addition, monitoring global changes in methylation pattern has been applied to molecular classification of cancers. Most recently, gene hypermethylation has been associated with clinical risk groups in neuroblastoma and hormone receptor status and response to tamoxifen in breast cancer.

Lung cancer is the second most common cancer among both men and women and is the leading cause of cancer death in both sexes. There is no established early detection test for the disease, and only 15% of lung cancer cases are diagnosed when the disease is localized. The ability to accurately detect malignant cells in a wide range of clinical specimens including sputum, blood, or tissue would provide significant implications for screening high-risk individuals for this cancer.

A Human Epigenome Consortium was formed in 1999 with a mission to systematically map and catalogue the genomic positions of distinct methylation variants. It is likely that large-scale discovery of methylation patterns through de novo DNA sequencing of bisulfite-treated DNA is be carried out in the near future. This would provide a resource for methylation studies analogous to SNP databases for genetic studies, and would be expected to greatly increase the demand for high-throughput, cost-effective methods of carrying out site-specific methylation assays. A publicly accessible database, which carries information about methylation patterns in various biologically significant samples would be the first outcome of these efforts. There is a need for methods for analysis of large sample sets useful for discovering such associations.

Presently, the analysis of DNA methylation patterns in genomic DNA has been significantly hampered by the fact that methylation information is not retained during standard DNA amplification steps such as PCR or biological amplification by cloning in bacteria. Therefore, DNA methylation analysis methods generally rely on a methylation-dependent modification of the original genomic DNA before any amplification step. A battery of DNA methylation detection methods has been developed, including methylation-specific enzyme digestion (Singer-Sam, et al., Nucleic Acids Res. 18(3): 687 (1990), Taylor, et al., Leukemia 15(4): 583-9 (2001)), bisulfite DNA sequencing (Frommer, et al., Proc Natl Acad Sci U S A. 89(5): 1827-31 (1992), Feil, et al., Nucleic Acids Res. 22(4): 695-6 (1994)), methylation-specific PCR (MSP) (Herman, et al., Proc Natl Acad Sci U S A. 93(18): 9821-6 (1996)), methylation-sensitive single nucleotide primer extension (MS-SnuPE) (Gonzalgo, et al., Nucleic Acids Res. 25(12): 2529-31 (1997)), restriction landmark genomic scanning (RLGS) (Kawai, Mol Cell Biol. 14(11): 7421-7 (1994), Akama, et al., Cancer Res. 57(15): 3294-9 (1997)), and differential methylation hybridization (DMH) (Huang, et al., Hum Mol Genet. 8(3): 459-70 (1999)). However, none of these methods combines random access to specific sequences in the genome with high throughput and low cost, which facilitates analysis of methylation profiles at high resolution in large sample sets. In addition, many prior art methods are insensitive to low levels of methylation changes in diseased tissues, e.g. 10% or 20% hypermethylation.

Thus, a need exists for a highly reproducible and multiplexed method for high-throughput quantitative measurement of DNA methylation that provides not just a discrete measure of positive versus negative DNA methylation, but a continuous measure of levels of DNA methylation to classify and predict different types and stages of cancer, cancer therapeutic outcomes and patient survival. This invention satisfies this need and provides related advantages as well.

SUMMARY OF THE INVENTION

The present invention provides a method for identification of differentially methylated genomic CpG dinucleotide sequences associated with cancer in an individual by obtaining a biological sample comprising genomic DNA from the individual measuring the level or pattern of one or more methylated genomic CpG dinucleotide sequences in two or more of the genomic targets in the sample, and comparing the level of said one or more methylated genomic CpG dinucleotide sequences in the sample to a reference level of methylated genomic CpG dinucleotide sequences, wherein a difference in the level or pattern of methylation of the genomic CpG dinucleotide sequences in the sample compared to the reference level identifies differentially methylated genomic CpG dinucleotide sequences associated with cancer.

The methods of the invention enable detection of differentially methylated genomic CpG dinucleotide sequences associated with lung cancer. In a particular embodiment, the present invention provides genomic targets that are differentially methylated in adenocarcinoma of the lung. Notably, the invention also discloses a novel cancer marker. As disclosed herein, the methods of the invention have numerous diagnostic and prognostic applications. The methods of the invention can be combined with a miniaturized array platform that allows for a high level of assay multiplexing and scalable automation for sample handling and data processing.

BRIEF DESCRIPTION OF THE DRAWINGS

The patent or application file contains at least one drawing executed in color. Copies of this patent or application publication with color drawings will be provided by the Office upon request and payment of the necessary fee.

FIG. 1 shows an assembly of a randomly ordered fiber optic array. Panel A shows a collection of bead types, each with a distinct oligonucleotide capture probe, is pooled. An etched fiber optic bundle is dipped into the bead pool, allowing individual beads to assemble into the microwells at the bundle's end. Panel B shows a scanning electron micrograph of an assembled array containing 3 micron diameter silica beads with 5 micron core-to-core spacing between features. The beads are stably associated with the wells under standard hybridization conditions.

FIG. 2 shows a photograph of a 96-array matrix. Each array is located on the end of an optical fiber bundle containing ~50,000 individual fibers. The spacing of the arrays matches that of a 96-well plate, allowing 96 separate samples to be processed simultaneously.

FIG. 31 shows methylation measurement with internal controls. Methylated, unmethylated and semi-methylated (generated by pre-mixing the methylated and unmethylated at 1:1 ratio) plasmid DNAs were spiked into human genomic DNA at 1:1 molar ratio, and 96 assays were run in parallel. Green, yellow and red colors represent low, medium and high methylation levels, respectively FIG. 32 provides information about 55 CpG sites disclosed herein as differentially methylated in cancer. For each CpG site, the following information is provided: (A) Target ID (B) Contig (C) PromoterStart-PromoterEnd; (D) CpG position relative to TSS; (E) Orientation; (F) Strand; (G) Start; (H) End; (I) Length; (J) CpG-Position; (K) Target sequence (SEQ ID NOS: 1555-1609, respectively, in order of appearance); (L) ASO_C (Probe Sequence) (SEQ ID NOS: 1610-1664, respectively, in order of appearance); (M) ASO_T (Probe Sequence) (SEQ ID NOS: 1665-1719, respectively, in order of appearance); (N) LSO_C (Probe Sequence) (SEQ ID NOS: 1720-1774, respectively, in order of appearance); (O) LSO_T (Probe Sequence) (SEQ ID NOS: 1775-1829 respectively, in order of appearance).

DETAILED DESCRIPTION OF THE INVENTION

This application file contains drawings executed in color. Copies of this patent or application publication with color drawings will be provided by the Office upon request and payment of the necessary fee.

The invention disclosed herein provides diagnostic and prognostic methods for a condition that is characterized by differential methylation of genomic CpG dinucleotide sequences. Also provided are populations of genomic targets and corresponding nucleic acid probes that useful for the detection of differentially methylated genomic CpG dinucleotide sequences that can be correlated to the presence of or susceptibility to cancer in an individual.

In particular, the present invention provides genomic targets that are differentially methylated in adenocarcinoma of the lung. The following 14 genomic targets are disclosed herein as differentially methylated in adenocarcinoma: ADCYAP1__2, CDH13__3 (CDH13-1358), GDF10__2, GDF10__3, HOXA5__2 (HOXA5-1247), MAGEA1__3, RUNX3__1, SCGB3A1__3, SERPINB5__1, SFN__2, SFTPA1__2, TERT__1, TERT__2, and TNF__2 (TNF-1343). The 14 genomic targets correspond to twelve gene targets.

The following 52 genomic target sites also are disclosed herein as differentially methylated in adenocarcinoma: ADCYAP1-1103, APBA2-1397, ASCL2-856, ASCL2-1038, ASCL2-1048, ASCL2-1339, CCND2-604, CD2-1433, CFTR-1051, CFTR-1191, DBC1-1053, DIO3-1355, DLC1-1012, DLK1-1119, DLK1-1185, DLK1-1226, DLK1-1287, GABRB3-1408, GALR1-1270, GDF10-1224, HOXA5-75, HOXA11-802, HOXA11-558, HOXA5-1094, HS3ST2-311, HTR2A-1387, HTR1B-315, HTR1B-1278, IGF2AS-1145, IGF2-112, NEFL-524, NEFL-600, NEFL-1341, NEFL-1367, NPY-793, NPY-931, NPY-1009, OPCML-967, PAX6-1337, PENK-1480, PENK-1293, POMC-1303, PTPN6-1214, PTPRO-1206, RET-1149, RUNX3-368, SEZ6L-1046, TERT-900, TNF-1371, TP73-358, TWIST1-1348, TWIST1-524. The 52 target sites correspond to 35 gene targets.

Figure 23A:
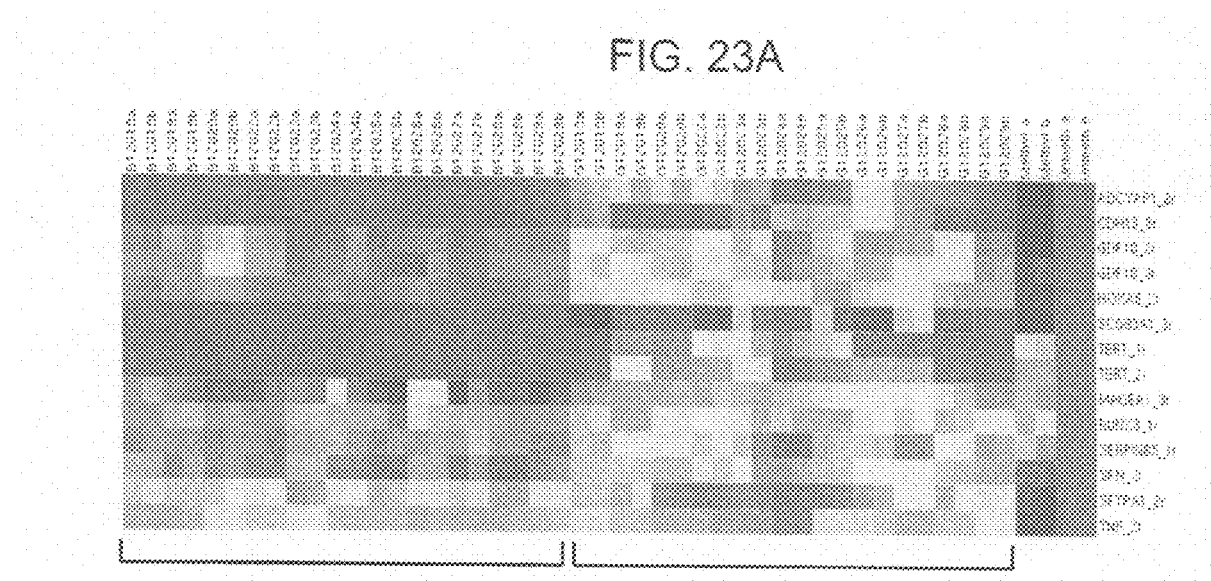
FIG. 23 shows methylation profiles of the lung adenocarcinoma markers and the squamous cell carcinoma markers in the training set of samples. Panel 23A shows 11 adenocarcinomas and 11 matching normal tissues. Panel 23B shows 14 squamous cell carcinomas and 10 matching normal tissues. Replicate measurements are shown in adjacent for each sample.
Figure 23B:
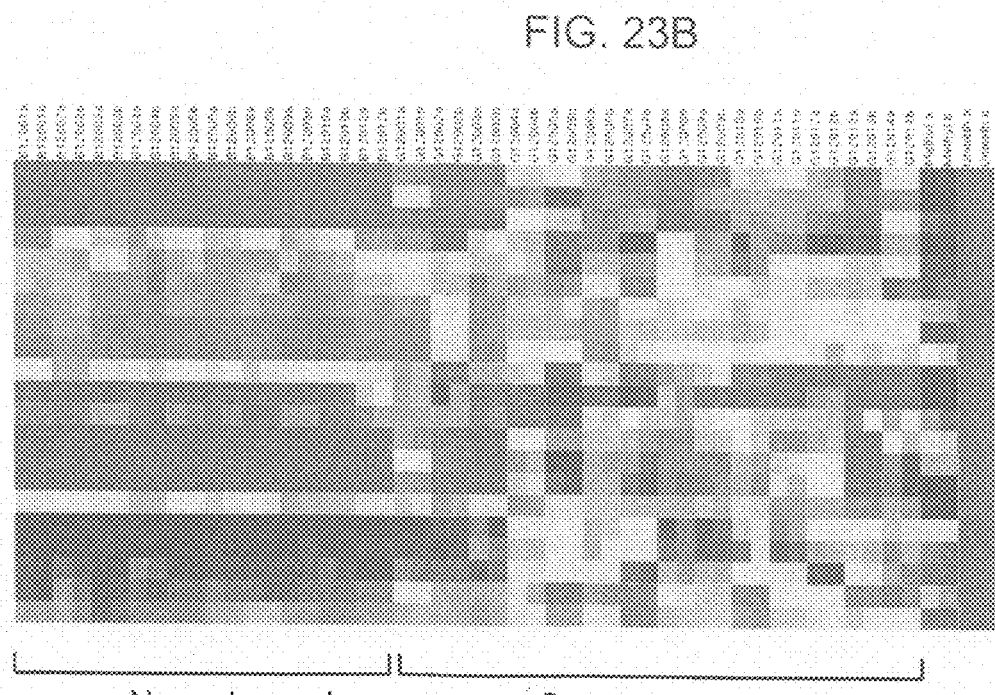

In a further embodiment, the present invention provides genomic targets that are differentially methylated in squamous cell carcinoma of the lung. The following 21 genomic targets are disclosed herein as differentially methylated in squamous cell carcinoma: ADCYAP1__1, ADCYAP1__2, ADCYAP1__3, BCR__2, CALCA__1, GDF10__3, HOXA5__1, HOXA5__2, HOXA5__3, MAGEA1__1, MAGEA1__2, PGR__2, PRKCDBP__3, SCGB3A1__3, SERPINB5__1, SFN__2, SFTPC__3, TERT__1, TERT__2, TERT__3, TNF__2 (FIG. 23B). The 21 genomic targets correspond to 14 gene targets.

Notably, the invention also discloses a novel cancer marker. As described herein, the gene target adenylate cyclase activating polypeptide 1 (ADCYAP1) provided by the present invention and shown to be methylated in adenocarcinoma and squamous cell carcinoma represents a novel cancer marker based on methylation status. Genomic targets designated SEQ ID NOS: 264, 265 and 266 correspond to gene target adenylate cyclase activating polypeptide 1 (ADCYAP1) and are shown herein to be methylated in squamous cell carcinoma, while SEQ ID NOS: 265 and 1555 (corresponding to ADCYAP1-1103) are shown to be methylated in adenocarcinoma (FIGS. 23A and B).

The methods of the invention are directed to methods for diagnosing an individual with a condition that is characterized by a level and/or pattern of methylated genomic CpG dinucleotide sequences distinct from the level and/or pattern of methylated genomic CpG dinucleotide sequences exhibited in the absence of the particular condition. This invention also is directed to methods for predicting the susceptibility of an individual- to a condition that is characterized by a level and/or pattern of methylated genomic CpG dinucleotide sequences that is distinct from the level and/or pattern of methylated genomic CpG dinucleotide sequences exhibited in the absence of the condition.

Because methylation detection interrogates genomic DNA, rather than RNA or protein, it offers several technological advantages in a clinical diagnostic setting: (1) readily available source materials, particularly important for prognostic research, because typically DNA can be more reliably extracted than RNA from archived biological samples for study; (2) capability for multiplexing, allowing simultaneous measurement of multiple targets to improve assay specificity; (3) easy amplification of assay products to achieve high sensitivity; and (4) the ability to detect a positive signal in tumors that arises from methylation inactivation of one allele of tumor suppressor genes. Detecting the appearance of a positive signal is a more robust and reliable measurement than detecting a two-fold gene expression change at the mRNA level in these tumors.

In various distinct embodiments, the present invention is based, in part, on the identification of reliable CpG methylation markers for the improved prediction of susceptibility, diagnosis and staging of lung cancer. The invention provides a population of reliable genomic target sequences or genomic targets for use in the diagnostic and prognostic methods provided by the present invention, which have been designated herein as SEQ ID NOS: 57, 58, 59, 72, 76, 139, 140, 141, 174, 264, 265, 266, 293, 294, 305, 309, 313, 314, 315, 345, 350, 353, 360, 364, 371 and 373. The genomic targets provided by the invention are associated with the following gene targets: ADCYAP1, APBA2, ASCL2, BCR, CALCA, CCND2, CD2, CDH13, CTFR, GALR1, GDF10, HOXA5, HOXA11, HS3ST2, HTR2A, HTR1B, DBC1, DIO3, DLC1, DLK1, GABRB3, IGF2AS, IGF2, NEFL, NPY, MAGEA1, OPCML, PAX6, PENK, PGR, POMC, PRKCDBP, PTPN6, PTPRO, RET, RUNX3, SCGB3A1, SERPINB5, SEZ6L, SFNT, SFTPA1, SFTPC, TERT, TNF, TP73, and TWIST1 (Table 1 and FIG. 32). The genomic targets provided by the invention thus represent gene targets for methylation of genomic CpG dinucleotide sequences associated with lung cancer. Also provided are nucleic acid probes that correspond to the genomic target sites of the invention and that can be used to detect differential methylation of selected genomic CpG dinucleotide sequences that serve as markers associated with lung cancer.

It is understood that the genomic target sequences provides the context for the one or more selected genomic CpG dinucleotide sequences being measured within a particular genomic target sequence. Furthermore, according to the invention, any fraction of the total genomic CpG dinucleotide sequences within a genomic target sequence can be measured, including one or more, two or more three or more, four or more, five or more or all of the genomic CpG dinucleotide sequences within a genomic target sequence. In addition, since it is understood that the genomic target sequence provides the context for the one or more selected genomic CpG dinucleotide sequences being, measured, the invention encompasses measurement of the particular genomic CpG dinucleotide sequences encompassed within any of the genomic target sequences designated as SEQ ID NOS: 1-366, regardless of the particular nucleic probes that may be used for detecting the methylation of the particular genomic CpG dinucleotide sequence. Although Table 1 sets forth particular nucleic acid probes provided by the invention that correspond to the genomic targets of SEQ ID NOS: 1-366, the skilled person can practice the invention using any desired nucleic acid probe capable of detecting the methylation status of one or more genomic CpG dinucleotide sequences within a particular genomic target sequence.

The genomic targets and nucleic acid probes provided by the present invention are set forth in Table 1, below, and provide diagnostic and prognostic tools based on their ability to detect differential methylation of selected genomic CpG dinucleotide sequences associated with cancer. In the methods provided by the invention, the genomic targets and nucleic acid probes capable of detecting markers located within the genomic targets can be employed to detect altered levels of methylation of genomic CpG dinucleotide sequences in a biological sample compared to a reference level. Furthermore, the methods of the invention allow for use of the genomic markers and nucleic acid probes for the determination of methylation patterns, which are represented by differential methylation of selected genomic CpG dinucleotide sequences that serve as markers in particular sets or subsets of genomic targets. In embodiments directed to the detection of methylation patterns, it is possible to diagnose or predict the susceptibility of an individual to a specific tumor-type based on the correlation between the pattern and the tumor type.

DNA methylation is a mechanism for changing the base sequence of DNA without altering its coding function. DNA methylation is a heritable, reversible and epigenetic change. Yet, DNA methylation has the potential to alter gene expression, which has profound developmental and genetic consequences. The methylation reaction involves flipping a target cytosine out of an intact double helix to allow the transfer of a methyl group from S adenosylmethionine in a cleft of the enzyme DNA (cystosine-5)-methyltransferase (Klimasauskas et al., Cell 76:357-369, 1994) to form 5-methylcytosine (5-mCyt). This enzymatic conversion is the most common epigenetic modification of DNA known to exist in vertebrates and is essential for normal embryonic development (Bird, Cell 70:5-8, 1992; Laird and Jaenisch, Human Mol. Genet. 3:1487-1495, 1994; and Bestor and Jaenisch, Cell 69:915-926, 1992). The presence of 5-mCyt at CpG dinucleotides has resulted in a 5-fold depletion of this sequence in the genome during vertebrate evolution, presumably due to spontaneous deamination of 5-mCyt to T (Schoreret et al., Proc. Natl. Acad. Sci. USA 89:957-961, 1992). Those areas of the genome that do not show such suppression are referred to as "CpG islands" (Bird, Nature 321:209-213, 1986; and Gardiner-Garden et al., J Mol. Biol. 196:261-282, 1987). These CpG island regions comprise about 1% of vertebrate genomes and also account for about 15% of the total number of CpG dinucleotides. CpG islands are typically between 0.2 to about 1 kb in length and are located upstream of many housekeeping and tissue-specific genes, but may also extend into gene coding regions. Therefore, the methylation of cytosine residues within CpG islands in somatic tissues can modulate gene expression throughout the genome (Cedar, Cell 53:3-4, 1988; Nature 421:686-688, 2003).

Methylation of cytosine residues contained within CpG islands of certain genes has been inversely correlated with gene activity. Thus, methylation of cytosine residues within CpG islands in somatic tissue is generally associated with decreased gene expression and can be the effect a variety of mechanisms including, for example, disruption of local chromatin structure, inhibition of transcription factor-DNA binding, or by recruitment of proteins which interact specifically with methylated sequences indirectly preventing transcription factor binding. Despite a generally inverse correlation between methylation of CpG islands and gene expression, however, most CpG islands on autosomal genes remain unmethylated in the germline and methylation of these islands is usually independent of gene expression. Tissue-specific genes are usually unmethylated at the receptive target organs but are methylated in the germline and in non-expressing adult tissues. CpG islands of constitutively-expressed housekeeping genes are normally unmethylated in the germline and in somatic tissues.

Abnormal methylation of CpG islands associated with tumor suppressor genes can cause decreased gene expression. Increased methylation of such regions can lead to progressive reduction of normal gene expression resulting in the selection of a population of cells having a selective growth advantage. Conversely, decreased methylation (hypomethylation) of oncogenes can lead to modulation of normal gene expression resulting in the selection of a population of cells having a selective growth advantage.

The present invention harnesses the potential of genomic methylation of CpG islands as indicators of the presence of a condition in an individual and provides a reliable diagnostic and/or prognostic method applicable to any condition associated with altered levels or patterns of genomic methylation of CpG islands. CpG islands are contiguous regions of genomic DNA that have an elevated frequency of CpG dinucleotides compared to the rest of the genome. CpG islands are typically, but not always, between about 0.2 to about 1 kb in length, and may be as large as about 3 Kb in length. Generally, for the methods provided by the invention at least two or more, at least three or more, at least four or more CpG dinucleotide sequences are selected that are located within a genomic marker so as to allow for determination of co-methylation status in the genomic DNA of a given tissue sample. Preferably the primary and secondary CpG dinucleotide sequences are co-methylated as part of a larger co-methylated pattern of differentially methylated CpG dinucleotide sequences in the genomic marker. The size of such context regions varies, but generally reflects the size of CpG islands as described above, or the size of a gene promoter region, including the first one or two exons.

With particular regard to cancer, changes in DNA methylation have been recognized as one of the most common molecular alternations in human neoplasia. Hypermethylation of CpG islands located in the promoter regions of tumor suppressor genes is a well-established and common mechanism for gene inactivation in cancer (Esteller, Oncogene 21(35): 5427-40 (2002)). In contrast, a global hypomethylation of genomic DNA is observed in tumor cells; and a correlation between hypomethylation and increased gene expression has been reported for many oncogenes (Feinberg, Nature 301(5895): 89-92 (1983), Hanada, et al., Blood 82(6): 1820-8 (1993)). Thus, a detailed study of methylation pattern in selected, staged tumor samples compared to matched normal tissues from the same patient offers a novel approach to identify unique molecular markers for cancer classification.

Monitoring global changes in methylation pattern has been applied to molecular classification in breast cancer (Huang, et al., Hum Mol Genet. 8(3): 459-70 (1999)). In addition, many studies have identified a few specific methylation patterns in tumor suppressor genes, for example, p16, a cyclin-dependent kinase inhibitor, in certain human cancer types (Otterson, et al., Oncogene 11(6): 1211-6 (1995), Herman, et al., Cancer Res. 55(20): 4525-30 (1995)). Some of the most recent examples include the discoveries of causal relationship between the loss of RUNX3 expression, due to hypermethylation, and gastric cancer (Li, et al., Cell 109(1): 113-24 (2002)); loss of IGF2 imprinting in colorectal cancer (Cui, et al., Science 299(5613): 1753-5 (2003); and reduced Hic gene expression in several types of human cancer (Chen, et al., Nat Genet. 33(2): 197-202 2003), Fujii, et al., Oncogene 16(16): 2159-64 (1998), Kanai, et al., Hepatology 29(3): 703-9 (1999)).

In one embodiment, the invention provides a method for identification of differentially methylated genomic CpG dinucleotide sequences associated with cancer in an individual by obtaining a biological sample comprising genomic DNA from the individual; measuring the level of one or more methylated genomic CpG dinucleotide sequences in two or more of the genomic target sequences set forth herein and designated as SEQ ID NOS: 1-366 in the sample, and comparing the level of the one or more methylated genomic CpG dinucleotide sequences in the sample to a reference level of methylated genomic CpG dinucleotide sequences, wherein a difference in the level of methylation of said one or more genomic CpG dinucleotide sequences in the sample compared to the reference level identifies differentially methylated genomic CpG dinucleotide sequences associated with cancer. In additional embodiments, the level of methylated genomic CpG dinucleotide sequences is measured for one or more, three or more, four or more, five or more, six ore more, seven or more, eight or more, nine or more, ten or more, eleven or more, twelve or more, thirteen or more, fourteen or more, fifteen or more, twenty or more, twenty-five or more, thirty or more, fifty or more, of the genomic target sequences set forth herein and designated as SEQ ID NOS: 1-377 in the sample. A subset of the genomic target sequences or nucleic acid probes of the invention can be one ore more nucleic acid sequences.

In a further embodiment, the invention provides a method for identification of differentially methylated genomic CpG dinucleotide sequences associated with lung cancer in an individual by obtaining a biological sample comprising genomic DNA from the individual; measuring the level of one or more methylated genomic CpG dinucleotide sequences in two or more of the genomic target sequences set forth herein and designated as SEQ ID NOS: 57, 58, 59, 72, 76, 139, 140, 141, 174, 264, 265, 266, 293, 294, 305, 309, 313, 314, 315, 345, 350, 353, 360, 364, 371, 373, and any of the sequences set forth in FIG. 32 designated SEQ ID NOS: 1555-1609, in the sample, and comparing the level of the one or more methylated genomic CpG dinucleotide sequences in the sample to a reference level of methylated genomic CpG dinucleotide sequences, wherein a difference in the level of methylation of said genomic CpG dinucleotide sequences in the sample compared to the reference level identifies differentially methylated genomic CpG dinucleotide sequences associated with cancer. In additional embodiments, the level of one or more methylated genomic CpG dinucleotide sequences is measured for one or more, three or more, four or more, five or more, six ore more, seven or more, eight or more, nine or more, ten or more, eleven or more, twelve or more, thirteen or more, fourteen or more, fifteen or more, twenty or more, twenty-two or more, twenty-four or more, of the markers set forth herein and designated as SEQ ID NOS: 57, 58, 59, 72, 76, 139, 140, 141, 174, 264, 265, 266, 293, 294, 305, 309, 313, 314, 315, 345, 350, 353, 360, 364, 371, 373, and any of the sequences set forth in FIG. 32 designated SEQ ID NOS: 1555-1609, in the sample. A subset of the genomic markers or nucleic acid probes of the invention can be one or more nucleic acid sequences.

In one embodiment, the invention provides a method for identification of differentially methylated genomic CpG dinucleotide sequences associated with adenocarcinoma of the lung in an individual by obtaining a biological sample comprising genomic DNA from the individual; measuring the level of one or more methylated genomic CpG dinucleotide sequences for two or more of the markers set forth herein and designated as SEQ ID NOS: 59, 140, 266, 293, 294, 140, 174, 371, 313, 314, 353, 360, 364, 373, and any of the sequences set forth in FIG. 32 designated SEQ ID NOS: 1555-1609, in the sample, and comparing the level of one or more methylated genomic CpG dinucleotide sequences in the sample to a reference level of methylated genomic CpG dinucleotide sequences, wherein a difference in the level of methylation of said genomic CpG dinucleotide sequences in the sample compared to the reference level identifies differentially methylated genomic CpG dinucleotide sequences associated with cancer. In additional embodiments, the level of one or more methylated genomic CpG dinucleotide sequences is measured for one or more, three or more, four or more, five or more, six ore more, seven or more, eight or more, nine or more, ten or more, twelve or more, thirteen or more, of the markers set forth herein and present in SEQ ID NOS: 59, 140, 266, 293, 294, 140, 174, 371, 313, 314, 353, 360, 364, 373, and any of the sequences set forth in FIG. 32 designated SEQ ID NOS: 1555-1609, in the sample. A subset of the genomic markers or nucleic acid probes of the invention can be one or more nucleic acid sequences.

In one embodiment, the invention provides a method for identification of differentially methylated genomic CpG dinucleotide sequences associated with squamous cell carcinoma of the lung in an individual by obtaining a biological sample comprising genomic DNA from the individual; measuring the level of one or more methylated genomic CpG dinucleotide sequences for two or more of the markers set forth herein and designated as SEQ ID NOS: 57, 58, 72, 76, 139, 140, 141, 174, 264, 265, 266, 294, 305, 309, 313, 314, 315, 345, 350, 360 and 371, in the sample, and comparing the level of one or more methylated genomic CpG dinucleotide sequences in the sample to a reference level of methylated genomic CpG dinucleotide sequences, wherein a difference in the level of methylation of said genomic CpG dinucleotide sequences in the sample compared to the reference level identifies differentially methylated genomic CpG dinucleotide sequences associated with cancer. In additional embodiments, the level of one or more methylated genomic CpG dinucleotide sequences is measured for one or more, three or more, four or more, five or more, six ore more, seven or more, eight or more, nine or more, ten or more, eleven or more, twelve or more, thirteen or more, fourteen or more, fifteen or more, twenty or more, of the markers set forth herein and designated as SEQ ID NOS: 57, 58, 72, 76, 139, 140, 141, 174, 264, 265, 266, 294, 305, 309, 313, 314, 315, 345, 350, 360 and 371, in the sample. A subset of the genomic markers or nucleic acid probes of the invention can be one ore more nucleic acid sequences.

The level of methylation of the differentially methylated genomic CpG dinucleotide sequences can provide a variety of information about the cancer and can be used, for example, to diagnose cancer in the individual; to predict the course of the cancer in the individual; to predict the susceptibility to cancer in the individual, to stage the progression of the cancer in the individual; to predict the likelihood of overall survival for the individual; to predict the likelihood of recurrence of cancer for the individual; to determine the effectiveness of a treatment course undergone by the individual.

As described herein, the level of methylation that is detected in a biological sample can be decreased or increased in comparison to the reference level and alterations that increase or decrease methylation can be detected and provide useful prognostic or diagnostic information. For example, hypermethylation of CpG islands located in the promoter regions of tumor suppressor genes have been established as common mechanisms for gene inactivation in cancers (Esteller, *Oncogene* 21(35): 5427-40 (2002)). Thus, a detailed study of methylation pattern in selected, staged tumor samples compared to matched normal tissues from the same patient can identify unique molecular markers for cancer classification.

In addition to detecting levels of methylation, the present invention also allows for the detection of patterns of methylation. It has been confirmed previously that neoplastic cells can exhibit unusual patterns of gene methylation (Feinberg and Vogelstein, *Nature* 301:89-92 (1983)). Previous genetic studies of various conditions, for example, schizophrenia and bipolar disorder, seemed to implicate regions of particular chromosomes 22, but studies failed to identify a susceptibility gene. Analysis of methylation patterns across these chromosome in biological samples from afflicted individuals can reveal epigenetic changes in the form of altered levels of methylation of subsets of genomic CpG dinucleotide sequences that make up a pattern of affected genomic targets that can be correlated with a condition.

In one embodiment of the invention, an altered level of methylation of genomic CpG dinucleotide sequences is observed only in a subset of the genomic targets set forth in Table 1 and designated SEQ ID NOS: 1-377. In this embodiment, the subset can represent a methylation pattern characteristic of a particular type of cancer. A particular subset provided by the invention encompasses genomic targets that are differentially methylated in lung cancer and set forth herein and designated as SEQ ID NOS: 57, 58, 59, 72, 76, 139, 140, 141, 174, 264, 265, 266, 293, 294, 305, 309, 313, 314, 315, 345, 350, 353, 360, 364, 371 and 373. A further subset provided by the invention encompasses genomic targets that are differentially methylated in adenocarcinoma of the lung and set forth herein and designated as SEQ ID NOS: 59, 140, 266, 293, 294, 140, 174, 371, 313, 314, 353, 360, 364, 373, and any of the sequences set forth in FIG. 32 designated SEQ ID NOS: 1555-1609. An additional subset provided by the invention encompasses genomic targets that are differentially methylated in squamous cell carcinoma of the lung and set forth herein and designated as SEQ ID NOS: 57, 58, 72, 76, 139, 140, 141, 174, 264, 265, 266, 294, 305, 309, 313, 314, 315, 345, 350, 360 and 371. Therefore, as described herein with reference to cancer, methylation patterns can be correlated with a particular type, class or origin of a condition and detection and comparison of methylation patterns across samples that share a phenotypic characteristic can be useful to identify further methylation patterns.

In a further embodiment the present invention provides a population of genomic targets comprising nucleic acid sequences designated SEQ ID NOS: 1-377, and set forth in Table 1. Also provided in a distinct, but related embodiment is a population of genomic targets selected from the group consisting of nucleic acid sequences designated SEQ ID NOS: 1-377. In a further embodiment the invention provides a population of genomic targets comprising a subset of the nucleic acid sequences designated SEQ ID NOS: 1-366, and set forth in Table 1. Differential methylation of genomic CpG dinucleotide sequences in a subset of SEQ ID NOS: 1-366 can be characteristic of a particular type, class or origin of cancer. Detection of differential methylation in a subset of genomic targets can be useful to diagnose or predict susceptibility for a particular type, class or origin of cancer.

In a further embodiment the invention provides a population of genomic targets comprising a subset of the nucleic acid sequences designated SEQ ID NOS: 1-377, and set forth in FIG. 32 designated SEQ ID NOS: 1555-1609. Differential methylation of genomic CpG dinucleotide sequences in a subset of SEQ ID NOS: 1-377 and 1555-1609 can be characteristic of a particular type, class or origin of cancer. Detection of differential methylation in a subset of genomic targets can be useful to diagnose or predict susceptibility for a particular type, class or origin of cancer.

In one embodiment, a population of genomic targets selected from the group consisting of nucleic acid sequences designated SEQ ID NOS: 1-366 can encompass SEQ ID NOS: 57, 58, 59, 72, 76, 139, 140, 141, 174, 264, 265, 266, 293, 294, 305, 309, 313, 314, 315, 345, 350, 353, 360, 364, 371 and 373. In yet another embodiment, a population of genomic targets selected from the group consisting of nucleic acid sequences designated SEQ ID NOS: 1-377 can encompass SEQ ID NOS: 59, 140, 266, 293, 294, 140, 174, 371, 313, 314, 353, 360, 364, 373, and any of the sequences set forth in FIG. 32 designated SEQ ID NOS: 1555-1609. In a further embodiment, a population of genomic targets selected from the group consisting of nucleic acid sequences designated SEQ ID NOS: 1-377 can encompass SEQ ID NOS: 57, 58, 72, 76, 139, 140, 141, 174, 264, 265, 266, 294, 305, 309, 313, 314, 315, 345, 350, 360 and 371. In a further embodiment, a population of genomic targets selected from the group consisting of nucleic acid sequences designated SEQ ID NOS: 1-377 can encompass SEQ ID NOS: 57, 58, 59, 72, 76, 139, 141, 264, 265, 293, 309, 315, 345, 350, 353, 364 and 373. In a further embodiment, a population of genomic targets selected from the group consisting of nucleic acid sequences designated SEQ ID NOS: 1-377 can encompass SEQ ID NOS: 59, 293, 353, 364 and 373. The genomic targets are capable of exhibiting altered levels of methylation of genomic CpG dinucleotide sequences that are predictive of the presence or susceptibility of an individual for cancer.

Also provided by the present invention is a population of nucleic acid probes capable of detecting methylation of genomic CpG dinucleotide sequences of two or more genomic targets selected from the group consisting of the nucleic acid sequences designated SEQ ID NOS: 1-377, and set forth in Table 1. The population of nucleic acid probes provided by the invention consists of two or more nucleic acid sequences selected from the group consisting of SEQ ID NOS: 378-1508, and set forth in Table 1, which sets forth four probes for each genomic target of SEQ ID NOS: 1-377. Also provided by the present invention is a population of nucleic acid probes capable of detecting methylation of genomic CpG dinucleotide sequences of two or more genomic targets selected from the group consisting of the nucleic acid sequences designated SEQ ID NOS: 378-1508, and set forth in FIG. 32 designated SEQ ID NOS: 1610-1829. The population of nucleic acid probes provided by the invention consists of two or more nucleic acid sequences selected from the group consisting of SEQ ID NOS: 378-1508, and set forth in FIG. 32 designated SEQ ID NOS: 1610-1829, which sets forth four probes for each genomic target of SEQ ID NOS: 378-1508 and 1610-1829. The nucleic acid probes of the invention are capable of detecting altered levels of methylation of genomic CpG dinucleotide sequences of two or more genomic targets, wherein altered levels are predictive of the presence or susceptibility of an individual for cancer. Based on the observation that adjacent CpG sites tend to be co-methylated or co-de-methylated, a design scheme can be applied in which a "CG" sequence was used for all the CpG sites within the vicinity of the design, in particular for the landing sites for both ASO and LSO, to target any methylated CpG site; while a "TG" sequence was used for all the CpG sites within the vicinity of the design, to target any un-methylated CpG site. This approach requires two separate LSO oligos, but adds better discrimination between the methylated and unmethylated alleles.

In a further embodiment aimed at determination of patterns of DNA methylation, a population of nucleic acid probes is utilized that is capable of detecting altered levels of methylation of genomic CpG dinucleotide sequences of a subset of a population of two or more genomic targets. Thus, the detection of differential methylation of genomic CpG dinucleotide sequences in only a subset of genomic targets can be used to identify a pattern that correlates with a particular type, class or origin of cancer.

As disclosed herein, the present invention provides a subset of genomic targets consisting of nucleic acid sequences set forth in Table 1 and designated SEQ ID NOS: 57, 58, 72, 76, 139, 140, 141, 174, 264, 265, 266, 294, 305, 309, 313, 314, 315, 345, 350, 360 and 371 which exhibits differential methylation of genomic CpG dinucleotide sequences associated with lung squamous cell carcinoma. FIG. 23B shows the differential methylation pattern observed for genomic targets designated SEQ ID NOS: 57, 58, 72, 76, 139, 140, 141, 174, 264, 265, 266, 294, 305, 309, 313, 314, 315, 345, 350, 360 and 371, which correspond to gene targets MAGEA1 (SEQ ID NOS: 57 and 58), BCR (SEQ ID NO: 72), CALCA (SEQ ID NO: 76), HOXA5 (SEQ ID NOS: 139, 140, and 141), TNF (SEQ ID NO: 174), ADCYAP1 (SEQ ID NOS: 264, 265 and 266), GDF10 (SEQ ID NO: 294), SFN (SEQ ID NO: 305), SFTPC (SEQ ID NO: 309), TERT (SEQ ID NOS: 313, 314 and 315), PRKCDBP (SEQ ID NO: 345), PGR (SEQ ID NO: 350), SERPINB (SEQ ID NO: 360) and SCGB3A1 (SEQ ID NO: 371).

As disclosed herein, the present invention provides a subset of genomic targets consisting of nucleic acid sequences set forth in FIG. 32 and designated SEQ ID NOS: 1555-1609, which exhibit differential methylation of genomic CpG dinucleotide sequences associated with lung adenocarcinoma. FIG. 32 lists the differential methylation pattern observed for genomic targets designated SEQ ID NOS: 1555-1609, which correspond to gene targets ADCYAP1 (SEQ ID NO: 1555), APBA2 (SEQ ID NO: 1556), ASCL2 (SEQ ID NO: 1557-1560), CCND2 (SEQ ID NO: 1561), CD2 (SEQ ID NO: 1562), CDH13 (SEQ ID NO: 1563), CTFR (SEQ ID NO: 1564-1565), DBC1 (SEQ ID NO: 1566), DIO3 (SEQ ID NO: 1567), DLC1 (SEQ ID NO: 1568), DLK1 (SEQ ID NO: 1569-1572), GABRB3 (SEQ ID NO: 1573), GALR1 (SEQ ID NO: 1574), GDF 10 (SEQ ID NO: 1575), HOXA5 (SEQ ID NO: 1578-1580), HOXA11 (SEQ ID NO: 1576-1577), HS3ST2 (SEQ ID NO: 1581), HTR2A (SEQ ID NO: 1584), HTR1B (SEQ ID NO: 1582-1583), IGF2AS (SEQ ID NO: 1586), IGF2 (SEQ ID NO: 1585), NEFL (SEQ ID NO: 1587-1590), NPY (SEQ ID NO: 1591-1593), OPCML (SEQ ID NO: 1594), PAX6 (SEQ ID NO: 1595), PENK (SEQ ID NO: 1596-1597), POMC (SEQ ID NO: 1598), PTPN6 (SEQ ID NO: 1599), PTPRO (SEQ ID NO: 1600), RET (SEQ ID NO: 1601), RUNX3 (SEQ ID NO: 1602), SEZ6L (SEQ ID NO: 1603), TERT (SEQ ID NO: 1604), TNF (SEQ ID NO: 1605-1606), TP73 (SEQ ID NO: 1607), and TWIST1 (SEQ ID NO: 1608-1609).

In a further embodiment, the present invention provides a subset of genomic targets consisting of nucleic acid sequences set forth in Table 1 and designated SEQ ID NOS: 59, 140, 265, 293, 294, 140, 174, 371, 313, 314, 353, 360, 364 and 373 which exhibits differential methylation of genomic CpG dinucleotide sequences associated with lung adenocarcinoma. FIG. 23A shows the differential methylation pattern observed for genomic targets designated SEQ ID NOS: 59, 140, 174, 265, 293, 294, 305, 313, 314, 353, 360, 364, 371, and 373, which correspond to gene targets MAGEA1 (SEQ ID NO: 59), HOXA5 (SEQ ID NO: 140), ADCYAP1 (SEQ ID NO: 265), GDF10 (SEQ ID NOS: 293 and 294), TNF (SEQ ID NO: 174), ADCYAP1 (SEQ ID NO: 265), GDF10 (SEQ ID NO: 293, 294), SFN (SEQ ID NO: 305), TERT (SEQ ID NO: 313, and 314), CDH13 (SEQ ID NO: 353), SERPINB (SEQ ID NO: 360) RUNX3 (SEQ ID NO: 364) and SFTPA1 (SEQ ID NO: 373).

As demonstrated in Example IV, the differentially methylated markers identified from squamous cell carcinomas largely overlap with those identified from adenocarcinomas. Methylation of the gene target adenylate cyclase activating polypeptide 1 (ADCYAP1) as shown in the present disclosure for adenocarcinoma and squamous cell carcinoma has not previously been reported. Genomic targets designated SEQ ID NOS: 264, 265 and 266 correspond to gene target adenylate cyclase activating polypeptide 1 (ADCYAP1) and are shown herein to be methylated in squamous cell carcinoma, while SEQ ID NO: 265 is shown to be hypermethylated in adenocarcinoma and squamous cell carcinoma (FIGS. 23A and B). Gene targets ADCYAP1, CDH13, GDF10, HOXA5, SCGB3A1 and TERT had increased methylation levels in adenocarcinoma samples compared to normal (FIGS. 23A & 26), while MAGEA1, RUNX3, SERPINB5, SFN, SFTPA1 and TNF were less methylated in cancer (FIG. 23A). Methylation of CDH13, HoxA5, SCGB3A1 and GDF10 is associated with tumor progression in various types of cancer as described by Hibi et al., *Br J Cancer* 91:1139-1142 (2004); Hibi et al., *Br J Cancer* 90, 1030-3 (2004); Ogama et al. *Int J Oncol* 25, 685-9-1 (2004); Chen et al., *Am J Pathol* 163, 37-45 (2003); Fackler et al., *Int J Cancer* 107, 970-5 (2003); Aldred et al., *Cancer Res,* 63, 2864-71 (2003). The human telomerase reverse transcriptase gene (TERT) is shown to be inactivated in most differentiated cells, but is reactivated in the majority of cancer cells (Liu et al., *Genes Chromosomes Cancer* 41, 26-37 (2004)).

Figure 4:
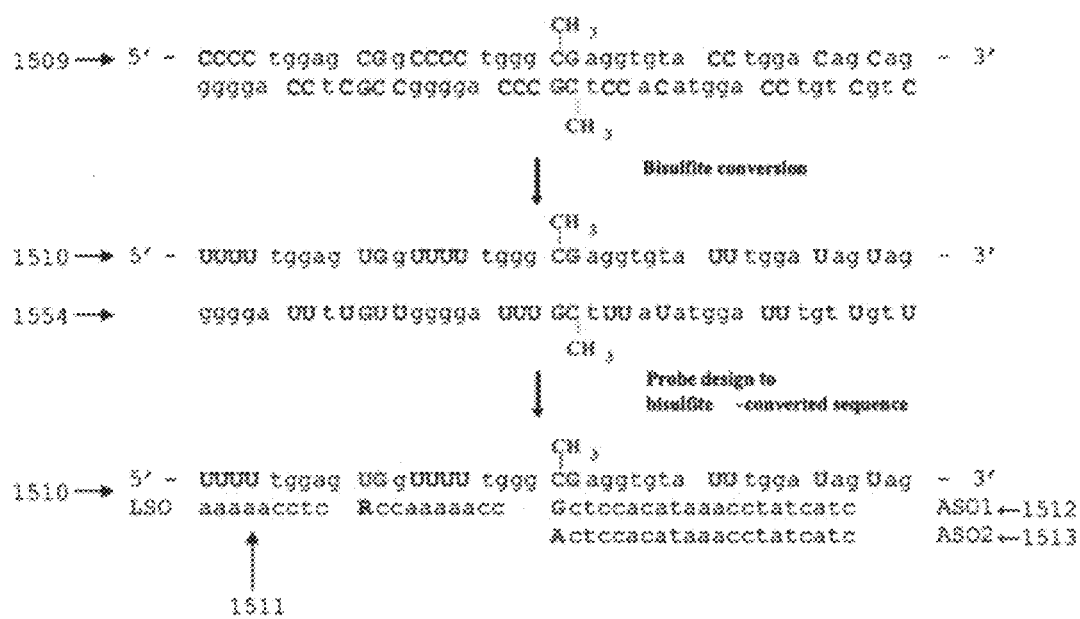
FIG. 4 shows an oligonucleotide design scheme (SEQ ID NOS: 1509-1513 and 1554).

As shown in Examples IV and V, the method disclosed herein provides not just a discrete measure of positive versus negative DNA methylation, but a continuous measure of levels of DNA methylation. For a 17% difference in absolute methylation level (e.g. 10% vs. 27%), signals are expected to have largely non-overlapping distributions. The assay can detect as little as 2.5% of methylation for some CpG sites. Unlike restriction enzyme-based methods, assay probes can be specifically designed for most of the CpG sites in the genome, and assay oligos can be designed to interrogate either the Watson or Crick strand or both at each CpG site (FIG. 4). Assay results can be read out on a universal array. As a result, gene (or CpG) sets can be refined iteratively, if desired, because no custom arrays need to be developed. The invention method can detect changes in methylation status at up to 1536 different CpG sites simultaneously using as little as 200 nanograms of genomic DNA.

Lung cancer is the second most common cancer among both men and women and is the leading cause of cancer death in both genders. There is no established early detection test for the disease, and only 15% of lung cancer cases are diagnosed when the disease is localized. The ability to accurately detect malignant cells in a wide range of clinical specimens including sputum, blood, or tissue has significant implications for screening high-risk individuals for this cancer.

Also provided are target nucleic acid probes for detection of a subset of genomic targets consisting of nucleic acid sequences designated SEQ ID NOS: 1610-1829 which exhibits differential methylation of genomic CpG dinucleotide sequences associated with squamous cell carcinoma (FIG. 23B). In the presence of differentially methylated genomic CpG dinucleotide sequences, the subsets of genomic targets signify a pattern distinctive of a particular type of cancer, for example, adenocarcinoma or squamous cell carcinoma of the lung tissue. The p value can be calculated for each individual marker. More than one CpG dinucleotide sequence that serves as genomic marker can be selected from the same gene if desired. Thus a gene can provide the context for more than one genomic CpG dinucleotide sequence such that methylation is determined for more than one CpG dinucleotide sequence within a single gene.

The p-value can be calculated based on a t-test of the level of methylation [i.e. methylation allele intensity/(methylation allele intensity+un-methylation allele intensity)] as is shown among 9 lung squamous cell carcinoma and 5 matching normal samples or 14 other normal samples in Table 2 and among 16 lung adenocarcinoma and 11 normal samples in Table 3.

As demonstrated in Example IV, a data matrix of β values can be used to identify CpG loci which show differential methylation in cancer. A p-value cutoff can be chosen by the skilled person to minimize the number of false positives and additional filters can be incorporated to select markers which have the largest difference between cancer and normal tissues. As shown in FIG. 23A for adenocarcinoma, a list of 14 differentially methylated markers was obtained: ADCYAP1_2, CDH13_3, GDF10_2, GDF10_3, HOXA5_2, MAGEA1_3, RUNX3_1, SCGB3A1_3, SERPINB5_1, SFN_2, SFTPA1_2, TERT_1, TERT_2, and TNF_2. Utilizing the same methylation analysis with the normal and squamous cell carcinoma samples, a list 21 differentially methylated markers was obtained: ADCYAP1_1, ADCYAP1_2, ADCYAP1_3, BCR_2, CALCA_1, GDF10_3, HOXA5_1, HOXA5_2, HOXA5_3, MAGEA1_1, MAGEA1_2, PGR_2, PRKCDBP_3, SCGB3A1_3, SERPINB5_1, SFN_2, SFTPC_3, TERT_1, TERT_2, TERT_3, TNF_2 (FIG. 23B).

The invention also provides subsets of target nucleic acid probes capable of detecting a pattern of methylation of genomic CpG dinucleotide sequences that is associated with a particular type of cancer. Thus, the invention provides a subset of genomic targets consisting of nucleic acid sequences designated SEQ ID NOS: 59, 140, 266, 293, 294, 140, 174, 371, 313, 314, 353, 360, 364, 373, and the nucleic acid sequences set forth in FIG. 32 and designated SEQ ID NOS: 1555-1609, which exhibits differential methylation of genomic CpG dinucleotide sequences associated with adenocarcinoma (FIG. 23A and FIG. 32). The population of nucleic acid probes capable of detecting altered levels of methylation of genomic CpG dinucleotide sequences of a subset of said two or more genomic targets associated with adenocarcinoma are set forth in Table 1 and designated as SEQ ID NOS: 378-1508.

In a further embodiment, the invention provides a subset of genomic targets consisting of nucleic acid sequences set forth in FIG. 23B and designated SEQ ID NOS: 57, 58, 72, 76, 139, 140, 141, 174, 264, 265, 266, 294, 305, 309, 313, 314, 315, 345, 350, 360 and 371, which exhibits differential methylation of genomic CpG dinucleotide sequences associated with squamous cell carcinoma. The population of nucleic acid probes capable of detecting altered levels of methylation of genomic CpG dinucleotide sequences of a subset of said two or more genomic targets associated with squamous cell carcinoma are set forth in Table 1 and designated as SEQ ID NOS: 378-1508.

In one embodiment, this invention provides diagnostic markers for cancer. The markers of the invention are genomic sequences having methylation states that are diagnostic or prognostic of the presence or severity of cancer. A list of exemplary genes for which methylation state can be used to determine the presence or severity of cancer is provided in Table 1. Cancer diagnosis or prognosis in a method of the invention can be made in a method of the invention based on the methylation state of particular sequence regions of the gene including, but not limited to, the coding sequence, the 5'-regulatory regions, or other regulatory regions that influence transcription efficiency.

The prognostic methods of the invention are useful for determining if a patient is at risk for recurrence. Cancer recurrence is a concern relating to a variety of types of cancer. For example, of patients undergoing complete surgical removal of colon cancer, 25-40% of patients with stage II colon carcinoma and about 50% of patients with stage III colon carcinoma experience cancer recurrence. One explanation for cancer recurrence is that patients with relatively early stage disease, for example, stage II or stage III, already have small amounts of cancer spread outside the affected organ that were not removed by surgery. These cancer cells, referred to as micrometastases, cannot typically be detected with currently available tests.

The prognostic methods of the invention can be used to identify surgically treated patients likely to experience cancer recurrence so that they can be offered additional therapeutic options, including preoperative or postoperative adjuncts such as chemotherapy, radiation, biological modifiers and other suitable therapies. The methods are especially effective for determining the risk of metastasis in patients who demonstrate no measurable metastasis at the time of examination or surgery.

The prognostic methods of the invention also are useful for determining a proper course of treatment for a patient having cancer. A course of treatment refers to the therapeutic measures taken for a patient after diagnosis or after treatment for cancer. For example, a determination of the likelihood for cancer recurrence, spread, or patient survival, can assist in determining whether a more conservative or more radical approach to therapy should be taken, or whether treatment modalities should be combined. For example, when cancer recurrence is likely, it can be advantageous to precede or follow surgical treatment with chemotherapy, radiation, immunotherapy, biological modifier therapy, gene therapy, vaccines, and the like, or adjust the span of time during which the patient is treated. As described herein, the diagnosis or prognosis of cancer state is typically correlated with the degree to which one or more of the genes in Table I is methylated. Thus, the invention can include a determination made based on the methylation state for the entire set of genes in Table I or a subset of the genes.

Furthermore, as the list in Table I is exemplary, the methylation state of other genes or genomic sequences can also be used in a method of the invention to determine the presence or severity of cancer. Exemplary cancers that can be evaluated using a method of the invention include, but are not limited to hematoporetic neoplasms, Adult T-cell leukemia/lymphoma, Lymphoid Neoplasms, Anaplastic large cell lymphoma, Myeloid Neoplasms, Histiocytoses, Hodgkin Diseases (HD), Precursor B lymphoblastic leukemia/lymphoma (ALL), Acute myclogenous leukemia (AML), Precursor T lymphoblastic leukemia/lymphoma (ALL), Myclodysplastic syndromes, Chronic Myeloproliferative disorders, Chronic lymphocytic leukemia/small lymphocytic lymphoma (SLL), Chronic Myclogenous Leukemia (CML), Lymphoplasmacytic lymphoma, Polycythemia Vera, Mantle cell lymphoma, Essential Thrombocytosis, Follicular lymphoma, Myelofibrosis with Myeloid Metaplasia, Marginal zone lymphoma, Hairy cell leukemia, Hemangioma, Plasmacytoma/plasma cell myeloma, Lymphangioma, Glomangioma, Diffuse large B-cell lymphoma, Kaposi Sarcoma, Hemanioendothelioma, Burkitt lymphoma, Angiosarcoma, T-cell chronic lymphocytic leukemia, Hemangiopericytoma, Large granular lymphocytic leukemia, head & neck cancers, Basal Cell Carcinoma, Mycosis fungoids and sezary syndrome, Squamous Cell Carcinoma, Ceruminoma, Peripheral T-cell lymphoma, Osteoma, Nonchromaffin Paraganglioma, Angioimmunoblastic T-cell lymphoma, Acoustic Neurinoma, Adenoid Cystic Carcinoma, Angiocentric lymphoma, Mucoepidermoid Carcinoma, NK/T-cell lymphoma, Malignant Mixed Tumors, Intestinal T-cell lymphoma, Adenocarcinoma, Malignant Mesothelioma, Fibrosarcoma, Sarcomotoid Type lung cancer, Osteosarcoma, Epithelial Type lung cancer, Chondrosarcoma, Melanoma, cancer of the gastrointestinal tract, olfactory Neuroblastoma, Squamous Cell Carcinoma, Isolated Plasmocytoma, Adenocarcinoma, Inverted Papillomas, Carcinoid, Undifferentiated Carcinoma, Malignant Melanoma, Mucoepidermoid Carcinoma, Adenocarcinoma, Acinic Cell Carcinoma, Gastric Carcinoma, Malignant Mixed Tumor, Gastric Lymphoma, Gastric Stromal Cell Tumors, Amenoblastoma, Lymphoma, Odontoma, Intestinal Stromal Cell tumors, thymus cancers, Malignant Thymoma, Carcinids, Type I (Invasive thymoma), Malignant Mesothelioma, Type II (Thymic carcinoma), Non-mucin producing adenocarcinoma, Squamous cell carcinoma, Lymph epithelioma, cancers of the liver and biliary tract, Squamous Cell Carcinoma, Hepatocellular Carcinoma, Adenocarcinoma, Cholangiocarcinoma, Hepatoblastoma, papillary cancer, Angiosarcoma, solid Bronchioalveolar cancer, Fibrolameller Carcinoma, Small Cell Carcinoma, Carcinoma of the Gallbladder, Intermediate Cell carcinoma, Large Cell Carcinoma, Squamous Cell Carcinoma, Undifferentiated cancer, cancer of the pancreas, cancer of the female genital tract, Squamous Cell Carcinoma, Cystadenocarcinoma, Basal Cell Carcinoma, Insulinoma, Melanoma, Gastrinoma, Fibrosarcoma, Glucagonamoa, Intaepithelial Carcinoma, Adenocarcinoma Embryonal, cancer of the kidney, Rhabdomysarcoma, Renal Cell Carcinoma, Large Cell Carcinoma, Nephroblastoma (Wilm's tumor), Neuroendocrine or Oat Cell carcinoma, cancer of the lower urinary tract, Adenosquamous Carcinoma, Urothelial Tumors, Undifferentiated Carcinoma, Squamous Cell Carcinoma, Carcinoma of the female genital tract, Mixed Carcinoma, Adenoacanthoma, Sarcoma, Small Cell Carcinoma, Carcinosarcoma, Leiomyosarcoma, Endometrial Stromal Sarcoma, cancer of the male genital tract, Serous Cystadenocarcinoma, Mucinous Cystadenocarcinoma, Sarcinoma, Endometrioid Tumors, Speretocytic Sarcinoma, Embyonal Carcinoma, Celioblastoma, Choriocarcinoma, Teratoma, Clear Cell Carcinoma, Leydig Cell Tumor, Unclassified Carcinoma, Sertoli Cell Tumor, Granulosa-Theca Cell Tumor, Sertoli-Leydig Cell Tumor, Disgerminoma, Undifferentiated Prostatic Carcinoma, Teratoma, Ductal Transitional carcinoma, breast cancer, Phyllodes Tumor, cancer of the bones joints and soft tissue, Paget's Disease, Multiple Myeloma, Insitu Carcinoma, Malignant Lymphoma, Invasive Carcinoma, Chondrosacrcoma, Mesenchymal Chondrosarcoma, cancer of the endocrine system, Osteosarcoma, Adenoma, Ewing Tumor, endocrine Carcinoma, Malignant Giant Cell Tumor, Meningnoma, Adamantinoma, Cramiopharlingioma, Malignant Fibrous Histiocytoma, Papillary Carcinoma, Histiocytoma, Follicular Carcinoma, Desmoplastic Fibroma, Medullary Carcinoma, Fibrosarcoma, Anoplastic Carcinoma, Chordoma, Adenoma, Hemangioendothelioma, Memangispericytoma, Pheochromocytoma, Liposarcoma, Neuroblastoma, Paraganglioma, Histiocytoma, Pineal cancer, Rhabdomysarcoms, Pineoblastoma, Leiomyosarcoma, Pineocytoma, Angiosarcoma, skin cancer, cancer of the nervous system, Melanoma, Schwannoma, Squamous cell carcinoma, Neurofibroma, Basal cell carcinoma, Malignant Periferal Nerve Sheath Tumor, Merkel cell carcinoma, Sheath Tumor, Extramamary Paget's Disease, Astrocytoma, Paget's Disease of the nipple, Fibrillary Astrocytoma, Glioblastoma Multiforme, Brain Stem Glioma, Cutaneous T-cell lymphoma, Pilocytic Astrocytoma, Xanthorstrocytoma, Histiocytosis, Oligodendroglioma, Ependymoma, Gangliocytoma, Cerebral Neuroblastoma, Central Neurocytoma, Dysembryoplastic Neuroepithelial Tumor Medulloblastoma, Malignant Meningioma, Primary Brain Lymphoma, Primary Brain Germ Cell Tumor, cancers of the eye, Squamous Cell Carcinoma, Mucoepidermoid Carcinoma, Melanoma, Retinoblastoma, Glioma, Meningioma, cancer of the heart, Myxoma, Fibroma, Lipoma, Papillary Fibroelastoma, Rhasdoyoma, or Angiosarcoma among others.

This invention provides methods for determining a prognosis for survival for a cancer patient. One method involves (a) measuring a level of methylation for one or more of the genes listed in Table 1 in a neoplastic cell-containing sample from the cancer patient, and (b) comparing the level of methylation in the sample to a reference level of methylation for the gene, wherein a low level of methylation for the gene in the sample correlates with increased survival of the patient.

In a particular embodiment, the invention provides methods for determining a prognosis for survival for a lung cancer patient. In this embodiment, the method involves (a) measuring a level of methylation for one or more of the genes listed in Table 1 and described herein to be associated with genomic targets differentially methylated in lung cancer in a neoplastic cell-containing sample from the lung cancer patient, and (b) comparing the level of methylation in the sample to a reference level of methylation for the one or more genes, wherein a low level of methylation for the one or more genes in the sample correlates with increased survival of the patient. In this embodiment, the level of methylation can be measured for one or more gene targets, including, for example, ADCYAP1, BCR, CALCA, CDH13, GDF10, HOXA5, MAGEA1, PGR, PRKCDBP, RUNX3, SCGB3A1, SERPINB5, SFN, SFTPA1, SFTPC, TERT, and TNF. Genomic markers associated with each of these genes are described throughout this application and are set forth in Table 1 along with their corresponding proble sequences.

Another method involves (a) measuring a level of methylation for one or more of the genes listed in Table 1 in a neoplastic cell-containing sample from the cancer patient, and (b) classifying the patient as belonging to either a first or second group of patients, wherein the first group of patients having low levels of methylation for a gene is classified as having an increased likelihood of survival compared to the second group of patients having high level of methylation for a gene.

In a particular embodiment, the invention provides methods for determining a prognosis for survival for a lung cancer patient. In this embodiment, the method involves (a) measuring a level of methylation for one or more of the genes listed in Table 1 and described herein to be associated with genomic targets differentially methylated in lung cancer in a neoplastic cell-containing sample from the cancer patient, and (b) classifying the patient as belonging to either a first or second group of patients, wherein the first group of patients having low levels of methylation for a gene is classified as having an increased likelihood of survival compared to the second group of patients having high level of methylation for a gene. In this embodiment, the level of methylation can be measured for one or more gene targets, including, for example, ADCYAP1, BCR, CDH13, CALCA, GDF10, HOXA5, PRKCDBP, SCGB3A1 SFTPC, TERT. Genomic markers associated with each of these genes are described throughout this application and are set forth in Table 1 along with corresponding probe sequences.

Another method involves (a) measuring a level of methylation for one or more of the genes listed in Table 1 in a neoplastic cell-containing sample from the cancer patient, and (b) classifying the patient as belonging to either a first or second group of patients, wherein the first group of patients having high levels of methylation for a gene is classified as having an increased likelihood of survival compared to the second group of patients having low level of methylation for a gene.

In a particular embodiment, the invention provides methods for determining a prognosis for survival for a lung cancer patient. In this embodiment, the method involves (a) measuring a level of methylation for one or more of the genes listed in Table 1 and described herein to be associated with genomic targets differentially methylated in lung cancer in a neoplastic cell-containing sample from the cancer patient, and (b) classifying the patient as belonging to either a first or second group of patients, wherein the first group of patients having high levels of methylation for a gene is classified as having an increased likelihood of survival compared to the second group of patients having low level of methylation for a gene. In this embodiment, the level of methylation can be measured for one or more gene targets, including, for example, MAGEA1, PGR, RUNX3, SERPINB5, SFN, SFTPA1, and TNF. Genomic markers associated with each of these genes are described throughout this application and are set forth in Table 1 along with their corresponding proble sequences.

The invention also provides a method for monitoring the effectiveness of a course of treatment for a patient with cancer. The method involves (a) determining a level of one or more of the genes listed in Table 1 in a neoplastic cell containing sample from the cancer patient prior to treatment, and (b) determining the level of methylation for the gene in a neoplastic cell-containing sample from the patient after treatment, whereby comparison of the level of methylation for the gene prior to treatment with the level of methylation for the gene after treatment indicates the effectiveness of the treatment.

In a particular embodiment, the invention also provides a method for monitoring the effectiveness of a course of treatment for a patient with lung cancer. The method involves (a) determining a level of one or more of the genes listed in Table 1 and described herein to be associated with genomic targets differentially methylated in lung cancer in a neoplastic cell containing sample from the lung cancer patient prior to treatment, and (b) determining the level of methylation for the gene in a neoplastic cell-containing sample from the patient after treatment, whereby comparison of the level of methylation for the gene prior to treatment with the level of methylation for the gene after treatment indicates the effectiveness of the treatment. In this embodiment, the level of methylation can be measured for one or more gene targets, including, for example, ADCYAP1, BCR, CALCA, CDH13, GDF10, HOXA5, MAGEA1, PGR, PRKCDBP, RUNX3, SCGB3A1, SERPINB5, SFN, SFTPA1, SFTPC, TERT, and TNF. Genomic markers associated with each of these genes are described throughout this application and are set forth in Table 1 along with their corresponding proble sequences.

For adenocarcinoma, the level of methylation is elevated compared to normal tissue samples for genomic targets corresponding to gene targets, including, for example, ADCYAP1, CDH13, GDF10, HOXA5, SCGB3A1, SERPINB5, SFN, SFTPA1, TERT; and decreased compared to normal tissue samples for genomic targets corresponding to gene targets, including, for example, MAGEA1, RUNX3, SERPINB5, SFN, SFTPA1, and TNF (Table 23 A). For squamous cell carcinoma, the level of methylation is elevated compared to normal tissue samples for genomic targets corresponding to gene targets, including, for example, ADCYAP1, BCR, CALCA, GDF10, HOXA5, PRKCDBP, SCGB3A1, SFTPC, and TERT; and decreased compared to normal tissue samples for genomic targets corresponding to gene targets, including, for example, TNF, MAGEA1, PGR, SERPINB5 and SFN (Table 23 B). Based on discovery of these differential methylation states associated with lung cancer, the skilled person can design various application of the present invention by selecting whether to measure for elevated or decreased methylation within one or more gene targets.

As used herein, the term "reference level" refers to a control level of expression of a marker used to evaluate a test level of expression of a biomarker in a neoplastic cell-containing sample of a patient. For example, when the level of methylation of one or more genes, referred to herein as "genomic targets," in the neoplastic cells of a patient are higher than the reference level of methylation for the genes, the cells are considered to have a low level of expression of the gene. Conversely, when the level of methylation of one or more genes in the neoplastic cells of a patient are lower than the reference level, the cells are considered to have a low level of expression, of the gene. It is also possible that the level of methylation of one or more genes in the neoplastic cells of a patient can be higher than the reference level and the cells are considered to have a high level of expression, of the gene. Furthermore, the level of methylation of one or more genes in the neoplastic cells of a patient can be lower than the reference level and the cells are considered to have a low level of expression, of the gene.

A reference level can be determined based on reference samples collected from age-matched normal classes of adjacent tissues, and with normal peripheral blood lymphocytes. The reference level can be determined by any of a variety of methods, provided that the resulting reference level accurately provides a level of a marker above which exists a first group of patients having a different probability of survival than that of a second group of patients having levels of the biomarker below the reference level. The reference level can be determined by, for example, measuring the level of expression of a biomarker in non-tumorous cells from the same tissue as the tissue of the neoplastic cells to be tested. The reference level can also be a level of a biomarker of in vitro cultured cells which can be manipulated to simulate tumor cells, or can be manipulated in any other manner which yields expression levels which accurately determine the reference level. The reference level can also be determined by comparison of the level of a biomarker, such as methylation of one or more genes, in populations of patients having the same cancer. This can be accomplished, for example, by histogram analysis, in which an entire cohort of patients are graphically presented, wherein a first axis represents the level of the biomarker, and a second axis represents the number of patients in the cohort whose neoplastic cells express the biomarker at a given level.

Two or more separate groups of patients can be determined by identification of subset populations of the cohort which have the same or similar levels of the biomarker. Determination of the reference level can then be made based on a level which best distinguishes these separate groups. A reference level also can represent the levels of two or more markers. Two or more markers can be represented, for example, by a ratio of values for levels of each biomarker. The reference level can be a single number, equally applicable to every patient, or the reference level can vary, according to specific subpopulations of patients. For example, older individuals might have a different reference level than younger individuals for the same cancer. In another example, the reference level might be a certain ratio of a biomarker in the neoplastic cells of a patient relative to the biomarker levels in non-tumor cells within the same patient. Thus the reference level for each patient can be proscribed by a reference ratio of one or more genomic markers, such as methylation of one or more genes, wherein the reference ratio can be determined by any of the methods for determining the reference levels described herein.

It is understood that the reference level has to correspond to the level of one or more methylated genomic CpG dinucleotide sequences present in a corresponding sample that allows comparison to the desired phenotype. For example, in a diagnostic application a reference level can be based on a sample that is derived from a cancer-free origin so as to allow comparison to the biological test sample for purposes of diagnosis. In a method of staging a cancer it can be useful to apply in parallel a series of reference levels, each based on a sample that is derived from a cancer that has been classified based on parameters established in the art, for example, phenotypic or cytological characteristics, as representing a particular cancer stage so as to allow comparison to the biological test sample for purposes of staging. In addition, progression of the course of a condition can be determined by determining the rate of change in the level or pattern of methylation of genomic CpG dinucleotide sequences by comparison to reference levels derived from reference samples that represent time points within an established progression rate. It is understood, that the user will be able to select the reference sample and establish the reference level based on the particular purpose of the comparison.

As used herein, the term "neoplastic cell" refers to any cell that is transformed such that it proliferates without normal homeostatic growth control. Such cells can result in a benign or malignant lesion of proliferating cells. Such a lesion can be located in a variety of tissues and organs of the body. Exemplary types of cancers from which a neoplastic cell can be derived are set forth above.

As used herein, the term "cancer" is intended to mean a class of diseases characterized by the uncontrolled growth of aberrant cells, including all known cancers, and neoplastic conditions, whether characterized as malignant, benign, soft tissue or solid tumor. Specific cancers include digestive and gastrointestinal cancers, such as anal cancer, bile duct cancer, gastrointestinal carcinoid tumor, colon cancer, esophageal cancer, gallbladder cancer, liver cancer, pancreatic cancer, rectal cancer, appendix cancer, small intestine cancer and stomach (gastric) cancer; breast cancer; ovarian cancer; lung cancer; renal cancer; CNS 30 cancer; leukemia and melanoma. By exemplification, a list of known cancers is set forth above.

As used herein, the term "sample" is intended to mean any biological fluid, cell, tissue, organ or portion thereof, that contains genomic DNA suitable, for methylation detection via the invention methods. A test sample can include or be suspected to include a neoplastic cell, such as a cell from the colon, rectum, breast, ovary, prostate, kidney, lung, blood, brain or other organ or tissue that contains or is suspected to contain a neoplastic cell. The term includes samples present in an individual as well as samples obtained or derived from the individual. For example, a sample can be a histologic section of a specimen obtained by biopsy, or cells that are placed in or adapted to tissue culture. A sample further can be a subcellular fraction or extract, or a crude or substantially pure nucleic acid molecule or protein preparation. A reference sample can be used to establish a reference level and, accordingly, can be derived from the source tissue that meets having the particular phenotypic characteristics to which the test sample is to be compared.

A sample may be obtained in a variety of ways known in the art. Samples may be obtained according to standard techniques from all types of biological sources that are usual sources of genomic DNA including, but not limited to cells or cellular components which contain DNA, cell lines, biopsies, bodily fluids such as blood, sputum, stool, urine, cerebrospinal fluid, ejaculate, tissue embedded in paraffin such as tissue from eyes, intestine, kidney, brain, heart, prostate, lung, breast or liver, histological object slides, and all possible combinations thereof. In particular embodiments, the methods described herein can be performed on one or more samples from lung cancer patients at the time of bronchoscopy: bronchoaveolar lavage (BAL) fluid, sputum, or whole blood. The multiplexed methylation analysis system can be applied to early and non-invasive diagnosis of lung cancer, or to monitor cancer progression or response to treatment. In general, this technology can be useful for comprehensive DNA methylation analyses in large populations, with potential application to the classification or diagnosis of a broad range of cancers and other diseases.

A suitable biological sample can be sourced and acquired subsequent to the formulation of the diagnostic aim of the marker. A sample can be derived from a population of cells or from a tissue that is predicted to be afflicted with or phenotypic of the condition. The genomic DNA can be derived from a high-quality source such that the sample contains only the tissue type of interest, minimum contamination and minimum DNA fragmentation. In particular, samples should be representative of the tissue or cell type of interest that is to be handled by the diagnostic assay. It is understood that samples can be analyzed individually or pooled depending on the purpose of the user. In addition, a population or set of samples from an individual source can be analyzed to maximize confidence in the results and can be a sample set size of 10, 15, 20, 25, 50, 75, 100, 150 or sample set sizes in the hundreds.

In subsequent steps of the method, the methylation levels of CpG positions are compared to a reference sample, to identify differentially methylated CpG positions. Each class may be further segregated into sets according to predefined parameters to minimize the variables between the at least two classes. In the following stages of the method, all comparisons of the methylation status of the classes of tissue, are carried out between the phenotypically matched sets of each class. Examples of such variables include, age, ethnic origin, sex, life style, patient history, drug response etc.

As used herein, the term "disease-free survival" refers to the lack of tumor recurrence and/or spread and the fate of a patient after diagnosis, for example, a patient who is alive without tumor recurrence.

The phrase "overall survival" refers to the fate of the patient after diagnosis, regardless of whether the patient has a recurrence of the tumor. As used herein, the term "risk of recurrence" refers to the probability of tumor recurrence or spread in a patient subsequent to diagnosis of cancer, wherein the probability is determined according to the process of the invention. Tumor recurrence refers to further growth of neoplastic or cancerous cells after diagnosis of cancer. Particularly, recurrence can occur when further cancerous cell growth occurs in the cancerous tissue. Tumor spread refers to dissemination of cancer cells into local or distant tissues and organs, for example during tumor metastasis. Tumor recurrence, in particular, metastasis, is a significant cause of mortality among patients who have undergone surgical treatment for cancer. Therefore, tumor recurrence or spread is correlated with disease free and overall patient survival.

The methods of the invention can be applied to the characterization, classification, differentiation, grading, staging, diagnosis, or prognosis of a condition characterized by a pattern of one or more methylated genomic CpG dinucleotide sequences that is distinct from the pattern of one or more methylated genomic CpG dinucleotide sequences exhibited in the absence of the condition. A condition that is suitable for practicing the methods of the invention can be, for example, cell proliferative disorder or predisposition to cell proliferative disorder; metabolic malfunction or disorder; immune malfunction, damage or disorder; CNS malfunction, damage or disease; symptoms of aggression or behavioural disturbance; clinical, psychological and social consequences of brain damage; psychotic disturbance and personality disorder; dementia or associated syndrome; cardiovascular disease, malfunction and damage; malfunction, damage or disease of the gastrointestinal tract; malfunction, damage or disease of the respiratory system; lesion, inflammation, infection, immunity and/or convalescence; malfunction, damage or disease of the body as an abnormality in the development process; malfunction, damage or disease of the skin, the muscles, the connective tissue or the bones; endocrine and metabolic malfunction, damage or disease; headache or sexual malfunction, and combinations thereof.

Methylation of CpG dinucleotide sequences can be measured using any of a variety of techniques used in the art for the analysis of specific CpG dinucleotide methylation status. For example, methylation can be measured by employing a restriction enzyme based technology, which utilizes methylation sensitive restriction endonucleases for the differentiation between methylated and unmethylated cytosines. Restriction enzyme based technologies include, for example, restriction digest with methylation-sensitive restriction enzymes followed by Southern blot analysis, use of methylation-specific enzymes and PCR, restriction landmark genomic scanning (RLGS) and differential methylation hybridization (DMH).

Restriction enzymes characteristically hydrolyze DNA at and/or upon recognition of specific sequences or recognition motifs that are typically between 4- to 8-bases in length. Among such enzymes, methylation sensitive restriction enzymes are distinguished by the fact that they either cleave, or fail to cleave DNA according to the cytosine methylation state present in the recognition motif, in particular, of the CpG sequences. In methods employing such methylation sensitive restriction enzymes, the digested DNA fragments can be separated, for example, by gel electrophoresis, on the basis of size, and the methylation status of the sequence is thereby deduced, based on the presence or absence of particular fragments. Preferably, a post-digest PCR amplification step is added wherein a set of two oligonucleotide primers, one on each side of the methylation sensitive restriction site, is used to amplify the digested genomic DNA. PCR products are not detectable where digestion of the subtended methylation sensitive restriction enzyme site occurs. Techniques for restriction enzyme based analysis of genomic methylation are well known in the art and include the following: differential methylation hybridization (DMH) (Huang et al., Human Mol. Genet. 8, 459-70, 1999); Not I-based-differential methylation hybridization (see e.g., WO 02/086163 A1); restriction landmark genomic scanning (RLGS) (Plass et al., *Genomics* 58:254-62, 1999); methylation sensitive arbitrarily primed PCR (AP-PCR) (Gonzalgo et al., *Cancer Res.* 57: 594-599, 1997); methylated CpG island amplification (MCA) (Toyota et. al., *Cancer Res.* 59: 2307-2312, 1999). Other useful methods for detecting genomic methylation are described, for example, in US Pat. App. pub. No. 2003/0170684 or WO 04/05122.

Methylation of CpG dinucleotide sequences also can be measured by employing cytosine conversion based technologies, which rely on methylation status-dependent chemical modification of CpG sequences within isolated genomic DNA, or fragments thereof, followed by DNA sequence analysis. Chemical reagents that are able to distinguish between methylated and non methylated CpG dinucleotide sequences include hydrazine, which cleaves the nucleic acid, and bisulfite treatment. Bisulfite treatment followed by alkaline hydrolysis specifically converts non-methylated cytosine to uracil, leaving 5-methylcytosine unmodified as described by Olek A., *Nucleic Acids Res.* 24:5064-6, 1996 or Frommer et al., *Proc. Natl. Acad. Sci. USA* 89:1827-1831 (1992). The bisulfite-treated DNA can subsequently be analyzed by conventional molecular techniques, such as PCR amplification, sequencing, and detection comprising oligonucleotide hybridization.

Techniques for the analysis of bisulfite treated DNA can employ methylation-sensitive primers for the analysis of CpG methylation status with isolated genomic DNA as described by Herman et al., *Proc. Natl. Acad. Sci. USA* 93:9821-9826, 1996, and in U.S. Pat. Nos. 5,786,146 and 6,265,171. Methylation sensitive PCR (MSP) allows for the detection of a specific methylated CpG position within, for example, the regulatory region of a gene. The DNA of interest is treated such that methylated and non-methylated cytosines are differentially modified, for example, by bisulfite treatment, in a manner discernable by their hybridization behavior. PCR primers specific to each of the methylated and non-methylated states of the DNA are used in a PCR amplification. Products of the amplification reaction are then detected, allowing for the deduction of the methylation status of the CpG position within the genomic DNA. Other methods for the analysis of bisulfite treated DNA include methylation-sensitive single nucleotide primer extension (Ms-SNuPE) (Gonzalgo & Jones, Nucleic Acids Res. 25:2529-2531, 1997; and see U.S. Pat. No. 6,251,594), and the use of real time PCR based methods, such as the art-recognized fluorescence-based real-time PCR technique MethyLight™ (Eads et al., Cancer Res. 59:2302-2306, 1999; U.S. Pat. No. 6,331,393 to Laird et al.; and see Heid et al., Genome Res. 6:986-994, 1996). It is understood that a variety of methylation assay methods can be used for the determination of the methylation status of particular genomic CpG positions. Methods which require bisulfite conversion include, for example, bisulfite sequencing, methylation-specific PCR, methylation-sensitive single nucleotide primer extension (Ms-SnuPE), MALDI mass spectrometry and methylation-specific oligonucleotide arrays and are described, for example, in U.S. patent application Ser. No. 10/309,803 and international application International Patent Application No.: PCT/US03/38582.

In one embodiment, methylation of genomic CpG positions in a sample can be detected using an array of probes. In particular embodiments, a plurality of different probe molecules can be attached to a substrate or otherwise spatially distinguished in an array. Exemplary arrays that can be used in the invention include, without limitation, slide arrays, silicon wafer arrays, liquid arrays, bead-based arrays and others known in the art or set forth in further detail below. In preferred embodiments, the methods of the invention can be practiced with array technology that combines a miniaturized array platform, a high level of assay multiplexing, and scalable automation for sample handling and data processing.

An array of arrays, also referred to as a composite array, having a plurality of individual arrays that is configured to allow processing of multiple samples can be used. Exemplary composite arrays that can be used in the invention are described in U.S. Pat. No. 6,429,027 and US 2002/0102578 and include, for example, one component systems in which each array is located in a well of a multi-well plate or two component systems in which a first component has several separate arrays configured to be dipped simultaneously into the wells of a second component. A substrate of a composite array can include a plurality of individual array locations, each having a plurality of probes and each physically separated from other assay locations on the same substrate such that a fluid contacting one array location is prevented from contacting another array location. Each array location can have a plurality of different probe molecules that are directly attached to the substrate or that are attached to the substrate via rigid particles in wells (also referred to herein as beads in wells).

In a particular embodiment, an array substrate can be fiber optical bundle or array of bundles, such as those generally described in U.S. Pat. Nos. 6,023,540, 6,200,737 and 6,327, 410; and PCT publications WO9840726, WO9918434 and WO9850782. An optical fiber bundle or array of bundles can have probes attached directly to the fibers or via beads. Other substrates having probes attached to a substrate via beads are described, for example, in US 2002/0102578. A substrate, such as a fiber or silicon chip, can be modified to form discrete sites or wells such that only a single bead is associated with the site or well. For example, when the substrate is a fiber optic bundle, wells can be made in a terminal or distal end of individual fibers by etching, with respect to the cladding, such that small wells or depressions are formed at one end of the fibers. Beads can be non-covalently associated in wells of a substrate or, if desired, wells can be chemically functionalized for covalent binding of beads. Other discrete sites can also be used for attachment of particles including, for example, patterns of adhesive or covalent linkers. Thus, an array substrate can have an array of particles each attached to a patterned surface.

In a particular embodiment, a surface of a substrate can include physical alterations to attach probes or produce array locations. For example, the surface of a substrate can be modified to contain chemically modified sites that are useful for attaching, either-covalently or non-covalently, probe molecules or particles having attached probe molecules. Chemically modified sites can include, but are not limited to the linkers and reactive groups set forth above. Alternatively, polymeric probes can be attached by sequential addition of monomeric units to synthesize the polymeric probes in situ. Probes can be attached using any of a variety of methods known in the art including, but not limited to, an ink-jet printing method as described, for example, in U.S. Pat. Nos. 5,981,733; 6,001,309; 6,221,653; 6,232,072 or 6,458,583; a spotting technique such as one described in U.S. Pat. No. 6,110,426; a photolithographic synthesis method such as one described in U.S. Pat. No. 6,379,895 or 5,856,101; or printing method utilizing a mask as described in U.S. Pat. No. 6,667, 394. Accordingly, arrays described in the aforementioned references can be used in a method of the invention.

The size of an array used in the invention can vary depending on the probe composition and desired use of the array. Arrays containing from about 2 different probes to many millions can be made. Generally, an array can have from two to as many as a billion or more probes per square centimeter. Very high density arrays are useful in the invention including, for example, those having from about 10,000,000 probes/cm$^2$ to about 2,000,000,000 probes/cm$^2$ or from about 100,000, 000 probes/cm$^2$ to about 1,000,000,000 probes/cm$^2$. High density arrays can also be used including, for example, those in the range from about 100,000 probes/cm$^2$ to about 10,000, 000 probes/cm$^2$ or about 1,000,000 probes/cm$^2$ to about 5,000,000 probes/cm$^2$. Moderate density arrays useful in the invention can range from about 10,000 probes/cm$^2$ to about 100,000 probes/cm$^2$, or from about 20,000 probes/cm$^2$ to about 50,000 probes/cm$^2$. Low density arrays are generally less than 10,000 probes/cm$^2$ with from about 1,000 probes/cm$^2$ to about 5,000 probes/cm$^2$ being useful in particular embodiments. Very low density arrays having less than 1,000 probes/cm$^2$, from about 10 probes/cm$^2$ to about 1000 probes/cm$^2$, or from about 100 probes/cm$^2$ to about 500 probes/cm$^2$ are also useful in some applications.

Thus, the invention provides a robust and ultra highthroughput technology for simultaneously measuring methylation at many specific sites in a genome. The invention further provides cost-effective methylation profiling of thousands of samples in a reproducible, well-controlled system. In particular the invention allows implementation of a process, including sample preparation, bisulfite treatment, genotyping-based assay and PCR amplification that can be carried out on a robotic platform.

The methods of the invention can be carried out at a level of multiplexing that is 96-plex or even higher including, for example, as high as 1,500-plex. An advantage of the invention is that the amount of genomic DNA used for detection of methylated sequences is low including, for example, less that 1 ng of genomic DNA per locus. In one embodiment, the throughput of the methods can be 96 samples per run, with 1,000 to 1,500 methylation assays per sample (144,000 data points or more per run). In the embodiment exemplified herein, the system is capable of carrying out as many as 10 runs per day or more. A further object of the invention is to provide assays to survey methylation status the 5'-regulatory regions of at least 1,000 human genes per sample. Particular genes of interest are tumor suppressor genes or other cancer-related genes, as well as genes identified through RNA profiling.

Therefore, the invention makes available diagnostic and/or prognostic assays for the analysis of the methylation status of CpG dinucleotide sequence positions as markers for disease or disease-related conditions. As exemplified herein for lung cancer, the invention provides a systematic method for the identification, assessment and validation of genomic targets as well as a systematic means for the identification and verification of multiple condition relevant CpG positions to be used alone, or in combination with other CpG positions, for example, as a panel or array of markers, that form the basis of a clinically relevant diagnostic or prognostic assay. The inventive method enables differentiation between two or more phenotypically distinct classes of biological matter and allows for the comparative analysis of the methylation patterns of CpG dinucleotides within each of the classes.

A further object of the invention is to provide assays for specific identifying methylation patterns in different cancer types and cancer stages. The invention provides assays for specific methylation patterns characteristic of different cancer types and cancer stages. For example, the invention provides genomic targets that give rise to differential methylation patterns characteristic of lung cancer in general, adenocarcinoma of the lung, squamous cell carcinoma of the lung as well as methylation patterns that can distinguish between adenocarcinoma and squamous cell carcinoma of the lung. As described herein, the genomic targets designated SEQ ID NOS: 57, 58, 59, 72, 76, 139, 140, 141, 174, 264, 265, 266, 293, 294, 305, 309, 313, 314, 315, 345, 350, 353, 360, 364, 371 and 373 show differential methylation patterns characteristic of lung cancer. The subset of genomic targets designated SEQ ID NOS: 59, 140, 266, 293, 294, 140, 174, 371, 313, 314, 353, 360, 364 and 373 shows differential methylation patterns characteristic of adenocarcinoma of the lung, while the genomic targets designated SEQ ID NOS: 57, 58, 72, 76, 139, 140, 141, 174, 264, 265, 266, 294, 305, 309, 313, 314, 315, 345, 350, 360 and 371 show differential methylation patterns characteristic of squamous cell carcinoma of the lung. The genomic targets designated SEQ ID NOS: 59, 293, 353, 364 and 373 show differential methylation patterns in adenocarcinoma of the lung, but not in squamous cell carcinoma of the lung and can thus be used to distinguish between the two types of lung cancer. The genomic targets designated SEQ ID NOS: 57, 58, 59, 72, 76, 139, 141, 264, 265, 293, 309, 315, 345, 350, 353, 3-64 and 373 show differential methylation patterns in squamous cell carcinoma of the lung, but not in adenocarcinoma of the lung and can also be used to distinguish between the two types of lung cancer.

A further object of the invention is to provide software to retrieve and annotate CpG island sequence information, design and analyze primers, track sample information, and analyze and report results obtained from methylation profiling methods of the invention. An advantage of the invention is that it provides a high throughput methylation analysis system that can be commercialized, both through a service business—in which customers can provide samples and a gene list (CpG site list) for analysis in the methods—and through products that can used in standard laboratory conditions.

RLGS profiling of the methylation pattern of 1184 CpG islands in 98 primary human tumors revealed that the total number of methylated sites is variable between and in some cases within different tumor types, suggesting there may be methylation subtypes within tumors having similar histology (Costello, et al., Nat Genet. 24(2): 132-8 (2000)). Aberrant methylation of some of these genes correlates with loss of gene expression. Based on these observations, it should be feasible to use the methylation pattern of a sizable group of tumor suppressor genes or other cancer-related genes to classify and predict different kinds of cancer, or the same type of cancer in different stages. It promises to provide a useful tool for cancer diagnosis, or preferably, for detection of premalignant changes. When combined with the development of sensitive, non-invasive methods (e.g. a blood test; indeed, circulating tumor nucleic acids in blood have been demonstrated to reflect the biologic characteristics of tumors (Cui, et al., Science 299 (5613): 1753-5 (2003)), to detect such methylation signatures) this may provide a viable method to screen subjects at risk for cancer as well as to monitor cancer progression and response to treatment.

Because methylation detection interrogates genomic DNA, but not RNA or protein, it offers several technological advantages in a clinical diagnostic setting: (1) readily available source materials. This is particularly important for prognostic research, when only DNA can be reliably extracted from archived paraffin-embedded samples for study; (2) capability for multiplexing, allowing simultaneous measurement of multiple targets to improve assay specificity; (3) easy amplification of assay products to achieve high sensitivity; (4) robust measurement in tumors that arise from methylation inactivation of one allele of tumor suppressor genes—a process called "functional haploinsufficiency" (Balmain, et al., Nat Genet. 33 Suppl: 238-44 (2003)). It is much easier to detect a methylation change (from negative to positive) than to detect a two-fold gene expression change in these tumors. In summary, when combined with RNA-based gene expression profiling and/or protein-based immunoassays, DNA methylation profiling should provide a sensitive, accurate and robust tool for cancer diagnosis and prognosis (Wong, et al., Curr Oncol Rep. 4(6): 471-7 (2002)).

The present invention is directed to a method for the identification of differentially methylated CpG dinucleotides within genomic DNA that are particularly informative with respect to disease states. These may be used either alone or as components of a gene panel in diagnostic and/or prognostic assays.

In particular embodiments, the invention is directed to methods of prediction and diagnosis of conditions characterized by a pattern of one or more methylated genomic CpG dinucleotide sequences that is distinct from the pattern of methylated genomic CpG dinucleotide sequences exhibited in the absence of the particular condition, for example, cell proliferative disorders, such as cancer; dysfunctions, damages or diseases of the central nervous system (CNS), including aggressive symptoms or behavioral disorders; clinical, psychological and social consequences of brain injuries; psychotic disorders and disorders of the personality, dementia and/or associates syndromes; cardiovascular diseases, malfunctions or damages; diseases, malfunctions or damages of the gastrointestine diseases; malfunctions or damages of the respiratory system; injury, inflammation, infection, immunity and/or reconvalescence, diseases; malfunctions or damages as consequences of modifications in the developmental process; diseases, malfunctions or damages of the skin, muscles, connective tissue or bones; endocrine or metabolic diseases malfunctions or damages; headache; and sexual malfunctions; or combinations thereof.

It is understood that modifications which do not substantially affect the activity of the various embodiments of this invention are also included within the definition of the invention provided herein. Accordingly, the following examples are intended to illustrate but not limit the present invention.

EXAMPLE I

Design of Target Nucleic Acid Probes

This Example shows design of target nucleic acid probes for detection of genomic loci.

First, a human gene promoter database was prepared that includes all CpG regions of potential interest for methylation profiling. A fully automated SNP genotyping assay design program was adapted for methylation application and CpG islands of interest are selected and "converted by bisulfite" computationally. For each CpG locus, three probes are designed: two allele-specific oligonucleotides, one corresponding to the methylated, and the other to the unmethylated state of the CpG site and one locus-specific oligo (FIG. 4). If other CpG loci are present in the close vicinity of the chosen CpG site, a wobble base [A or G] is used for the corresponding probe position. Assays for more than 60 CpG sites from 20 different genes were designed, mostly selected from the methylation database on the world-wide-web at methdb.de. Approximately half of the sites were used in the assay development.

EXAMPLE II

Development of Internal Controls and Confirmation of Completeness of Bisulfite Conversion This example shows the development of internal controls that allow optimization of protocols, determination of assay specificity, troubleshooting, and evaluation of overall assay performance.

Plasmids pUC19, pACYC184 and phage phiX174 were selected to serve as control DNAs. These DNAs can be spiked into the genomic DNA assays to provide internal controls, and would not interfere with human genomic DNA reactions. It is easy to prepare completely unmethylated plasmid DNAs and then methylate them in vitro using Sss I (CpG) methylase to produce substrates with known methylation status. Plasmids can be methylated virtually to completion. The quality of in vitro methylation was tested by restriction enzyme digestion of unmethylated and methylated DNAs using the methylation sensitive enzyme Hpa II and its isoschisomer Msp I, which is not sensitive to methylation. It was not possible to detect any bands resulting from restriction digest on the agarose gel after incubation of methylated pUC19, pACYC184 and phiX174 with Hpa II for two hours at 37° C., while the unmethylated DNAs were completely digested. Both methylated and unmethylated DNAs were completely digested by Msp I.

Figure 5:
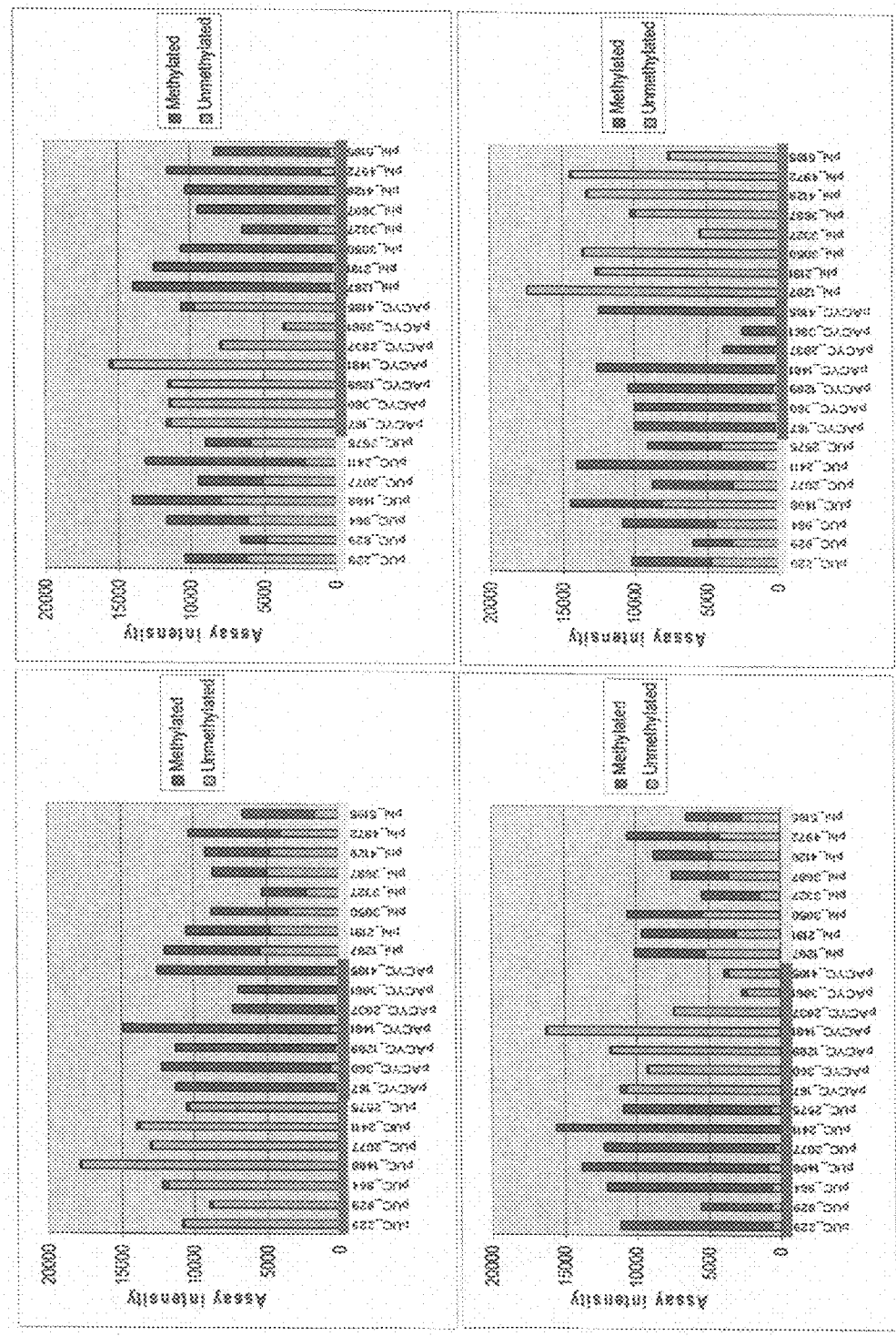
FIG. 5 shows plasmid controls used in the assay development. Unmethylated (green), semi-methylated (yellow) and fully-methylated (red) plasmid loci can be correctly scored in the human genomic DNA background.

Plasmid controls (unmethylated, methylated or mixed at a 1:1 ratio) were spiked into human genomic DNA at a 1:1 molar ratio (at approximately 2-4 pg plasmid DNA/1 µg gDNA, depending on the plasmid size), and were used in every methylation experiment to monitor both bisulfite conversion efficiency and accuracy of methylation detection. As shown in FIG. 5, unmethylated, semi-methylated and fully-methylated loci can be easily distinguished by the assay.

Figure 6:
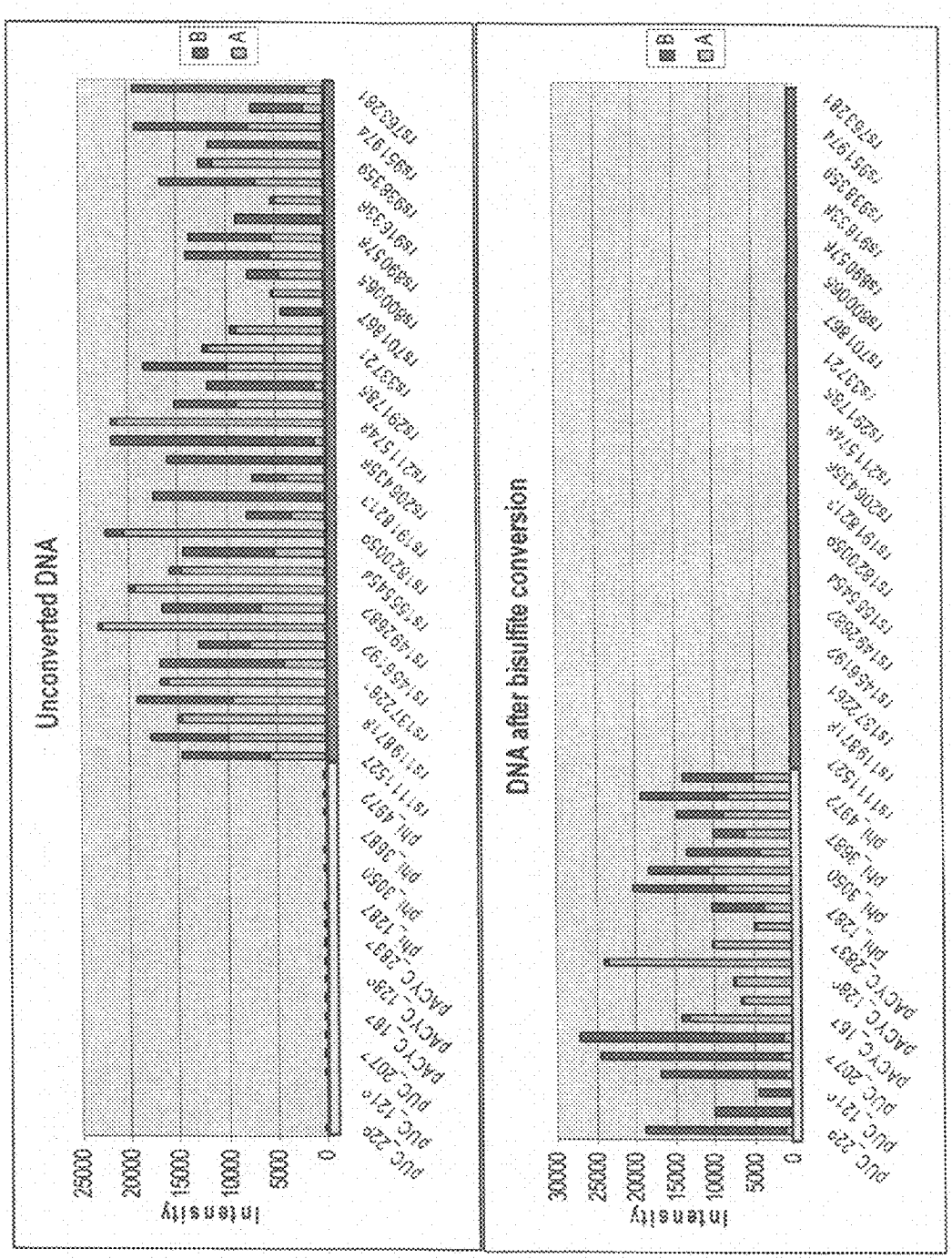
FIG. 6 shows bisulfite conversion of DNA monitored with internal controls. Top panel: unconverted DNA; bottom panel: DNA after bisulfite conversion. Query oligonucleotides for converted plasmid loci (yellow) and unconverted genomic loci (green) are present in both assays. After bisulfite conversion, signal corresponding to unconverted loci disappears, and signal from converted loci becomes detectable.

The utility of bisulfite conversion of DNA for methylation detection is based on the different sensitivity of cytosine and 5-methylcytosine to deamination by bisulfite. Under acidic conditions, cytosine undergoes conversion to uracil, while methylated cytosine remains unreactive. An efficient bisulfite conversion protocol facilitates a high-throughput methylation profiling assay. Incomplete conversion of cytosine to uracil by bisulfite can result in appearance of false-positive signals for 5-methylcytosine, and reduce the overall quality of the assay data. In order to monitor the effectiveness of bisulfite treatment, a set of oligonucleotides (a standard set of SNP genotyping probes) designed for unconverted genomic DNA sequences was included with the plasmid control oligos in the assay. As shown in FIG. 6, if bisulfite conversion is successful, the signal from oligonucleotides targeted to the unconverted DNA (the SNP set) will disappear, and signals from oligonucleotides targeted to the converted DNA will be present. Incomplete conversion will result in low and inconsistent signals across all targeted loci.

Data Processing

Figures 7A, 7B:
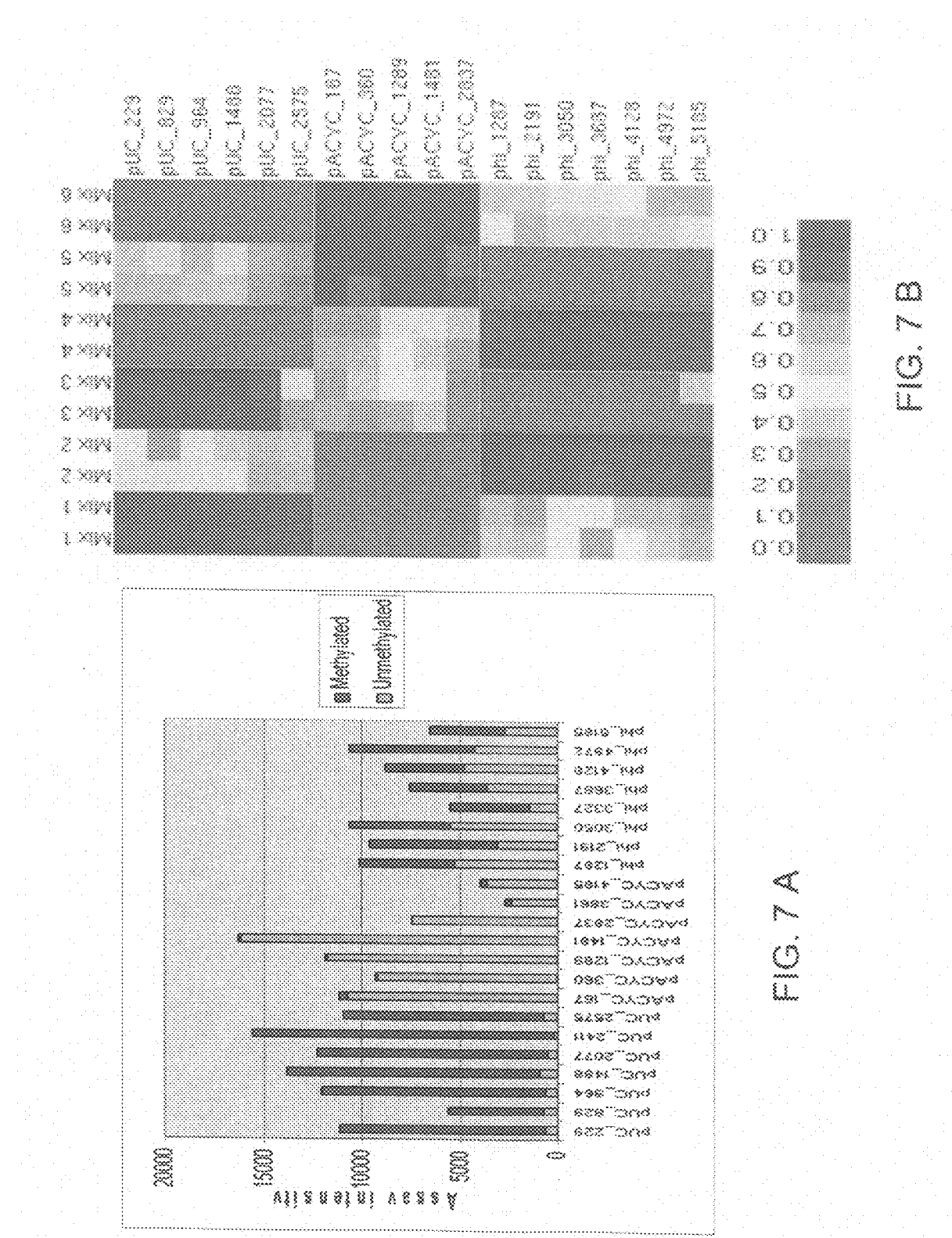
FIG. 7 shows methylation assay development and data processing. Left panel: unmethylated, semi-methylated, and fully-methylated loci on the plasmids can be distinguished in the human genomic DNA background. These plasmid DNAs were spiked into human genomic DNA at a 1:1 molar ratio. Right panel: each data point is represented in a red/green/yellow plot, where red indicates a methylated state, green—unmethylated, and yellow—semi-methylated. The whole left panel (bar graph) is represented by one column on a red/green/yellow plot.

Development of a robust and high-throughput method for simultaneous measurement of methylation at many specific sites in many samples requires a highly efficient analysis and data export process. Each data point in the methylation assay can be represented as a ratio of the fluorescent signals from M (methylated) and U (unmethylated) specific PCR products after array hybridization. This value indicates the methylation status of the CpG locus and may range from 0 in the case of completely unmethylated sites to 1 in completely methylated sites. The value also can be visually presented as a red/green/yellow plot (FIG. 7). In addition, each locus is characterized by a locus intensity value, which allows filtering of failed loci. This combination of numerical and color outputs allows for quick comparison of genes and samples of interest, and processing of thousands of loci across hundreds of samples.

Reference Samples for Genome-Wide Methylation Profiling

Figure 8:
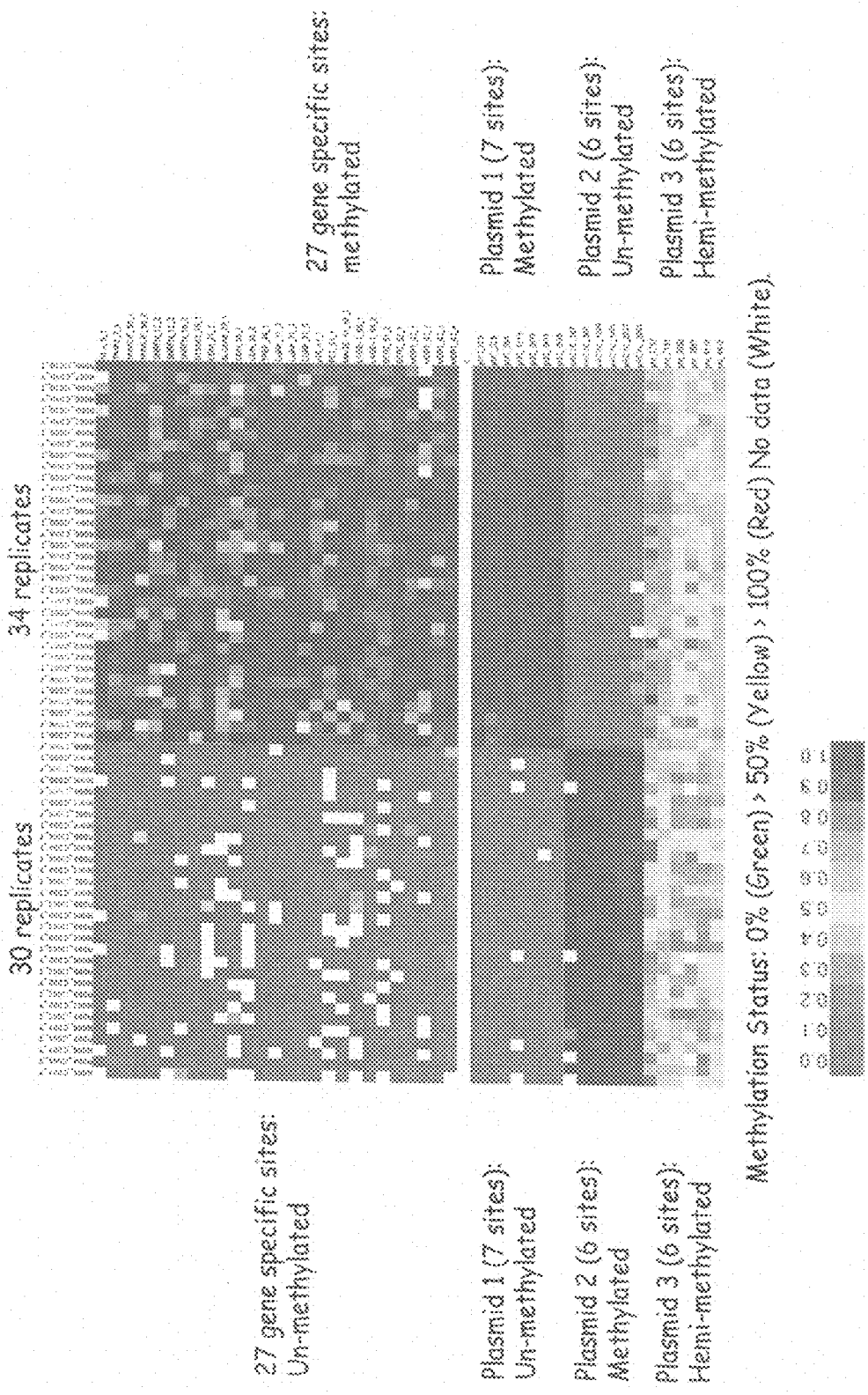
FIG. 8 shows reproducible methylation detection in two human reference DNAs: unmethylated (left panel) and methylated (right panel). The red color indicates a methylated state, green—unmethylated, and yellow—semi-methylated. White squares represent the loci with low intensity values, for which the methylation status call could not be made. In the case of amplified gDNA (left panel), some genomic loci may become underrepresented after amplification procedure.

To calibrate quantitative measurements of methylation, "fully methylated" and "unmethylated" genomic templates were developed (FIG. 8). The fully unmethylated templates were generated by genome-wide amplification of human genomic DNA. With more than 1000-fold amplification, any endogenous methylation is effectively "diluted/erased", and the sample can be used as an "unmethylated" reference DNA. Methylated templates were generated by in vitro methylation of amplified gDNA using Sss I (CpG-methylase) enzyme. The reproducibility of the methylation detection method was confirmed by typing 27 human gene-specific CpG sites in these reference DNAs over 30 times. A high degree of reproducibility was obtained (FIG. 8).

Methylation Profiles of Randomly Selected Human Genomic DNAs

Figure 9:
FIG. 9 shows methylation measurement in 15 Coriell genomic DNAs and the reference DNAs.

We have also monitored a set of CpG sites in randomly selected human genomic DNAs. The DNA samples were obtained from the Human Genetic Cell Repository, Coriell Institute for Medical Research, NJ. In this experiment, we measured 7 females, 5 males and 3 of unknown gender specificity; each was done in duplicate and the results are shown in columns next to each other in FIG. 9. Distinguishable methylation patterns were obtained with DNAs isolated from male and female cell lines, especially in genes that are located on the X-chromosome (FIG. 9). The overall methylation profiles are quite reproducible among the duplicates.

Assay Reproducibility

One of the most important assay characteristics is its reproducibility. This was addressed by monitoring several plasmid loci with known methylation status across multiple replicates in several independent experiments. The experimental setup also allowed for estimation of the assay accuracy. A mixture of unmethylated, methylated and 1:1 mixed plasmid DNAs was prepared, and spiked into 1 µg of human genomic DNA in a 1:1 molar ratio. Each experiment included three plasmid mixtures:

| 1 | pUC19 U | pACYC 184 M | phiX174 U:M |
| 2 | pUC19 U:M | pACYC 184 U | phiX174 M |
| 3 | pUC19 M | pACYC 184 U:M | phiX174 U |

Figure 10:
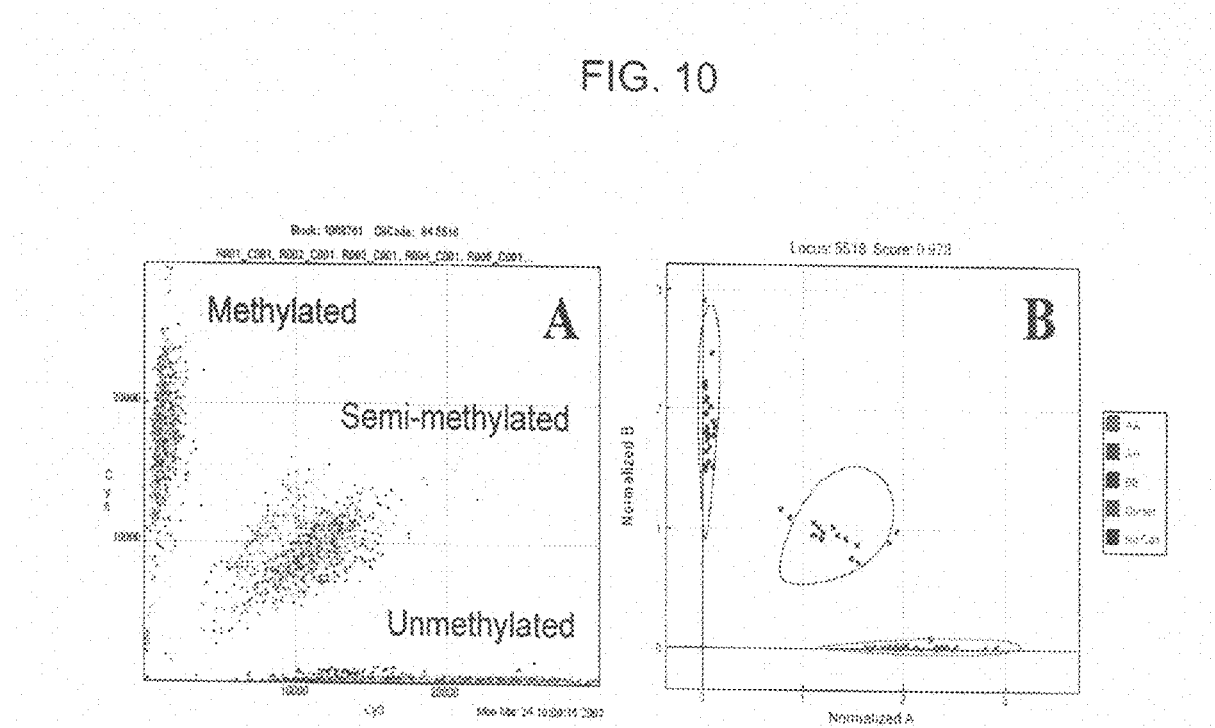
FIG. 10 shows methylation status of any particular locus determined using a clustering algorithm. Panel A shows raw intensity data (of each bead) for one locus across all 96 replicates. Panel B shows analyzed clusters. Unmethylated, methylated and semi-methylated loci can be distinguished and called correctly by this algorithm.
Figure 11:
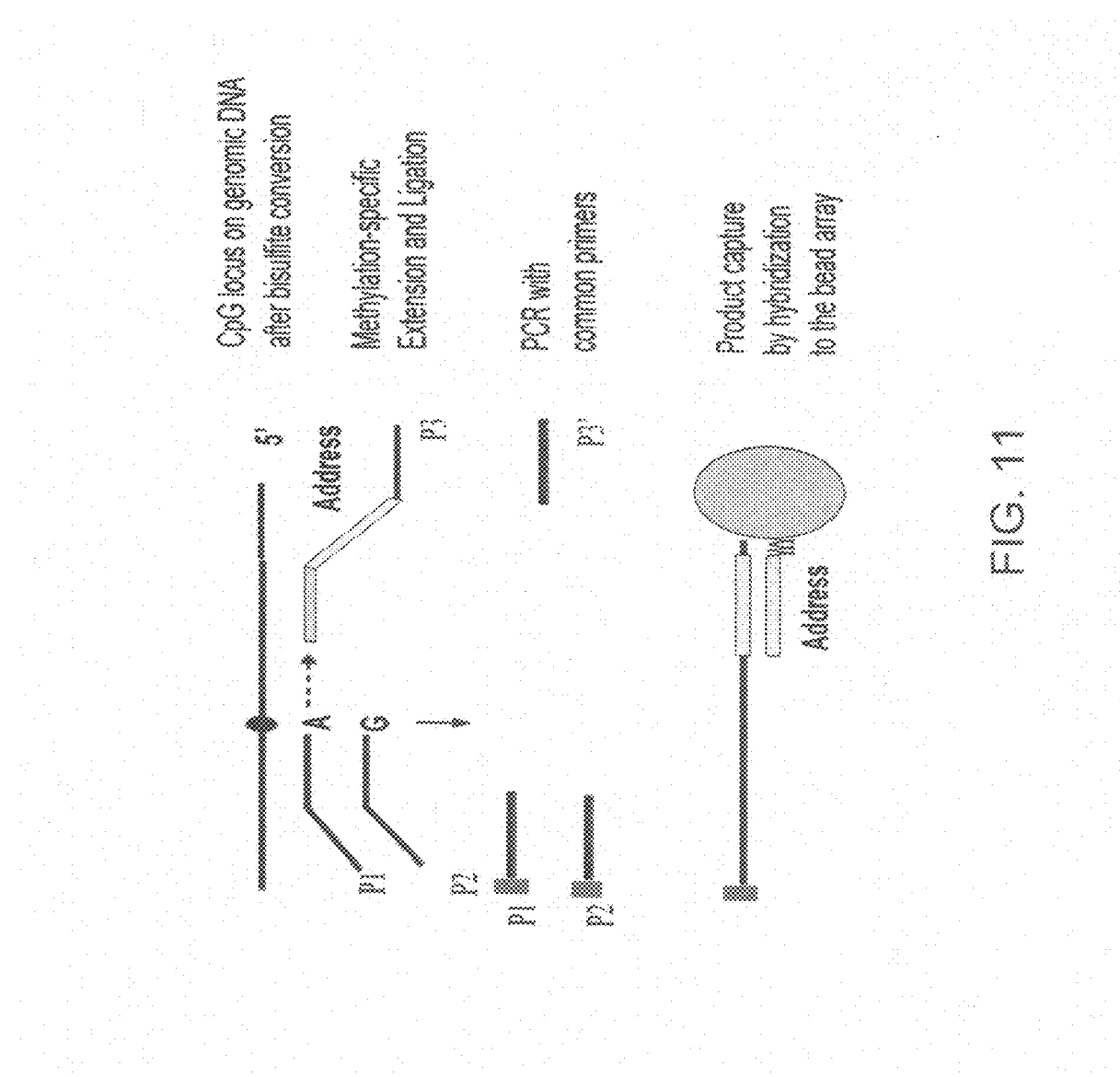
FIG. 11 shows a schematic overview of a methylation assay that incorporates bisulfite conversion and a bead array format.
Figure 12:
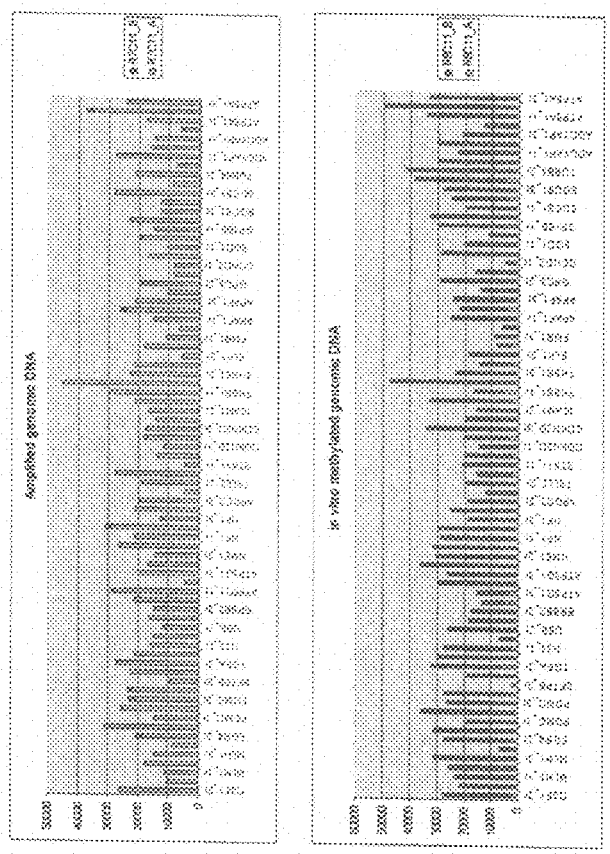
FIG. 12 shows reference samples for a methylation assay encompassing amplified genomic DNA in Panel A and corresponding in vitro methylated genomic DNA in Panel B.
Figure 13:
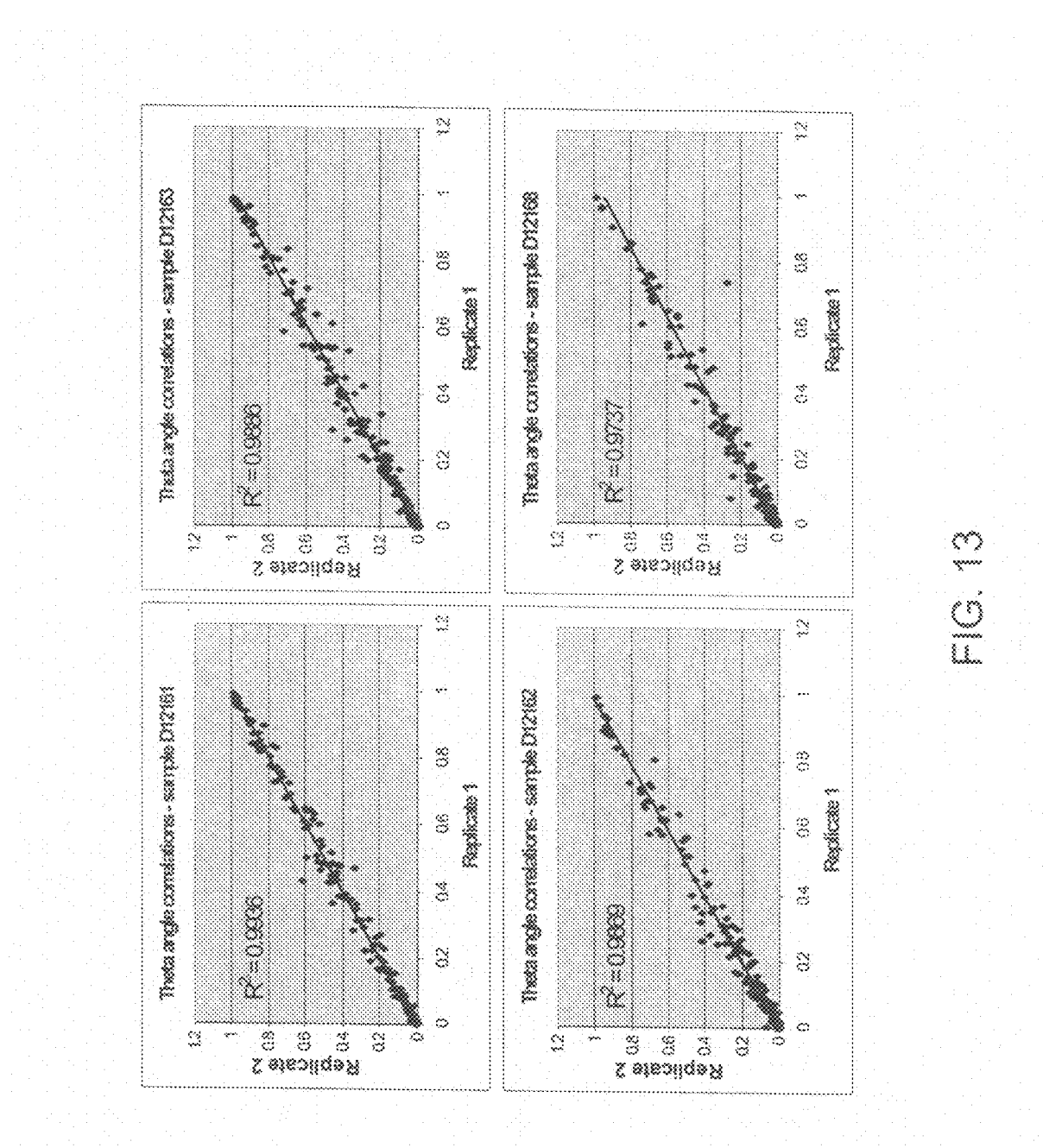
FIG. 13 shows correlation in methylation status between replicates of lung cancer clinical samples containing 389 loci across four independent arrays.
Figure 14:
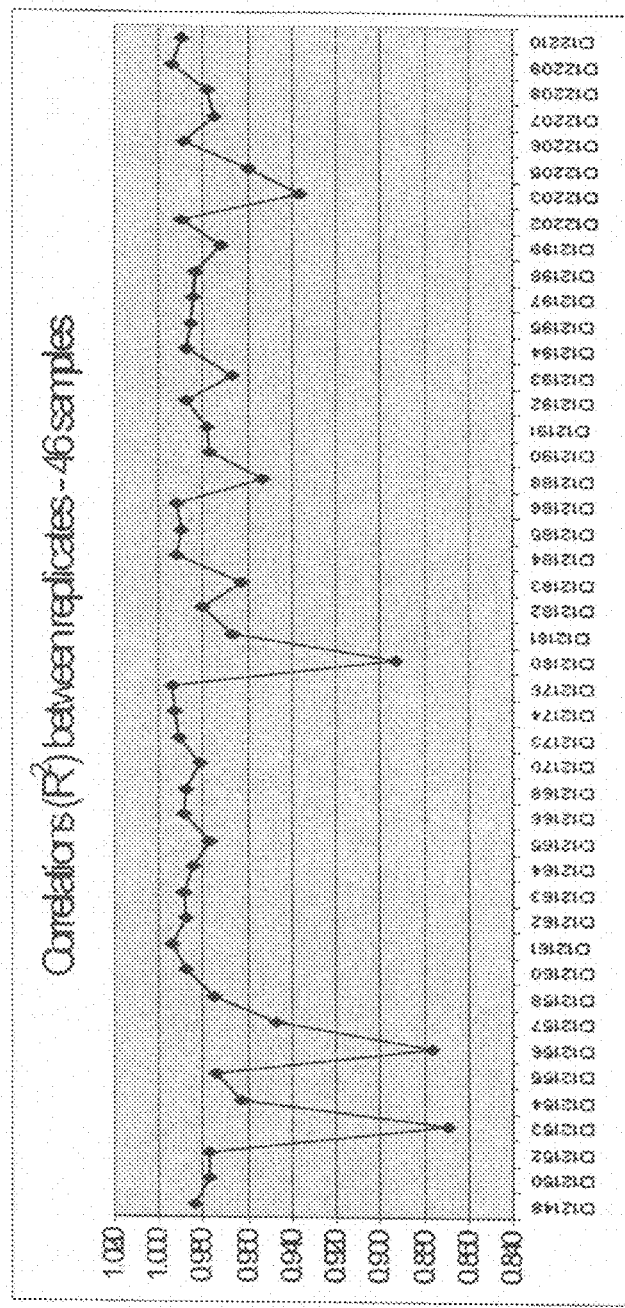
FIG. 14 shows reproducibility of the methylation assay between technical replicates as observed in 46 lung cancer clinical samples containing 389 loci across four independent arrays.
Figure 15:
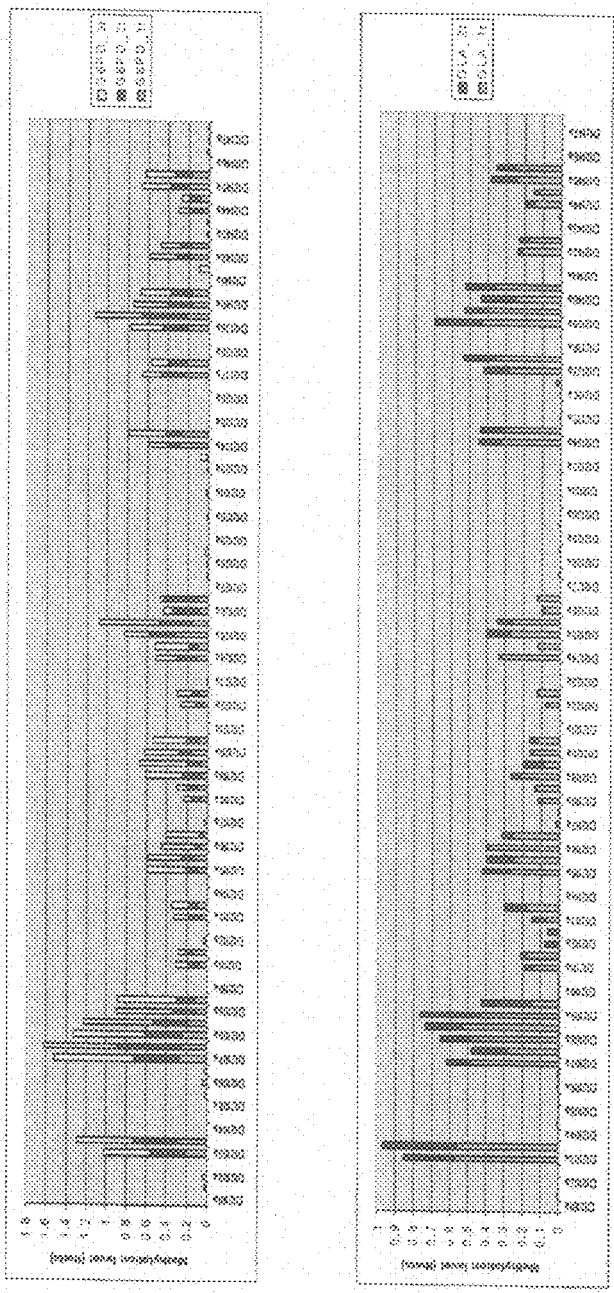
FIG. 15 shows methylation status of two housekeeping genes located on the X chromosome. In females X inactivation correlates with promoter methylation, and methylation pattern determined for both genes in 46 samples (in duplicates) allows to match the methylation status of the promoter with the gender of the sample source.

A typical experiment included 32 replicates of each set of the three plasmid mixtures assayed on a 96 fiber bundle array matrix. Results of the reproducibility study are summarized in Table 2, which involve (79+96+95+95) replicates×14 CpG sites=5,110 measurements. It is noticeable that some loci (e.g. phi_4972) tend to perform better than others (e.g. pACYC_360). There are also some performance variations from experiment to experiment. The overall call accuracy is averaged at ~97% with a high call rate of 99.6%. The accuracy was calculated using our existing SNP genotyping software, which uses a clustering algorithm to determine if a locus is methylated, unmethylated or semi-methylated (FIG. 10).

TABLE 5

| | Methylation measurement with 14 plasmid CpG loci. | | | | | | | | |
| --- | --- | --- | --- | --- | --- | --- | --- | --- | --- |
| | Experiment 1, 79 replicates | | | Experiment 2, 96 replicates | | | Experiment 3, 95 replicates | | |
| Locus | No call, % | Correct, % | Wrong call, % | No call, % | Correct, % | Wrong call, % | No call, % | Correct, % | Wrong call, % |
| pUC_229 | 0 | 100 | 0 | 0 | 93.75 | 6.25 | 0 | 93.68 | 6.32 |
| pUC_964 | 0 | 100 | 0 | 0 | 89.58 | 10.42 | 0 | 94.74 | 5.26 |
| pUC_1488 | 1.27 | 100 | 0 | 0 | 96.88 | 3.13 | 0 | 91.58 | 8.42 |

TABLE 5-continued

Methylation measurement with 14 plasmid CpG loci.

| | | | | | | | | | |
|---|---|---|---|---|---|---|---|---|---|
| pUC_2077 | 0 | 100 | 0 | 8.33 | 88.64 | 11.36 | 6.32 | 91.01 | 8.99 |
| pUC_2575 | 0 | 100 | 0 | 0 | 88.54 | 11.46 | 0 | 90.53 | 9.47 |
| pACYC_167 | 0 | 100 | 0 | 0 | 88.54 | 11.46 | 0 | 97.89 | 2.11 |
| pACYC_360 | 0 | 98.73 | 1.27 | 1.04 | 74.74 | 25.26 | 0 | 91.58 | 8.42 |
| pACYC_1289 | 0 | 100 | 0 | 1.04 | 89.47 | 10.53 | 0 | 95.79 | 4.21 |
| pACYC_1481 | 0 | 100 | 0 | 1.04 | 92.63 | 7.37 | 0 | 95.79 | 4.21 |
| phi_2191 | 0 | 100 | 0 | 0 | 98.96 | 1.04 | 0 | 95.79 | 4.21 |
| phi_3050 | 0 | 100 | 0 | 0 | 100 | 0 | 0 | 98.95 | 1.05 |
| phi_3687 | 0 | 97.47 | 2.53 | 2.08 | 94.68 | 5.32 | 3.16 | 92.39 | 7.61 |
| phi_4128 | 0 | 100 | 0 | 0 | 100 | 0 | 0 | 98.95 | 1.05 |
| phi_4972 | 0 | 100 | 0 | 0 | 100 | 0 | 0 | 100 | 0 |
| Total: | 0.09 | 99.73 | 0.27 | 0.97 | 92.60 | 7.40 | 0.68 | 94.90 | 5.10 |

| | Experiment 4, 95 replicates | | | Summary | | | |
|---|---|---|---|---|---|---|---|
| Locus | No call, % | Correct, % | Wrong call, % | No call, % | Wrong call, % | Correct, % | Correct, CV (%) |
| pUC_229 | 0 | 100 | 0 | 0 | 3.14 | 96.86 | 3.75 |
| pUC_964 | 0 | 100 | 0 | 0 | 3.92 | 96.08 | 5.20 |
| pUC_1488 | 0 | 100 | 0 | 0.32 | 2.89 | 97.11 | 4.09 |
| pUC_2077 | 0 | 96.84 | 3.16 | 3.66 | 5.88 | 94.12 | 5.55 |
| pUC_2575 | 0 | 100 | 0 | 0 | 5.23 | 94.77 | 6.43 |
| pACYC_167 | 0 | 100 | 0 | 0 | 3.39 | 96.61 | 5.66 |
| pACYC_360 | 0 | 97.89 | 2.11 | 0.26 | 9.26 | 90.73 | 12.27 |
| pACYC_1289 | 0 | 97.89 | 2.11 | 0.26 | 4.21 | 95.79 | 4.75 |
| pACYC_1481 | 0 | 100 | 0 | 0.26 | 2.89 | 97.11 | 3.69 |
| phi_2191 | 0 | 100 | 0 | 0 | 1.31 | 98.69 | 2.02 |
| phi_3050 | 0 | 98.95 | 1.05 | 0 | 0.53 | 99.47 | 0.61 |
| phi_3687 | 0 | 97.89 | 2.11 | 1.31 | 4.39 | 95.61 | 2.69 |
| phi_4128 | 0 | 98.95 | 1.05 | 0 | 0.53 | 99.47 | 0.61 |
| phi_4972 | 0 | 100 | 0 | 0 | 0 | 100 | 0 |
| Total: | 0 | 99.17 | 0.83 | 0.43 | 3.40 | 96.60 | 4.09 |

Note:
Experiment 1 included 80 replicates of bisulfite converted DNA and 16 replicates of unconverted samples for background control. The other 3 experiments included only bisulfite converted DNA.

As demonstrated above, assay sensitivity and specificity were shown to be sufficient to detect changes in methylation status at more than 50 loci simultaneously in 1 microgram of human genomic DNA. A minimum of three levels of methylation was clearly distinguished: fully methylated, hemi-methylated, and unmethylated. The ability to distinguish three levels of methylation was confirmed by using plasmid control DNAs with known methylation status, spiked into human genomic DNA in a 1:1 molar ratio. Furthermore, reproducibility of methylation determination was shown to be 96.6% (which is a more stringent measurement than reproducibility), at a call rate exceeding 90% (Table 2). A set of three reference samples for 14 CpG sites was analyzed in four independent experiments. The number of measurements in each experiment was 1106, 1344, 1330 and 1330 respectively.

Overall, this example demonstrates the development of a microtiter plate based, high throughput bisulfite conversion, which as described in the following Example, can be fully integrated into the SNP genotyping system for high-throughput methylation profiling. The methylation assays can be enlarged in both the scope and capacity of methylation detection with as many as 1500 methylation sites in each assay, while using reduced amounts of genomic DNA. Since the data collection and processing are largely automated, it is possible to do at least one, two, five or ten array matrix runs per day per system, with each run providing data from 96 samples at a time, creating a highly scalable system where multiple instruments can be run in parallel if needed.

EXAMPLE III

Integration of Microtiter Plate Based, High-Throughput Bisulfite Conversion Into Genotyping System for High Throughput Methylation Profiling This example demonstrates the integration of a microtiter plate based, high throughput bisulfite conversion as described in Example II, into the SNP genotyping system for high-throughput methylation profiling.

The assay optimization process includes measuring the array-to-array experimental variability, both within a matrix and between matrices, and dissect out contributions to variability from samples, sample processing (bisulfite conversion, allele-specific extension, ligation, and PCR amplification), and array hybridization, using carefully designed controls. The resulting data also is useful in determining thresholds of significance for analyzing and interpreting results.

Improve Assay Performance with Fully "Methylated" and "Un-Methylated" Genomic Templates Currently, all the methods used to validate methylation status of any methylation site in any given sample, such as bisulfite sequencing and methylation-specific PCR, are either laborious and time consuming, or inaccurate and expensive. Indeed, a high performance methylation quantitation (or calibration) system is needed for large-scale genome-wide methylation assay development and validation. As described in Example II, a system has been developed that uses fully "methylated" and "un-methylated" genomic templates.

The un-methylated templates can be generated by genome-wide amplification of any genomic DNA, using random primed DNA amplification with enzymes such as Phi-29, Taq DNA polymerase or Klenow Fragment (3'->5'-exo-). After this amplification, the endogenous DNA methylation is diluted at least 100 to 1000-fold, effectively rendering the amplified genome DNA "un-methylated".

The methylated templates can be generated by in vitro methylation using the SssI CpG-methylase. However, not all the CpG sites can be fully methylated in vitro. Some of these can result from base substitution at the CpG sites in the DNA tested, in particular, these sites become "methylation-resistant". It is well known that CpG sites are mutation hot spots. In order to achieve higher levels of genomic DNA methylation, different experimental conditions are tested, for example, varying the concentration of magnesium in the methylation reaction and using multiple methylases.

The above-described templates are used for assay development and calibration. The fully methylated and unmethylated genomic DNA templates can be mixed at different ratio, for example, 0%, 25%, 50%, 75%, and 100% of methylated template. Methylation assays on these mixed templates generate a calibration curve for quantitative methylation measurement in unknown samples for any CpG site in the genome. The mixed templates can also be used to determine the sensitivity of methylation detection, for example, what percentage of the methylated template can be detected in the presence of un-methylated template.

Since this approach can be used to evaluate the methylation assay designed for any specific CpG site across the entire genome, it greatly aids methylation assay development such as assay specificity. For example, if an assay gives the same methylation "report" for both the unmethylated and the methylated DNA templates, it confirms that the assay is not working properly.

Finally, protocols for measuring DNA methylation in formalin-fixed, paraffin-embedded samples are created. Robust large-scale DNA methylation detection on these samples opens up a huge sample resource, for which clinical history is already available.

Improvement of Assay Sensitivity by Genomic DNA Amplification After Bisulfite Conversion In order to improve assay sensitivity, DNA is amplified after bisulfite conversion, using a random priming approach. But, instead of using all possible random primers, advantage is taken of the unique sequence feature of genomic DNAs after bisulfite treatment, i.e. that un-methylated cytosines are converted to uracil. Therefore, these DNA templates contain mostly three bases, A, G and T (and U). The genomic amplification is carried out using (i) through (iii) as set forth in the following paragraphs.

(i) A mixture of two sets of primers that contain all possible combinations of three nucleotides: (i.e. A, T and C for one set, and A, T and G for the other set). Primers from the first set have higher affinity to the original bisulfite converted DNA strand, while primers from the second set preferentially anneal to the newly synthesized complementary strand. Using this scheme, having G and C in the same primer is avoided, thus preventing the primers from crossing over any CpG sites to be interrogated. Bias that may be introduced by the un-balanced annealing efficiency of primers corresponding to the two alleles (C or T) also is avoided. Lastly, since each primer set contains all possible combinations of three, but not four nucleotides, effective primer concentration is increased.

(ii) Simple primer sequences that contain only Adenines (A). The homopoly-A primers (for example, 6-mer, 9-mer, or longer) is used for the first strand synthesis. After that, a homopoly-T tail is added to the 3'-ends of the first strand products, using terminal deoxyribonucleotide transferase (TdT). A standard PCR is then be carried out to amplify the DNAs using a poly-A primer. Human chromosome 1 sequence was used to calculate the poly-T frequencies in the genome after bisulfite conversion: on average, the physical distance between any two poly-(T)n sequences (n>=9) is 330 bp, a perfect amplicon size range for robust amplifications.

(iii) Similar to approach (i), except that oligo-A primer is used for the first strand synthesis and primers containing combinations of A, T and G for the complementary strand synthesis.

Probe design is one of the critical components for a successful methylation assay. The fully automated SNP genotyping assay design program described herein can be used for methylation assay development. As shown above, for each CpG locus, three probes are designed: two allele-specific oligonucleotides, one corresponding to the methylated and the other to the unmethylated state of the CpG site, and one locus-specific oligo. If other CpG loci are present close to the chosen CpG site, a wobble base [A or G] is used in the corresponding position of the probes. Based on the observation that adjacent CpG sites tend to be co-methylated or co-de-methylated, a simpler design scheme is applied in which a "CG" sequence is used for all the CpG sites within the vicinity of the design, in particular for the landing sites for both ASO and LSO, to target any methylated CpG site; while a "TG" sequence is used for all the CpG sites within the vicinity of the design, to target any un-methylated CpG site. This approach requires two LSO oligos for some loci, but adds better discrimination between the methylated and unmethylated alleles.

A human gene promoter database, which includes all CpG regions of potential interest for methylation profiling was constructed by combining NCBI's RefSeq annotation, existing knowledge of some well-studied promoters, gene and promoter prediction algorithms, as well as observations of certain cancer-related genes. This database is continuously expanded by integrating more public information from literature and databases, and experimental observations. For the methylation study, a new database searching strategy is integrated into the primer design software. A modified genome database is generated in which all "C"s (except those located within a CpG dinucleotide sequence) are converted to "T"s in silico. The probe design program searches against this converted database to find unique sequences and compute melting temperature (Tm), self-complementarity and length for an optimal probe. An optimization program is applied to match address sequences with locus-specific oligos to minimize self-complementarities of combined address and probe sequences. A locus filtering program is used to filter out sequences predicted to be unsuitable on the basis of data from SNP genotyping experiments already carried out. Some sequence features have been shown to be troublesome, e.g. runs of six or more consecutive bases of a single type, extreme GC or AT content, inverted repeats (mostly due to, secondary structure), and high numbers of hits in the human genome sequence based on similarity searches by BLAST. All of these parameters can be computed in advance. These parameters are stored in a relational database for further data analysis. In addition, the program computes the sequence complementarity between the probes designed for a given set of methylation sites, especially the sequence complementary at their 3' ends. This calculation allows assessment of the compatibility of the assays, which in turn provides guidance regarding grouping of the assays properly for multiplexing.

The main problem for the methylation assay primer design lies in the reduced complexity of the genome after bisulfite conversion of the genomic DNA. Analysis of 5'-regulatory sequences from 1200 human genes was performed and preliminary computer simulation analysis indicates that the length of the primers designed for the bisulfite-converted DNAs will have to be increased by several bases as compared to the un-converted ones to achieve the same primer specificity and melting temperature. If necessary, longer primers along with increased assay stringency is used.

In another in-silico experiment, three BLAST searchable human genomic sequence databases were created. The first database mimics methylated condition (after bisulfite treatment), where all the C residues in CpG dinucleotide sequence remains as C; the second mimics un-methylated conditions, where all the C residues in CpG dinucleotide sequence are converted into T; both of these databases have C residues from non-CpG sites converted into T. The third database has normal genomic sequences. BLAST searching against these databases using designed probes as queries was performed and, as predicted, the probes had much larger number of hits to the database that have "C" converted into "T" (the first two databases), and less number of hits to the normal database (the third database). Subsequent empirical experiments with probes that have either large or small number of BLAST hits suggested that the probes with small number of hits usually generate good assay results, while the probes with large number of hits do not. In the future, this BLAST search process is automated and integrated into the probe design software. Furthermore, probes is designed for all the CpG sites in the promoter regions. After a subsequent BLAST filtering process, only three probes are synthesized for each gene. For a small number of genes that can't have three qualified probes designed due to limited number of CpG sites in the promoter region or CpG sites too close to each other, or/and severe sequence similarity to other genomic regions.

In order to search for specific methylation patterns in different cancer types or cancer stages, we first develop methylation assays for at least 1000 human genes. These genes are selected based on the following criteria:

(i) Biological relevance. Methylation patterns in previously characterized tumor suppressor genes and oncogenes are an initial focus (Esteller, Oncogene 21(35): 5427-40 (2002), Adorjan, et al., Nucleic Acids Res. 30(5): p. e21 (2002)). Then, the target group is enlarged to include genes that are indirectly involved in cancer development, for example, DNA repair genes; metastasis-inhibitor genes, genes regulated by various signaling pathways, and/or responsible for altered cell growth and differentiation; or genes considered to be targets for oncogenic transformation.

(ii) Previous knowledge, e.g. genes located within published recurrent loss of hetrozygosity (LOH) regions or amplified genomic regions (Pollack, et al., Proc Natl Acad Sci U S A. 99(20): 12963-8 (2002)).

(iii) Gene expression profiling information, for example, genes differentially expressed in cancer and normal tissues. In the past few years, due to the rapid development of microarray technology, many specific gene-expression signatures have been identified for different cancer types (Golub, et al., Science 286(5439): 531-7 (1999), Ramaswamy, et al., Proc Natl Acad Sci U S A. 98(26): 15149-54 (2001), Perou, et al., Nature 406(6797): 747-52 (200) Bhattacharjee, et al., Proc Natl Acad Sci U S A 98(24): 13790-5 (2001), Chen, et al., Mol Biol Cell 13(6): 1929-39 (2002), Welsh, et al., Proc Natl Acad Sci U S A. 98(3): 1176-81 (2001)), cancer stages (Dhanasekaran, et al., Nature 412(6849): 822-6 (2001), Ramaswamy, et al., Nat Genet. 33(1): 49-54 (2003)), and cancer therapeutic outcomes (Shipp, et al., Nat Med. 8(1): 68-74 (2002)). Some of these differential expressions are regulated by imprinted or somatic methylation.

The methylation targets are grouped-into functionally relevant sets that are useful for focused research (e.g. based on association with a particular pathway or disease; or expressed in particular tissues of interest; or representing a particular genomic region), as well as for more global studies. For example, genes can be grouped according to their biochemical properties, such as, oncogenes/tumor suppressor genes, kinases, phosphatases, and cell surface receptors. Genes can be also grouped based on their involvement in different biological pathways/functions, for example, tumor antigen, signal transduction, apoptosis, angiogenesis, cell cycle control, cell differentiation, DNA repair, cancer metastasis/invasion, drug resistance and detoxification, and transcriptional regulation, etc. The assays are then optimized to achieve a high degree of reliability and specificity within each set.

Selection of CpG Sites to be Interrogated

Several CpG sites within each 5'-regulatory region, including CpGs over the transcriptional start site is targeted, since redundant information from multiple CpG sites can provide a better measurement of the overall methylation status in the interrogated gene. While there are many CpG sites within each CpG island, only those for which robust assays can be designed is used. Each potential CpG site is BLAST searched against human dbSNP databases to avoid any potential "polymorphic" CpG site (i.e. the "methylation-resistant" site), to ensure clean data interpretation. If desired, the consequence of the polymorphic CpG sites, for example, their effect on methylation of adjacent CpG sites, and subsequently on gene expression level can be determined.

It has been estimated that the human genome has 26,000 to 45,000 CpG islands (Antequera, et al., *Proc Natl Acad Sci USA*. 90(24): 11995-9 (1993), Ewing, et al., Nat Genet. 25(2): 232-4 (2000)). Among them, those found in gene 5'-regulatory regions are the most biologically significant ones. The work does not only utilize CpG rich promoters, but also investigates less CpG rich promoters since they might also be subjected to aberrant methylation and silencing.

In order to correctly identify genes and their upstream regulatory regions, public databases such as NCBI RefSeq, UCSC Human Genome Project (HGP) Working Draft, ENSEMBL and Unigene are utilized. These databases annotate known or verified genes according to sequence similarity to mRNA, EST and protein sequences, and novel genes predicted using gene prediction programs. They also contain reference links to genetic and physical mapping data, as well as other features such as CpG islands. The accuracy of these annotated features is confirmed by re-running gene prediction programs and searching for sequence similarity to mRNA, EST, and known protein sequences. Existing promoter databases such as Eukaryotic Promoter Database (EPD) (Praz, V., et al., Nucleic Acids Res. 30(1): 322-4 (2002)), are used to identify the 5'-regulatory sequences. Meantime, promoter and first exon prediction algorithms such as FirstEF (Davuluri, et al., Nat Genet. 29(4): 412-7 (2001)) are used to identify potential regulatory sequences. This approach provides a well-annotated collection of regulatory sequences of human genes and allow for identification of the CpG sites within these regulatory regions and design assay probes as described above.

A CpG site within a CpG island doesn't automatically qualify it as a biologically significant methylation target and art knowledge is applied in order to design most valuable methylation assays. In the past few years, tremendous progress has been made in the epigenetics field, which uncovered many epigenetic regulation mechanisms in various biological pathways (Strichman-Almashanu, et al., Genome Res. 12(4): 543-54 (2002)), and cancers (Widschwendter, et al., Oncogene 21(35): 5462-82 (2002), Tsou, et al., 21(35): p. 5450-61 (2002)). Moreover, large methylation projects such as bisulfite sequencing of CpG island-enriched libraries (Cross, et al., Nat Genet. 6(3): 236-44 (1994)), or entire human chromosomes or even the entire genome are likely to be developed. These efforts should produce tremendous amounts of methylation data and reveal hundreds of thousands of new methylation sites in many different tissue types.

Assay Development, and Array Data Extraction and Analysis

Once the assays are designed, they are tested with publicly available genomic DNAs isolated from various cancerous or normal human tissues or cell lines of different tissue origins, and obtain tissue-specific methylation profiles for individual genes (CpG sites). These methylation profiles serve as references for analyzing unknown samples. Building on SNP genotyping technology, a quantitative metric to guide the methylation assay development is formulated and provide a quality assurance to data-generated in a production setting. The metric takes into consideration all aspects of assay performance and data quality (e.g. assay specificity and quantitation), including efficiency of bisulfite conversion, overall signal intensity of all targeted CpG sites, concordance among the measurements of the three CpG sites within each gene, specificity of detection in control samples (e.g. plasmids, reference samples as well mixtures of the reference samples), and measurement variations in replicated samples, etc.

In addition the quantitative performance of methylation detection is tested at various multiplexing levels, for example, high (>1000-plex), medium (~300-plex), and low (<100-plex), and validate the specificity and sensitivity of the assays at high multiplexing levels. Meanwhile, as a measurement of the assay specificity, concordance of methylation profiles generated from a given sample at different multiplexing levels are compared. Finally, methylation-specific PCR is used to validate some of the array results (Herman, et al., Proc Natl Acad Sci U S A. 93(18): 9821-6 (1996)). All qualified assays are re-pooled and used for large-scale DNA methylation profiling.

Figure 3:
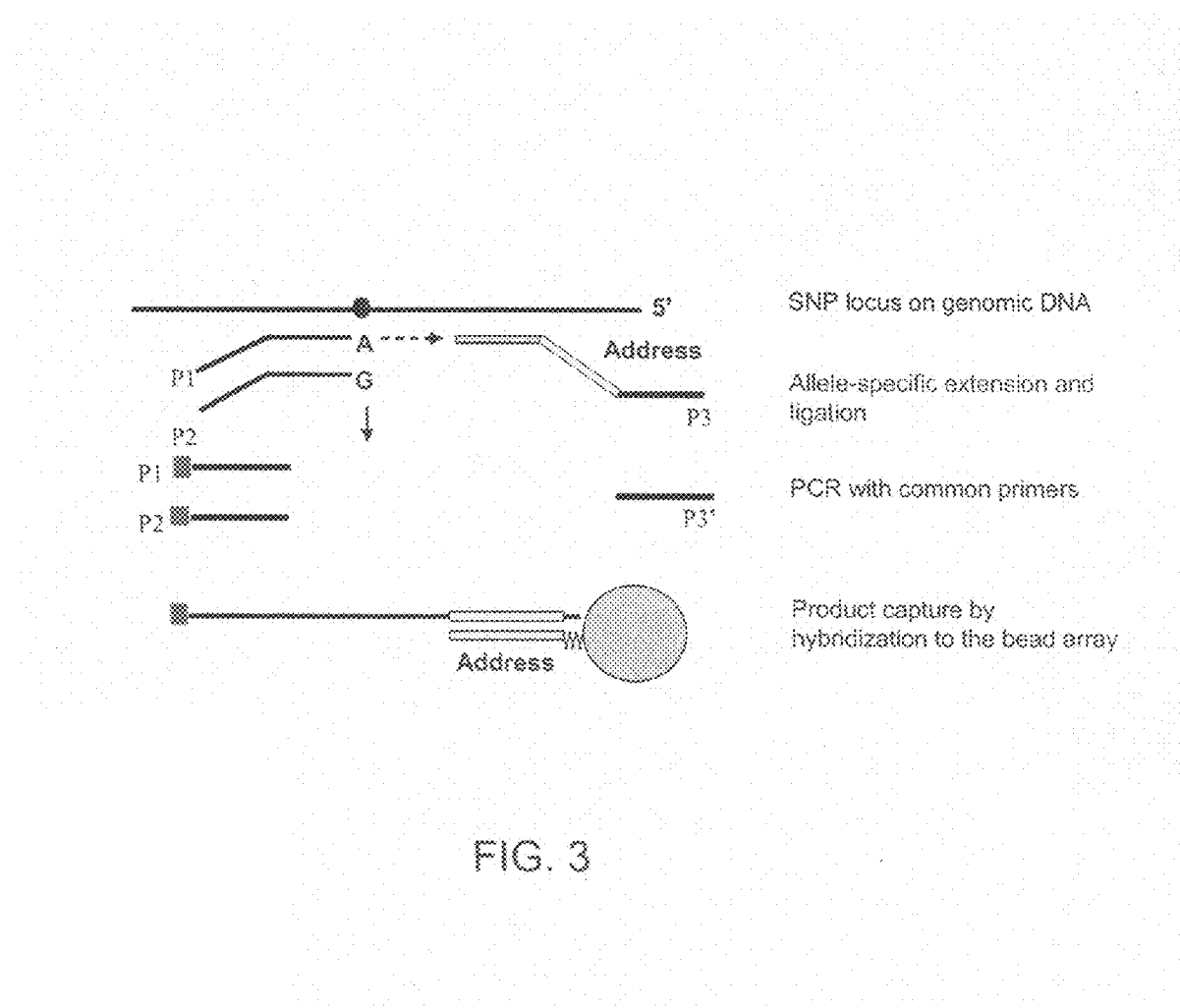
FIG. 3 shows Illumina's SNP genotyping format.

Since the sequence complexity is significantly reduced following bisulfite conversion of the genomic DNA, the assay oligo/genomic DNA annealing protocol is optimized to minimize cross-hybridization. Tetramethylammonium (TMACl) (De Murcia, et al., Biophys Chem. 8(4): 377-83 (1978), Sorg, et al., Nucleic Acids Res. 19(17): 4782 (1991)), and/or Betaine (Rees, et al., Biochemistry, 32(1): 137-44 (1993)) is used to normalize the base composition dependence of DNA/oligo hybridization. Nevertheless, high locus specificity should be achieved by the requirement that both ASO and LSO oligos need to hybridize to the same genomic target site and then get extended and ligated (FIG. 3).

The existing SNP genotyping software is modified and adapted for the methylation data analysis. The current software takes the raw intensity data and transforms them into a genotype call using a clustering algorithm (FIG. 10). However, for most of the methylation data analysis cluster analysis cannot be utilized due to the need not only to distinguish three methylation states of each locus (unmethylated, methylated and semi-methylated), but do it in a more quantitative manner, for example, estimate percentage of methylation of certain loci in a given sample. The methylated and unmethylated reference samples and assay controls are used in every experiment for software calibration. Assay intensity data of unknown sample is compared to those obtained with the reference samples, and used to calculate the methylation level of the locus of interest. Software is developed for comparison of various samples and detection of differential methylation profiles to allow for identification of differences between normal tissues and tumors, and/or create tissue-specific methylation profiles for genes and loci of interest.

Search for Specific Methylation Patterns in Different Cancer Types or Cancer Stages Once the gene-specific methylation assays are developed as described above, a large-scale DNA methylation survey is carried out in a large number of samples. The experiment is designed to compare methylation patterns in (1) normal and cancerous tissues; (2) different cancer types or cancer stages; (3) or responsive to (or associated with) treatment with certain growth factors or drugs, activation of oncogenes or inactivation of tumor suppressor genes, changes in a developmental program, etc. The main objective is to find unique methylation patterns for specific cancer types/stages and develop molecular markers for classification and diagnosis of cancers, which can be used to complement existing morphological and clinical parameters. This can be particularly useful for cancer types which appear similar by histological assessments, but follow different clinical courses (e.g. different therapeutic responses). The results also provide important clues to the mechanisms of specific cellular responses; and this information can prove critical for devising strategies for cancer prevention and treatment.

Malignant tissues obtained by laser capture microdissection (LCM) are used to identify specific cell and tissue types for methylation profiling. In these cases, a more sensitive strategy is employed, which involves DNA amplification after bisulfite conversion. If an assay can be established to detect tumor-specific methylation patterns in a very small amount of diseased tissue in the presence of a large amount of normal tissue, it may find wide application in clinical cancer diagnosis.

As a pilot study, DNA samples isolated from 50 or more lung tissues, for example, 98 lung tissues and 50 or more breast tissues, for example, 101 breast tissues, including both normal and cancerous tissues, are used. Among these tissues, a portion, for example, 169 (98 lung and 71 breast) are frozen and the remainder, for example, 30 (breast) are paraffin-fixed. These tumor tissues are classified upon resection, and basic (anonymous) data about each tumor is kept in the tumor bank database. The tissues were resected, sent to the Pathology Department for pathological examination, and then sent to the tumor bank with the initial pathology report. The tissue was quickly frozen and stored at −80° C. The tissue procurement, storage, and documentation of clinical specimens are very well documented, in accordance with guidelines for human subject research. Thirty of the 101 breast tumor tissues are formalin-fixed, paraffin-embedded tissues. Slides were made from the fixed tissue block and stored at room temperature. Each tumor sample was examined by a pathologist to confirm the clinical diagnosis. Basic (anonymous) data about each tumor, such as the information on the gender, age, and ethnic background of the patient as well as diagnosis are available to us for data analysis.

Initially, DNA methylation profiles are generated for these samples for a list of 141 genes, selected fully based on their biological functions (see Appendix I). If both DNA and RNA samples are available for a subject in the study, both DNA methylation and gene expression is measured, including allele-specific expression, using a sensitive RNA profiling method (Fan, et al., Genome Res. 14:878-885 (2003), Yeakley, et al., Nat Biotechnol. 20(4): 353-8 (2002)). Gene-specific as well as allele-specific probes are designed to measure expression levels of specific transcripts and their isoforms. Cross-referencing gene expression results to DNA methylation data confirms not only the gene silencing caused by DNA methylation, but also helps interpret the association study results. Once specific methylation patterns are derived from this preliminary study, they are validated in (larger) independent sample sets.

Finally, comparing results obtained from human and animal studies sheds light on the underlying molecular mechanisms of tumorigenesis. For example, there is a well-characterized rat mammary tumor model involving mammary glands from virgin and parlous animals exposed to MNU (Sivaraman, et al., Carcinogenesis 19(9): 1573-81 (1998)). It provides an excellent biological model for studying molecular events in human breast cancer, especially those occurred in early cancer developments leading to mammary tumorigenesis (Russo, et al., Br J Cancer 64(3): 481-4 (1991)).

Bioinformatics, Array Information Management, and Statistical Data Analysis

Software development focuses on algorithms and software tools to process and analyze the large amount of methylation assay data as efficiently as possible. A database developer/administrator organizes, track and maintain all the methylation site information, primer design, sample information, the day-to-day experimental data, as well as design and implement web browser interfaces to provide search, query and report functions.

To develop a robust and high-throughput technology for simultaneous measurement of methylation at many specific sites in many samples, a highly efficient analysis and data export process is needed. Algorithms for analyzing data to determine methylation status automatically are developed. Again, this is based on experience with analysis of SNP genotyping data. There are some important differences in how the data is analyzed, such as the requirement for more quantitative analysis and output as described above. Experiments is designed and analysis procedures developed to determine the quantitative limits of our system, such as the limit of detection of methylated DNA in a mixed sample, and linearity of signal as a function of amount of methylated DNA.

Once tools are developed to extract information about methylation status from raw data, and to determine the significance of the measurements and assign confidence indices, the focus is on analyses of patterns of methylation and their correlations with different phenotypes. For example, analyses are carried out to detect and verify any correlations between specific methylation patterns and particular cancer types. Techniques (methods) to perform this type of analysis are the subject of intensive research in the microarray field. Many powerful algorithms/tools have been developed, such as supervised or unsupervised hierarchical clustering analysis (Dhanasekaran, et al., Nature 412(6849): 822-6 (2001), Eisen, et al., Proc Natl Acad Sci U S A. 1998. 95(25): 14863-8 (1991), Khan, et al., Nat Med. 7(6): 673-9 (2001)), K-means clustering, bootstrapping or jackknife (Kerr, M. K. et al. Proc Natl Acad Sci U S A. 98(16): 8961-5 (2001)), principal component analysis, etc. However, each of these methods has its own advantages and limitations; no clear advantage exists for any given algorithm in application to our study. Therefore, multiple algorithms are tested and the most suitable ones are selected to carry out the analyses.

The technology is upscaled to meet commercial requirements by implementing the entire process, including sample preparation, bisulfite treatment, genotyping-based assay and PCR amplification on a robotic platform; increasing the level of multiplexing to at least 96-plex, and as high as 1,500-plex; and reducing the amount of genomic DNA required such that, on average, <1 ng of genomic DNA is used per methylation site analyzed.

The assay described herein allows measurement of the methylation status in at least 10, 100, or 1,000 human genes' 5'-regulatory regions, and validate the sensitivity and specificity of the assays at low or high multiplexing levels. The assay further allows for a systematic search for specific methylation patterns in different cancer types and cancer stages.

Overall, this Example describes a system for methylation detection by leveraging various technologies for high-throughput array-based assays and SNP genotyping, and to validate the technology in real-world applications. The technology is highly scalable, both in terms of the number of assays carried out on a single sample, and the number of samples that can be processed in parallel. Furthermore, it can be used has the potential for broad application in many areas of cancer and fundamental biomedical research. The assays and assay protocols, and the specific methylation patterns (in various cancers) to be developed in this study can generally be useful to the research community.

EXAMPLE IV

DNA Methylation Profiling in Lung Cancer

This Example demonstrates the identification of adenocarcinoma markers by virtue of differential methylation patterns and use of the identified markers to distinguish adenocarcinoma from normal tissue with high specificity and sensitivity.

As described in detail above, the SNP genotyping system was adapted for DNA methylation detection based on "SNP" genotyping of bisulfite-converted genomic DNA. In this assay, non-methylated cytosines (C) are converted to uracil (U) when treated with bisulfite, while methylated cytosines remain unchanged. Hybridization behavior of uracil is similar to that of thymine (T). The detection of the methylation status of a particular cytosine can thus be carried out using a genotyping assay for a C/T polymorphism.

Assay Probe Design

Figure 20:
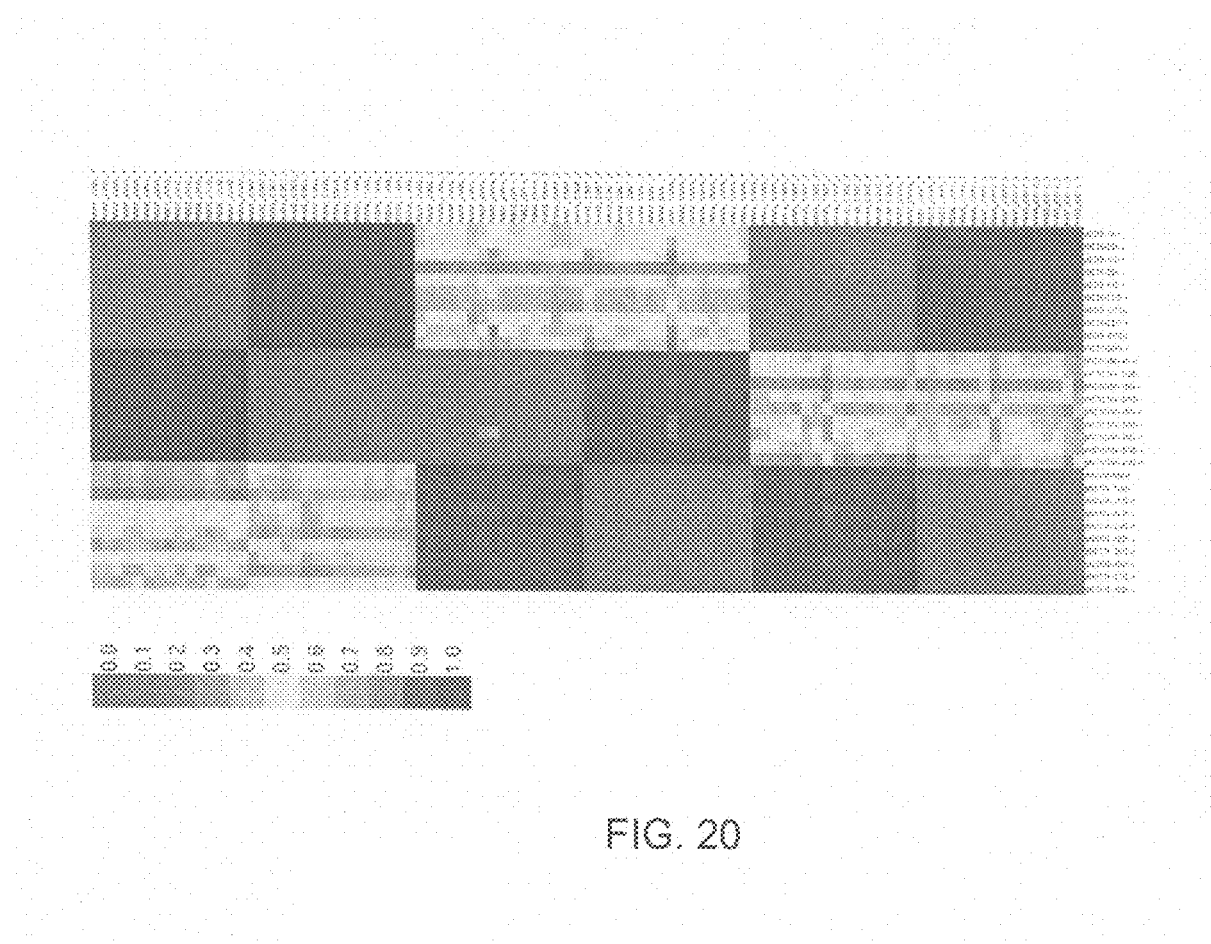
FIG. 20 shows internal methylation assay controls. Methylated, unmethylated or semi-methylated (generated by mixing the methylated and unmethylated at 1:1 ratio) plasmid DNAs were spiked into human genomic DNA at 1:1 molar ratio. Methylation states were determined in 46 such samples at 29 CpG sites from 3 plasmids: Unmethylated (Green), semi-methylated (Yellow) and fully-methylated (Red).

A 1.5 kb sequence from the 5'-regulatory region (in some cases, including the first exon) is extracted for each target gene based on human genome public databases NCBI RefSeq build 33 released on Jun. 6, 2003. CpG islands of interest from this 1.5 kb region were selected and "converted by bisulfite" computationally. As described in Example 1, an automated SNP genotyping assay design program was adapted for methylation application. For each CpG locus, four probes were designed: two allele-specific oligos and two locus-specific oligos, each corresponding to the methylated or unmethylated state of the CpG site respectively (FIG. 20). If other CpG loci were present in the close vicinity of the chosen CpG site, an assumption is made that it has the same methylation status as the site of interest. While there are many CpG sites within each CpG island, only those for which robust assays could be designed were used. Assays were designed for 389 CpG sites from 141 genes: 114 genes with three CpG assays, 20 genes with two and 7 genes with only one assay. The designed site sequence information is included in Table 1.

DNA Samples for Methylation Analysis

Lung tissue specimens were collected from subjects with lung cancer. Under an Institutional Review Board approved protocol, the samples of lung tissue classified as cancerous and samples adjacent to the cancerous tissue but classified as normal were utilized in this study. After pathological classification upon resection, the tissues were frozen and stored at −80° C. Forty-six samples were obtained from Philipps-University of Marburg, Germany, and 25 samples were from The Pennsylvania State University College of Medicine Tumor Bank. Specifically, a total of 38 lung cancer and 33 normal tissues were used, including 22 matched pairs (Table 4). The cancer samples included 14 squamous cell carcinoma and 24 adenocarcinoma cancer tissues. The samples were pulverized under liquid nitrogen. DNA was extracted from the tissue powder by QIAamp DNA Mini Kit (Qiagen Inc. Valencia, Calif.) according to manufacturer's instruction. The DNA was eluted from the column with dH2O, and stored at −80° C. until use.

Plasmid DNA Controls.

Plasmids pUC19, pACYC184 and phage phiX174 served as control DNAs as described above in Example II.

Bisulfite Conversion of DNA and Methylation Assay

The EZ DNA methylation kit (Zymo Research, Orange Calif.) was used for bisulfite conversion of DNA samples, according to manufacturer's recommendations. One and a half microgram of genomic DNA was used for each conversion. Bisulfite-converted genomic DNA from one conversion was then used for up to 8 array experiments. After bisulfite conversion of genomic DNA, the remaining assay steps were identical to the GoldenGate™ assay (Fan et al., *Cold Spring Harbor Symposia on Quantitative Biology* 68: 69-78 (2003)), using manufacturer's reagents and conditions (BeadLab User Manual, Illumina).

Briefly, bisulfite-converted, biotinylated genomic DNA was immobilized on paramagnetic beads and washed. Pooled query oligos were annealed to the gDNA under a controlled hybridization program, and then washed to remove excess or mishybridized oligos. Hybridized oligos were then extended and ligated to generate amplifiable templates. A PCR reaction was performed with fluorescently labeled universal PCR primers. Single stranded PCR products were prepared by denaturation, then hybridized to a Sentrix® Array Matrix (Fan et al., *Cold Spring Harbor Symposia on Quantitative Biology* 68: 69-78 (2003)). The array hybridization was conducted under a temperature gradient program, and arrays were imaged using a BeadArray Reader 1000 scanner (Barker et al. *Proc. SPIE* 4966:1-11 (2003)). Image processing and intensity data extraction software were as describe previously (Galinsky, *Bioinformatics* 19, 1832-6 (2003)).

Microarrays were assembled by loading pools of glass beads (3 μm in diameter) derivatized with oligos onto the etched ends of fiber-optic bundles (Barker et al., supra, 2003). About 50,000 optical fibers are hexagonally packed to form an approximately 1.4 mm diameter bundle. The fiber optic bundles are assembled into a 96-array matrix, Sentrix® Array Matrix, which matches the dimensions of standard microtiter plates. This arrangement allows simultaneous processing of 96 samples using standard robotics (Fan et al. supra, 2003). Because the beads are positioned randomly, a decoding process is carried out to determine the location and identity of each bead in every array location (Gunderson, *Genome Res* 14, 870-7 (2004)). Decoding is an automated part of array manufacture.

Methylation Data Analysis

Each methylation data point is represented by fluorescent signals from the M (methylated) and U (unmethylated) alleles. M and U signals were initially computed and normalized by requiring each sample to have the same average signal in each of the two fluorescent channels. Background intensity computed from a set of negative controls was subtracted from each of the analytical data point prior to normalization. The ratio of fluorescent signals from the two alleles $$\beta = \frac{\max(M, 0)}{|U| + |M| + 100}.$$

The β value reflects the methylation status of each CpG locus, ranging from 0 in the cases of completely unmethylated sites to 1 in completely methylated sites. A constant offset of 100 was added to the denominator of the formula, as a compensation for any "negative signals" which may arise from global background subtraction (i.e. over-subtraction). Hierarchical clustering was performed using average linkage method and Pierson's correlation coefficient (r) as a similarity measure. K-nearest neighbor class prediction was done using 1-r for distance calculation and k=1 (nearest neighbor).

To choose optimal number of neighbor k, classification of the training set was performed first with different values of k. Leave-one-out cross validation gave misclassification rate of 0.03 (one out of 32 samples) using k=1. This result did not improve with a larger k.

According to the above-described protocols, for each CpG locus, four probes were designed: two allele-specific oligos (ASOs) and two locus-specific oligos (LSOs), each corresponding to the methylated or unmethylated state of the CpG site respectively (FIG. 1). Each ASO consists of a 3' portion that hybridizes to the bisulfite-converted genomic DNA, with the 3' base complementary to either the "C" or "T" allele of the targeted CpG locus, and a 5' portion that incorporates a universal PCR primer sequence (P1 or P2, each associated with an allele respectively). The LSOs consists of three parts: At the 5' end is a CpG locus-specific sequence; in the middle is an address sequence, complementary to a corresponding capture sequence on the array; and at the 3' end is a universal PCR priming site (P3). The flexibility in primer design (the gap size between the ASO and LSO oligos varies from 1 base to 20 bases) is particularly important for methylation studies, since it can be implemented in a way that will avoid difficult sequences or ambiguous bases in the CpG islands of interest. In this study, assay oligos were designed for 389 CpG sites from the 5'-regulatory region of 141 genes.

Typically, 144-160 CpG sites were assayed together. Pooled assay oligos were first annealed to bisulfite-converted genomic DNA. An allele-specific primer extension step was then carried out; ASOs got extended if their 3' base is complementary to their cognate CpG site in the gDNA template. Allele-specific extension was followed by ligation of the extended ASOs to their corresponding LSOs, to create PCR templates. Requiring the joining of two fragments to create a PCR template provides an additional level of genomic specificity. Any incorrectly hybridized ASOs and LSOs are unlikely to be adjacent, and therefore should not be able to ligate.

The ligated products were then amplified by PCR using common primers P1, P2, and P3, and hybridized to a microarray bearing the complementary address sequences. P1 and P2 are fluorescently labeled, each with a different dye, and associated with the "T" (unmethylated) allele or the "C" (methylated) allele respectively. As described in this example, methylation status of an interrogated locus is determined by quantifying β, which is defined as the ratio of the fluorescent signal from the methylated allele to the sum of the fluorescent signals of both methylated and unmethylated alleles.

Development of reliable internal controls is a prerequisite for development of a robust methylation detection method.

Plasmids pUC19, pACYC184 and phage phiX174 as internal control DNAs. These DNAs (unmethylated, methylated or mixed at a 1:1 ratio) were spiked into 200 ng human genomic DNA at a 1:1 molar ratio (at approximately 2-4 pg plasmid DNA/1 µg gDNA, depending on the plasmid size), and were used in every methylation experiment to monitor both bisulfite conversion efficiency and accuracy of methylation detection. As shown in FIG. 2, unmethylated, semi-methylated and fully-methylated plasmid loci can be easily distinguished by the assay.

"Methylated" and "fully unmethylated" genomic templates were developed to calibrate quantitative measurements of methylation. The fully unmethylated templates were generated by genome-wide amplification of human genomic DNA using Repli-g DNA amplification kit (Molecular Staging). After this amplification, the endogenous DNA methylation is diluted at least 100 to 1000-fold, effectively rendering the amplified genomic DNA "unmethylated". Methylated templates were generated by in vitro methylation using Sss I (CpG-methylase) enzyme (New England BioLabs). Among the 389 CpG sites targeted, 70 of them can only be methylated to less than 50% completion. Some of these sites may be less accessible to methylase because of the DNA secondary structure; some may result from base substitution at the CpG sites in the DNA tested, i.e. these sites become "methylation-resistant" (it is well known that CpG sites are mutation hot spots).

The above two reference templates were used for assay development and 20 CpG assays were disqualified due to similar β values for both unmethylated and methylated templates (a threshold of Δβ>0.1 was applied). Therefore, the data analyses is based on the remaining 369 functional CpG assays.

As described above, the use of bisulfite conversion of DNA for methylation detection is based on the different sensitivity of cytosine and 5-methylcytosine to deamination by bisulfite. Under acidic conditions, cytosine undergoes conversion to uracil, while methylated cytosine remains unreactive. Thus, an effective bisulfite conversion protocol facilitates a robust methylation profiling assay. Incomplete conversion of cytosine to uracil by bisulfite can result in appearance of false-positive signals for 5-methylcytosine, and reduce the overall quality of the assay data. In order to monitor the effectiveness of bisulfite treatment, a set of oligos (a standard set of SNP genotyping probes) designed for unconverted genomic DNA sequences was used in the assay. If bisulfite conversion is successful, the signal from assays designed against the unconverted DNA (i.e. the SNP set) will disappear, and only signals from assays designed against the converted DNA are present. Incomplete conversion results in low and inconsistent signals across all loci targeted to both unconverted and converted DNA.

Figure 21:
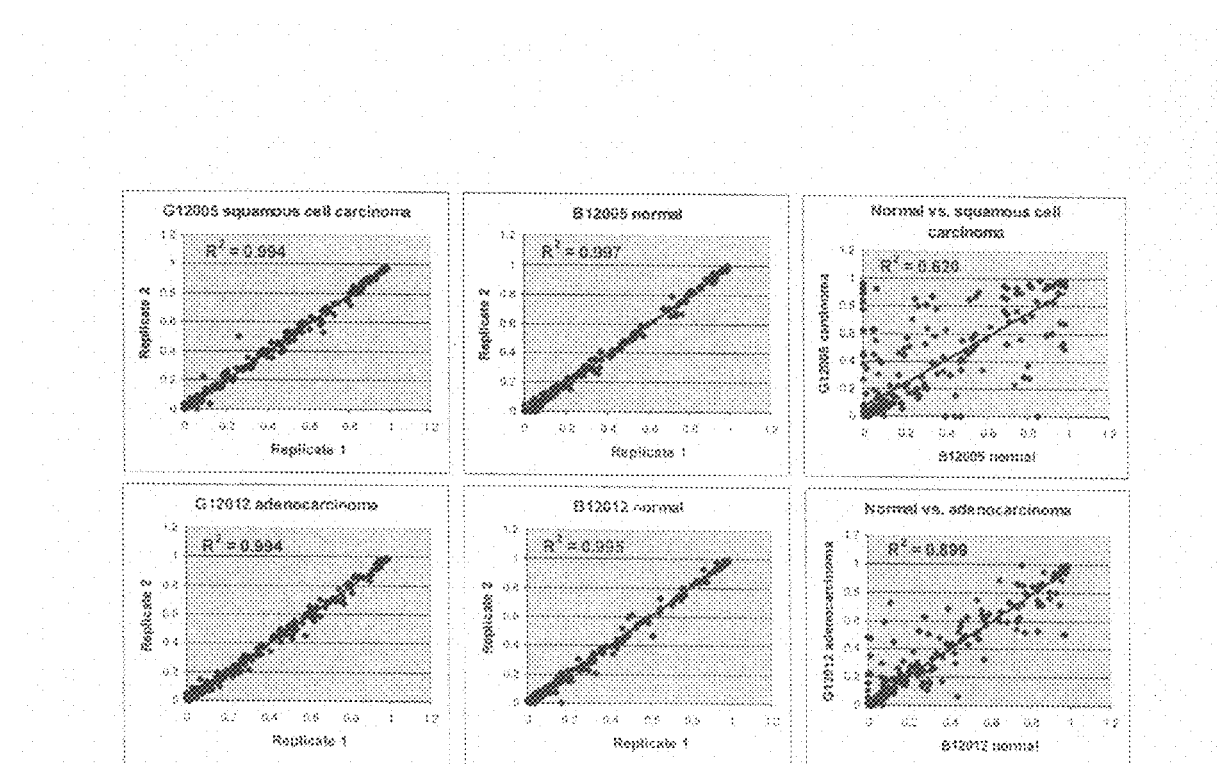
FIG. 21 shows a comparison of methylation profiles among lung cancer and matching normal tissues. The β-value (i.e. the methylation ratio measured for all the functional CpG sites) obtained from one replicate experiment is plotted against that obtained from another replicate experiment. The upper panels show the reproducibility of replicate assays on DNA derived from squamous cell carcinoma G12005 (left) and its matching normal tissue (center), and a comparison between the normal and the squamous cell carcinoma (right). The lower panels show the reproducibility of replicate assays on DNA derived from lung adenocarcinoma G12012 (left) and its matching normal tissue (center), and a comparison between the normal and the adenocarcinoma (right).

Each gDNA sample was assayed in duplicate (Table 4). According to the methods described herein, highly reproducible DNA methylation profiles within replicates were obtained with 200 ng genomic DNA (average $r^2$ was 0.97) (FIG. 21, left and center panels). As a result, differential methylation between different samples was readily detected (FIG. 3, right panel).

Figure 16:
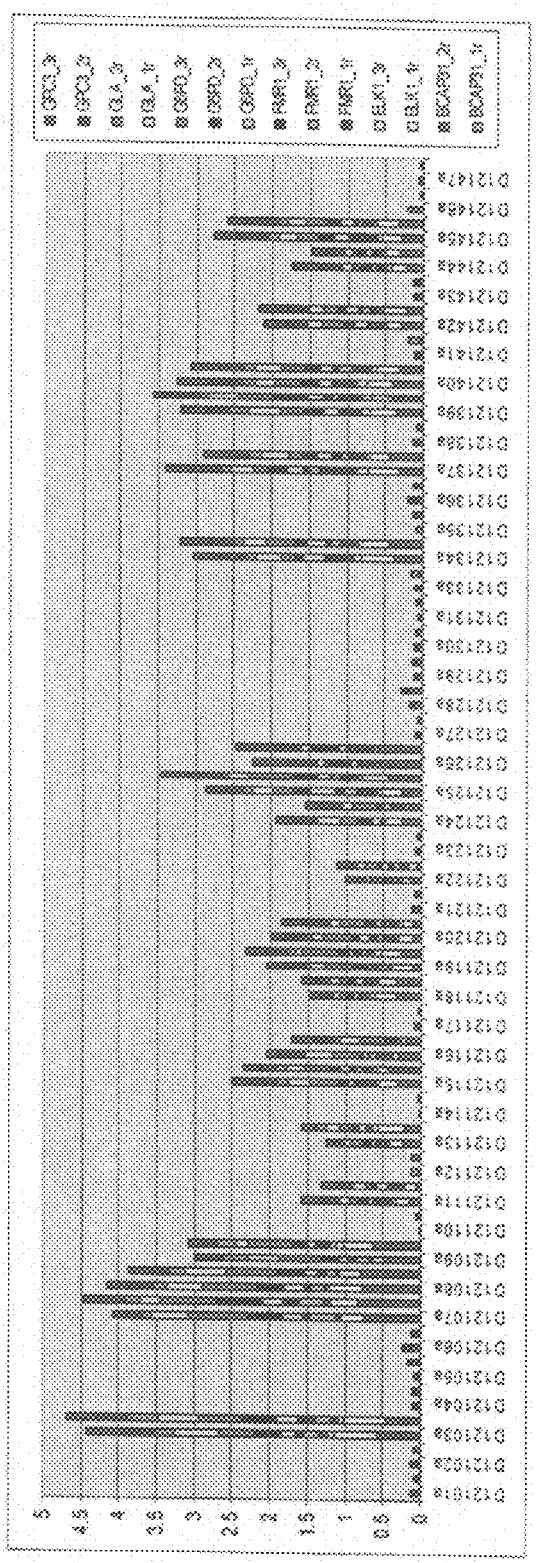
FIG. 16 shows correlation between methylation levels and gender based on methylation status of 6 genes located on the X-chromosome as monitored in 46 samples.
Figure 17:
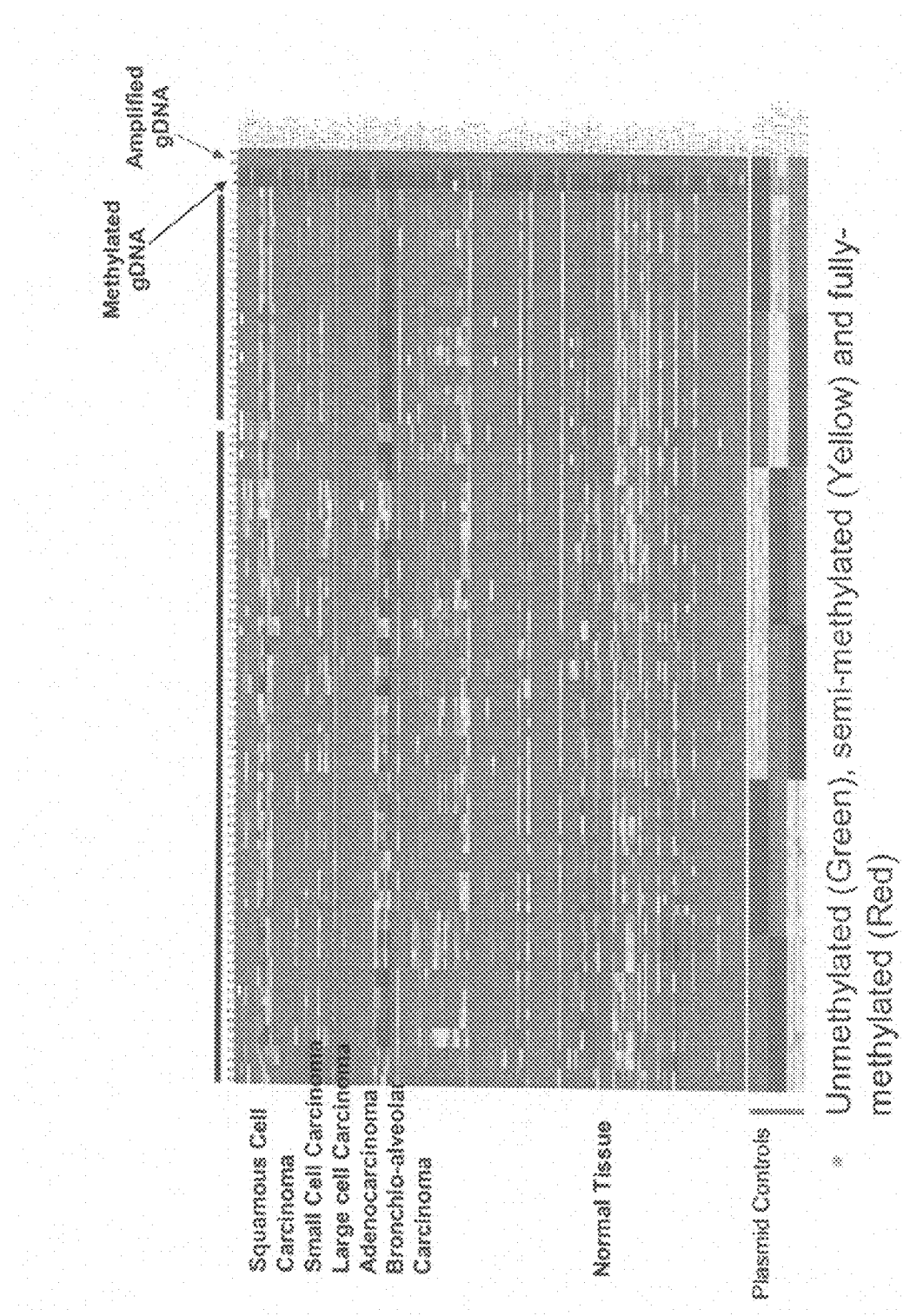
FIG. 17 shows methylation profiling in 46 lung cancer and matched normal tissues based on interrogation of 162 CpG sites. Unmethylated (green), semi-methylated (yellow), methylated (red).
Figure 18:
FIG. 18 shows distinct methylation patterns observed for 14 markers in squamous cell carcinoma versus normal matching tissue.
Figure 19:
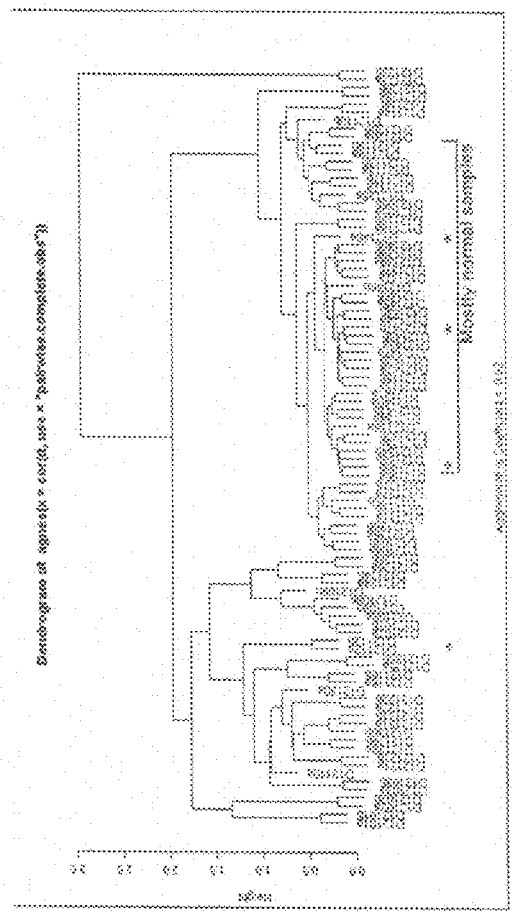
FIG. 19 shows cluster analysis of methylation profiles in 46 lung cancer samples which demonstrates good separation of cancer samples from normal matching pairs.
Figure 22:
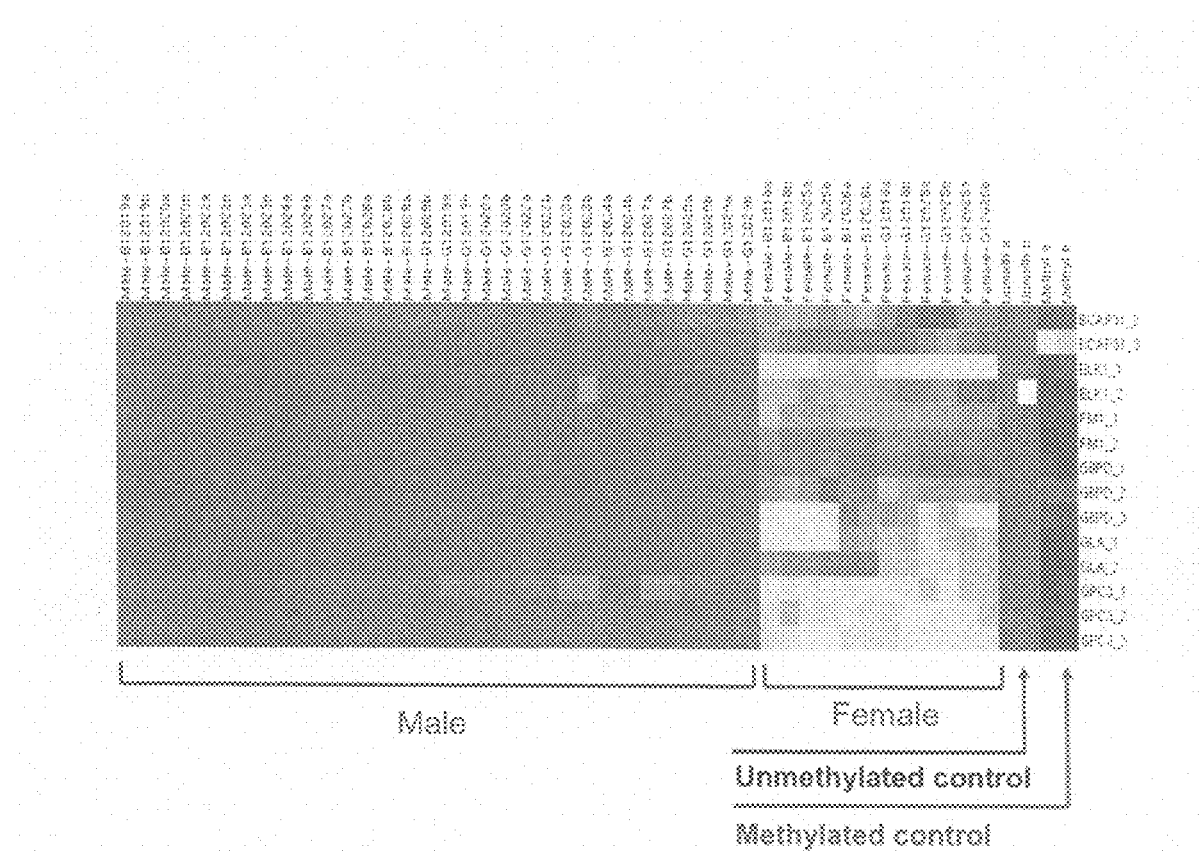
FIG. 22 shows methylation profiles of 6 housekeeping genes located on the X-chromosome. Data are shown for 14 CpG loci in 16 males and 6 females, which include adenocarcinomas and their matching normal tissue samples, and the two reference samples. Replicate measurements are shown in adjacent for each sample.

As described above, DNA methylation is involved in transcriptional inactivation of genes on one of the two X-chromosomes in female somatic cells (i.e. X-chromosome silencing), compensating the dosage of functional X-linked genes between male and female. The methylation status of six X-linked housekeeping genes—BCAP31, GPC3, FMR, ELK1, G6PD and GLA, was analyzed to test if the assay could detect the methylation difference between males and females. As shown in FIGS. 16 and 22, methylation levels of these genes correlated well with the gender of the sample source.

There are four major histologic types of lung carcinomas: squamous cell carcinoma, small cell carcinoma, large cell carcinoma, and adenocarcinoma. The methylation status of 369 CpG sites located in the 5'-regulatory regions of 141 genes in 14 squamous cell carcinoma, 24 adenocarcinoma and 33 normal tissue samples was measured. The genes were selected based on their biological relevance. These include tumor suppressor genes and oncogenes, genes that are indirectly involved in cancer development, for example, DNA repair genes; metastasis-inhibitor genes, genes regulated by various signaling pathways, and/or responsible for altered cell growth, differentiation and apoptosis; genes considered to be targets for oncogenic transformation; imprinting genes; previously reported differentially methylated genes (Esteller, *Oncogene* 21, 5427-40 (2002), Tsou et al., Oncogene 21, 5450-61 (2002); Adodjan et al., *Nucleic Acids Res* 30, e21 (2002)).

A data matrix of β values was used to identify CpG loci that show differential methylation in cancer. Using a Mann-Whitney test, 21 normal samples were first compared to 11 adenocarcinoma samples referred thereafter the "training set". With a p-value cutoff of 1/369, 79 differentially methylated loci were identified. By choice of this p-value threshold, only one false positive marker was expected and this prediction was verified by randomly permuting columns in the data matrix and repeating Mann-Whitney test. Since the permutation process is independent of disease status, it provides an accurate estimate of actual false positive rate. On average, 0.63 differentially methylated markers were observed, indicating a lower than expected actual false positive rate, which is not surprising since not all CpG loci can be considered as independent variables. To select markers which have the largest difference between cancer and normal tissues (assuming this would cause the largest biological changes), an additional filter requiring |Δβ|>0.2 was required. Ultimately, a list of 14 differentially methylated markers was obtained: ADCYAP1_2, CDH13_3, GDF10_2, GDF10_3, HOXA5_2, MAGEA1_3, RUNX3_1, SCGB3A1_3, SERPINB5_1, SFN_2, SFTPA1_2, TERT_1, TERT_2, and TNF_2 (FIG. 23A).

The same differential methylation analysis was subsequently performed for the same 21 normal samples and 14 squamous cell carcinoma samples. When the same p-value threshold and |Δβ|>0.2 filtering was used, the following list of 21 differentially methylated markers was obtained: ADCYAP1_1, ADCYAP1_2, ADCYAP1_3, BCR_2, CALCA_1, GDF10_3, HOXA5_1, HOXA5_2, HOXA5_3, MAGEA1_1, MAGEA1_2, PGR_2, PRKCDBP_3, SCGB3A1_3, SERPINB5_1, SFN_2, SFTPC_3, TERT_1, TERT_2, TERT_3, TNF_2 (FIG. 23B).

Figure 24A:
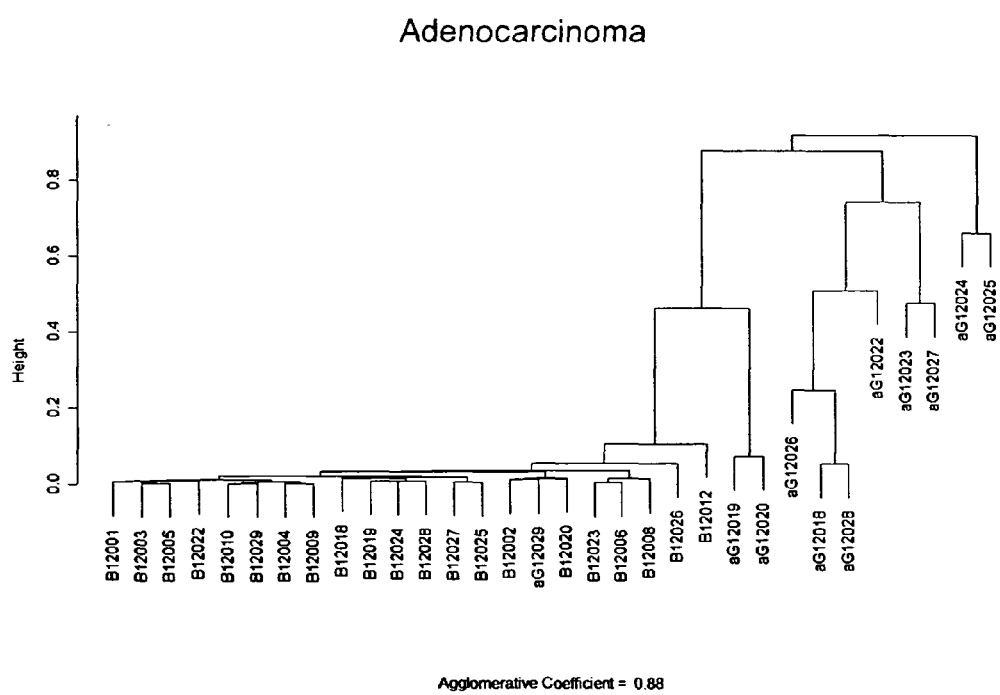
FIG. 24 shows a cluster analysis of lung cancer samples based on methylation profiles. Panel 24A shows adenocarcinoma (training set). Panel 24B shows squamous cell carcinoma (training set). Panel 24C shows adenocarcinoma (test set).
Figure 24B:
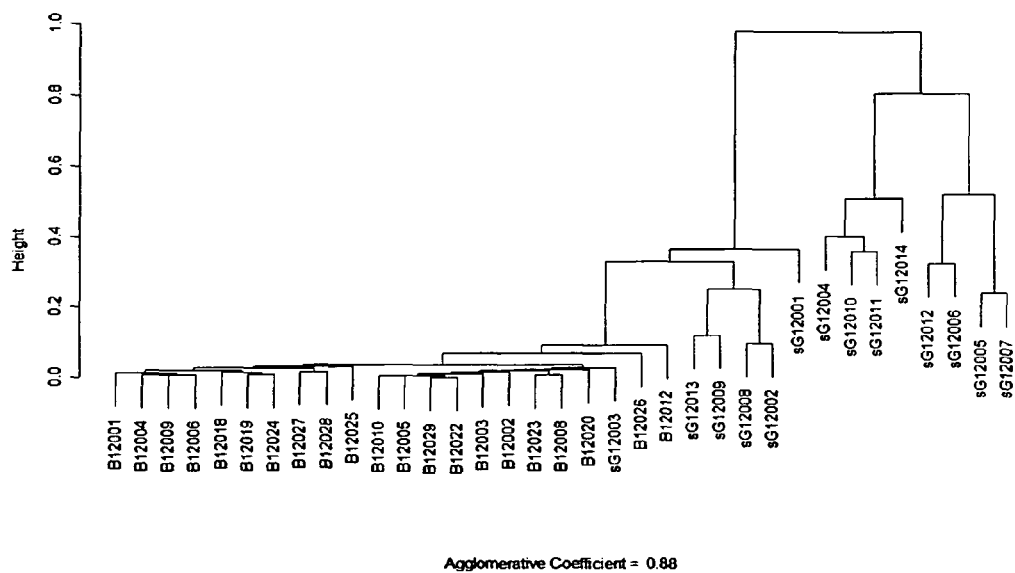

In addition, methylation profiles of the cancer and normal samples were clustered using the selected markers. Normal samples formed a tight cluster (i.e. small cluster distances) in both adenocarcinoma and squamous cell carcinoma groups (FIGS. 24A & 24B). Two early stage cancer samples, G12029 (FIG. 24A) and G12003 (FIG. 24B), were co-clustered with normal samples. Quite large cluster distances existed among cancer samples which may reflect different disease stages.

An independent set of test samples was used to assess the specificity and sensitivity of the 14 adenocarcinoma markers. This test set contained 11 normal and 14 adenocarcinoma samples. We classified these samples using a k-nearest neighbor algorithm. The misclassification rate in the test set was 0.04, with one cancer sample (D12190) misclassified as normal. The 14 markers also were evaluated by measuring their p-values from Mann-Whitney test with the test sample set. The p-values ranged between 0.00017 and 0.029. Finally, the classification accuracy derived from these 14 specific markers and randomly selected 1,000 sets of 14 CpG loci was measured. Only 2.2% of the 1,000 random sets produced same or lower misclassification rates as compared to the 14 markers, with an average misclassification rate being 28%. The above-described analyses indicate that the differential methylation pattern for the identified markers is preserved in the two completely unrelated sample sets and the identified markers can be used to distinguish adenocarcinoma from normal tissue with high specificity and sensitivity.

Figure 24C:
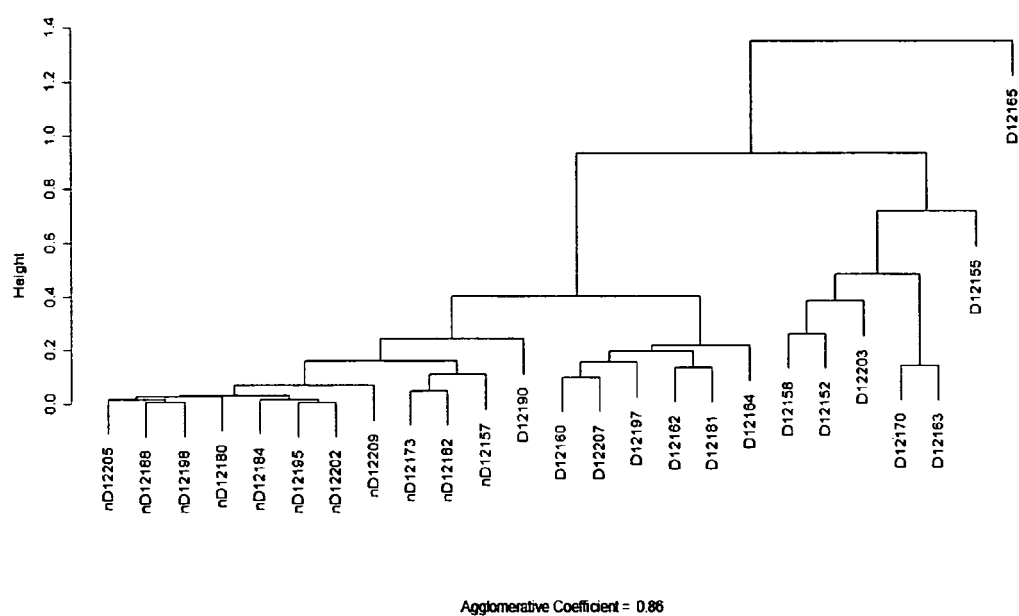
Figure 25:
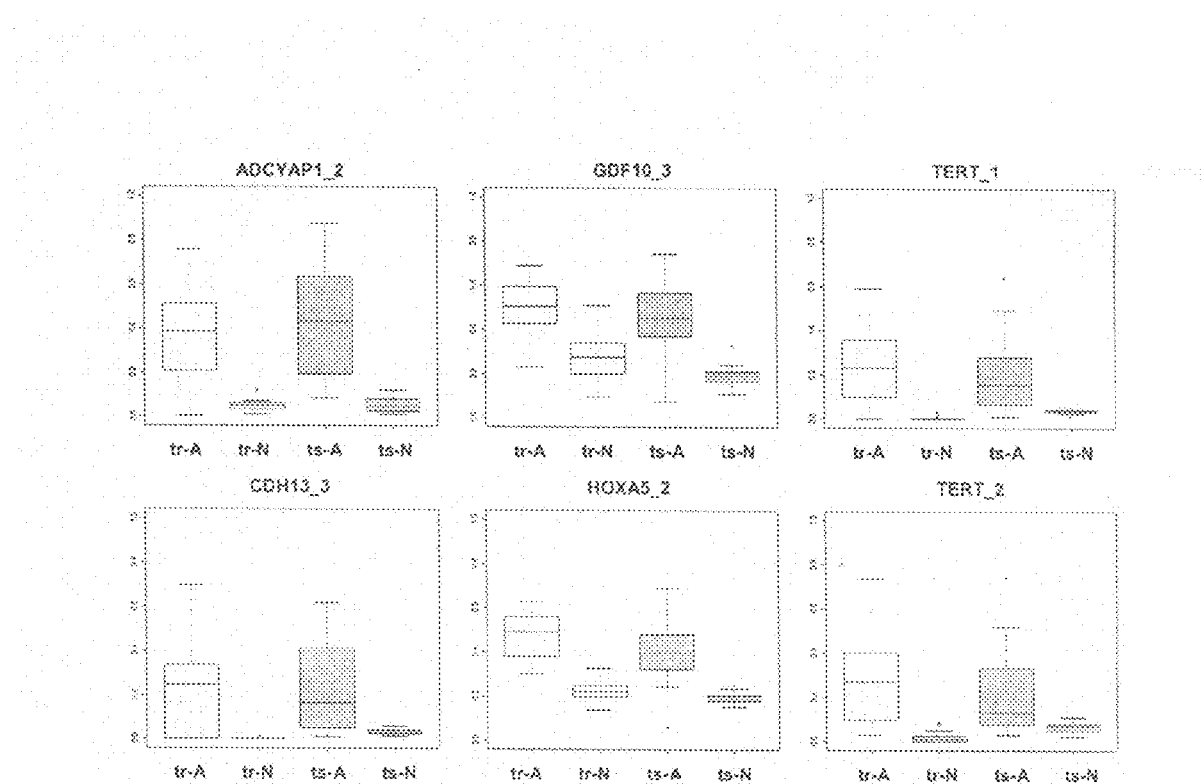
FIG. 25 shows box plots of the array data for selected cancer-specific methylation markers. β-values (y-axis) were calculated for the six adenocarcinoma cancer markers. For the training set (yellow plots), 11 adenocarcinoma and 21 normal tissues were used. For the validation set (grey plots), 13 adenocarcinoma and 12 normal tissues were used. The black bar represents the mean β-value. The box defines quartiles (25% and 75%, respectively). The error bars are upper and lower adjacent limits (median +/−1.5*IQR). Dots represent the outliers.

These results are further demonstrated by cluster analysis of the methylation patterns of the 14 identified markers in the test set samples. As shown in FIG. 24C, the cancer and normal samples are clearly separated. The array data for some of the markers which show increased methylation in cancer samples was plotted to illustrate their performance in both training set and test set of samples (FIG. 25).

EXAMPLE V

DNA Methylation Profiling in Lung Cancer

This example provides a further demonstration of the identification of adenocarcinoma markers by virtue of differential methylation patterns and use of the identified markers to distinguish adenocarcinoma from normal tissue with high specificity and sensitivity.

The methods in this Example were performed generally as described in the preceeding Examples.

Briefly, as described in Example IV, 1.5 kb sequence from the 5'-regulatory region was extracted for each target gene based on human genome RefSeq build 34, version 3 (released on Mar. 10, 2004). CpG islands of interest from this 1.5 kb region were selected and "bisulfite-converted" computationally. As described in Example 1, an automated SNP genotyping assay design program was adapted for methylation application. For each CpG site, four probes were designed: two allele-specific oligos (ASO) and two locus-specific oligos (LSO). Each ASO-LSO oligo pair corresponded to either the methylated or unmethylated state of the CpG site (FIG. 4). The gap size between the ASO and LSO oligos varied from 1 base to 20 bases, which allowed difficult sequences or ambiguous bases in CpG islands of interest to be avoided. This flexibility is particularly important for methylation studies because of a decrease in sequence complexity as a result of bisulfite treatment.

As described above, if other CpG sites were present in close vicinity of the target CpG site, we made the assumption that they had the same methylation status as the site of interest. This design hypothesis was based on previously reported bisulfite sequencing results, in which a majority (>90%) of the adjacent CpG sites was shown to be co-methylated or co-de-methylated (Bird A., *Genes Dev.* 16:6-21 (2002); Grunau et al., *J. Nutr.* 132:2435S-2439S (2002); Rakyan et al., *PLoS Biol.* 2:e405 (2004); Tost et al., *Nucleic Acids Res.* 31: e50 (2003)). This assumption was also confirmed by our own bisulfite sequencing results. This design strategy is used in methylation-specific PCR primer design (Herman, et al., *Proc Natl Acad Sci USA*. 93(18): 9821-6 (1996)) and other microarray-based DNA methylation analysis (Adorjan et al. 2002). While there were many CpG sites within each CpG island, only those for which robust assays could be designed were selected.

DNA from breast cancer cell lines MCF-7, MDA-MB-435, MDA-MB-468 and T-47D, colon cancer cell lines Fet, HT29, HCT116, LS174 and SW480, and prostate cancer cell lines PC3 and LNCaP was extracted using a modified Trizol method according to the manufacturer's recommendations (Invitrogen, Carlsbad, Calif.). DNA from lung cancer cell lines NCI-H69 (HTB-119D), NCI-H526 (CRL-5807D), NCI-H358 (CRL-5811D), NCI-H1299 (CRL-5803D), NCI-H1395 (CRL-5868D) and NCI-H2126 (CCL-256D) was purchased from ATCC (Manassas, Va.). DNA from normal lung, ovary, breast, colon and prostate tissues was purchased from Clinomics Biosciences (Frederick, Md.). DNA samples NA06999, NA07033, NA10923 and NA10924 were purchased from the Coriell Institute for Medical Research (Camden, N.J.).

Samples of lung tissue classified as cancerous and samples adjacent to the cancerous tissue but classified as normal were utilized in this study, under Human Subjects Institutional Review Board approved protocols. After pathological classification upon resection, the tissues were frozen and stored at −80° C. Twenty-two samples (the training set) were obtained from Philipps-University of Marburg, Germany, and 24 samples (the test set) were from The Pennsylvania State University College of Medicine Tumor Bank. Specifically, 23 lung adenocarcinoma and 23 normal tissues were used, of which 11 were matched pairs (Table 6). The samples were pulverized under liquid nitrogen. DNA was extracted from the tissue powder by QIAamp DNA Mini Kit (Qiagen Inc. Valencia, Calif.) according to the manufacturer's instructions. The DNA was eluted from the column with dH2O, and stored at −80° C. until use.

Methylation Profiling Assay with the SNP Genotyping Platform

Applying the protocols described above and in the previous examples, assays were designed and performed for 1536 CpG sites from the 5'-regulatory region of 371 genes (1-9 CpG sites per gene). These genes (shown in Table 5) were selected based on their biological relevance. They include tumor suppressor genes and oncogenes; genes that are indirectly involved in cancer development, for example, DNA repair genes; metastasis-inhibitor genes; genes regulated by various signaling pathways, and/or responsible for altered cell growth, differentiation and apoptosis; genes considered to be targets for oncogenic transformation; genes of innate host defense; genes involved in surfactant function of the lung; imprinted genes; and previously reported differentially methylated genes (Esteller, *Oncogene* 21, 5427-40 (2002), Tsou et al., *Oncogene* 21, 5450-61 (2002); Adordan et al., *Nucleic Acids Res* 30, e21 (2002)).

The assay procedure is similar to that described previously for standard SNP genotyping ((Fan et al., *Cold Spring Harbor Symposia on Quantitative Biology* 68: 69-78 (2003)), except that four oligos, two allele-specific oligos (ASOs) and two locus-specific oligos (LSOs) are used for each assay site rather than three. For each CpG site, two pairs of probes were designed to interrogate either the top or bottom strand: an allele-specific oligo (ASO) and locus-specific oligo (LSO) probe pair for the methylated state of the CpG site and a corresponding ASO-LSO pair for the unmethylated state. Each ASO consists of a 3' portion that hybridizes to the bisulfite-converted genomic DNA, with the 3' base complementary to either the "C" or "T" allele of the targeted CpG site, and a 5' portion that incorporates a universal PCR primer sequence P1 or P2. The LSOs consist of three parts: at the 5' end is a CpG locus-specific sequence; in the middle is an address sequence, complementary to a corresponding capture sequence on the array; and at the 3' end is a universal PCR priming site (P3). Pooled assay oligos were first annealed to bisulfite-converted genomic DNA. An allele-specific primer extension step was then carried out; ASOs were extended only if their 3' base was complementary to their cognate CpG site in the gDNA template. Allele-specific extension was followed by ligation of the extended ASOs to their corresponding LSOs, to create PCR templates. The ligated products were then amplified by PCR using common primers P1, P2, and P3', and hybridized to a microarray bearing the complementary address sequences. P1 and P2 were fluorescently labeled, each with a different dye, and associated with the "T" (unmethylated) allele or the "C" (methylated) allele respectively.

Bisulfite-treated, biotinylated genomic DNA (gDNA) was immobilized on paramagnetic beads. Pooled query oligos were annealed to the gDNA under a controlled hybridization program, and then washed to remove excess or mishybridized oligos. Hybridized oligos were then extended and ligated to generate amplifiable templates. Requiring the joining of two fragments to create a PCR template in this scheme provided an additional level of locus specificity. It is unlikely that any incorrectly hybridized ASOs and LSOs will be adjacent, and therefore should not be able to ligate after ASO extension. A PCR reaction was performed with fluorescently labeled universal PCR primers. Methylation status of an interrogated CpG site was determined by calculating β, which is defined as the ratio of the fluorescent signal from the methylated allele to the sum of the fluorescent signals of both methylated and unmethylated alleles.

As described in Example IV above, each methylation data point is represented by fluorescent signals from the M (methylated) and U (unmethylated) alleles. Background intensity computed from a set of negative controls was subtracted from each analytical data point. The ratio of fluorescent signals was then computed from the two alleles $$\beta = \frac{\max(M, 0)}{|U| + |M| + 100}.$$

The β-value reflects the methylation level of each CpG site. An absolute value was used in the denominator of the formula, as a compensation for any "negative signals" which may arise from global background subtraction (i.e. over-subtraction; a constant bias of 100 was added to regularize β when both U and M values were small). For cluster analysis, a matrix of correlation coefficients between calculated methylation signals was computed. Agglomerative nesting was applied using the Agnes function in the R package with Ward's method. Thus, the β-value provides a continuous measure of levels of DNA methylation in samples, ranging from 0 in the case of completely unmethylated sites to 1 in completely methylated sites.

Internal Controls for the Methylation Assay

Plasmids pUC19, pACYC184 and phage φX174 served as internal control DNAs in the methylation assay as described above (see Example II). Very low methylation values were obtained for most of the 1536 CpG sites in the unmethylated reference DNA sample as expected, with approximately 95% of the CpG sites showing methylation level lower than 50%. In contrast, about 93% of the CpG sites were methylated to over 50% of completion in the in vitro methylated reference DNA. In general, these results confirm that the assay is specific, and faithfully reports the methylation status of most of the targeted CpG sites in tested samples. Some degree of cross-hybridization can explain those outlier CpG sites where elevated methylation was observed in the unmethylated reference DNA and the sites that were "under-methylated" in the in vitro methylated reference DNA, as can be expected by the reduced complexity of bisulfite-converted DNA. All such un-validated sites were still included and monitored in the assay reactions, but excluded from consideration for methylation marker development (see below).

Bisulfite Conversion Efficiency

As described above, an effective bisulfite conversion protocol facilitates a robust methylation profiling assay. To estimate the conversion efficiency, an analysis was performed of 7097 cytosines in 173 independent DNA fragments derived from eight genomic regions by bisulfite sequencing as described by Frommer et al., *Proc. Natl. Acad. Sci. USA* 89:1827-1831 (1992). To avoid ambiguity, only the cytosines from non-CpG sites were counted. Primers were designed flanking the CpG sites of interest (Table 9). The primer landing sites did not contain CpG dinucleotides and therefore the nucleotide sequences remained unchanged after bisulfite treatment. As a result, the methylated and unmethylated alleles would be equally amplified in the same reaction with the designed primer pair. The PCR amplified fragments were cloned into the pCR4-TOPO vector (Invitrogen) followed by transformation into *Escherichia coli* TOP10 competent cells (Invitrogen). Transformants containing recombinant plasmids were selected by blue/white colony screening. PCR inserts were directly amplified from the white colonies in the reaction mixture (35 μl) containing 3.5 μl GeneAmp 10×PCR buffer (Applied Biosystems), 1.5 units of AmpliTaq Gold (Applied Biosystems), 1.5 mM $MgCl_2$, 200 nM of dNTP, and 200 nM each of M13 forward (5'-GTAAAACGACGGC-CAGT-3' (SEQ ID NO: 1514)) and reverse primer (5'-CAG-GAAACAGCTATGAC-3' (SEQ ID NO: 1515)). The reaction was subjected to the following cycling conditions: 94° C. for 10', followed by 35 cycles of 94° C. 30", 50° C. 30", 72° C. 30", and a final cycle of 72° C. for 5'. The PCR products were sequenced by Agencourt Bioscience Corporation (Beverly, Mass.). The sequence data indicated that the DNA conversion rate was 99.7%.

Methylation Assay Reproducibility

Figure 26:
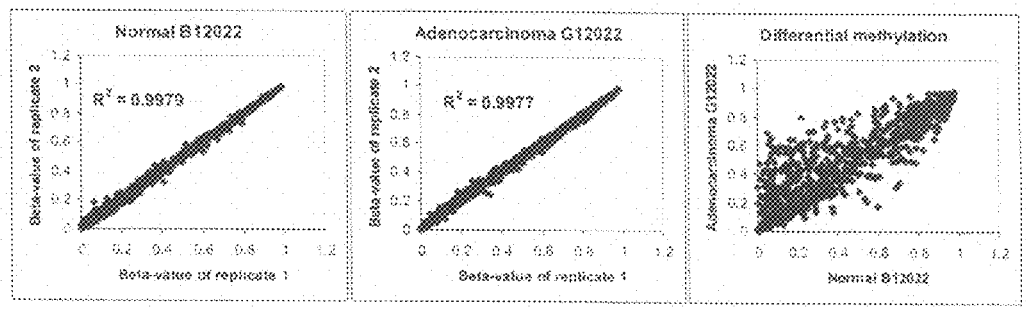
FIG. 26 shows methylation assay reproducibility and differential methylation detection. Comparison of methylation profiles between lung cancer and matching normal tissue. The β-value (i.e. the methylation ratio measured for all 1536 CpG sites) obtained from one replicate experiment is plotted against that obtained from another technical replicate experiment. The left and middle panels show the reproducibility of replicated assays on DNAs derived from lung adenocarcinoma G12022 (left) and its matching normal tissue (center). The right panel shows the comparison between the normal and the matching adenocarcinoma samples.

For each sample, 1 μg of genomic DNA was used for each bisulfite conversion. 20% of the converted DNA (corresponding to 200 ng starting gDNA) was then used to assay the 1536 CpG sites simultaneously on an array. Technical replicates were done for each sample using the same converted DNA. Highly reproducible DNA methylation profiles were obtained between these technical replicates (FIG. 26, left and center panels), with an average $R^2$ of 0.98±0.02 when the β-values were compared (Table 6). When β-values for matching normal and carcinoma clinical samples were compared, differential methylation was readily detected (FIG. 26, right panel).

DNA methylation is involved in transcriptional inactivation of genes on one of the two X-chromosomes in female somatic cells (i.e. X-chromosome silencing), which compensates for the dosage of functional X-linked genes between male and female (Carrel and Willard, *Nature* 434:400-404 (2005)) The methylation status of six X-linked housekeeping genes—EFNB1, ELK1, FMR1, G6PD, GPC3 and GLA was measured together with the rest of the 371 genes in male and female genomic DNAs. In general, methylation levels of these genes correlated well with the gender of the sample source, i.e. no or very low methylation was detected in male DNA samples and hemi-methylation was detected in female DNA samples.

The best 18 "gender-specific" CpG sites were subsequently selected from these X-chromosomal genes (with β<0.1 in male genomic DNA) to estimate the assay's ability for detecting difference of methylation levels between samples. Female genomic DNA was diluted into male genomic DNA at ratios of 5:95, 10:90, 20:80 and 50:50, prior to bisulfite conversion. Two independent sets of mixtures were made and measured in parallel (FIG. 27 Panel A); and four replicates were done for each mixture. The standard deviation of the β-value obtained for all the 1536 CpG sites across the four replicates was less than 0.06 in 99% of cases, and the average slope of β vs. expected methylation level for the selected X-chromosomal sites was equal to one. Therefore, the method can discriminate levels of methylation (β-values) that differ by as little as 0.17 ($1.96 \times \sqrt{2} \times 0.06$). Since the tails of their respective signal distributions did not have large overlapping areas (less than 16% assuming Gaussian error), there is a high probability that the response produced at one methylation level will be significantly different from the expected signal produced at another.

Figure 27A:
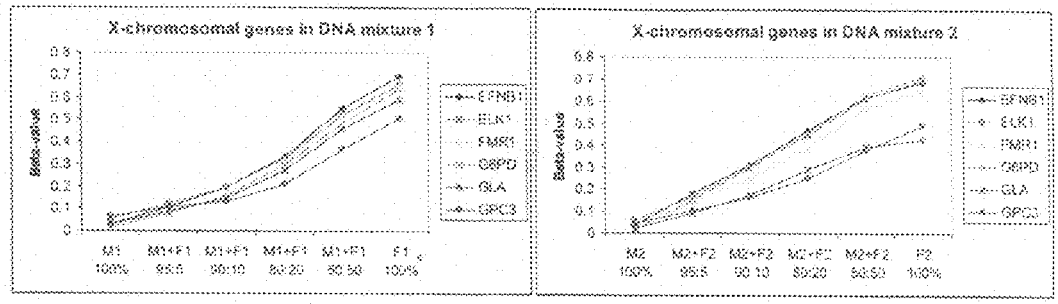
FIG. 27 shows methylation detection in gDNA mixtures. (A) Female genomic DNA was diluted with male genomic DNA at ratios of 5:95, 10:90, 20:80 and 50:50. Two sets of mixtures were made and measured: M1 (male NA10923)/F1 (female NA10924) and M2 (male NA07033)/F2 (female NA06999). Methylation levels of six X-chromosome linked genes were calculated as the average of several (1-5) CpG sites for each gene. (B) Methylation profiles of individual CpG sites (only four are shown). Error bars represent the standard deviation of β-values calculated from four replicate experiments, done with the first set of mixtures (NA10923/NA10924).
Figure 27B:
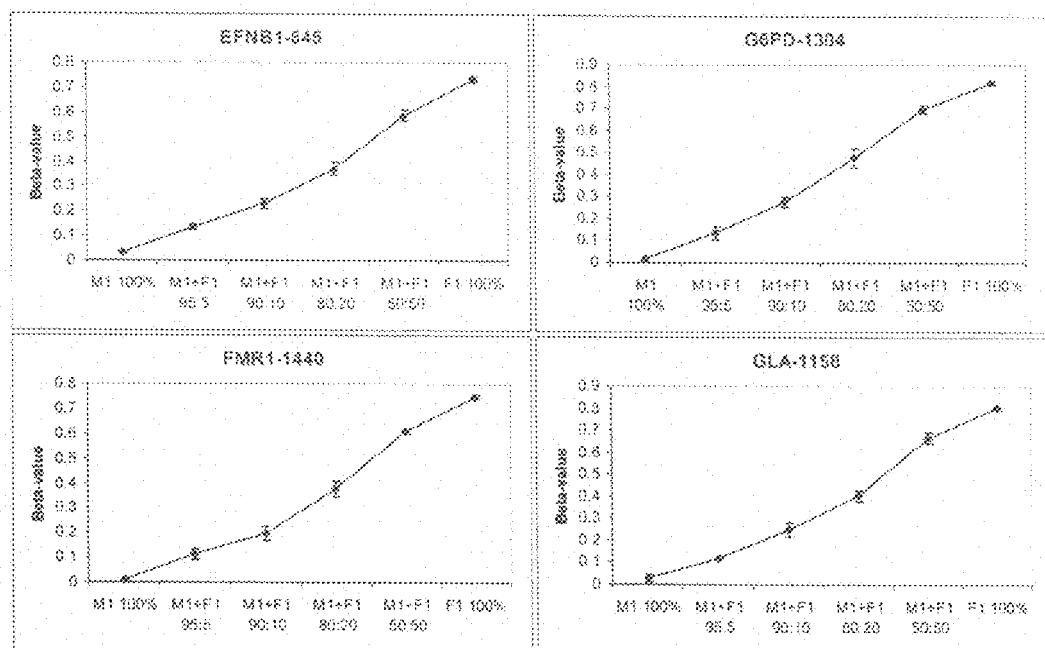

The standard deviation of these measurements was not uniform across the range of β-values. It had a parabolic shape with the maximum peak around β=0.5. Therefore, the absolute performance of the assay depends on the methylation level itself. For example, for 16 out of the 18 CpG sites, methylation levels from 5:95 and 0:100 mixtures could be unambiguously distinguished from each other (i.e. the maximum β-value in the 0:100 mixtures was less than the minimum β-value in the 5:95 mixtures) (FIG. 27 Panel B). This indicates that the method can detect as little as 2.5% methylation for well-performing CpG sites in the optimal range of the response curve.

Methylation Profiling in Cancer Cell Lines

Figure 28:
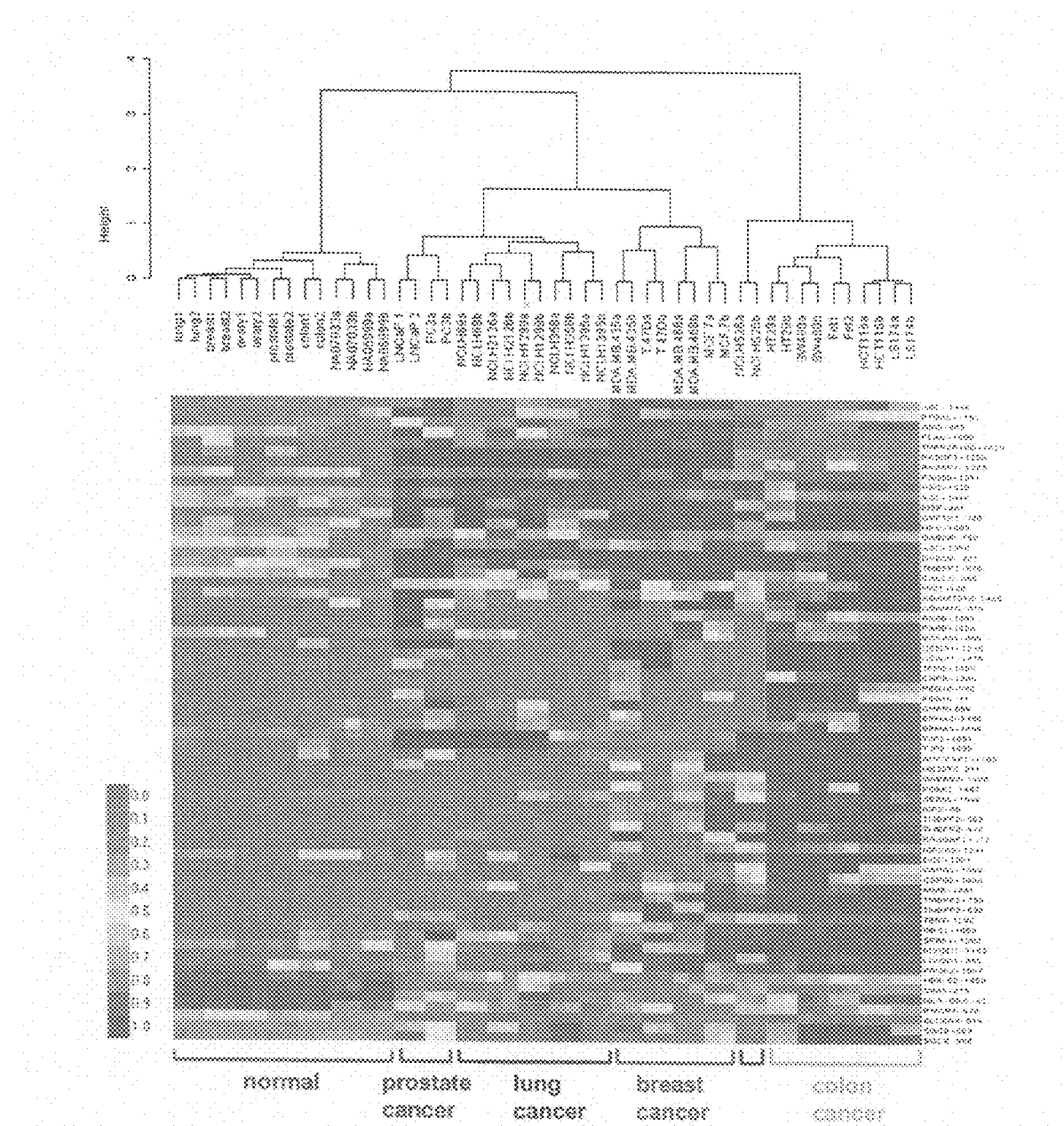
FIG. 28 shows methylation profiling in cancer cell lines. Seven DNA samples derived from different normal tissues and 17 colon, breast, lung and prostate cancer cell lines were profiled. All cancer samples were correctly separated from normal samples using agglomerative clustering based on 64 cancer-specific methylation makers, and highly specific methylation signatures were obtained for each cancer type. Green, yellow and red colors represent low, medium and high methylation levels, respectively.

To demonstrate the applicability of the disclosed method for studying DNA methylation in cancer, the assay developed for the 1536 CpG sites was applied to a panel of 17 colon, breast, lung and prostate cancer cell lines, as well as seven DNA samples derived from different normal tissues. Sixteen CpG sites distinguishing cancer from normal samples were selected based on a Mann-Whitney test (p<0.00001) and an additional filter of mean change of methylation level greater than 0.34 (0.17×2). Forty-eight CpG sites distinguishing individual cancer types were selected based on a Kruskal-Wallis test (p<0.035) and a standard deviation across cancer samples greater than 0.34. This gave us a balanced list of 16 cancer-specific markers and 48 cancer type-specific markers. Using these markers, all cancer samples were correctly separated from normal samples by hierarchical clustering, with Ward's linkage method and correlation-based distance metric. This separation of cancer samples was not sensitive to the choice of distance metric or linkage method (data not shown). FIG. 28 shows the differential methylation profiles in normal vs. cancer samples as well as specific methylation signatures that were obtained for individual cancer types. In general, our data correlate well with previous cell line methylation profiling results (Melnikov, et al., *Nucleic Acids Res* 33: e93 (2005); Paz et al., *Cancer Res* 63: 1114-1121 (2003)). For example, GSTP1 was completely methylated in the LNCaP prostate cancer cell line and semi-methylated in PC3 cell line, as previously reported by Singal et al., *Cancer Res* 61: 4820-4826 (2001). The overall methylation level in colon cancer cell lines appears to be higher as compared to the other cell lines, also consistent with previous results Paz et al. supra, 2003.

Validation of Microarray Data by Methylation-Specific PCR (MSP)

Methylation-specific PCR (MSP) has been widely used to monitor methylation status of individual genes (Eads et al., *Nucleic Acids Res* 28: E32 (2000); Herman, et al., *Proc Natl Acad Sci USA*. 93(18): 9821-6 (1996)). MSP was used to confirm the methylation status of CpG sites from five genes that were identified by our microarray analysis as showing distinct methylation profiles in normal lung tissue and lung cancer cell lines.

MSP primers that are specific to either methylated or unmethylated DNA were designed to target corresponding CpG sites within the promoter regions of CFTR, DBC1, DLK1, EYA4 and NPY genes (Table 5). In addition, a pair of primers recognizing a non-CpG-containing region of the β-actin gene (ACTB) was used to measure DNA input. The specificity of each set of MSP primers was first tested using in vitro methylated and unmethylated reference DNAs described above. MSP conditions were optimized to maximize the discrimination between the two methylation states. Bisulfite-treated genomic DNAs derived from one normal lung tissue and six lung cancer cell lines were analyzed using real-time MSP. The methylated and unmethylated alleles in each genomic DNA sample were amplified in separate reactions.

Briefly, the bisulfite-converted genomic DNA was amplified by real-time quantitative PCR using two sets of locus-specific MSP primers, which recognize methylated or unmethylated DNA, respectively. The MSP primers (Table 8) were designed using CpGWare, software provided by Chemicon (Temecula, Calif.). Real-time PCR analysis was performed on an ABI Prism 7900HT Sequence Detection System (Applied Biosystems, Foster City, Calif.).

The PCR reaction was performed using a 384-well optical tray in a final volume of 10 μl. The reaction mixture consists of 5 μl of 2×SYBR Green PCR master mix (Applied Biosystems) and 250 nM each of primers and bisulfite-converted DNA template (~50 ng, measured prior to bisulfite treatment). The real-time PCR cycling conditions were as follows: 50° C. for 2 min, 95° C. for 12', followed by 40 cycles at 95° C. for 20", 56° C. for 30", and 72° C. for 1'.

After PCR, a thermal melt profile was performed to examine the homogeneity of PCR amplicons. Each DNA sample was analyzed in duplicate and the mean was used for further analysis. The difference of the threshold cycle number (the $C_t$-values) between the methylated and unmethylated alleles, $\Delta C_t = C_t$ (unmethylated)$-C_t$ (methylated), was first determined. The percentage of methylated DNA, designated as the methylation level "c", can be correlated to the ΔCt value through the equation: $\Delta C_t = \text{Log } 2[c/(1-c)]$ ((Martens et al., *Cancer Res* 65: 4101-4117 (20055); Zeschnigk et al. Nucleic Acids Res 32: e125 (2004)). The resulting methylation level thereby equals $2^{\Delta Ct}/(1+2^{\Delta Ct})$.

Figure 29:
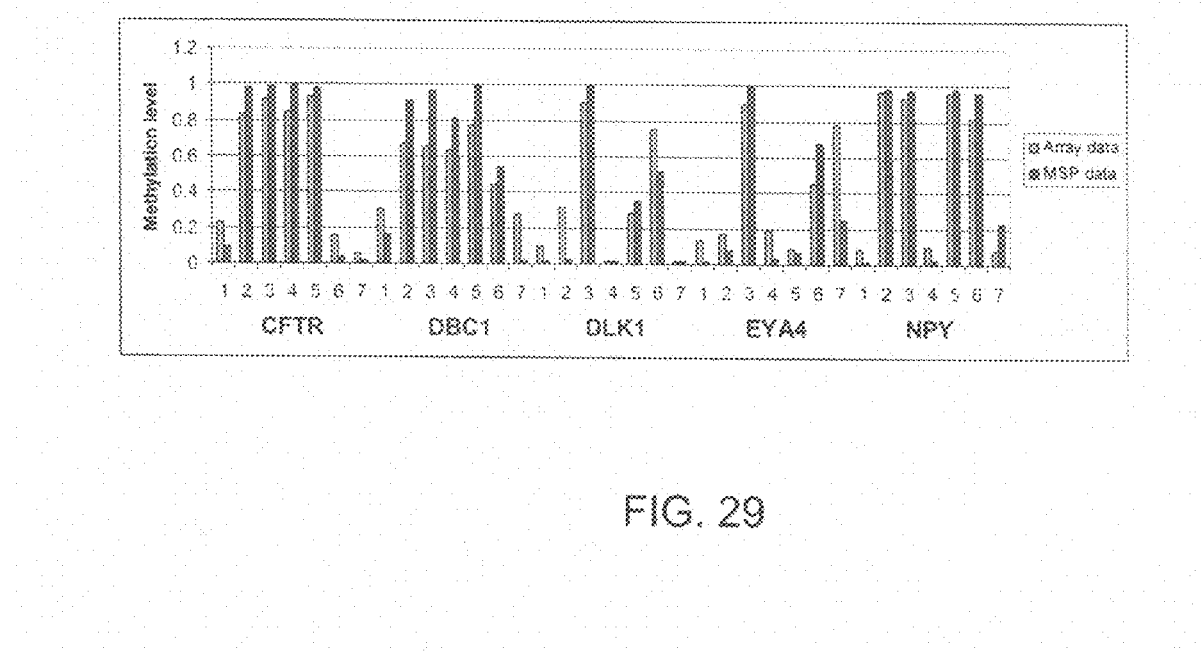
FIG. 29 shows a comparison of methylation-specific PCR and array-based methylation data. MSP was used to confirm the methylation status of CpG sites within the promoter regions of five genes that showed distinct methylation profiles in one normal lung tissue and six lung cancer cell lines from array-based methylation analysis (1: normal lung tissue, 2: NCI-H69, 3: NCI-H526, 4: NCI-H358, 5: NCI-H1299, 6: NCI-H1395, and 7: NCI-H2126). Methylation level is represented as bars, blue for microarray data and red for MSP data.

Of the 35 MSP data points, 34 were highly concordant with the methylation status determined by the genotyping-based microarray analysis, with a Spearman correlation coefficient, r=0.89 (FIG. 29). These results confirm the overall validity of the method.

Methylation Marker Identification in Lung Adenocarcinomas

The methylation status of the 1536 CpG sites in 23 lung adenocarcinoma and 23 normal lung tissue samples was measured using a data matrix of β-values to identify CpG sites that showed differential methylation in cancers. Using a Mann-Whitney test, 11 normal samples were initially compared to 11 adenocarcinoma samples (a training set of samples obtained from Philipps-University of Marburg, Germany). A false discovery rate (FDR) approach was used as described by Benjamini, Y. and Y. Hochberg, *J. R. Statist. Soc.* B 57: 289-300 (1995), to select a list of differentially methylated CpG sites. At an FDR=0.001 cutoff, 207 differentially methylated sites were identified. To select markers which had the largest difference between cancer and normal tissues, an additional filter was applied that required a minimum difference of 0.15 in β between the two groups.

A list of 55 differentially methylated markers for lung adenocarcinoma was thus obtained (Table 7). Among these markers, more were hypermethylated in adenocarcinoma, including the genes ASCL2, CDH13, HOXA11, HOXA5, NPY, RUNX3, TERT and TP73 that were selected for validation by bisulfite sequencing (see below). Of these genes, methylation of CDH13 (Ogama et al., *Int J Oncol* 25: 685-691 (2004); Toyooka et al., *Cancer Res* 61: 4556-4560 (2001)); HOXA5 (Chen et al., *Am J Pathol* 163: 37-45 (2003)); RUNX3 (Li et al., *Biochem Biophys Res Commun* 314: 223-228 (2004)); and TP73 (Lomas et al., *Cancer Genet Cytogenet* 148: 148-151 (2004)) is known to be associated with tumor progression in various types of cancer. The human telomerase reverse transcriptase gene (TERT) was shown to be inactivated in most differentiated cells, but reactivated in the majority of cancer cells ((Liu et al., *Genes Chromosomes Cancer* 41, 26-37 (2004)) However, a recent study reported methylation of TERT in cervical cancer and its correlation with poor prognosis (Widschwendter et al., *Gynecol Oncol* 93: 407-416 (2004)). One of the markers on the list, neuropeptide Y (NPY), which was shown to be hypermethylated in 19 out of the 23 analyzed adenocarcinoma samples and had no or very low methylation in the normal samples, was not previously reported as a cancer marker. NPY may influence lipid metabolism and is potentially associated with hypertension (Tomaszewski et al., *Hypertension* 44: 689-694 (2004)). Accordingly, it is contemplated that NPY plays a role in lung surfactant-related function.

Figure 30:
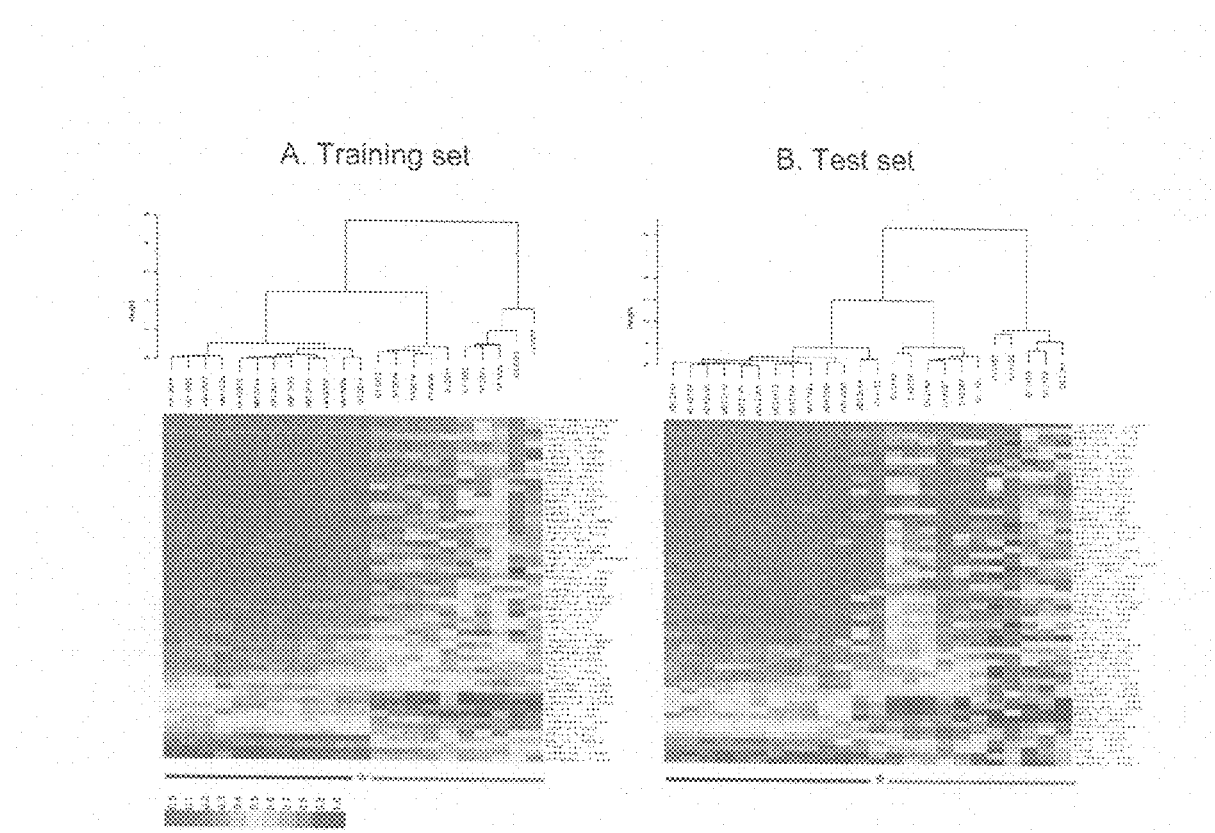
FIG. 30 shows a cluster analysis of lung adenocarcinoma samples. Panel (A) shows eleven cancer and 11 normal tissue samples were used as a training set to identify a list of 55 CpG sites, that are differentially methylated in cancer vs. normal tissues with high confidence level (adjusted p-value<0.001) and significant change in absolute methylation level (|Δβ|>0.15). Cancer sample G12029 was mistakenly co-clustered with normal samples. Panel (B) shows use of the selected 55 CpG sites for classification of an independent test sample set of 12 lung adenocarcinoma and 12 normal tissue samples, collected from a different institute. All the normal and cancer samples were separated into two distinguished groups with a single error—cancer sample D12162 was co-clustered with normal samples. Normal samples are underlined in green, cancer, in red. The asterisks indicate misclassified samples.

Clustering of Independent Sample Sets Based on the Identified Methylation Markers Agglomerative nesting with the Ward method and correlation-based distance were used to cluster the training set samples, i.e. the German samples mentioned above, based on the methylation profiles of the 55 selected markers. Cancer samples were clearly distinguishable from normal samples with one error—cancer sample G12029 co-clustered with the normal samples (FIG. 30 Panel A).

To assess the power of the selected methylation markers for reliable classification of prospective cancer and normal samples, clustered an independent test set of samples was clustered based on the methylation profiles of these markers. This test set contained 12 normal and 12 adenocarcinoma samples, collected from The Pennsylvania State University College of Medicine Tumor Bank. A 100% specificity (12/12) and 92% sensitivity (11/12) was obtained. The specificity was calculated as True Negative (TN)/(TN+False Positive (FP)), and the sensitivity was calculated as True Positive (TP)/(TP+False Negative (FN)). One cancer sample D12162 was co-clustered with the normal samples in this test set (FIG. 30 Panel B). This analysis indicates that the differential methylation pattern for the identified markers was preserved in the two completely unrelated training and test sample sets and that methylation profiling of these markers allows the identification of cancer samples with high specificity and sensitivity.

Methylation Marker Validation by Bisulfite Sequencing

Eight CpG sites which showed elevated methylation in the adenocarcinoma samples were validated using bisulfite sequencing (Frommer, et al., *Proc Natl Acad Sci USA*. 89(5): 1827-31 (1992)). This method was selected over other methylation detection methods for several reasons: (1) to provide another validation of the disclosed method, in addition to the MSP method; (2) it requires less input DNA as compared to other methods; and (3) the bisulfite sequencing data was used to estimate the bisulfite conversion rate as described above).

PCR primers were designed flanking the CpG sites of interest (Table 9). DNAs from two normal and four adenocarcinoma samples were treated with bisulfite and regions of interest were amplified by PCR. PCR fragments were cloned and individual colonies were picked for sequencing as described above. Twelve cloned fragments were sequenced for each CpG site in selected samples. In all cases an increase in methylation in cancer samples was observed compared to normal samples. Even though the absolute levels of methylation detected by the two different methods were somewhat different (Table 10), a strong correlation was obtained between these two data sets, with a Spearman correlation coefficient, r=0.70. Overall, these results confirm that the disclosed methods can reliably detect methylation differences in clinical samples for more than 1,000 CpG sites and that the assay can be used for both marker discovery and validation.

This Example demonstrates measurement of the methylation status of 1536 CpG sites (derived from 371 genes) in 11 lung adenocarcinomas and 11 matching normal tissue samples. A panel of 55 adenocarcinoma-specific methylation markers was identified by combining p-value and magnitude of change thresholds (FIG. 30 Panel A). Furthermore, adenocarcinoma markers in an independent sample set (N=24) were validated with high sensitivity and specificity (FIG. 30 Panel B). The results described above demonstrate the utility of the invention method for marker identification and validate the robustness of the markers identified.

Throughout this application various publications have been referenced. The disclosures of these publications in their entireties are hereby incorporated by reference in this application in order to more fully describe the state of the art to which this invention pertains.

The term "comprising" is intended herein to be open-ended, including not only the cited elements, but further encompassing any additional elements.

Unless defined otherwise, all technical and scientific terms used herein have the same meaning as commonly understood by one of ordinary skill in the art to which the invention pertains.

Although the invention has been described with reference to the disclosed embodiments, those skilled in the art will readily appreciate that the specific examples and studies detailed above are only illustrative of the invention. It should be understood that various modifications can be made without departing from the spirit of the invention. Accordingly, the invention is limited only by the following claims.

TABLE 1

Cancer-associated genomic markers and corresponding target nucleic acid probes.

| TARGET CPG SITE | GENBANK ACCESSION # | TARGET SEQUENCE SEQ ID NOS: 1-377 | PROBE SEQUENCE (ASO1) SEQ ID NOS: 378-754 | PROBE SEQUENCE (LSO1) SEQ ID NOS: 755-1131 | PROBE SEQUENCE (ASO2) SEQ ID NOS: 1132-1508 |
|---|---|---|---|---|---|
| GI29736559_ESR2_1R (SEQ ID 1) | NT_026437 | GGATGCTCCTCAGCTCTGGGG ACGCGGTGCAGAAGTGTGAGG GCGCC | GCCCTCACACTTCTAC ACCG | GTCCCCAAAACTAAAA AACATCC | AACACCCTCACACTTC TACACCA |
| GI29736559_ESR2_2R (SEQ ID 2) | NT_026437 | CTTCCGACTTTGTCACACACC TGCGCCGCCAGACTGGGGTCG GGCCCC | CCGACTTTATCACACA CCTACG | CGCCAAACTAAAATCG AACC | CTTCCAACTTTATCAC ACACCTACA |

TABLE 1-continued

Cancer-associated genomic markers and corresponding target nucleic acid probes.

| TARGET CPG SITE | GENBANK ACCESSION # | TARGET SEQUENCE SEQ ID NOS: 1-377 | PROBE SEQUENCE (ASO1) SEQ ID NOS: 378-754 | PROBE SEQUENCE (LSO1) SEQ ID NOS: 755-1131 | PROBE SEQUENCE (ASO2) SEQ ID NOS: 1132-1508 |
|---|---|---|---|---|---|
| GI29735559_ESR2_3R (SEQ ID 3) | NT_026437 | CCCGGCTTCCAGGCAGTAATG GGCGGGTCCCTGCGCGGGAGC GTGGCGGGCG | CGACTTCCAAACAATA ATAAACG | ATCCCTACGCGAAAAC GTAAC | CCCAACTTCCAAACAA TAATAAACA |
| GI29791372_TGFBR2_1R (SEQ ID 4) | NT_022517 | AATCTGAAGAAAGCTGAGGGG AGGCGGCAGATGTTCTGATCT ACTAGGGA | CCCTAATAAATCAAAA CATCTACCG | CTCCCCTCAACTTTCT TCAAATT | TCCCTAATAAATCAAA ACATCTACCA |
| GI29791372_TGFBR2_2R (SEQ ID 5) | NT_022517 | AACTCCTGAGTGGTGTGGGAG GGCGGTGAGGGGCAGCTGAAA GTC | ACTTTCAACTACCCCT CACCG | CCTCCCACACCACTCA AAAATT | AACTTTCAACTACCCC TCACCA |
| GI29791372_TGFBR2_3R (SEQ ID 6) | NT_22517 | TGGTCTAGGAAACATGATTGG CAGCTACGAGAGAGCTAGGGG CTGGACGT | GTCCAACCCCTAACTC TCTCG | AACTACCAATCATATT TCCTAAACCA | ACATCCAACCCCTAAC TCTCTCA |
| GI29791384_TP73_1R (SEQ ID 7) | NT_004321 | CCGAGGAGCCCAGCGCTAGTG GCGGCGGCCAGGAGAGACCCG GGTGTCA | ACCCGAATCTCTCCTA ACCG | CGCCACTAACGCTAAA CTCCT | TAACACCCAAATCTCT CCTAACCA |
| GI29791384_TP73_2R (SEQ ID 8) | NT_004321 | GACAGCAGGGAGTCCGGGGGA AACGCAGGCGTCGGGCACAGA GTCGG | ACTCTATACCCGACGC CTACG | TTCCCCCGAACTCCCT ACTAT | CCAACTCTATACCCAA CACCTACA |
| GI29791384_TP73_3R (SEQ ID 9) | NT_004321 | GGCCCTGGCGCCGACCTGCT TCGGCCCTGCGTGGGCGGCCT CGCCGG | CTAACGCCGAACCTAC TTCG | CCCTACGTAAACGACC TCGC | AACCCTAACACCCAAAC CTACTTCA |
| GI29791621_PTGS2_1R (SEQ ID 10) | NT_004487 | TCGGAAGCGCTCGGGCAAAGA CTGCGAAGAAGAAAAGACATC TGGCGG | CGCCAAATATCTTTTC TTCTTCG | AATCTTTACCCGAACG CTTCC | CCACCAAATATCTTTT CTTCTTCA |
| GI29791621_PTGS2_3R (SEQ ID 11) | NT_004487 | AGTCTGTCCCGACGTGACTTC CTCGACCCTCTAAAGACGTAC AGACCAGA | TATCCCGACGTAACTT CCTCG | CCCTCTAAAACGTAC AAACCAA | AATCTATCCCAACATA ACTTCCTCA |
| GI29793179_DAPK1_1R (SEQ ID 12) | NT_023935 | GCGCCGGCCTGGCAGGGCAGC TCGGAGGTGGGTGGGCCGCGC CGCCAGC | CCGACCTAACAAAACA ACTCG | AAATAAATAAACCGCG CCG | ACACCAACCTAACAAA ACAACTCA |
| GI29793179_DAPK1_3R (SEQ ID 13) | NT_023935 | AAACCTTCTTGCCTTCAAGCC TCGGCTCCAACACCAGTCCGG CAGA | AACCTTCTTACCTTCA AACCTCG | CTCCAACACCAATCCG ACA | AAACCTTCTTACCTTC AAACCTCA |
| GI29794150_CASP8_1R (SEQ ID 14) | NT_005403 | GGAAGTGAGAAACAAGTGTGT GATAACGGTGGAGAATGGGA GCACTCTC | AAATACTCCCATTCTC CACCG | TTATCACACACTTATT TCTCACTTCC | AAAAATACTCCCATTC TCCACCA |
| GI29794150_CASP8_2R (SEQ ID 15) | NT_005403 | GCGGGAGGGAGACGAGGAGGGC GTTCCCTGGGGAGTGGCAGTG AAACG | ACTACCACTCCCCAAA | CCTCCTCGTCTCCTCC C | CACTACCACTCCCCAA AAAACA |
| GI29794150_STAT1_1R (SEQ ID 16) | NT_005403 | AAGCCGGCGGAAATACCCCAG CGCGTGGGCGGAGCAGCGGCC GCGCAGA | CGACGAAAATACCCCA ACG | GTAAACGAAACAACGA CCCG | AAACCAACAAAAATAC CCCAACA |
| GI29794150_STAT1_2R (SEQ ID 17) | NT_005403 | GGCGGTGGCGCCCACGGAACA GCCGCGTCTAATTGGCTGAGC GCGGAGC | GCGCTCAACCAATTAA ACG | GACTATTCCGTAAACG CCACC | ACTCCACACTCAACCA ATTAAACA |
| GI29794159_STAT1_3R (SEQ ID 18) | NT_005403 | CCAGTTCCCAGCGTGGCAACA CGGGACTGGGCTGCACCTCAC CCAGCCG | AATTCCCAACGTAACA ACACG | AACTAAACTACAACTC ACCCAACC | CCAATTCCCAACATAA CAACACA |
| GI29794559_CDKN2A_1R (SEQ ID 19) | NT_008413 | GACTCACCCCTCCTTTCTGCC GCTCCTTCCTTTCCTTGCCCT GCTTT | ACTCACCCCTCCTTTC TACCG | TCCTTCCTTTCCTTAC CCTACTTT | AACTCACCCCTCCTTT CTACCA |
| GI29794559_CDKN2A_2R (SEQ ID 20) | NT_008413 | GCCCGCGTCCGAGTTCCTGGA CGAGAGCCGAGCCTCGCTTAG ACCGC | GCGTCCGAATTCCTAA ACG | AAACCGAACCTCGCTT AAACC | ACCCACATCCAAATTC CTAAACA |
| GI29794559_CDKN2A_3R (SEQ ID 21) | NT_008413 | TCCAGCCCGCGAGGTTTAGGA CGGATCCAGGCAGACCGCAGG CTCC | AACCCGCGAAATTTAA AACG | ATCCAAACAAACCGCA AACT | TCCAACCCACAAAATT TAAAACA |
| GI29794559_CDKN2B_1R (SEQ ID 22) | NT_008413 | AGCAGTGCAGCCAGCATTCCT GGCGGCTCCCTGGCCCAGTCT CTGGCGCA | CAATACAACCAACATT CCTAACG | CTCCCTAACCCAATCT CTAACG | AACAATACAACCAACA TTCCTAACA |
| GI29794559_CDKN2B_2R (SEQ ID 23) | NT_008413 | GGCTGAAGGAACAGAAATCCT CTGCTCCGCCTACTGGGGATT AGGAGCTG | CAACTCCTAATCCCCA ATAAACG | AACAAAAATTTCTAT TCCTTCAACC | CAACTCCTAATCCCCA ATAAACA |
| GI29794559_CDKN2B_3R (SEQ ID 24) | NT_008413 | AGCATCTTTGGGCAGGCTTCC CCGCCCTCGTGACGCGTCGGC CCGGGC | CATCTTTAAACAAACT TCCCG | CCTCGTAACGCGTCGA C | AACATCTTTAAACAAA CTTCCCCA |
| GI29796774_MYC_1R (SEQ ID 25) | NT_008046 | AGAGCAGGCAACCTCCCTCTC GCCCTAGCCCAGCTCTGGAAC AGGCAG | AAACAAACAACCTCCC TCTCG | CCTAACCCAACTCTAA AACAACAA | AAAACAAACAACCTCC CTCTCA |
| GI29796774_MYC_2R (SEQ ID 26) | NT_008046 | ACCTTTGATTTCTCCCAAACC CGGCAGCCCGAGACTGTTGCA AACCGG | CTTTAATTTCTCCCAA CCCCG | CAACCCGAAACTATTA CAAACG | ACCTTTAATTTCTCCC AAACCCA |

TABLE 1-continued

Cancer-associated genomic markers and corresponding target nucleic acid probes.

| TARGET CPG SITE | GENBANK ACCESSION # | TARGET SEQUENCE SEQ ID NOS: 1-377 | PROBE SEQUENCE (ASO1) SEQ ID NOS: 378-754 | PROBE SEQUENCE (LSO1) SEQ ID NOS: 755-1131 | PROBE SEQUENCE (ASO2) SEQ ID NOS: 1132-1508 |
|---|---|---|---|---|---|
| GI29796774_MYC_3R (SEQ ID 27) | NT_008046 | CAAGGGTCTCTGCTGACTCCC CCGGCTCGGTCCACAAGCTCT CCACTT | AAAAATCTCTACTAAC TCCCCCG | CTCGATCCACAAACTC TCCACT | CAAAAATCTCTACTAA CTCCCCCA |
| GI29797939_APC_1R (SEQ ID 28) | NT_034772 | CAGCAACACCTCTCACGCATG CGCATTGTAGTCTTCCCACCT CCCAC | AACAACACCTCTCACG CATACG | ATTATAATCTTCCCAC CTCCCAC | CAACAACACCTCTCAC ACATACA |
| GI29197939_APC_2R (SEQ ID 29) | NT_034772 | GACGAACAGCGAAGCAGTGC CCGGCAAGCGGAGCGCAGCAC CCATTG | CAAAACAACGAAACAA TACCCG | CAAACGAAACGCAACA CC | AACAAAACAACAAAAC AATACCCA |
| GI29797939_APC_3R (SEQ ID 30) | NT_034772 | CGCCGGAAGCCTAGCCGCTGC TCGGGGGGACCTGCGGGCTC AGGCCCG | CGAAAACCTAACCGCT ACTCG | AAAAAACCTACGAACT CAAACCC | CACCAAAAACCTAACC ACTACTCA |
| GI29798364_HIC1_1R (SEQ ID 31) | NT_010718 | TGCCCAGGCCGCAGGGCTGAT GCCCCCGCTCAGCTGAGGGAA GGGGAAG | CCCCTTCCCTCAACTA AACG | AAACATCAACCCTACG ACCTAAA | CTTCCCCTTCCCTCAA CTAAACA |
| GI29798364_HIC1_2R (SEQ ID 32) | NT_010718 | CTCCTGCTCCTTCTCCTGGTC CGGGCGGGCCGGCCTGGGCTC CCACT | CTCCTACTCCTTCTCC TAATCCG | ACGAACCGACCTAAAC TCCC | CTCCTACTCCTTCTCC TAATCCA |
| GI29798364_HIC1_3R (SEQ ID 33) | NT_010718 | AACTGGGGCAACTTCCCCGA GGCGGGAGGCGCTGGTTCCTC GGCTCCC | TAAAACAACTTCTCCC GAAACG | AAAACGCTAATTCCTC GACTCC | AACTAAAACAACTTCT CCCAAAACA |
| GI29798364_TP53_1R (SEQ ID 34) | NT_010718 | GTTAGTATCTACGGCACCAGG TCGGCGAGAATCCTGACTCTG CACCCTCCTC | TATCTACGACACCAAA TCGACG | AAATCCTAACTCTACA CCCTCCTC | ATTAATATCTACAACA CCAAATCAACA |
| GI29798364_TP53_2R (SEQ ID 35) | NT_010718 | CTCCATTTCCTTTGCTTCTC CGGCAGGCGGATTACTTGCCC TTACTTGTCA | CCATTTCCTTTACTTC CTCCG | CAAACGAATTACTTAC CCTTACTTATCA | CTCCATTTCCTTTACT TCCTCCA |
| GI29798364_TP53_3R (SEQ ID 36) | NT_010718 | CCCCGCCGCCTGCAGAGGGCG CAGCAGGTCTTGCACCTCTTC TGCATCTC | CGCCGCCTACAAAAAA CG | AACAAATCTTACACCT CTTCTACATCTC | CCCCACCACCTACAAA AAACA |
| GI29798595_BRCA1_1R (SEQ ID 37) | NT_010755 | TTTCGTATTCTGAGAGGCTGC TGCTTAGCGGTAGCCCCTTGG TTTCCGTGG | CACGAAAACCAAAAAA CTACCG | TAAACAACAACCTCTC AAAATACG | CCACAAAAACCAAAAA ACTACCA |
| GI29798595_BRCA1_2R (SEQ ID 38) | NT_010755 | TGGGTGGCCAATCCAGAGCCC CGAGAGACGCTTGGCTCTTTC TGTCCCTCC | AATAACCAATCCAAAA CCCCG | AAAAACGCTTAACTCTT TCTATCCC | AAAATAACCAATCCAA AACCCCA |
| GI29798595_BRCA1_3R (SEQ ID 39) | NT_010755 | CTCAGGTAGAATTCTTCCTCT TCCGTCTCTTTCCTTTTACGT CATCCGGGG | CAAATAAAATTCTTCC TCTTCCG | CTCTTTCCTTTTACGT CATCCG | CTCAAATAAAATTCTT CCTCTTCCA |
| GI29800185_PTEN_1R (SEQ ID 40) | NT_030059 | AGACTCGAGTCAGTGACACTG CTCAACGCACCCATCTCAGCT TTCATCATCA | CTCGAATCAATAACAC TACTCAACG | ACCCATCTCAACTTTC ATCATCA | AAACTCAAATCAATAA CACTACTCAACA |
| GI29800185_PTEN_2R (SEQ ID 41) | NT_030059 | AGGGTATTCCCCTTGCAGGGA CCGTCCCTGCATTTCCCTCTA CACTGAG | AAATATTCCCCTTACA AAAACCG | CCCTACATTTCCCTCT ACACTAAA | AAAATATTCCCCTTAC AAAAACCA |
| GI29800185_PTEN_3R (SEQ ID 42) | NT_030059 | AAGGGAGCCGGATGAGGTGAT ACACGCTGGCGACACAATAGC AGGTTGCTCT | CAACCTACTATTATAT CGCCAACG | ATATCACCTCATCCGA CTCCCTT | AAAACAACCTACTATT ATATCACCAACA |
| GI29800407_RET_1R (SEQ ID 43) | NT_033985 | CGGCTCTGCGTAGGTGCGCGG ACCCGGGCTCCTGGGTTCCAT CCCCGC | TACGTAAATACGCGAA CCCG | ACTCCTAAATTCCATC CCCG | CAACTCTACATAATAC ACAAACCCA |
| GI29800407_RET_2R (SEQ ID 44) | NT_033985 | GTCGGCCAGACCTGCATCCCG CGTAGCATCCCTGCCCTCTCT GTGCAGCG | CAAACCTACATCCCGC G | AACATCCCTACCCTCT CTATACAA | ATCAACCAAACCTACA TCCCACA |
| GI29800407_RET_3R (SEQ ID 45) | NT_033985 | CCGCGGAGAGCCTGGAGGCGG GGCGCCCTTCTCTGAGTCCGC GGGGTCGC | CGAAAACCTAAAAAC GAAACG | CCTTCTCTAAATCCGC GAAAT | CCACAAAAACCTAAA AACAAAACA |
| GI29800594_TGFB1_1R (SEQ ID 46) | NT_011109 | CCCGTGCGCTTCCTGGGTGGG GCCGGGGGCGGCTTCAAAACC CCCTGCC | CGTACGCTTCCTAAAT AAAACCG | AAACGACTTCAAAACC CCCTAC | CCCATACACTTCCTAA ATAAAACCA |
| GI29800594_TGFB1_2R (SEQ ID 47) | NT_011109 | CTCTTTCTCTGGTGACCCACA CCGCCCGCAAAGCACAGCGCA TCTGG | TCTTTCTCTAATAACC CACACCG | CCGCAAAACCACAACG C | CTCTTTCTCTAATAAC CCACACCA |
| GI29800594_TGFB1_3R (SED ID 48) | NT_011109 | CCCAGCCTGACTCTCCTTCCG TTCTGGGTCCCCCTCCTCTGG TCG | CCAACCTAACTCTCCT TCCG | TCTAAATCCCCCTCCT CTAATCG | CCCAACCTAACTCTCC TTCCA |
| GI29802188_SNRPN_1R (SEQ ID 49) | NT_026446 | TCTCTTGAATCTTGACAATCC CCGAACACTGCTCCCCGCTTT ATTTGTTTAG | CTTTAAATCTTAACAA TCCCCG | ACACTACTCCCCGCTT TATTTATT | TCTCTTAAATCTTAAC AATCCCCA |
| GI29802188_SNRPN_2R (SEQ ID 50) | NT_026446 | TCCCTGGGTGCCTCCTGCGCA AGCGCAGTTGTCCTCCTGCGC CGACCTCG | CCTAAATACCCTCCTAC GCAAACG | AATTATCCTCCTACGC CGACCT | TCCCTAAATACCCTCCT ACACAAACA |

TABLE 1-continued

Cancer-associated genomic markers and corresponding target nucleic acid probes.

| TARGET CPG SITE | GENBANK ACCESSION # | TARGET SEQUENCE SEQ ID NOS: 1-377 | PROBE SEQUENCE (ASO1) SEQ ID NOS: 378-754 | PROBE SEQUENCE (LSO1) SEQ ID NOS: 755-1131 | PROBE SEQUENCE (ASO2) SEQ ID NOS: 1132-1508 |
|---|---|---|---|---|---|
| GI29892395_GLA_1R (SEQ ID 51) | NT_011651 | GAAAGGAAGAGGGTGATTGGT TAGCGGAACGTCTTACGTGAC TGATTATTG | ATCAATCACGTAAAAC GTTCCG | TAACCAATCACCCTCT TCCTTTC | CAATAATCAATCACAT AAAACATTCCA |
| GI29802395_GLA_2R (SEQ ID 52) | NT_011651 | ACACACCAACCTCTAACGATA CCGGGTAATTTTCCTCCTTCT TCCCTC | ACACCAACCTCTAACG ATACCG | ATAATTTTCCTCCTTC TTCCCTC | ACACACCAACCTCTAA CAATACCA |
| GI29802395_GLA_3R (SEQ ID 53) | NT_011651 | AACTCAGGGCCGTGGTTTTCA AACGTTTTCGCCTTACGGTC ACCCTTAG | CTCAAAACCGTAATTT TCAAACG | TTTTCGCCTTACGATC ACC | AACTCAAAACCATAAT TTTCAAACA |
| GI29802670_AR_1R (SEQ ID 54) | NT_011669 | TAGAGCTAGCCTCTCCTGCCC TCGCCCACGCTGCGCCAGCAC TTGTTTCT | AAAACTAACCTCTCCT ACCCTCG | CCACGCTACGCCAACA CTTAT | TAAAACTAACCTCTCC TACCCTCA |
| GI29802670_AR_2R (SEQ ID 55) | NT_011669 | TCCTAGAGCAAATGGCACAAT GCCACGAGGCCCGATCTATCC CTATGACGGA | CCTAAAACAAATAACA CAATACCACG | AACCCGATCTATCCCT ATAACGA | TCCTAAAACAAATAAC ACAATACCACA |
| GI29802670_AR_3R (SEQ ID 56) | NT_011669 | CCGGTGGGGCGGGACCCGAC TCGCAAACTGTTGCATTTGCT CTCCACCTCC | ATAAAAACGAAACCCG ACTCG | AAACTATTACATTTAC TCTCCACCTCC | CCAATAAAAACAAAAC CCAACTCA |
| GI29802882_MAGEA1_1R (SEQ ID 57) | NT_011726 | TCCCGCCAGGAAACATCCGGG TGCCCGGATGTGACGCCACTG ACTTGCG | CAAATCAATAACGTCA CATCCG | ACACCCGAATATTTCC TAACGAA | CACAAATCAATAACAT CACATCCA |
| GI29802882_MAGEA1_2R (SEQ ID 58) | NT_011726 | CTCAACCCTGATGCCCATCCG CCCAGCCATTCCACCCTCA | CTCAACCCTAATACCC ATCCG | CCAACCATTCCACCCT CA | CTCAACCCTAATACCC ATCCA |
| GI29802882_MAGEA1_1R (SEQ ID 59) | NT_011726 | CCACTCCAATGCTCACTCCCG TGACCCAACCCCCTCTTCATT GT | CCACTCCAATACTCAC TCCCG | AACCCAACCCCCTCTT CATTAT | CCACTCCAATACTCAC TCCCA |
| GI29804485_CTAG2_1R (SEQ ID 60) | NT_025965 | GACGGACAGGGCAGGCAGGGT CCGGGACGATGGCCGCACAGT CCCGGC | CGAACAAAACAAACAA AATCCG | AACGATAACGCACAA TCC | AACACAAAACAAACAA AATCCA |
| GI29804485_CTAG2_2R (SEQ ID 61) | NT_025965 | GAGACCTTGGCTGGCGCGAGG CCACGCCCACCAGACATGCAG TTCCAGCT | CTTAACTAACGCGAAA CCACG | CCACCAAACATACAAT TCCAACT | AAAACCTTAACTAACA CAAAACCACA |
| GI29804485_CTAG2_3R (SEQ ID 62) | NT_025965 | GGGCGACTAGGACAGGGACAG AACCCGTTGAACCCAGGAGTG AGATCCGG | GAATCTCACTCCTAAA TTCAACG | ATTCTATCCCTATCCT AATCGCC | CCAAATCTCACTCCTA AATTCAACA |
| GI29804485_G6PD_1R (SEQ ID 63) | NT_025965 | TCCCGCTCCGGAGAGAAGTCT GAGTCCGCCAGGCTCTGCAGG CCCGCGGA | GCGAACCTACAAAACC TAACG | ACTCAAACTTCTCTCC GAAACG | TCCACAAACCTACAAA ACCTAACA |
| GI29804485_G6PD_2R (SEQ ID 64) | NT_025965 | CGGAAGCTCGGTAATGATAAG CACGCCGGCCACTTTGCAGGG CGTCACCGCC | ACTCGATAATAATAAA CACGCCG | CCACTTTACAAAACGT CACCG | CAAAAACTCAATAATA ATAAACACACCA |
| GI29804485_G6PD_3R (SEQ ID 65) | NT_025965 | CCCAATAGGGCCGGCTTGACC CGCGAACAGGCGAGGGTTCCC GGGGG | CCAATAAAACCGACTT AACCCG | GAACAAACGAAAATTC CCGA | CCCAATAAAACCAACT TAACCCA |
| GI29804485_SLC6A8_1R (SEQ ID 66) | NT_025965 | GGGAAGCTGTAGCCCCCAGTG GGCAGCGGTGGAGAGAGCTCA AGGAAGG | CTTCCTTAAACTCTCT CCACCG | TACCCACTAAAAACTA CAACTTCCC | CCTTCCTTAAACTCTC TCCACCA |
| GI29804485_SLC6A8_2R (SEQ ID 67) | NT_025965 | GGTAGCAACCATCCTGCCTCC CGCTGGAGCGGCGTCTCCTCC CCGG | ATAACAACCATCCTAC CTCCCG | TAAAACGACGTCTCCT CCCC | AATAACAACCATCCTA CCTCCCA |
| GI29804485_SLC6A8_3R (SEQ ID 68) | NT_025965 | CCGGCCGGCCGTGGGGTGGG GCGATAGTGACATCACCCCGG AGTCGG | GACCGACCGTAAAAAT AAAACG | TAATAACATCACCCCG AAATCG | CCAACCAACCATAAAA ATAAAACA |
| GI29805823_GSTP1_2R (SEQ ID 69) | NT_033903 | CCTCTCCCCTGCCCTGTGAAG CGGGTGTGCAAGCTCCGGGAT CGCAGCGG | CCTCTCCCCTACCCTA TAAAACG | ATATACAAACTCCGAA ATCGCAA | CCTCTCCCCTACCCTA TAAAACA |
| GI29805823_GSTP1_3R (SEQ ID 70) | NT_033903 | CGGCCAGCTGCGCGGCGACTC CGGGGACTCCAGGGCGCCCCT CTGCG | AACTACGCGACGACTC CG | AAACTCCAAAACGCCC CTCTAC | CAACCAACTACACAAC AACTCCA |
| GI2980729_BCR_1R (SEQ ID 71) | NT_011520 | GCTGTGAGGTGTGAGGAACTT ACCTGCGTCTCCATGGAAGGT GCCCTCCG | GAAAACACCTTCCAT AAAACG | AAATAAATTCCTCACA CCTCACAAC | CAAAAAACACCTTCCA TAAAAACA |
| GI2980729_BCR_2R (SEQ ID 72) | NT_011520 | CTCTGACACGACGACTGGGCA GTGCCGGTGACGCTTATGGCA CTGCGGC | GCAATACCATAAACGT CACCG | CACTACCCAATCGTCG TATCAAA | ACCACAATACCATAAA CATCACCA |
| GI2980729_BCR_3R (SEQ ID 73) | NT_011520 | GGGCTGCGAGTTGCACAGTCC AATTCGCTGTTGTTAGGGCCT CAGTTTCCCAAA | ACGAATTACACAATCC AATTCG | TATTATTAAAACCTCA ATTTCCCAA | AAACTACAAATTACAC AATCCAATTCA |
| GI29807292_TMP3_1R (SEQ ID 74) | NT_011520 | AAGGAGCAGTGGAAAGGGGTG ACGAGTTCCTGGCTGGCCACC AATCATC | AATTAATAACCAAAAA CTCG | CACCCCTTTCCACTAC TCCTT | AATAATTAATAACCAA CCAAAAACTCA |
| GI29807292_TMP3_2R (SEQ ID 75) | NT_011520 | AACTTGTGGCATTTCTAACAG GATGAAGCGGAAGAGAAAGGG AAAGAGA | TCTCTTTCCCTTTCTC TTCCG | TTCATCCTATTAAAAA TACCACAAATT | TCTCTTTCCCTTTCTC TTCCA |

TABLE 1-continued

Cancer-associated genomic markers and corresponding target nucleic acid probes.

| TARGET CPG SITE | GENBANK ACCESSION # | TARGET SEQUENCE SEQ ID NOS: 1-377 | PROBE SEQUENCE (ASO1) SEQ ID NOS: 378-754 | PROBE SEQUENCE (LSO1) SEQ ID NOS: 755-1131 | PROBE SEQUENCE (ASO2) SEQ ID NOS: 1132-1508 |
|---|---|---|---|---|---|
| GI29807454_CALCA_1R (SEQ ID 76) | NT_009237 | GGGGCGAGGGTTCAAAACCAG GCCGGACTGAGAGGTGAAATT CACCATG | AATAAATTTCACCTCT CAATCCG | CCTAATTTTAAACCCT CGCCC | CATAATAAATTTCACC TCTCAATCCA |
| GI29807454_CALCA_2R (SEQ ID 77) | NT_009237 | CAGGTTCTGGAAGCATGAGGG TGACGCAACCCAGGGGCAAAG GACCCCT | AAAATCCTTTACCCCT AAATTACG | CACCCTCATACTTCCA AAACCTA | AAAAATCCTTTACCCC TAAATTACA |
| GI29807454_KAI1_1R (SEQ ID 78) | NT_009237 | CAGGGCAGGGCAGGATTAGGA AGGCGCTGAGCCCAGGCTGGT GCGG | GCACCAACCTAAACTC AACG | CTTCCTAATCCTACCC TACCCTA | CCACACCAACCTAAAC TCAACA |
| GI29807454_KAI1_2R (SEQ ID 79) | NT_009237 | GATAGAGGAGAGACTCCGTAG CGGGGCGGGGCCTCAGCTCCA GCTGGGC | CCCAACTAAAACTAAA ACCCCG | CCCGCTACGAAATCTC TCCT | ACCCAACTAAAACTAA AACCCCA |
| GI29807454_KAI1_3R (SEQ ID 80) | NT_009237 | GCCGCCTCCTGATAGAGGCCC CGACTTAGGACACAAACCGCT CCCAC | GCCTCCTAATAAAAAC CCCG | CTTAAAACACAAACCG CTCCC | ACCACCTCCTAATAAA AACCCCA |
| GI29807454_MYOD1_1R (SEQ ID 81) | NT_009237 | TTGCCTCTCTCCAAATCTCTC ACGACCTGATTTCTACAGCCG CTCTACCC | TACCTCTCTCCAAATC TCTCACG | CCTAATTTCTACAACC GCTCTACC | TTACCTCTCTCCAATC TCTCACA |
| GI29807454_MYOD1_2R (SEQ ID 82) | NT_009237 | CTTTCTGCGTGTCTCTCAGCC TCTTTCGGTCCCTCTTTCACG GTCTCACTCC | TACGTATCTCTCAACC TCTTTCG | TCCCTCTTTCACGATC TCACTC | CTTTCTACATATCTCT CAACCTCTTTCA |
| GI29807454_MYOD1_3R (SEQ ID 83) | NT_009237 | GGAATATCAGAGCCTCTACGA CCCGTTTGTCTCGGGCTCGCC CACTTCAA | AATATCAAAACCTCTA CGACCCG | TTATCTCGAACTCGCC CACTT | AAAATATCAAAACCTC TACAACCCA |
| GI29808625_CDH1_2R (SEQ ID 84) | NT_010498 | CGAACCCAGTGGAATCAGAAC CGTGCAGGTCCCATAACCCAC CTAGA | GAACCCAATAAAATCA AAACCG | ACAAATCCCATAACCC ACCTAAA | CAACCCAATAAAATCA AAACCA |
| GI29880625_CDH1_3R (SEQ ID 85) | NT_010498 | ACCCTCAGCCAATCAGCGGTA CGGGGGGCGGTGCCTCCGGGG CTCACC | CCTCAACCAATCAACG ATACG | AAAACGATACCTCCGA AACTCAC | ACCCTCAACCAATCAA CAATACA |
| GI29823164_TYMS_1R (SEQ ID 86) | NT_010859 | CTGTGCTGCTGGCTTAGAGAA GGCGCGGTCGACCAGACGGTT CCCAAAGG | TTAAAAACCGTCTAAT CGACCG | GCCTTCTCTAAACCAA CAACACA | CCTTTAAAACCATCT AATCAACCA |
| GI29823164_TYMS_2R (SEQ ID 87) | NT_010859 | GGCTCCGTTCTGTGCCACACC CGTGGCTCCTGCGTTTCCCCC TGGCG | TCCGTTCTATACCACA CCCG | AACTCCTACGTTTCCC CCTAAC | AACTCCATTCTATACC ACACCCA |
| GI29823171_BCL2_1R (SEQ ID 88) | NT_025028 | CGTGTGACGTTACGCACAGGA AACCGGTCGGGCTGTGCAGAG AATGAAGTAAG | TACTTCATTCTCTACA CAACCCG | CCGATTTCCTATACGT AACGTCA | CTTACTTCATTCTCTA CACACCCA |
| GI29823171_BCL2_2R (SEQ ID 89) | NT_025828 | CGGGAGGCGGCCGTAGCCAGC GCCGCCGCAGGACCAGGAG GAGG | CCTCCTAATCCTACGC GACG | CGCTAACTACGACCGC CTC | CCTCCTCCTAATCCTA CACAACA |
| GI29823171_BCL2_3R (SEQ ID 90) | NT_025028 | CCGTCAGCGCTCGGAGCGGGC TGCGCGGCGGGAGCTCCGGGA GGCGCC | AACGCTCGAAACGAAC TACG | GACGAAAACTCCGAAA AACGAC | CCATCAACACTCAAAA CAAACTACA |
| GI29734309_SYK_1R (SEQ ID 91) | NT_008476 | GCCCAGCTCCGGGCTCATGGG CGCGGTCAGCAGGGCGGGCCA GGGCGG | CCAACTCCGAACTCAT AAACG | GATCAACAAAACGAAC CAAAACG | ACCCAACTCCAAACTC ATAACCA |
| GI29734309_SYK_2R (SEQ ID 92) | NT_008476 | GGGCTCCTCTACACCTGCCGC CGCCTGGGCCGATTCCGCGGG CCTCG | ACTCCTCTACACCTAC CGCCG | CTAAACCGATTCCGCG AAC | AAACTCCTCTACACCT ACCACCA |
| GI29734309_SYK_3R (SEQ ID 93) | NT_008476 | GGACCGATGCGGTCCATGTCC CGGGCAGCCCCACCTTCTCTG CCTGC | ACCGATACGATCCATA TCCCG | ACAACCCACCTTCTC TACCTAC | AAACCAATACAATCCA TATCCCA |
| GI29740881_HTR1B_1R (SEQ ID 94) | NT_007299 | GGGAATGCAAGATCTCGGGAC CTCTCGCTCGGCCTGCAAGCTT TGGTCTC | AAACCAAAACTTACAA ACCAACG | AAAATCCCGAAATCTT ACATTCC | AAAACCAAAACTTACA AACCAACA |
| GI29740881_HTR1B_2R (SEQ ID 95) | NT_007299 | GGCGGAGGAATAATTGAGGAA CTCACGGAACTATCAACTGGG GACAAACC | TTATCCCCAATTAATA ATTCCG | AAATTCCTCAATTATT CCTCCGC | AATTTATCCCCAATTA ATAATTCCA |
| GI29740881_HTR1B_3R (SEQ ID 96) | NT_007299 | CCCTTTTATGGCTCCGTCTCC GCGGGGCAGCTCGTCCGAGTG GCCAGA | TTTATAACTCCGTCTC CGCG | AACAACTCGTCCGAAT AACCAA | CCCTTTTATAACTCCA TCTCCACA |
| GI29741420_MGMT_1R (SEQ ID 97) | NT_008818 | GGCTTGTACCGGCCGAAGGGC CATCCGGGTCAGGCGCACAGG GCAGCGG | CTACCCTATACGCCTA ACCCG | ATAACCCTTCGACCGA TACAAAC | CCACTACCCTATACAC CTAACCCA |
| GI29741420_MGMT_2R (SEQ ID 98) | NT_008818 | GCCCGGCCGTGCCGGCGTCCAG CGAGGATGCGCAGACTGCCTC AGGCCCG | ACGTACCGACGTCCAA CG | AAATACGCAAACTACC TCAAACC | AACCAACATACCAACA TCCAACA |
| GI29741420_MGMT_3R (SEQ ID 99) | NT_008818 | GACCACTCGGGCACGTGGCAG GTCGCTTGCACGCCCGCGGAC TATCCCT | CACTCGAACACGTAAC AAATCG | TTACACGCCCGCGAAC TAT | AACCACTCAAACACAT AACAAATCA |

TABLE 1-continued

Cancer-associated genomic markers and corresponding target nucleic acid probes.

| TARGET CPG SITE | GENBANK ACCESSION # | TARGET SEQUENCE SEQ ID NOS: 1-377 | PROBE SEQUENCE (ASO1) SEQ ID NOS: 378-754 | PROBE SEQUENCE (LSO1) SEQ ID NOS: 755-1131 | PROBE SEQUENCE (ASO2) SEQ ID NOS: 1132-1508 |
|---|---|---|---|---|---|
| GI29791697_CDC25A_1R (SEQ ID 100) | NT_005825 | GAAGTTGCTTACTGATTGTG GATTCCGTTTGGCGCCAACTA GGAAAGGG | CTTTCCTAATTAACGC CAAACG | AATCCACCAATCAATA ACAACTTC | CCCTTTCCTAATTAAC ACCAAACA |
| GI29791697_CDC25A_2R (SEQ ID 101) | NT_005825 | GAGGCCGAGCCAAGGCTGGAT CCGGCCAGACCTCCACAGGTC TTCCTT | AACCGAACCAAAACTA AATCCG | CCAAACCTCCACAAAT CTTCCTT | AAAACCAAACCAAAC TAAATCCA |
| GI29791697_CDC25A_3R (SEQ ID 102) | NT_005825 | CTCCAGAGTTGGGCCCTGGTG GTCGAGTCCAGTCCTGGGGGT CATTG | AATAACCCCCAAAACT AAACTCG | CCACCAAAACCCAACT CTAAAA | CAATAACCCCCAAAAC TAAACTCA |
| GI29791697_PTHR1_1R (SEQ ID 103) | NT_005825 | GGGCCCAGCCCTGGGCATCTG AACACCGGCACACTTGGATCT GCCTCTGTT | CAAAAACAAATCCAAA TATACCG | TATTCAAATACCCTAA AACTAAACCC | AACAAAAACAAATCCA AATATACCA |
| GI29791697_PTHR1_2R (SEQ ID 104) | NT_005825 | CAGCCCTGGGCATCTGAACAC CGGCACACTTGGATCTGCCTC TGTTGCCTCC | CAACCCTAAACATCTA AACACCG | CACACTTAAATCTACC TCTATTACCTCC | CAACCCTAAACATCTA AACACCA |
| GI29791697_PTHR1_3R (SEQ ID 105) | NT_005825 | GGGGCTGTAGGGGTCAGGACA CGGGCTGGAGTGGAATGA | TCATTCCACTCCAACC CG | ATCCTAACCCCTACAA CCCC | TCATTCCACTCCAACC CA |
| GI29792366_SOD3_1R (SEQ ID 106) | NT_006316 | TCTGGGAAGTCTCCCTCTTAT CTCGCAGAATGCCTGTCCCTG GATAAAGATCATT | CTAAAAAATCTCCCTC TTATCTCG | AAAATACCTATCCCTA AATAAAAATCATT | TCTAAAAAATCTCCCT CTTATCTCA |
| GI29792366_SOD3_2R (SEQ ID 107) | NT_006316 | TTCTCAGCGGGCCAGAAGGAA GGACGGTAGGGTGGAAGGGCT G | AACCCTTCCACCCTAC CG | CCTTCCTTCTAACCCG CTAAA | CAACCCTTCCACCCTA CCA |
| GI29792366_SOD3_3R (SEQ ID 108) | NT_006316 | CACAAGTCCTAGAATACCAGA ACGGAGACGTGCTTTCTTGGA CCTTAAACGAAA | CACAATCCTAAAATAC CAAAACG | AAACGTACTTTCTTAA ACCTTAAAGG | CACAAATCCTAAAATA CCAAAACA |
| GI29792503_VHL_1R (SEQ ID 109) | NT_005027 | CAAGGCTGCAGTGAGCCAAGC TCGCGCCACTGCACTCCAGCC CGGGCGAC | AACTACAATAAACCAA ACTCGCG | CACTACACTCCAACCC GAAC | CAAAACTACAATAAAC CAAACTCACA |
| GI29792503_VHL_1R (SEQ ID 110) | NT_005927 | CCCGTGTGAGATGCGCCACCC TCGAACCTTGTTACGACGTCG GCACATTGCG | GTATAAAATACGCCAC CCTCG | ACCTTATTACGACGTC GACACAT | CCCATATAAAATACAC CACCCTCA |
| GI2979312_CD1A_1R (SEQ ID 111) | NT_004668 | GGGGAATTAAGACCCAATGGG CAATCCGTGACTATTAGGGGA TGGGA | CCCATCCCCTAATAAT CACG | ATTACCCATTAAATCT TAATTCCCC | TCCCATCCCCTAATAA TCACA |
| GI29793120_CD1A_2R (SEQ ID 112) | NT_004668 | CATAGCAGTAGCAGACATCTC TTGTACCGTGCCTTACACCTC AGCCCATTT | AACAATAACAAACATC TCTTATACCG | ACCTTACACCTCAACC CATTT | CATAACAATAACAAAC ATCTCTTATACCA |
| GI29793120_S100A2_1R (SEQ ID 113) | NT_004668 | AGACTGTGGCCCAGCCCAACT GCGGCTGTGTGTAGAGCAACC CCATTTCTCA | ACTATAACCCAACCCA ACTACG | CTATATATAAAACAAC CCCATTTCTCA | AAACTATAACCCAACC CAACTACA |
| GI29793120_S100A2_2R (SEQ ID 114) | NT_004668 | GAGCACTGGACCATGAAGTCT CAGCGTGTGCTCACAGCCTCT CACACAGGA | AACACTAAACCATAAA ATCTCAACG | ATACTCACAACCTCTC ACACAAA | AAACACTAAACCATAA AATCTCAACA |
| GI29793234_ABCC5_1R (SEQ ID 115) | NT_005962 | GGGCAGTTGGTGTTAAAGTGA GAAAGGCGGTATCTGCGCAGA CTGCAGGGTC | CCTACAATCTACGCAA ATACCG | CTTTCTCACTTTAACA CCAACTACCC | AACCCTACAATCTACA CAAATACCA |
| GI29793234_ABCC5_2R (SEQ ID 116) | NT_005962 | CGCAGGGTGGGACTGCTCTGC CTACGAACAGCACTGTGTGCG AACACAGGG | CCTATATTCGCACACA ATACTATTCG | AAACAAAACAATCCCA CCCTAC | CCCTATATTCACACAC AATACTATTCA |
| GI29793234_ABCC5_3R (SEQ ID 117) | NT_005962 | CTGGCCGGCCTGACGACTCTC AACGGGTTAGACGCGGCTAC GATGACCTTCACG | ACCGACCTAACGACTC TCAACG | ATTAAACGCGAACTAC GATAACC | CTAACCAACCTAACAA CTCTCAACA |
| GI29793234_HRASLS_2R (SEQ ID 118) | NT_005962 | TGGAGGTCTCTGCTGGCTATC TGGCGTGTGTGTGTGTGTGGT GTG | ACACCACACACACACA CACG | CAAATAACCAACAAA ACCTCCA | CACACCACACACACAC ACACA |
| GI29793234_HRASLS-3R (SEQ ID 119) | NT_005962 | CAAAACCGATTATCTTTATAA CCGCGGCGCCTAGCACAGCGC CTGGTGCCCT | AACCGATTATCTTTAT AACCGCG | CGCCTAACACAACGCC TAATAC | CAAAACCAATTATCTT TATAACCA |
| GI29793705_CD2_1R (SEQ ID 120) | NT_004754 | GGAGCACATCAGAAGGGCTGG CTTGTGCGCGCTCTTGCTCTC TGTGTATGTG | CACAAAAACAAAACG CG | ACAAACCAACCCTTCT AATATACTCC | CACATACACAAAACAA CACA |
| GI29793872_RASSF_1R (SEQ ID 121) | NT_006014 | TCCTCACCCCAAGTGAAGGCT CGAGACTTCCTGCCCCACCCA GTGGG | CCTCACCCCAAATAAA AACTCG | AACTTCCTACCCCACC CAATAAA | TCCTCACCCCAAATAA AAACTCA |
| GI29793872_RASSF_2R (SEQ ID 122) | NT_006014 | CCTGCACCCAGGTTTCCATTG CGCGGCTCTCCTCAGCTCCTT CCCGC | CTACACCCAAAATTCC ATTACG | GACTCTCCTCAACTCC TTCCC | CCTACACCCAAATTTC CATTACA |
| GI29793872_RASSF1_3R (SEQ ID 123) | NT_006014 | AGATCACGGTCCAGCCTCTGC CGGAGCCCCAGTCTCCGCAGT GGAG | AATCACGATCCAACTC CTACCG | AACCCCAATCTCCGCA ATAAA | AAATCACAATCCAACC TCTACCA |
| GI29794089_PRDM2_1R (SEQ ID 124) | NT_004873 | CTGGAACATCGCGGGCACAGG GCAGCGTTGGTCACTGCTCCT GGGTACT | ATACCCAAAAACAATA AACCACG | TACCCTATACCCGCGA TATTCC | AATACCCAAAAACAAT AACCAACA |

TABLE 1-continued

Cancer-associated genomic markers and corresponding target nucleic acid probes.

| TARGET CPG SITE | GENBANK ACCESSION # | TARGET SEQUENCE SEQ ID NOS: 1-377 | PROBE SEQUENCE (ASO1) SEQ ID NOS: 378-754 | PROBE SEQUENCE (LSO1) SEQ ID NOS: 755-1131 | PROBE SEQUENCE (ASO2) SEQ ID NOS: 1132-1508 |
|---|---|---|---|---|---|
| GI29794089_PRDM2_2R (SEQ ID 125) | NT_004873 | GGGGGTCCCGGAGCCCCCAG CCCCGCAGGCCACTGCCTCGC CGCCCGA | GAACGACGAAACAATA ACCTACG | AACTAAAAAACTCCGA AACCCC | TCAAACAACAAAACAA TAACCTACA |
| GI29794089_PRDM2_3R (SEQ ID 126) | NT_004873 | TCTTCATCAGAACATCTATGA GTCGTCGTCTCTGCAGTCCAT TTGTTTGCCCGC | TCATCAAAACATCTAT AAATCGTCG | CTCTACAATCCATTTA TTTACCCG | TCTTCATCAAAACATC TATAAATCATCA |
| GI29794150_NCL_1R (SEQ ID 127) | NT_005403 | ACTCCAAGGCTGCCCAAGCCT ACGGACCCAGCCACATTGGCG AACCG | TCCAAAACTACCCAAA CCTACG | ACCCAACCACATTAAC GAACC | ACTCCAAAACTACCCA AACCTACA |
| GI29794150_NCL_2R (SEQ ID 128) | NT_005403 | ACTCCGCGGTCCCTGAACTTC CGGTGCTGGCGGACTCCTCGC TCCAGG | GCGATCCCTAAACTTC CG | TACTAACGAACTCCTC GCTCCAA | ACTCCACAATCCCTAA ACTTCCA |
| GI29794150_NCL_3R (SEQ ID 129) | NT_005403 | GGGGTGCCTCCGGCCCCATGC TCGCGGGCAAGCAGGGATAAG CTGTGCC | CACAACTTATCCCTAC TTACCCG | GAACATAAAACCGAAA ACACCC | AACACAACTTATCCCT ACTTACCCA |
| GI29794150_TMEFF2_1R (SEQ ID 130) | NT_005403 | GGCCATCCGGCAAAGACCCGA GTAAGGAACGCAGGGTCACTG CCTGGGCCAAC | TTAACCCAAACAATAA CCCTACG | TCCTTACTCGAATCTT TACCGAA | ATTAACCCAAACAATA ACCCTACA |
| GI29794150_TMEFF2_2R (SEQ ID 131) | NT_005403 | TTTCTCTCAGACCACTTGTCC CGACCAATCTGACCTTCCAAA CACAT | TTCTCTCAAACCACTT ATCCCG | CCAATCTAACCTTCCA AACACAT | TTTCTCTCAAACCACT TATCCCA |
| GI29794150_TMEFF2_3R (SEQ ID 132) | NT_005403 | CGCAGAGCCAGAGACTCCTGC CGAGTTAGACCTTCTCTCGTC GCCCC | GCAAAACCAAAAACTC CTACCG | ATTAAACCTTCTCTCG TCGCC | CACAAAACCAAAAACT CCTACCA |
| GI29795229_DBCCR1_1R (SEQ ID 133) | NT_008470 | GCGCGGTCCCTTTGGATGCTC GTGCGCATAGACACAACACCC TACACGCC | CGATCCCTTTAAATAC TCGTACG | ATAAACACAACACCCT ACACGC | ACACAATCCCTTTAAA TACTCATACA |
| GI29795229_DBCCR1_2R (SEQ ID 134) | NT_008470 | CCCCAGAAACACTCAGGTACT CGCGACACACACAGTACAGTC ACGCTTAA | CCCAAAAACACTCAAA TACTCG | GACACACACAATACAA TCACGCT | CCCCAAAAACACTCAA ATACTCA |
| GI29795229_DBCCR1_3R (SEQ ID 135) | NT_008470 | GCAGACACAAACGGACCCACA CGGGCAACTCCCGAGACAAAA CCC | ACACAAACGAACCCAC ACG | ACAACTCCCGAAACAA AACC | AACAAACACAAACAAAC CCACACA |
| GI29795229_TMEFF1_1R (SEQ ID 136) | NT_008470 | GGACACAAAGGGAAGGCGAGG AGGCGAGCAAGAGGCTGGGCC TGCCT | AACAAACCCAACCTCT TACTCG | CTCCTCGCCTTCCCTT TATATC | AAACAAACCCAACCTC TTACTCA |
| GI29795229_TMEFF1_2R (SEQ ID 137) | NT_008470 | CGGGCGGGCCGGGGTCTTTGT GACGCGGTGGCAACGGCCACG GACACAAAG | GAACCGAAATCTTTAT AACGCG | TAACAACGACCACGAA CACAA | CAAACAAACCAAAATC TTTATAACACA |
| GI29795229_TMEFF1_3R (SEQ ID 138) | NT_008470 | GACAGTCACCTTTACCTCTT CCGTGACTCAGTTTCTTCCAC CTAAAAAC | CAAATCACCTTTACCT CTTCCG | AACTCAATTTCTTCCA CCTAAAAAC | AACAAATCACCTTTAC CTCTTCCA |
| GI29796755_HOXA5_1R (SEQ ID 139) | NT_007819 | TGCAGCCCCCGGTCGGAAGCT GGGCGATGAGCCCTGCCTCCA GCGGGT | CCGCTAAAAACAAAAC TCATCG | CCAACTTCCGACCGAA AACTAC | ACCCACTAAAAACAAA ACTCATCA |
| GI29796755_HOXA5_2R (SEQ ID 140) | NT_007819 | GGGCGATGAGCCCTGCCTCCA GGGGTGGCGCTCGAGTCCGG CTGAACGGCG | CGATAAACCCTACCTC CAACG | ATAACGCTCGAATCCG ACTAAAC | AAACAATAAACCCTAC CTCCAACA |
| GI29796755_HOXA5_3R (SEQ ID 141) | NT_007819 | ATCCTCTGCATCCTCGCCGGG CGCGCGATCGGCAGCTGACGG CCTAACAA | CTACATCCTCGCCGAA CG | GCGATCGACAACTAAC GACCTAA | ATCCTCTACATCCTCA CCAAACA |
| GI29796755_IGFBP1_2R (SEQ ID 142) | NT_007819 | GGCGCGGCCTGTGCCCTTTAT AAGGTGCGCGCTGTGTCCAGC GAGCATCGGCC | ATACTCGCTAAACACA ACGCG | ACCTTATAAAAAACAC AAACCGC | AACCAATACTCACTAA ACACAACACA |
| GI29796755_IGFBP1_3R (SEQ ID 143) | NT_007819 | CGCGGCCTGTGCCCTTTATAA GGTGCGCGTGTGTCCAGCGA GCATCGGCCACC | GACCTATACCCTTTAT AAAATACGCG | TATATCCAACGAACAT CGACCA | CACAACCTATACCCTT TATAAAATACACA |
| GI29796755_IL6_1R (SEQ ID 144) | NT_007819 | TCTGCTTCTTAGCGCTAGCCT CAATGACGACCTAAGCTGCAC TTTTCCCCCT | TCTTAACGCTAACCTC AATAACG | CCTAAACTACACTTTT CCCCCT | TCTACTTCTTAACACT AACCTCAATAACA |
| GI29796755_IL6_2R (SEQ ID 145) | NT_007819 | CCTGGAGACGCCTTGAAGTAA CTGCACGAAATTTGAGGATGG CCAGGCAG | TACCTAACCATCCTCA AATTTCG | ACAATTACTTCAAAAC GTCTCCAA | CTACCTAACCATCCTC AAATTTCA |
| GI29796755_TWIST1_1R (SEQ ID 146) | NT_007819 | GTTTTGAATGGTTTGGGAGG ACGAATTGTTAGACCCCGAGG AAGG | CTTCCTCGAAATCTAA CAATTCG | CCTCCCAAACCATTCA AAAAC | CCTTCCTCAAAATCTA ACAATTCA |
| GI29796755_TWIST1_2R (SEQ ID 147) | NT_007819 | CCACTCCGGATGGGCTGCCA CCGCGGCCAGGACAGTCTCCT CCGAC | ACTCCGAATTAAAACT ACCACCG | GACCAAAACAATCTCC TCCGAC | CCACTCCAAATAAAAC TACCACCA |
| GI29796755_TWIST1_3R (SEQ ID 148) | NT_007819 | GGCCTTTGGAACTCCAAGGGG CCCACCCAATAATCAA TTCGTCTACCTGACCATTGGG TGGG | CCCACCCAATAATCAA AAACG | ACCCCTTAAAATTCCA AAAAC | CCCACCCAATAATCAA ATAAACA |

TABLE 1-continued

Cancer-associated genomic markers and corresponding target nucleic acid probes.

| TARGET CPG SITE | GENBANK ACCESSION # | TARGET SEQUENCE SEQ ID NOS: 1-377 | PROBE SEQUENCE (ASO1) SEQ ID NOS: 378-754 | PROBE SEQUENCE (LSO1) SEQ ID NOS: 755-1131 | PROBE SEQUENCE (ASO2) SEQ ID NOS: 1132-1508 |
|---|---|---|---|---|---|
| GI29796774_TRC8_1R (SEQ ID 149) | NT_008046 | GAAGCTAGAGTAAGCTGAGGA GGTGGCGGAAACCATGGCAA CCATGGGTG | ACCCATAATTACCATA ATTTCCG | CCACCTCCTCAACTTA CTCTAACTTC | CACCCATAATTACCAT AATTTCCA |
| GI29796774_TRC8_2R (SEQ ID 150) | NT_008046 | ACCACACCCAGCCTAGTGCCA CGCACCGCAAGCGCTCCATAA ACGCA | CACACCCAACCTAATA CCACG | ACCGCAAACGCTCCAT AA | ACCACACCCAACCTAA TACCACA |
| GI29796774_TRC8_3R (SEQ ID 151) | NT_008046 | CGCAGGCAGTGGGCGCGGACT CTGCGGTTCGCTTGACTGACG GCGCAGCCTCC | AAACAATAAACGCGAA CTCTACG | TTCGCTTAACTAACGA CGCAAC | CACAAACAATAAACAC AAACTCTACA |
| GI29804415_C4B_1R (SEQ ID 152) | NT_007592 | TTGTGAGGGCCTTTAAATATC CTGTACTCGTGGGCCATGTTG GGCCCT | AAACCCAACATAACCC ACG | ATACAAAATATTTAAA AACCCTCACAA | AAAACCCAACATAACC CACA |
| GI29804415_C4B_2R (SEQ ID 153) | NT_007592 | TCAGGCACTGGAATGAGAGGA GTTAACGGGGAAGGACAGGGT TATTTC | AACCCTATCCTTCCCC G | TAACTCCTCTCATTCC AATACCTAA | AAAATAACCCTATCCT TCCCCA |
| GI29804415_C4B_3R (SEQ ID 154) | NT_007592 | CCCATGGACACCCAGGTGTCC GGGGTGCCCCCACAACTCTGG GCCT | CCATAAACACCCAGAT ATCCG | AATACCCCCACAACTC TAAACCT | CCCATAAACACCCAAA TATCCA |
| GI29804415_CDKN1A_1R (SEQ ID 155) | NT_007592 | TGGCTCTGATTGGCTTTCTGG CCGTCAGGAACATGTCCCAAC ATGTTGAGC | TCAACATATTAAAACA TATTCCTAACG | CCAAAAAACCAATCAA AACCA | ACTCAACATATTAAAA CATATTCCTAACA |
| GI29804415_CSNK2B_1R (SEQ ID 156) | NT_007592 | CCCACATTACTTGAGGGCTCG GGCGTGCGCAAAGCTCCGGGT TCAGTTTC | CCACATTACTTAAAAA CTCGAACG | ACGCAAAACTCCGAAT TCAAT | CCCACATTACTTAAAA ACTCAAACA |
| GI29804415_CSNK2B_2R (SEQ ID 157) | NT_007592 | ACAATCAAATAGCCACACGGC ACGAAGACGCATGCGTGGCGA CAACAAC | AATCAAATAACCACAC GACACG | AAACGCATACGTAACG ACAACA | ACAATCAAATAACCAC ACAACACA |
| GI29804415_CSNK2B_3R (SEQ ID 158) | NT_007592 | CAGCCTGGCCCTTTAAGTCTT CCGCGATCCCATTTCGGAGTT TCCTCT | AACCTAACCCTTTAAA TCTTCCG | GATCCCATTTCGAAAT TTCCTCT | CAACCTAACCCTTTAA ATCTTCCA |
| GI29804415_EDN1_1R (SEQ ID 159) | NT_007592 | TCTTTTTCTTAGCCCTGCCCC CGAATTGTCAGACGGCGGGCG TCTGCCTCT | CTTTTTCTTAACCCTA CCCCCG | ATTATCAAACGACGAA CGTCTACC | TCTTTTTCTTAACCCT ACCCCCA |
| GI29804415_EDN1_2R (SEQ ID 160) | NT_007592 | GGCTGGCAGCTTCAAAGGGG AAGCGGACTCCAGCACTGCAC GGGCAGG | TACCCGTACAATACTA AAATCCG | TTCCCCTTTACAAACT ACCAACC | CCTACCCATACAATAC TAAAATCCA |
| GI29804415_EDN1_3R (SEQ ID 161) | NT_007592 | GGCCTGGCCTTATCTCCGGCT GCACGTTGCTGTTGGTGACT AATAACACAA | ATTATTAATCACCAAC AAACAACG | ACAACCGAAAATAAAA CCAAACC | TTATATTATTAATCAC CAACAAACAACA |
| GI29804415_HLA-F_1R (SEQ ID 162) | NT_007592 | AAGTTCAATCAAGGGACTGGG ATTTCGGAATGAATAATGAAG GGAGATG | TCTCCCTTCATTATTC ATTCCG | AATCCCAATCCCTTAA TTAAACTT | CATCTCCCTTCATTAT TCATTCCA |
| GI29804415_HLA-F_2R (SEQ ID 163) | NT_007592 | TCCTTCTTCCTGGATACTCAT AACGCGCCCATTTCTCACT CCCATTGG | TCTTCCTAAATACTCA TAACGCG | CCCCATTTCTCACTCC CATTAA | TCCTTCTTCCTAAATA CTCATAACACA |
| GI29804415_LY6G6E_1R (SEQ ID 164) | NT_007592 | GGGGCAGGCTGGGGGCCCCG CTGCCTGCTGGGTCAGGCTG | AACCTAACCCAACAAA CAACG | AAACCCCCAACCTACC CC | CAACCTAACCCAACAA ACAACA |
| GI29804415_LY6G6E_2R (SEQ ID 165) | NT_007592 | AACTCTACAAATCCCGGGATC TCGGGGTGCAGATCACCTCTC CCAGA | TCTACAAATCCCGAAA TCTCG | AATACAAATCACCTCT CCCAAA | AACTCTACAAATCCCA AAATCTCA |
| GI29804415_LY6G6E_3R (SEQ ID 166) | NT_007592 | CTGAAGCTGGGTGGGGTCCGC CCTTACACAGCTGGGCTTTGT GT | CACAAAACCCAACTAT ATAAAAACG | ACCCCACCCAACTTCA AA | ACACAAAACCCAACTA TATAAAACA |
| GI29804415_NEU1_1R (SEQ ID 167) | NT_007592 | GCTGAGGCAGGAGAATCGCTT GAACCCGGGAGGCAGAGGTTG CAGTGAGC | TCACTACAACCTCTAC CTCCCG | ATTCAAACGATTCTCC TACCTCA | ACTCACTACAACCTCT ACCTCCCA |
| GI29804415_NEU1_2R (SEQ ID 168) | NT_007592 | GAGGGCCAATCGGAAGGGCAA GCTTCGAGATGCTGCGTGATC ACGTGG | ACGTAATCACGCAACA TCTCG | AACTTACCCTTCCGAT TAACCCT | CCACATAATCACACA CATCTCA |
| GI29804415_NEU1_3R (SEQ ID 169) | NT_007592 | GGGCGGATCACCTGAGTCAGG AGTTCGAGACCAGCCTGGCCA ACATGGTGAAA | TCACCATATTAACCAA ACTAATCTCG | ACTCCTAACTCAAATA ATCCGCC | TTCACCATATTAACCA AACTAATCTCA |
| GI29804415_RDBP_1R (SEQ ID 170) | NT_007592 | GGTGAAGGAGGTTTGGACTCA ATGCGGGTCAAAGGTTAGGGT CAAAAG | TTTTAACCCTAACCTT TAACCCG | ATTAAATCCAAACCTC CTTCACC | CTTTTAACCCTAACCT TTAACCCA |
| GI29804415_RDBP_2R (SEQ ID 171) | NT_007592 | GGGATCTGGAGGGGTAGCAC TACGGGGAAAGGTCAAAAGTC AGGG | CCTAACTTTTAACCTT TCCCCG | AATACTACCCCCTCCA AATCCC | CCCTAACTTTTAACCT TTCCCCA |
| GI29804415_RDBP_3R (SEQ ID 172) | NT_007592 | TGGCAGCCCGGAAGTGCGGCA AGTAGTCGCTGCGAAGTAAGC CCGCCCCGG | AAACGAAACTTACTTC GCAACG | CTACTTACCGCACTTC CGAACTA | CCAAAACAAAACTTAC TTCACAACA |
| GI29804415_TNF_1R (SEQ ID 173) | NT_007592 | ATAGGTTTTGAGGGGATGGGG ACGGGGTTCAGCCTCCAGGGT CCT | AAACCCTAAAAACTAA CCCCG | CCCCATACCCCTCAAA ACCTAT | AAAACCCTAAAAACTA AAACCCCA |

TABLE 1-continued

Cancer-associated genomic markers and corresponding target nucleic acid probes.

| TARGET CPG SITE | GENBANK ACCESSION # | TARGET SEQUENCE SEQ ID NOS: 1-377 | PROBE SEQUENCE (ASO1) SEQ ID NOS: 378-754 | PROBE SEQUENCE (LSO1) SEQ ID NOS: 755-1131 | PROBE SEQUENCE (ASO2) SEQ ID NOS: 1132-1508 |
|---|---|---|---|---|---|
| GI29804415_TNF_2R (SEQ ID 174) | NT_007592 | CCCGCCCCGCGATGGAGAAG AAACCGAGACAGAAGGTGCAG GGCCCACTAC | AATAAACCCTACACCT TCTATCTCG | TTTCTTCTCCATCGCG AAA | ATAATAAACCCTACAC CTTCTATCTCA |
| GI29804415_TNF_3R (SEQ ID 175) | NT_007592 | CAGAAGGTGCAGGGCCCACTA CCGCTTCCTCCAGATGAGCTC ATGGGTTTC | AAAAAATACAAAACCC ACTACCG | TTCCTCCAAATAAACT CATAAATTTC | CAAAAAATACAAAACC CACTACCA |
| GI29804415_VEGF_1R (SEQ ID 176) | NT_007592 | GTCTCTGGACAGAGTTTCCGG GGGCGGATGGGTAATTTTCAG GCTGTG | ACAACCTAAAAATTAC CCATCCG | CCCCGAAAACTCTATC CAAAA | CACAACCTAAAAATTA CCCATCCA |
| GI29804415_VEGF_2R (SEQ ID 177) | NT_007592 | TCCCCTTCATTGCGGCGGGCT GCGGGCCAGGCTTCACTGAGC GTCCGCA | CCCTTCATTACGACGA ACTACG | ACCAAACTTCACTAAA CGTCCG | TCCCCTTCATTACAAC AAACTACA |
| GI29804415_VEGF_3R (SEQ ID 178) | NT_007592 | GAACGGCTCTCAGGCCCTGTC CGCACGTAACCTCACTTTCCT GCTCCCT | AACGACTCTCAAACCC TATCCG | ACGTAACCTCACTTTC CTACTCC | AAACAACTCTCAAACC CTATCCA |
| GI29807454_WT1_1R (SEQ ID 179) | NT_009237 | CATCTCTACTCCCACCGCATT CGACCCTGCCCGGACTCACTG CTTACC | CTACTCCCACCGCATT CG | CCCTACCCGAACTCAC TACTTAC | CATCTCTACTCCCACC ACATTCA |
| GI29824571_MOS_1R (SEQ ID 180) | NT_008193 | TCAGTCATGTTTCCAAAGTCC CGCGGTTTCCCCTAGTCTCTT CATTCA | CAATCATATTTCCAAA ATCCCG | GATTTCCCCTAATCTC TTCATTCA | TCAATCATATTTCCAA AATCCCA |
| GI29789877_CSF1_2R (SEQ ID 181) | NT_019273 | GTTTGCTGAAGGCTTGGAAGT GCAGCGCAGAAGACAGAGGGT GACTAGGAA | TCCTAATCACCCTCTA TCTTCTACG | TACACTTCCAAACCTT CAACAAAC | TTCCTAATCACCCTCT ATCTTCTACA |
| GI29789877_CSF1_3R (SEQ ID 182) | NT_019273 | TGTGTGTGTGTATGTGTGTGT CTGGCGCCTGGCCAGGGTGAT TTCCCAT | AAAAAATCACCCTAAC CAAACG | CAAACACACACATACA CACACACA | ATAAAAAATCACCCTA ACCAAACA |
| GI29789881_MTHFR_1R (SEQ ID 183) | NT_021937 | GAGCATCTCTGGTTGGAATCA TAATGCTTCGGCCTGAAGTGA CCAGGCCACTCACT | AAATAACCTAATCACT TCAAACCG | AACATTATAATTCCAA CCAAAAATACTC | AATAAATAACCTAATC ACTTCAAACCA |
| GI29791372_MLH1_1R (SEQ ID 184) | NT_002517 | CGGGAGGCCACAAGAGCAGGG CCAACGTTAGAAAGCCGCAAG GGGAGA | CCCCTTACGACCTTTC TAACG | TAACCCTACTCTTATA ACCTCCCG | TCTCCCCTTACAACCT TTCTAACA |
| GI29791372_MLH1_2R (SEQ ID 185) | NT_002517 | TGGCGTAAGCTACAGCTGAAG GAAGAACGTGAGCACGAGGCA CTGAGGTGA | CACCTCAATACCTCGT ACTCACG | TCTTCCTTCAACTATA ACTTACGCC | TCACCTCAATACCTCA TACTCACA |
| GI29791372_MLH1_3R (SEQ ID 186) | NT_002517 | CCGCCACATACCGCTCGTAGT ATTCGTGCTCAGCCTCGTAGT | CACATACCGCTCGTAA TATTCG | ACTCAACCTCGTAATA ACGCCTA | CCACCACATACCACTC ATAATATTCA |
| GI29791392_EGR4_1R (SEQ ID 187) | NT_022184 | CCACAGGAAATGCACAGGTGA GAAACTGACGTTAAGGGGGAC TGAGTGTCAA | TAACACTCAATCCCCC TTAACG | CAATTTCTCACCTATA CATTTCCTATAA | TTAACACTCAATCCCC CTTAACA |
| GI29791392_EGR4_2R (SEQ ID 188) | NT_022184 | AGGGCAGATTCAAACCCAACA AAACAAATTCAAACCC CGGTCCTCCCCTGCTGCCCCT CGGC | AAACAAATTCAAACCC AACACG | TCCTCCCCTACTACCC CTCG | AAAACAAATTCAAACC CAACACA |
| GI29791392_EGR4_3R (SEQ ID 189) | NT_022184 | CGGTCGGCCCGGTGAGGCGCA GCGCCCCAGACTGGCGCATCC GCGGC | ACCCGATAAAACGCAA CG | CCCAAACTAACGCATC CG | CAATCAACCCAATAAA ACACAACA |
| GI29791392_POMC_1R (SEQ ID 190) | NT_022184 | GGCGAGCGGCCAGGTGCGCCT TCGGCAGGACAGTGCTAATTC CAGCCCC | AACGACCAAATACGCC TTCG | CAAAACAATACTAATT CCAACCCC | AACAAACAACCAAATA CACCTTCA |
| GI29791392_POMC_2R (SEQ ID 191) | NT_022184 | CACACGGGGGTGCTAAGCCTC CCGCCCGTTCTAAGCGGAGAC CCAACG | CACGAAAATACTAAAC CTCCCG | CCGTTCTAAACGAAAC CCAAC | CACACAAAAATACTAA ACCTCCCA |
| GI29791392_POMC_3R (SEQ ID 192) | NT_022184 | CGCACGCAGGTAACTTCACCC TCGCCTCAACGACCTCAGAGG CTGCCC | ACGCAAATAACTTCAC CCTCG | CTCAACGACCTCAAAA ACTACCC | CACACACAATAACTTC ACCCTCA |
| GI29791392_SFTPB_1R (SEQ ID 193) | NT_022184 | GAGGTCGCTGCCACTCCTACA GAGCCCCCACGCCCCGCCCAG CTATAAGGGGCCATG | CCCCTTATAACTAAAC GAAACG | AAAAACTCTATAAAAA TAACAACGACCT | CATAACCCCTTATAAC TAAACAAAACA |
| GI29791392_SFTPB_2R (SEQ ID 194) | NT_022184 | ACTCCTACAGAGCCCCCACGC CCCGCCCAGCTATAAGGGGCC A | TCCTACAAAACCCCCA CG | CCCGCCCAACTATAAA AAA | ACTCCTACAAAACCCC CACA |
| GI29791392_TGFA_1R (SEQ ID 195) | NT_022184 | ACGGTAGCCGCCTTCCTATTT CCGCCCGGCGGGCAGCGCTGC GGGGCGA | TAACCGCCTTCCTAT TTCCG | CCGACGAACAACGCTA CG | ACAATAACCACCTTCC TATTTCCA |
| GI29791392_TGFA_2R (SEQ ID 196) | NT_022184 | CGCCCCTAGAGCCTGGAAGC CGCCACTGCGGCCCAGGACAA CGCCTAAAACCCTAAA TCCGG | CGCCTAAAACCCTAAA AACCG | CACTACGACCCAAAAC AATCC | CACCACCTAAAACCTA AAAACCA |
| GI29791392_TGFA_3R (SEQ ID 197) | NT_022184 | CCAAGTCTTGGCAAGCGGCCG GCGAAACTCACAGGTCCCTTT CCTGGC | AAATCTTAACAAACGA CCGACG | AACTCACAAATCCCTT TCCTAAC | CCAAATCTTAACAAAC AACCAACA |

TABLE 1-continued

Cancer-associated genomic markers and corresponding target nucleic acid probes.

| TARGET CPG SITE | GENBANK ACCESSION # | TARGET SEQUENCE SEQ ID NOS: 1-377 | PROBE SEQUENCE (ASO1) SEQ ID NOS: 378-754 | PROBE SEQUENCE (LSO1) SEQ ID NOS: 755-1131 | PROBE SEQUENCE (ASO2) SEQ ID NOS: 1132-1508 |
|---|---|---|---|---|---|
| GI29794065_N33_1R (SEQ ID 198) | NT_015280 | CTCCTCTCCTCAGCGCTGGTC CGGGAAAGGCAAGCTCCGGGC GGGAGCG | CTCTCCTCAACGCTAA TCCG | AAAAAACAAACTCCGA ACGAAA | CTCCTCTCCTCAACAC TAATCCA |
| GI29794065_N33_2R (SEQ ID 199) | NT_015288 | GGGAATAGAGATTGCTGGGGA CCGCAGGGGCCAGGTTGTCAT TCCC | AAAATAACAACCTAAC CCCTACG | TCCCCAACAATCTCTA TTCCC | AAAAATAACAACCTAA CCCCTACA |
| GI29794065_N33_3R (SEQ ID 200) | NT_015288 | CCCGAAGCCTGGCTCCCTCGC CACGCCCACTTCCTGCCCC | CCGAAACCTAACTCCC TCG | CACGCCCACTTCCTAC CC | CCCAAAACCTAACTCC CTCA |
| GI29798364_UBB_1R (SEQ ID 201) | NT_010718 | CACCAATCAGCGCCGACCTCG CCTTCGCAGGCCTAACCAATC AGT | AATCAACGCCGACCTC G | CTTCGCAAACCTAACC AATCAAT | CACCAATCAACACCAA CCTCA |
| GI29798364_UBB_2R (SEQ ID 202) | NT_010718 | CGCGCTCAGTTACTTAGCAAC CTCGGCGCTAAGCCACCCCAG GTGGAGC | CGCTCAATTACTTAAC AACCTCG | CGCTAAACCACCCCAA ATAAAAC | CACACTCAATTACTTA ACAACCTCA |
| GI29798364_UBB_3R (SEQ ID 203) | NT_010718 | GGAGAATCGCTTGAACCCGGG AGGCGGAGGTTGCGATGAGCC GAGAT | GACTCATCGCAACCTC CG | CTCCCGAATTCAAACG ATTCT | ATCTCAACTCATCACA ACCTCCA |
| GI29798595_ERBB2_1R (SEQ ID 204) | NT_010755 | GGCAGCCTAGGGAATTTATCC CGGACTCCGGGGGAGGGGCA GAGTCAC | CTCTACCCCCTCCCCC G | AATCCGAAATAAATTC CCTAAACT | ATAACTCTACCCCCTC CCCCA |
| GI29798595_ERBB2_2R (SEQ ID 205) | NT_010755 | GATTCTCCGAGGAAAAGTGTG AGAACGGCTGCAGGCAACCCA GGCGTCCCG | AACGCCTAAATTACCT ACAACCG | TCTCACACTTTTCCTC GAAAAAT | CAAAACACCTAAATTA CCTACAACCA |
| GI29798595_ERBB2_3R (SEQ ID 206) | NT_010755 | AGGAGGGACGCACCCAGGCCT GCGCGAAGAGAGGGAGAAAGT GAAGCT | ACTTCACTTTCTCCCT CTCTTCG | GCAAACCTAAATACGT CCCTCCT | AACTTCACTTTCTCCC TCTCTTCA |
| GI29799031_ATP5G1_1R (SEQ ID 207) | NT_010783 | GTGGCCCAAGCGCCCGAATGA AGGCTCGGGGCCAAAGTCATG TGTCTGACT | TCAAACACATAACTTT AACCCCG | ACCTTCATTCGAACGC TTAAAC | AATCAAACACATAACT TTAACCCCA |
| GI29799031_ATP5G1_2R (SEQ ID 208) | NT_010783 | CTGTGGAGGGAGAGGAAGCAG CTGCGGAAAGCCAATAAGAGT GGGGAA | TCCCCACTCTTATTAA CTTTCCG | AACTACTTCCTCTCCC TCCACAA | TTCCCCACTCTTATTA ACTTTCCA |
| GI29799031_ATP5G1_3R (SEQ ID 209) | NT_010783 | TCCCGCCAACTCTATGGTCGA GCGTTTCAGGGATCGGCCAAT CGTAATCC | CGCCAACTCTATAATC GAACG | TTCAAAAATCGACCAA TCGTAAT | TCCCACCAACTCTATA ATCAAACA |
| GI29799031_NME1_1R (SEQ ID 210) | NT_010783 | CTCGGGAAGCCAATTTGCTCG CGAACGAAGGAAGTGAGTCAG AGAACCCG | GAATTCTCTAACTCAC TTCCTTCG | TCGCGAACAAATTAAC TTCCC | CAAATTCTCTAACTCA CTTCCTTCA |
| GI29799031_NME1_2R (SEQ ID 211) | NT_010783 | GGGTGGAGAGAAGAAAGCAAG CAGCTAACCGGAAAGGTCTGA AAAAGCTAGCG | GCTAACTTTTTCAAAC CTTTCCG | TTAACTACTTACTTTC TTCTCTCCACCC | CACTAACTTTTTCAAA CCTTTCCA |
| GI29799031_NME1_3R (SEQ ID 212) | NT_010783 | CGCAACGTGTGAGCGCCACCT CTCGGGAAGCCAATTTGCTCG CGAACGAAG | AACGTATAAACGCCAC CTCTCG | AAAACCAATTTACTCG CGAACG | CACAACATATAAACAC CACCTCTCA |
| GI29799354_NF1_1R (SEQ ID 213) | NT_010799 | CTCCCGGGTCAGCTCTGGCAC TCGCCAGCTGAGCCCAGCGCC AGTCTAG | CCCGAATCAACTCTAA CACTCG | CAACTAAACCCAACGC CAATCTA | CTCCCAAATCAACTCT AACACTCA |
| GI29799354_NF1_2R (SEQ ID 214) | NT_010799 | GGGCGCCCTAACTTCCAACTC CGGGAGCAATCCAAACCCGGA GGCC | GCCCTAACTTCCAACT CCG | AAACAATCCAAACCCG AAAAC | AAACCCTAACTTCCAA CTCCA |
| GI29799354_NF1_3R (SEQ ID 215) | NT_010799 | TTTTCATTAATGAAACCGGCC GGCGCGGGCGCATGCGCGGCA GGCCGCC | TCATTAATAAAACCGA CCGACG | GAACGCATACGCGACA AAC | TTTTCATTAATAAAAC CAACCAACA |
| GI29800594_APOC2_1R (SEQ ID 216) | NT_011109 | TTCAGGAGGGTGAGGGCAGGA GCGTGGGTGGAGTCAGCAGGT CCCC | AAACCTACTAACTCCA CCCACG | TCCTACCCTCACCCTC CTAAA | AAAAACCTACTAACTC CACCCACA |
| GI29800594_APOC2_2R (SEQ ID 217) | NT_011109 | CAACCCAGCCTCTGTCGGAGG CGAATTCTCAGAGTGAGGGTT CCCTGTCA | AACCCAACCTCTATCG AAAACG | ATTCTCAAAATAAAAA TTCCCTATCA | CAACCCAACCTCTATC AAAAACA |
| GI29800594_APOC2_3R (SEQ ID 218) | NT_011109 | TTCCCTGTGACGTGACCTTGG GGGACGTCATTGCCCTTTCTG TCCCCACC | TCCCTATAACGTAACC TTAAAAACG | CATTACCCTTTCTATC CCCACC | TTCCCTATAACATAAC CTTAAAAACA |
| GI29800594_KLK10_3R (SEQ ID 219) | NT_011109 | GGTTTCACTATGTTGGCCAGG CTGGTCTCGAACTCCTGACCT CGTGATCCGCC | GAATCACGAAATCAAA AATTCG | AACCAACCTAACCAAC ATAATAAACC | AACAAATCACAAAATC AAAAATTCA |
| GI29800594_TSLL2_2R (SEQ ID 220) | NT_011109 | CGGTGGCTCAGCTCACAGCCT CTCGCTAGACTCCAGACACCC ACCTGCC | ATAACTCAACTCACAA CCTCTCG | TAAACTCCAAACACCC ACCTACC | CAATAACTCAACTCAC AACCTCTCA |
| GI29800594_TSLL2_3R (SEQ ID 221) | NT_011109 | ATCCTTGACCTGCCTCGACCT CCGGACCCTCCGGACCTCCAG CTGC | CTTAACCTACCTCGAC CTCCG | ACCCTCCGAACCTCCA ACTAC | ATCCTTAACCTACCTC AACCTCCA |
| GI29801019_STK11_1R (SEQ ID 222) | NT_011255 | AGCCAGCCTGGGGACTGGAGG GTGGCGGCTGCATCTGCTCAT TTCCTCCCA | ACCAACCTAAAAACTA AAAATAACG | CTACATCTACTCATTT CCTCCCA | AACCAACCTAAAAACT AAAAATAACA |

TABLE 1-continued

Cancer-associated genomic markers and corresponding target nucleic acid probes.

| TARGET CPG SITE | GENBANK ACCESSION # | TARGET SEQUENCE SEQ ID NOS: 1-377 | PROBE SEQUENCE (ASO1) SEQ ID NOS: 378-754 | PROBE SEQUENCE (LSO1) SEQ ID NOS: 755-1131 | PROBE SEQUENCE (ASO2) SEQ ID NOS: 1132-1508 |
|---|---|---|---|---|---|
| GI29801019_STK11_2R (SEQ ID 223) | NT_011255 | GGAGTCTTGCTGTGTCTCCA GGCCGGAGTGCAATGGCATGA CCTCTGCCTCCC | AAATCTTACTATATCT CCCAAACCG | AATACAATAACATAAC CTCTACCTCCC | AAAATCTTACTATATCT TCCCAAACCA |
| GI29801019_STK11_3R (SEQ ID 224) | NT_011255 | TGGAGTCTTGCTGTGTCTCCC AGGCCGGAGTGCAATGGCATG ACCTCTG | CAAAAATCATACCATT ACACTCCG | CCTAAAAACACAACA AAACTCCA | CAAAAATCATACCATT ACACTCCA |
| GI29801560_CDKN2D_1R (SEQ ID 225) | NT_011295 | GCCATTGCCGGCGGTCCACCG GTTGCCACACTCTGACCAATC AGGA | ATTACCGACGATCCAC CG | TTACCACACTCTAACC AATCAAAA | ACCATTACCAACAATC CACCA |
| GI29801560_CDKN2D_2R (SEQ ID 226) | NT_011295 | AGTTAAACCAGCCTTCTTTCC CGCCTGCCGGGTTCATTTGAA AACCGAAA | ATTAAACCAACCTTCT TTCCCG | CTACCGAATTCATTTA AAAACCG | AATTAAACCAACCTTC TTTCCCA |
| GI29801560_CDKN2D_3R (SEQ ID 227) | NT_011295 | CTCATCCACTCCGTCTCTCCG TTTCCCTTTCTTCACGGTGCT TGACA | CATCCACTCCGTCTCT CCG | TTCCCTTTCTTCACGA TACTTAACA | CTCATCCACTCCATCT CTCCA |
| GI29801560_ICAM_1R (SEQ ID 228) | NT_011295 | AGCTTGGAAATTCCGGAGCTG AAGCGGCCAGCGAGGGAGGAT GACCC | ATCCTCCCTCGCTAAC CG | TTCAACTCCGAAATTT CCAAACT | AAATCATCCTCCCTCA CTAACCA |
| GI29801560_ICAM1_2R (SEQ ID 229) | NT_011295 | TCCCCGGACGTGGTGAGACCG CGCTTCGTCACTCCCACGGTT AGCGG | CGAACGTAATATAACC GCG | TTCGTCACTCCCACGA TTAAC | TCCCCAAACATAATAA AACCACA |
| GI29801560_ICAM1_3R (SEQ ID 230) | NT_011295 | CCTGGCTCTGCTCTGGCCGCT TCTCGAGAAATGCCCGTGTCA GCTAGGTG | CCTAACTAACACGAAC ATTTCTCG | AAAACGACCAAAACAA AACCAA | CACCTAACTAACACAA ACATTTCTCA |
| GI29801767_THBS1_1R (SEQ ID 231) | NT_010194 | CCAGTCTCTAGTATCCACCTC TCGCCATCAACCAGGCATTCC GGGAG | CCAATCTCTAATATCC ACCTCTCG | CATCAACCAAACATTC CGAAA | CCAATCTCTAATATCC ACCTCTCA |
| GI29801767_THBS1_2R (SEQ ID 232) | NT_010194 | GGGCCAGCTCAGGACAGGCGC TCGGGGACGCGTGTCCTCAC CCCAC | CAACTCAAAACAAACG CTCG | AAAACGCGTATCCTCA CCC | AAACCAACTCAAAACA AACACTCA |
| GI29801767_THBS1_3R (SEQ ID 233) | NT_010194 | GTGGAGGAGAGTCAGCGAGGG CCCGAGGGGCAGGTACTTTAA CGAATG | TTCGTTAAAATACCTA CCCCTCG | ACCCTCGCTAACTCTC CTCC | CATTCATTAAAATACC TACCCCTCA |
| GI29801784_ELK1_1R (SEQ ID 234) | NT_011568 | GCCTTTTCAGTTGCTCACAGT CCGTCAGTCCTTGAGCCAATC GGCGTGGA | CCTTTTCAATTACTCA CAATCCG | CAATCCTTAAACCAAT CGACGTA | ACCTTTTCAATTACTC ACAATCCA |
| GI29801784_ELK1_2R (SEQ ID 235) | NT_011568 | AGCGCTTTGGCCAATCAGCGA GCGGCGGGACATTGGGCTCCT CCTCCTC | GCTTTAACCAATCAAC GAACG | CGAAACATTAAACTCC TCCTCCT | AACACTTTAACCAATC AACAAACA |
| GI29801784_ELK1_3R (SEQ ID 236) | NT_011568 | CCATTTCTATACAAGCCCTGC TTCCGCTGAGCAGCATGGCGT GCGACACCGCC | CATTTCTATACAAACC CTACTTCCG | TAAACAACATAACGTA CGACACCG | CCATTTCTATACAAAC CCTACTTCCA |
| GI29802832_FMR1_1R (SEQ ID 237) | NT_011681 | CGGGGGTTCGGCCTCAGTCAG GCGCTCAGCTCCGTTTCGGTT TCACTTC | AAAATTCGACCTCAAT CAAACG | TCAACTCCGTTTCGAT TTCACT | CAAAAATTCAACCTCA ATCAAACA |
| GI29802832_FMR1_2R (SEQ ID 238) | NT_011681 | CAGAAATGGGCGTTCTGGCCC TCGCGAGGCAGTGCGACCTGT CACCGCCCT | AATAAACGTTCTAACC CTCGCG | AACAATACGACCTATC ACCGC | CAAAAATAAACATTCT AACCCTCACA |
| GI29802832_FMR1_3R (SEQ ID 239) | NT_011681 | ACCTCCCGCTCAGTCAGACTG CGCTACTTTGAACCGGACCAA ACCAAA | TCCCGCTCAATCAAAC TACG | TACTTTAAACCGAACC AAACCAA | ACCTCCCACTCAATCA AACTACA |
| GI29802923_APAF1_1R (SEQ ID 240) | NT_019546 | TCCACTGCGATATTGCTCCAA ATCCGAGGAAATTCAACTCC CGGGCGCG | CACTACGATATTACTC CAAATCCG | AAAAATTCAAACTCCC GAACG | TCCACTACAATATTAC TCCAAATCCA |
| GI29802923_APAF1_2R (SEQ ID 241) | NT_019546 | AGCAGGGGCTCCCTTGGGCCC CGACTTCTTCCGGCTCTTCAC CTCAG | ACAAAAACTCCCTTAA ACCCCG | CTTCTTCCGACTCTTC ACCTCAA | AACAAAAACTCCCTTA AACCCCA |
| GI29802923_APAF1_3R (SEQ ID 242) | NT_019546 | CCCGAGTCCGGCATTGGTGGG AACGCGGCGCGTCCCTGAGGC TTAGCCACG | CGAATCCGACATTAAT AAAAACG | GACGCGTCCCTAAAAC TTAACC | CCCAAATCCAACATTA ATAAAAACA |
| GI29803889_GPC3_1R (SEQ ID 243) | NT_011786 | GCTGAAAGAAGGCCTGTGGCG AAGCGGAGGCGGACCTAAGTC AGG | CCTAACTTAAATCCCC CTCCG | TTCGCCACAAACCTTC TTTC | CCTAACTTAAATCCCC CTCCA |
| GI29803889_GPC3_2R (SEQ ID 244) | NT_011786 | CCAGAGCGCCCTGTGTAGAGC GGCTGCGAGCGGGCAGCTGGG CTCGGCTGCCGGG | ACGCCCTATATAAAAC GACTACG | ACGAACAACTAAACTC GACTACCG | CCAAAACACCCTATAT AAAACAACTACA |
| GI29803889_GPC3_3R (SEQ ID 245) | NT_011786 | CCAGAGCCAGTCAGAGCGGAC GGCTGCTGGGAAGCCAATCAG CGCGCTCG | CAAAACCAATCAAAAC GAACG | CTACTAAAAAACCAAT CAACGCG | CCAAACCAATCAAAA CAAACA |
| GI29805200_CCND2_1R (SEQ ID 246) | NT_009759 | AAATACAAGGGCAGGAGGATT AGGATCCGTTTTGAAGAAGCC AAAGTTGGAG | CCAACTTTAACTTCTT CAAAACG | ATCCTAATCCTCCTAC CCTTATATTT | CTCCAACTTTAACTTC TTCAAAACA |

TABLE 1-continued

Cancer-associated genomic markers and corresponding target nucleic acid probes.

| TARGET CPG SITE | GENBANK ACCESSION # | TARGET SEQUENCE SEQ ID NOS: 1-377 | PROBE SEQUENCE (ASO1) SEQ ID NOS: 378-754 | PROBE SEQUENCE (LSO1) SEQ ID NOS: 755-1131 | PROBE SEQUENCE (ASO2) SEQ ID NOS: 1132-1508 |
|---|---|---|---|---|---|
| GI29805200_CCND2_3R (SEQ ID 247) | NT_009759 | GGGAGGAGAGCTAACTGCCCA GCCAGCTTGCGTCACCGCTTC AGAGCGGAGAAGAG | TCTCCGCTCTAAAACG ATAACG | AAACTAACTAAACAAT TAACTCTCCTCCC | CTCTTCTCCACTCTAA AACAATAACA |
| GI29806267_SOD1_1R (SEQ ID 248) | NT_011512 | AGAAGGTTGTTTTCTCCACAT TTCGGGGTTCTGGACGTTTCC CGGCTGCGGG | AAAAATTATTTTCTCC ACATTTCG | AATTCTAAACGTTTCC CGACTAC | AAAAAATTATTTTCTC CACATTTCA |
| GI29806267_SOD1_2R (SEQ ID 249) | NT_011512 | TTTACATCATTTTGCCAATTT CGCGTACTGCAACCGGCGGGC CACGCC | ACATCATTTTACCAAT TTCGCG | ACTACAACCGACGAAC CACG | TTTACATCATTTTACC AATTTCACA |
| GI29806267_SOD1_3R (SEQ ID 250) | NT_011512 | CAGTCATTCCCGGCCACTCGC GACCCGAGGCTGCCGCAGGGG GC | AATCATTCCCGACCAC TCG | GACCCGAAACTACCGC AAA | CAATCATTCCCAACCA CTCA |
| GI29806588_GP1BB_1R (SEQ ID 251) | NT_011519 | CCCCAGCACCGCTGTGGTGTG CCGGGATCCTGAGCCTAGGCC TCCCGA | CCAACACCGCTATAAT ATACCG | AATCCTAAACCTAAAC CTCCCGA | CCCCAACACCACTATA ATATACCA |
| GI29806588_GP1BB_2R (SEQ ID 252) | NT_011519 | GAGACCCCATTTTCTGTCGAG GCGGGCCGAGTCTTCCCTTAT CCCC | AACCCCATTTTCTATC GAAACG | ACCGAATCTTCCCTTA TCCC | AAAACCCCATTTTCTA TCAAAACA |
| GI29806588_GP1BB_3R (SEQ ID 253) | NT_011519 | AAGGAGGCCAGAGGCTGCAAG GAGCGGGTCGTGACCGCTTA CACCCCG | AATATAAACGATCACG ACCCCG | TCCTTACAACCTCTAA CCTCCTT | AAAATATAAACAATCA CAACCCCA |
| GI29807454_WT1_2R (SEQ ID 254) | NT_009237 | TTTCTGCGCTTTCCTGAAGTT CCCGCCCTCTTGGAGCCTACC TGCCCCTC | TACGCTTTCCTAAAAT TCCCG | CCTCTTAAAACCTACC TACCCCTC | TTTCTACACTTTCCTA AAATTCCCA |
| GI29807454_WT1_3R (SEQ ID 255) | NT_009237 | CGCCCGGCTTATAACTGGTGC AACTCCCGGCCACCCAACTGA GGGACGTTC | AACGTCCCTCAATTAA ATAACCG | AAATTACACCAATTAT AAACCGAACG | AAACATCCCTCAATTA AATAACCA |
| GI29808062_SOCS1_1R (SEQ ID 256) | NT_010393 | CGAACAGGCGGGCAGAGGGCC CCGCGGGAGGGTCCAGAAGAG AGG | CCTCTCTTCTAAAACCC TCCCG | GAAACCCTCTACCCGC CTATT | CCTCTCTTCTAAACCC TCCCA |
| GI29808062_SOCS1_2R (SEQ ID 257) | NT_010393 | GGGTCCGAGAAGTGGCCGGAA GGCCAGGGTCGGGGCCAGAG CCCCTC | CCGAAAAATAACCGAA AAACG | AAAATCGAAACCAAAA CCCC | AAATCCAAAAAATAAC CAAAAAACA |
| GI29808062_SOCS1_3R (SEQ ID 258) | NT_010393 | CGGGCGCCGAACAGAGCGAGC TGCGGCCGTGGCAGCTGCACG GCTCCTGGCC | GCCGAACAAAACGAAC TACG | CCGTAACAACTACACG ACTCCTAA | CAAACACCAAACAAAA CAAACTACA |
| GI29808625_CDH3_2R (SEQ ID 259) | NT_010498 | GAGAATCGCTTCAGCCCGGGA GGTCGAGGCTGTAGTGAGCCG AGATCG | GATCTCGACTCACTAC AACCTCG | CCTCCCGAACTAAAAC GATTCT | CAATCTCAACTCACTA CAACCTCA |
| GI29808625_CDH3_3R (SEQ ID 260) | NT_010498 | CGAGATCGCGCTACTGCACTC CTGGGCGACAGAGCGAGACCC TGTCTCCAAA | CGCGCTACTACACTCC TAAACG | CAAAACGAAACCCTAT CTCCAA | CAAAATCACACTACTA CACTCCTAAACA |
| GI29808952_TUBB4_1R (SEQ ID 261) | NT_010542 | AAAGACAGGGAGCTGGGATGG TGCGGGTTGGTCTCTAAACCG GCGT | CCGATTTAAAAACCAA CCCG | ACCATCCCAACTCCCT ATCTTT | ACACCAATTTAAAACC AACCCA |
| GI29808952_TUBB4_2R (SEQ ID 262) | NT_010542 | CGCGCGGTGCGGAGCCTGCGG GCCGGGCGGGGCTCTGCGGCG GCGCCTCC | CGATACGAAACCTACG AACCG | ACGAAACTCTACGACG ACGC | CACACAATACAAAACC TACAAACCA |
| GI29808952_TUBB4_3R (SEQ ID 263) | NT_010542 | CCCGCGGTGACATCAGCCGAT GCGAAGGGCGGGGCCGCGGCT ATAAGAGCG | GCGATAACATCAACCG ATACG | AAAACGAAACCGCGAC TATAAA | CCCACAATAACATCAA CCAATACA |
| GI29823164_ADCYAP1_1R (SEQ ID 264) | NT_010859 | ATGCCTCTCGGGTGGTGACTC CAGCGCAGGAACTTGAAGAAG CGCTTTG | AACGCTTCTTCAAATT CCTACG | TAAAATCACCACCCGA AAACAT | CAAAACACTTCTTCAA ATTCCTACA |
| GI29823164_ADCYAP1_2R (SEQ ID 265) | NT_010859 | GGTAAGGGAGGGAAAATCTTA CCAAAGCGACCGGCTCACTCG ACTGCTGATTC | CAACAATCGAATAAAC CGATCG | TTTAATAAAATTTTCC CTCCCTTACC | AAATCAACAATCAAAT AAACCAATCA |
| GI29823164_ADCYAP1_3R (SEQ ID 266) | NT_010859 | TCCTGCTGCTCCCGCTGGTTC CTGCGGCTTCTGCTCAGACAC CAACGCCA | TACTACTCCCGCTAAT TCCTACG | CTTCTACTCAAACACC AACGCC | TCCTACTACTCCCACT AATTCCTACA |
| GI29823164_MC2R_1R (SEQ ID 267) | NT_010859 | CCTGAAGAATCAATCAAGTTT TCCGTGAAGTCAAGTCCAAGT AACATCCC | AAAAAATCAATCAAAT TTTCCG | AAAATCAAATCCAAAT AACATCCC | CCTAAAAAATCAATCA AATTTTCCA |
| GI29823167_ATP5A1_1R (SEQ ID 268) | NT_010966 | TCTCCTCCTGCGGCTCCATAG CTGCGGCTCCCGCCACTTTAC TAGGAACTCC | CCTCCTACGACTCCAT AACTACG | CTCCCGCCACTTTACT AAAAACT | TCTCCTCCTACAACTC CATAACTACA |
| GI29823167_ATP5A1_2R (SEQ ID 269) | NT_010966 | GGCTCTGGCATTGCAAGCCTC GCTTCGTTGCCACTTCCCAGC TCTTCCC | CTAACATTACAAACCT CGCTTCG | TACCACTTCCCAACTC TTCCC | AACTCTAACATTACAA ACCTCACTTCA |
| GI29823167_ATP5A1_3R (SEQ ID 270) | NT_010966 | CTCCCAGTGTTGGGATGCAGG GCGCGGAAGCAGTTCAGATGT GGAAGCCG | CTTCCACATCTAAACT ACTTCCG | GCCCTACATCCCAACA CTAAAA | CAACTTCCACATCTAA ACTACTTCCA |

TABLE 1-continued

Cancer-associated genomic markers and corresponding target nucleic acid probes.

| TARGET CPG SITE | GENBANK ACCESSION # | TARGET SEQUENCE SEQ ID NOS: 1-377 | PROBE SEQUENCE (ASO1) SEQ ID NOS: 378-754 | PROBE SEQUENCE (LSO1) SEQ ID NOS: 755-1131 | PROBE SEQUENCE (ASO2) SEQ ID NOS: 1132-1508 |
|---|---|---|---|---|---|
| GI17458490_PLAGL2_1R (SEQ ID 271) | NT_028392 | CGGGTCCCAGGAGCCCGCAGG CATCCCCGGGAGCGGCAGAAG CAGCAGCAGGAA | TACTACTACTTCTACC GCTCCCG | AAATACCTACGAACTC CTAAAACCC | TTCCTACTACTACTTC TACCACTCCCA |
| GI17458490_PLAGL2_2R (SEQ ID 272) | NT_028392 | ACGCTCAGCGGCCGTGCCCAC GCGGCGGCGCCCATGTCGGCC CG | TCAACGACCGTACCCA CG | GACGACGCCCATATCG AC | ACACTCAACAACCATA CCCACA |
| GI17458490_PLAGL2_3R (SEQ ID 273) | NT_028392 | GGCTTAGACCTCAAGCAAGTC ACGTAACCTCTCCCAGCCTCA GTTTT | ACTTAAACCTCAAACA AATCACG | AACCTCTCCCAACCTC AATTTT | AACTTAAACCTCAAAC AAATCACA |
| GI29732427_ABL1_1R (SEQ ID 274) | NT_035014 | AAAGCAGAGAAGCGAGAGCGG CCACTAGTTCGGCAGGAAATT TGTTGGAAGAT | TTCCAACAAATTTCCT ACCG | ACTAATAACCGCTCTC GCTTCT | ATCTTCCAACAAATTT CCTACCA |
| GI29732427_ABL1_2R (SEQ ID 275) | NT_035014 | CAATGCATTCCTTTTCGTCAG AGTCGAGGGCAAACTCGCTGA AATCTGGGTGACCC | ACATTCCTTTTCGTCA AAATCG | AAACAAACTCGCTAAA ATCTAAATAAC | CAATACATTCCTTTTC ATCAAAATCA |
| GI29732427_ABL1_3R (SEQ ID 276) | NT_035014 | GGATTGGTTCCACAGGCCTTT TAAAAAGCGGACTTAAAAGTT GCTGGCAATG | CATTACCAACAACTTT TAAATCCG | TTTTTAAAAAACCTAT AAAACCAATCC | CATTACCAACAACTTT TAAATCCA |
| GI29736559_CRIP1_1R (SEQ ID 277) | NT_026437 | GGGACAGACTCCGCCTGCAC CGGGACCATCCTCCGCCTCAA CTTTG | ACAAACTCCGCCTAAC ACCG | AACCATCCTCCGCCTC A | AAAACAAACTCCACCT AACACCA |
| GI29736559_CRIP1_2R (SEQ ID 278) | NT_026437 | GTGCCAGACGCCTGTGCCTTG GCCGTCCTACAGCCCTGCTGC CCCTGCC | CCAAACGCCTATACCT TAACCG | CCTACAACCCTACTAC CCCTACC | ATACCAAACACCTATA CCTTAACCA |
| GI29736559_CRIP1_3R (SEQ ID 279) | NT_026437 | CTGGAGTGTGGCCTCTGTGCC AGACGCCTGTGCCTTGGCCGT CCTACAG | TAAACGACCAAAACAC AAACG | CTAACACAAAACCACA CTCCAA | CTATAAACAACCAAA ACACAAACA |
| GI29736559_DAD1_1R (SEQ ID 280) | NT_026437 | CCTAGAGGAAGTTTAGTCCTT GGGACGCTTGGCCTGCCAGTC TCTGAAA | TCAAAAACTAACAAAC CAAACG | CCCAAAAACTAAACTT CCTCTAAA | TTTCAAAAACTAACAA ACCAAACA |
| GI29736559_DAD1_2R (SEQ ID 281) | NT_026437 | GATGGTGGTGGTGGTAGTGCA CGTTGGGTTGAGGGGAC | ATCCCCTCAACCCAAC G | ACACTACCACCACCAC CATC | ATCCCCTCAACCCAAC A |
| GI29736559_FOS_1R (SEQ ID 282) | NT_026437 | TCTGAGACAGGAACTGCGAAA TGCTCACGAGATTAGGACACG CGCCAAGGCGG | CCTTAACGCGTATCCT AATCTCG | AAACATTTCGCAATTC CTATCTC | CCACCTTAACACATAT CCTAATCTCA |
| GI29736559_FOS_2R (SEQ ID 283) | NT_26437 | CAAGGGTCCGCATTGAACAG GTGCGAATGTTCTCTCTCATT CTGCGCCGTTCC | AATCCGCATTAAACCA AATACG | ATATTCTCTCTCATTC TACGCCG | CAAAAATCCACATTAA ACCAAATACA |
| GI29736559_FOS_3R (SEQ ID 284) | NT_026437 | CGGGAGCCGAGGCTTAAGTCC TCGGGGTCCTGTACTCGATGC CGTTTCTCC | GAAACCGAAACTTAAA TCCTCG | AATCCTATACTCGATA CCGTTTCTC | CAAAAACCAAAACTTA AATCCTCA |
| GI29736559_HSPA2_1R (SEQ ID 285) | NT_026437 | AGACATAGGGTTTGGTGTGGC TGTGCGGGGTTCCCGGGCCTT GC | AAAACCCGAAAACCCC G | ACAACCACACCAAACC CTATATCT | ACAAAACCCAAAAACC CCA |
| GI29736559_HSPA2_2R (SEQ ID 286) | NT_026437 | GCTGGCCTGTCGGCCTCTGAT GCACTCGAACTTCAGCCCTTT GGAGCAGACA | CCTATCGACCTCTAAT ACACTCG | ACTTCCAACCCTTAAA ACAAACA | ACTAACCTATCAACCT CTAATACACTCA |
| GI29738185_ESR1_1R (SEQ ID 287) | NT_023451 | TCAGGGAAGCTGCTCTTTGGG ATCGCTCCAAATCGAGTTGTG CCTGGA | CAAACACAACTCGATT TAAAACG | TCCCAAAAACAACTT CCCTAA | TCCAAACACAACTCAA TTTAAAACA |
| GI29738185_ESR1_2R (SEQ ID 288) | NT_023451 | GGCCCCTGGATCCGTCTTTCG CGTTTATTTTAAGCCCAGTCT TCCCT | CCTAAATCCGTCTTTC GCG | TTATTTTAAACCCAAT CTTCCCT | AACCCCTAAATCCATC TTTCACA |
| GI29738185_ESR1_3R (SEQ ID 289) | NT_023451 | CCCCATTCTATCTGCCCTATC TCGGTTACAGTGTAGTCCTCC CCAGGGTC | CCCATTCTATCTACCC TATCTCG | TTACAATATAATCCTC CCCAAAATC | CCCCATTCTATCTACC CTATCTCA |
| GI29738645_RB1_1R (SEQ ID 290) | NT_024924 | CCTGGAAGGCGCCTGGACCCA CGCCAGGTTTCCCAGTTTAAT TCCTCA | TAAAAAACGCCTAAAC CCACG | CAAATTTCCCAATTTA ATTCCTCA | CCTAAAAAACACCTAA ACCCACA |
| GI29738645_RB1_3R (SEQ ID 291) | NT_024524 | GCGGGCGGAAGTGACGTTTTC CCGCGGTTGGACGCGGCGCTC AGTTGCCGGG | AACGAAAATAACGTTT TCCCG | GATTAAACGCGACGCT CAATTAC | ACAAACAAAAATAACA TTTTCCCA |
| GI29738863_GDF10_1R (SEQ ID 292) | NT_030772 | TCGCAGCCAGGGCAGGCTGCG GCGCCGACACACAGGAGCCGG CTGCGGG | GCAACCAAAACAAACT ACGACG | CGACACACAAAAACCG ACTAC | TCACAACCAAAACAAA CTACAACA |
| GI29738863_GDF10_2R (SEQ ID 293) | NT_030772 | TCATCTTGCAATCACATAGCC ATCGCATGCCATTGCAGGGGC AACCCAGCA | TCATCTTACAATCACA TAACCATCG | ATACCATTACAAAAAC CCCAACA | TCATCTTACAATCACA TAACCATCA |
| GI29738863_GDF10_3R (SEQ ID 294) | NT_030772 | CATACGCTGACTCCGAGGCAA CTGGGCGCACACATATCCCCT CTCTGGTCCTC | GCTAACTCCGAAACAA CTAAACG | ACACATATCCCCTCTC TAATCCTC | CATACACTAACTCCAA AACAACTAAACA |
| GI29739550_OAT_1R (SEQ ID 295) | NT_035040 | CAGGGTTCAAGGGCATGGGGC TCCCGCAGCTGTGGCTGGGGC AGAGC | CTCTACCCCAACCACA ACTACG | AAACCCCATACCCTTA AAACCCTA | ACTCTACCCCAACCAC AACTACA |

TABLE 1-continued

Cancer-associated genomic markers and corresponding target nucleic acid probes.

| TARGET CPG SITE | GENBANK ACCESSION # | TARGET SEQUENCE SEQ ID NOS: 1-377 | PROBE SEQUENCE (ASO1) SEQ ID NOS: 378-754 | PROBE SEQUENCE (LSO1) SEQ ID NOS: 755-1131 | PROBE SEQUENCE (ASO2) SEQ ID NOS: 1132-1508 |
|---|---|---|---|---|---|
| GI29739550_OAT_2R (SEQ ID 296) | NT_035040 | GCCCAACAGACTTTTCCTTTT CGGGCCTCAGTCTTCTCGTCA GCAAG | CCCAACAAACTTTTCC TTTTCG | ACCTCAATCTTCTCGT CAACAAA | ACCCAACAAACTTTTC CTTTTCA |
| GI29739550_OAT_1R (SEQ ID 297) | NT_035040 | CACGCGATTGGTATCCTGCCC TCCGCCCCAGCCAATGAGCGG CGAGGGT | GCGATTAATATCCTAC CCTCCG | CCCAACCAATAAACGA CGAAA | CACACAATTAATATCC TACCCTCCA |
| GI29789893_CTNNB1_1R (SEQ ID 298) | NT_037565 | TCCCCGATGCAGACCACAGCG CCCTCACGGGCTGCCCTCAGG CC | CCCGATACAAACCACA ACG | CCTCACGAACTACCCT CAAAC | TCCCCAATACAAACCA CAACA |
| GI29791372_RARB_1R (SEQ ID 299) | NT_022517 | AAAGGGAGAGAAGTTGGTGCT CAACGTGAGCCAGGAGCAGCG TCCCGGCT | GAAACGCTACTCCTAA CTCACG | TAAACACCAACTTCTC TCCCTTT | AACCAAAACACTACTC CTAACTCACA |
| GI29791372_RARB_2R (SEQ ID 300) | NT_022517 | CGTGAGCCAGGAGCAGCGTCC CGGCTCCTCCCCTGCTCATTT TAAAA | GTAAACCAAAAACAAC GTCCCG | CTCCTCCCCTACTCAT TTTAAAA | CATAAACCAAAAACAA CATCCCA |
| GI29791372_RARB_3R (SEQ ID 301) | NT_022517 | GAGCGGGCGCAGGCGGAACAC CGTTTTCCAAGCTAAGCCGCC GCAAA | AACGCAAACGAAACAC CG | TTTCCAAACTAAACCG CCG | AAACAAACACAAACAA AACACCA |
| GI29791375_ARH1_1R (SEQ ID 302) | NT_032977 | GGCTGGGGCACACAAAACCAG GTGCTACCGTCAACGACTAGG CCCATAGGGTACTG | ACCCTATAAACCTAAT CGTTAACG | TAACACCTAATTTTAT ATACCCCAACC | CAATACCCTATAAACC TAATCATTAACA |
| GI29791375_ARH1_2R (SEQ ID 303) | NT_032977 | AAGGGAGAAAGAAGCCAGACG GAGCTCGGAGATGTGGAGGGC AGACGCA | GTCTACCCTCCACATC TCCG | ACTCCGTCTAACTTCT TTCTCCC | TACATCTACCCTCCAC ATCTCCA |
| GI29791375_ARH1_3R (SEQ ID 304) | NT_032977 | CCCAAAACGCTCGGTAGGCGG TGGTGCGCAGCTTTCAATGCA TCCGCCGCCA | AACGCTCGATAAACGA TAATACG | AACTTTCAATACATCC GCCG | CCCAAAACACTCAATA AACAATAAATACA |
| GI29791382_SFN_2R (SEQ ID 305) | NT_037485 | CTCCTGAACCTTTATGGGCTC TGTCGAGGCTGAAGCAGCCAG GGGCT | ACCCCTAACTACTTCA ACCTCG | CAAAACCCATAAAAAT TCAAAA | AACCCCTAACTACTTC AACCTCA |
| GI29791382_SFN_3R (SEQ ID 306) | NT_037485 | GCAGGTCTTGGGCCCTGGTCC CGCCCCTGCTCCTCCCCAC | CAAATCTTAAACCCTA ATCCCG | CCCTACTCCTCCCCA C | ACAAATCTTAAACCCT AATCCCA |
| GI29794267_SFTPC_1R (SEQ ID 307) | NT_023666 | GAGGGGCTGGAGGAGGAAACG GGGAGGCCCACACAGAAGGG | CCCTTCTATATAAACC TCCCG | TTCCTCCTCCAACCCC TC | CCCTTCTATATAAACC TCCCCA |
| GI29794267_SFTPC_2R (SEQ ID 308) | NT_023666 | GGGCAACTGTCCCCACCCGTC CCTGGCACGGCTCTGCCCAGT | AAACAACTATCCCCAC CCG | CCCTAACACGACTCTA CCCAA | AAACAACTATCCCCAC CCA |
| GI29794267_SFTPC_3R (SEQ ID 309) | NT_023666 | TCCTTGCTGCCACACATTTAG CCGCCCTCCCCATGCCAGCTT GGGG | CCTTACTACCACACAT TTAACCG | CCTCCCCATACCAACT TAAAA | TCCTTACTACCACACA TTTAACCA |
| GI29794674_EGFR_1R (SEQ ID 310) | NT_033968 | GTTGGGTGCCCTCATTTCAGA TGATTTCGAGGGTGCTTGACA AGATCTGAA | TCAAATCTTATCAAAC ACCCTCG | AATCATCTAAAATAAA AACACCCAAC | TTCAAATCTTATCAAA CACCCTCA |
| GI29794674_EGFR_2R (SEQ ID 311) | NT_033968 | GGGGACCCTGGCACAGATTTG GCTCGACCTGGACATAGGCTG GGCCTG | AAACCCAACCTATATC CAAATCG | ACCAAATCTATACCAA AATCCCC | CAAACCCAACCTATAT CCAAATCA |
| GI29794674_EGFR_3R (SEQ ID 312) | NT_033968 | GGCAGTGCTGGGAACGCCCCT CTCGGAAATTAACTCCTCAGG GCACCCGC | AATACTAAAAACGCCC CTCTCG | AAATTAACTCCTCAAA ACACCCG | AACAATACTAAAAACA CCCCTCTCA |
| GI29796148_TERT_1R (SEQ ID 313) | NT_023089 | GACCTGGAGGCAGCCCTGGGT CTCCGGATCAGGCCAGCGGCC AAAGGG | CTTTAACCGCTAACCT AATCCG | AAACCCWAACTACCTC CAAATC | CCCTTTAACCACTAAC CTAATCCA |
| GI29796148_TERT_2R (SEQ ID 314) | NT_023089 | CCGCCCGGAGCAGCTGCGCTG TCGGGGCCAGGCCGGGCTCCC AGTGGA | CCCGAAACAACTACGC TATCG | AACCAAACCGAACTCC CAATAA | CCACCCAAAACAACTA CACTATCA |
| GI29796148_TERT_3R (SEQ ID 315) | NT_023089 | GGGTTACCCCACAGCCTAGGC CGATTCGACCTCTCTCCGCTG GGGCC | AATTACCCCACACCCT AAACCG | TTCGACCTCTCTCCGC TAAA | AAATTACCCCACACCC TAAACCA |
| GI29797939_IL13_1R (SEQ ID 316) | NT_034772 | GGCCGCGCAGATCCCGCTTAT CGGGCCCATCTCCCGTTACAT AAGGC | CGCAAATCCCGCTTAT CG | ACCCATCTCCCGTTAC ATAAAAC | AACCACACAAATCCCA CTTATCA |
| GI29797939_IL13_2R (SEQ ID 317) | NT_034772 | GAGCCGCTGGCCCGGGTGTCC AGCCGGCCCTTGCCCTGCCTG GCGCT | GCCAAACAAAACAAAA ACCG | CTAAACACCCGAACCA ACGACT | AACACCAAACAAAACA AAACCA |
| GI29797939_IL13_3R (SEQ ID 318) | NT_034772 | CACGCAGCGCATTGCAGGCAG GTGCGAGCCACATGCGCCAAG TGCCCGGA | GCAACGCATTACAAAC AAATACG | ACCACATACGCCAAAT ACCC | CACACAACACATTACA AACAAATACA |
| GI29797939_LOX_1R (SEQ ID 319) | NT_034772 | ATCCTGGGGTTTATTTGCTGA GGGCGCTTCCCATAAAAGCGA GAGAGTGTG | CACTCTCTCGCTTTTA TAAAAACG | CCTCAACAAATAAACC CAAAAT | CACACTCTCTCACTTT TATAAAAACA |
| GI29797939_LOX_2R (SEQ ID 320) | NT_034772 | GTGAACAAATAGCTGAGGGGC ATTACACAAACCGTTC GGCCGGGCCAGAACGGCTTGT GTAACTT | CCGCCCCTCAACTATT TATTC | AAATTACACAAACCAT TCTAACCCA | |

TABLE 1-continued

Cancer-associated genomic markers and corresponding target nucleic acid probes.

| TARGET CPG SITE | GENBANK ACCESSION # | TARGET SEQUENCE SEQ ID NOS: 1-377 | PROBE SEQUENCE (ASO1) SEQ ID NOS: 378-754 | PROBE SEQUENCE (LSO1) SEQ ID NOS: 755-1131 | PROBE SEQUENCE (ASO2) SEQ ID NOS: 1132-1508 |
|---|---|---|---|---|---|
| GI29797939_LOX_3R (SEQ ID 321) | NT_034772 | AGGCGAGGAGCTGTCCGCCTT GCACGTTTCCAATCGCATTAC GTGAACAAATAG | GAAAAACTATCCGCCT TACACG | TTCCAATCGCATTACG TAAACA | AAACAAAAACTATCC ACCTTACACA |
| GI29800185_SFTPD_1R (SEQ ID 322) | NT_030059 | TTGTGAATATCAGTGGCAGGT TTCCAGAACGCAGGTGGGGAT AAGAGTGAGT | TCACTCTTATCCCCAC CTACG | TCTAAAAACCTACCAC TAATATTCACAA | ACTCACTCTTATCCCC ACCTACA |
| GI29800185_SNCG_1R (SEQ ID 323) | NT_030059 | CGGTTTCATGGCAGCCCAGGG TCCAGCGGCATCCAGGATGCT GGTGGG | CCACCAACATCCTAAA TACCG | TAAACCCTAAACTACC ATAAAACCG | CCCCACCAACATCCTAA ATACCA |
| GI29800185_SNCG_2R (SEQ ID 324) | NT_030059 | AGCTGCACAGCCCAGGCCGCG GGAGGTTGGCTGCTCTCACCT AACAGGCC | ACACAACCCAAACCGC G | AAAATTAACTACTCTC ACCTAACAAACC | AACTACACAACCCAAA CCACA |
| GI29800185_SNCG_3R (SEQ ID 325) | NT_030059 | ACCTCAGATCCTCCAACCGGT TTCATGGCAGCCCAGGGTCCA | ACCTCAAATCCTCCAA CCG | TTTCATAACAACCCAA AATCCA | ACCTCAAATCCTCCAA CCA |
| GI29801752_PLAGL1_1R (SEQ ID 326) | NT_025741 | AGTGCCTGGCTCACGGTCAGT GCTCACGTTTGGGCAGCTGCA CTTGGGC | CCCAAATACAACTACC CAAACG | AAACACTAACCGTAAA CCAAACAC | ACCCAAATACAACTAC CCAAACA |
| GI29801752_PLAGL1_2R (SEQ ID 327) | NT_025741 | CCAGGCCGGCTCGGGTCTACC TGCGCAGCGCTGTACCTGGG CGACCTTGGCTT | AACCGACTCGAATCTA CCTACG | CAACGCTATACCTAAA CGACCTT | CCAAACCAACTCAAAT CTACCTACA |
| GI29801752_PLAGL1_3R (SEQ ID 328) | NT_025741 | GGGCTCTGGCGGCCCATCCTG GCGGAGACTTCGGCTAGCAGG CCCCGC | ACTCAACGACCCATC CTAACG | AAACTTCGACTAACAA ACCCCG | AAACTCTAACAACCCA TCCTAACA |
| GI29803948_CD63_1R (SEQ ID 329) | NT_029419 | CTGGCTTTGTCTTCTGGGATA AGACGGGGAAATCCAGAGGAT GTAAGC | CTTACATCCTCTAAAT TTCCCCG | CTTATCCCAAAAAACA AAACCAA | ACTTACATCCTCTAAA TTTCCCCA |
| GI29803948_CD63_2R (SEQ ID 330) | NT_029419 | GGCACCTTGATCCCCCTAGCC CGCTTCCAGCCCTCACCTGGC TTTGTC | ACAACTTAATCCCCCT AACCCG | TTCCAACCCTCACCTA ACTTTATC | AACAACTTAATCCCCC TAACCCA |
| GI29803948_CD63_3R (SEQ ID 331) | NT_029419 | GGTGTGACGGCCGGTCCTACT CTCCGGCCTGTTCAGATCAGC TCCTTCTGGG | ATAACGACCGATCCTA CTCTCCG | CCTATTCAAATCAACT CCTTCTAAA | AATATAACAACCAATC CTACTCTCCA |
| GI29803948_CDK4_1R (SEQ ID 332) | NT_029419 | TCCTGGGGACCCTTGACCCTC CGACACAAACAAGCGCTCCAG GAGTC | CTAAAAACCCTTAACC CTCCG | CACAAACAAACGCTCC AAAA | TCCTAAAAACCCTTAA CCCTCCA |
| GI29803948_CDK4_2R (SEQ ID 333) | NT_029419 | CCCTTAGCTTACGGAGACCCT GGGGCGAGGGAAATAGGAGAG AACAGCAGTC | ACTATTCTCTCCTATT CCCTCG | CCCAAAATCTCCGTAA ACTAAAA | AACTACTATTCTCTCC TATTTCCCTCA |
| GI29803948_CDK4_3R (SEQ ID 334) | NT_029419 | TGTTAATGGGTGAGAGGGATT TTGCGCTCTCCGGGGAGAAAG CCCCAC | TAAAACTTTCTCCCCG AAAAACG | AAAATCCCTCTCACCC ATTAACA | ATAAAACTTTCTCCCC AAAAAACA |
| GI29804485_BCAP31_1R (SEQ ID 335) | NT_025965 | GGCCCTCCAGGGTCGCGGCCT CTTCGGGCAGCCCAAGTGGAG GAACTT | AATTCCTCCACTTAAA CTACCCG | AAAAACCGCGACCCTA AAAA | AAATTCCTCCACTTAA ACTACCCA |
| GI29804485_BCAP31_2R (SEQ ID 336) | NT_025965 | GGGCTCAGGGCCCTCCAGGGT CGCGGCCTCTTCGGGCAGCCC AAGTG | AACTCAAAACCCTCCA CCAAATA | GACCTCTTCGAACAAC CCAAATA | AAACTCAAAACCCTCC AAAATCA |
| GI29804485_CTAG1_1R (SEQ ID 337) | NT_025965 | CCAGCTGGGCGACCAGGACAG GGACGGAGGCTGCTGAGCCCA GTTAGAG | CTAACTAAACTCAACA ACCTCCG | CCCTATCCTAATCGCC CAACTAA | CTCTAACTAAACTCAA CAACCTCCA |
| GI29804485_CTAG1_2R (SEQ ID 338) | NT_025965 | GAGACCTTGGCTGGCGCGAGG CCACGCCCACCAGACATGCAG TTCCAGCT | CTTAACTAACGCGAAA CCACG | CCACCAAACATACAAT TCCAACT | AAAAACCTTAACTAACA CAAAACCACA |
| GI29804485_CTAG1_3R (SEQ ID 339) | NT_025965 | GGGCGACTAGGACAGGGACAG AACCCGTTGAACCCAGGAGTG AGATCCGG | GAATCTCACTCCTAAA TTCAACG | ATTCTATCCCTATCCT AATCGCC | CCAAATCTCACTCCTA AATTCAACA |
| GI29804485_STK23_1R (SEQ ID 340) | NT_025965 | GGGGGGCCTCTGCCCGGGGGC CGGGCTCTCTGGGGCCGCCGT CGCGCC | AAAACCTCTACCCGAA AACCG | ACTCTCTAAAACCGCC GTCG | AAAAACCTCTACCCA AAAACCA |
| GI29804485_STK23_2R (SEQ ID 341) | NT_025965 | GGGGTACGGGCTGCTTCACCC CCGCGTGGACCTCCCCCTCAG CTGGGG | AATACGAACTACTTCA CCCCCG | GTAAACCTCCCCCTCA ACTAAAA | AAAATACAAACTACTT CACCCCCA |
| GI29804485_STK23_3R (SEQ ID 342) | NT_025965 | CTGGGAGCCAGAGCGCCAGGC AGCGTCGCAGGAGCAGGTTCT GGGCTGG | CAACCCAAAACCTACT CCTACG | CGCTACCTAACGCTCT AACTCC | CCAACCCAAAACCTAC TCCTACA |
| GI29804900_PRKCDBP_1R (SEQ ID 343) | NT_028310 | TGAAACAGGCACACCAGGGAA TTGGAGCGGAGGAGGGTAACT CAAACTCAGAG | AAATTTAAATTACCCT CCTCCG | TCCAATTCCCTAATAT ACCTATTTCA | CTCTAAATTTAAATTA CCCTCCTCCA |
| GI29804900_PRKCDBP_2R (SEQ ID 344) | NT_028310 | GGCCCCTCTGGTTATCTCTTT GCCGTGCCAACACAGTCTCTG CGCCCAC | CCCCTCTAATTATCTC TTTACCG | ACCAACACAATCTCTA CGCCC | AACCCCTCTAATTATC TCTTTACCA |
| GI29804900_PRKCDBP_3R (SEQ ID 345) | NT_028310 | GCAGCCTGTCCAAGTCACAAA GCGGGGCCTCGGGCCTTGACA GTTCGCG | CAACCTATCCAAATCA CAAAACG | AACCTCGAACCTTAAC AATCG | ACAACCTATCCAAATC ACAAAACA |

TABLE 1-continued

Cancer-associated genomic markers and corresponding target nucleic acid probes.

| TARGET CPG SITE | GENBANK ACCESSION # | TARGET SEQUENCE SEQ ID NOS: 1-377 | PROBE SEQUENCE (ASO1) SEQ ID NOS: 378-754 | PROBE SEQUENCE (LSO1) SEQ ID NOS: 755-1131 | PROBE SEQUENCE (ASO2) SEQ ID NOS: 1132-1508 |
|---|---|---|---|---|---|
| GI29805597_APOA1_1R (SEQ ID 346) | NT_033899 | AAGGGGATGAGTGCAGGGAAC CCCGACCCCACCCGGGAGACC TGCAAG | CAAATCTCCCGAATAA AATCG | AATTCCCTACACTCAT CCCCTT | CTTACAAATCTCCCAA ATAAAATCA |
| GI29805597_APOA1_2R (SEQ ID 347) | NT_033899 | GCAGACACTCCCCTCCCGCCC CCACTGAACCCTTGACCC | CAAACACTCCCCTCCC G | CCCCACTAAACCCTTA ACCC | ACAAACACTCCCCTCC CA |
| GI29805597_APOA1_3R (SEQ ID 348) | NT_033899 | CGAAACCTCAGTCTGGGAGCC ACGGAGGGCTCTCCCCTCTCC CC | AAACCTCAATCTAAAA ACCACG | AAAACTCTCCCCTCTC CCC | CAAAACCTCAATCTAA AACCACA |
| GI29805597_PGR_1R (SEQ ID 349) | NT_033889 | GCCCCTCCCCAGATGATCGAG GGGTCCAGGCTCCTTACCTCT AGT | CCCCTCCCCAAATAAT CG | AAAATCCAAACTCCTT ACCTCTAAT | ACCCCTCCCCAAATAA TCA |
| GI29805597_PGR_2R (SEQ ID 350) | NT_033099 | CATATTATATCCTGCCATTTG ATGCCCGGTGAACATTCTATA CCTGCTTCCCAGAA | CATATTATATCCTACC ATTTAATACCCG | TAAACATTCTATACCT ACTTCCCAAAA | CATATTATATCCTACC ATTTAATACCCA |
| GI29809602_CDH13_1R (SEQ ID 351) | NT_024797 | GAAAAGTGGAATCAGCTGGCA TTGCCCAGCGTGATTTGTGAG GCTGAGCCCCAA | AAACTCAACCTCACAA ATCACG | TAAACAATACCAACTA ATTCCACTTTTC | TTAAAACTCAACCTCA CAAATCACA |
| GI29809602_CDH13_2R (SEQ ID 352) | NT_024797 | ACGAGGGAGCGTTAGGAAGGA ATCCGTCTTGTAAAGCCATTG GTCCTGG | CCAAAACCAATAACTT TACAAAACG | ATTCCTTCCTAACGCT CCCTC | CCAAAACCAATAACTT TACAAAACA |
| GI29809602_CDH13_3R (SEQ ID 353) | NT_024797 | AAGCAAATGGGATGCCACCTC CGCGGGGCTCGCTCCTCGCGA GGTGCTCAC | AAATAAAATACCACCT CCGCG | AACTCGCTCCTCGCGA AATAC | AAACAAATAAAATACC ACCTCCACA |
| GI29809804_ASC_1R (SEQ ID 354) | NT_024812 | GGTTCGGGGAACCGCGGAGGT TTCGGGGTTCTAGAAATCCGA GGTTCTAAGCC | AAAAACCGCGAAAATT TCG | AATTCTAAAAATCCGA AATTCTAAACC | AATTCAAAAACCACA AAAATTTCA |
| GI29809804_ASC_2R (SEQ ID 355) | NT_024812 | GGAGGTTTCGGGGTTCTAGAA ATCCGAGGTTCTAAGCCTAGG TGCTCCAA | AAAACACCTAAACTTA AAACCTCG | ATTTCTAAAACCCCGA AACCTC | TTAAAACACCTAAACT TAAAACCTCA |
| GI29809804_ASC_3R (SEQ ID 356) | NT_024812 | GTGAGAGCCAGCCCAGGTTTC CGGTCTGTACCCGCTGGTGCA AGCCCAGA | AAACCAACCCAAATTT CCG | TCTATACCCGCTAATA CAAACCC | ATAAAAACCAACCCAA ATTCCA |
| GI29809804_PRSS8_1R (SEQ ID 357) | NT_024812 | CACCACATACACACTACACAC CGGGACACACACACAAAAGGC CTATGCA | ACCACATACACACTAC ACACCG | AACACACACACAAAAA ACCTATACA | CACCACATACACACTA CACACCA |
| GI29809804_PRSS8_2R (SEQ ID 358) | NT_024812 | CACACACACAAACCACATGCA CGTGCATGCACGCACACTCAG ACACAC | ACACACACAAACCACA TACACG | ACATACACGCACACTC AAACA | CACACACACAAACCAC ATACACA |
| GI29809804_PRSS8_3R (SEQ ID 359) | NT_024812 | TGAGCTCAGGGCTCAAGGGGG ACGGGGCTGGTGCCTGTTTT | AAACAAACACCAACCC CG | CCCCCTTAAACCCTAA ACTCA | AAAACAAACACCAACC CCA |
| GI29823171_SERPINB5_1R (SEQ ID 360) | NT_025028 | TTCACCTTCCGGTCCTGCTGTG GGCCGAGAGGATTGCCGTACG CATGTCTG | ACATACGTACGACAAT CCTCTCG | CCCACGCAAAACCGAA AA | CAAACATACATACAAC AATCCTCTCA |
| GI29823171_SERPINB5_1R (SEQ ID 361) | NT_025020 | CAAACTCCTGGGCTCAAGCAA TCCGCTCACGTCAACCTCCCC AAATGCT | AACTCCTAAACTCAAA CAATCCG | TCACGTCAACCTCCCC AAATA | CAAACTCCTAAACTCA AACAATCCA |
| GI29789893_CTNNB1_2R (SEQ ID 362) | NT_037565 | AGCGGTACTCGAAGGCCGGGG CCGAGATGCCACCTTCCGCAG GCCGC | GATACTCGAAAACCGA AACCG | AATACCACCTTCCGCA AACC | AACAATACTCAAAAAC CAAAACCA |
| GI29789893_CTNNB1_3R (SEQ ID 363) | NT_037565 | GGGTGCTGTGAGACTGGGCTG CGACCCAGGTCCAGCAGGGAG TGTG | CACACTCCCTACTAAA CCTAAATCG | AACCCAATCTCACAAC ACCC | CACACTCCCTACTAAA CCTAAATCA |
| GI29794147_RUNX3_1R (SEQ ID 364) | NT_077383 | TGAGCCAAGGCCGCGAGCAGG CTTCTCGCATCCTGTGAGCTG AGGTTGG | CCAACCTCAACTCACA AAATACG | AAAACCTACTCGCGAC CTTAACT | CCAACCTCAACTCACA AAATACA |
| GI29794147_RUNX3_2R (SEQ ID 365) | NT_077383 | GTGACATCACGGCCCAGGTGA CCGCGGCCCAGCCAATGAGCC AAGGCC | TAACATCACGACCCAA ATAACCG | GACCCAACCAATAAAC CAAAAC | ATAACATCACAACCCA AATAACCA |
| GI29794147_RUNX3_3R (SEQ ID 366) | NT_077383 | TGGTGGACAATGGCAGGGAGT CAGCCGCAGCCCAGGGGCGAG GTGGCAT | ACCTCGCCCCTAAACT ACG | CTAACTCCCTACCATT ATCCACCA | ATACCACCTCACCCCT AAACTACA |
| GI29794313_MYCL1_1R (SEQ ID 367) | NT_077386 | CCCAGCTCGGAGTGGGCAAGG AGCACGGTTTAGCTCAGCCGG CTGGCACCG | TACCAACCGACTAAAC TAAACCG | ACTCCTTACCCACTCC GAACTAA | CAATACCAACCAACTA AACTAAACCA |
| GI29794313_MYCL1_2R (SEQ ID 368) | NT_077386 | CGACGGGTGACCAGACGGACG CCGGGACCAGCCCAAGTTCAG GGCTGA | AATAACCAAACGAACG CCG | AACCAACCCAAATTCA AAACTAA | CAACAATAACCAAAC AAACACCA |
| GI29799662_SCGB3A1_1R (SEQ ID 369) | NT_077451 | GGCAGGGACCAGGGAGCCAGG AACTGCGCCGCCCCGCCCCT GCCCTGGC | CAAAACAAAACGAAA ACGACG | AATTCCTAACTCCCTA ATCCCTACC | ACCAAAACAAAACAA AAACAACA |

TABLE 1-continued

Cancer-associated genomic markers and corresponding target nucleic acid probes.

| TARGET CPG SITE | GENBANK ACCESSION # | TARGET SEQUENCE SEQ ID NOS: 1-377 | PROBE SEQUENCE (ASO1) SEQ ID NOS: 378-754 | PROBE SEQUENCE (LSO1) SEQ ID NOS: 755-1131 | PROBE SEQUENCE (ASO2) SEQ ID NOS: 1132-1508 |
|---|---|---|---|---|---|
| GI29799662_SCGB3A1_2R (SEQ ID 370) | NT_077451 | GGCGAGGACCGGGTATAAGAAGCCTCGTGGCCTTGCCCGGGCAGCCGC | ACTACCCGAACAAAACCACG | AACTTCTTATACCCGATCCTCG | ACAACTACCCAAACAAAACCACA |
| GI29799662_SCGB3A1_3R (SEQ ID 371) | NT_077451 | CGCGTGGGGTCAGACCGCAAAGCGAAGGTGCGGGCCGGGGTGGGCCTCGCG | GTAAATCAAACCGCAAAACG | AAATACGAACCGAAATAAACCTC | CACATAAAATCAAACCACACAAAACA |
| GI29801002_SFTPA1_1R (SEQ ID 372) | NT_077575 | TGGGGCTCATGGCTGAGCCAGGTCGCAGGACAGACAAGTTGGCCTGGA | CCAAACCAACTTATCTATCCTACG | CCTAACTCAACCATAAACCCCA | TCCAAACCAACTTATCTATCCTACA |
| GI29801002_SFTPA1_2R (SEQ ID 373) | NT_077575 | TTACAGACCTGGAGTTCCTCTTTCGCAGGTTCTGTGCTCCCCTCAAGGGTC | CAAACCTAAAATTCCTCTTTCG | AAATTCTATACTCCCCTCAAAATC | TTACAAACCTAAAATTCCTCTTTCA |
| GI29801002_SFTPA1_3R (SEQ ID 374) | NT_077575 | AGACAGAAACTGCAGCTCTCCCGTGACCTTCCAGGTGCTGCCCTGACTC | AACAAAAACTACAACTCTCCCG | AACCTTCCAATACTACCCTAACTC | AAACAAAAACTACAACTCTCCCA |
| GI29804083_UNG_1R (SEQ ID 375) | NT_078089 | CCGAGAGACAGGGTCTCGCTCTGTCGCCCAGGCCTGGAGTGCATTGGC | CCAATACACTCCAAACCTAAACG | CAAAACGAAACCCTATCTCTCG | ACCAATACACTCCAAACCTAAACA |
| GI29804083_UNG_2R (SEQ ID 376) | NT_078089 | GCTAGGATTACAGGCGTGGGCCACCGCGCCTGACCAGTCTTCTCTTCTTGCAG | AAAATTACAAACGTAAACCACCG | GCCTAACCAATCTTCTCTTCTTACA | CACTAAAATTACAAACATAAACCACCA |
| GI29804083_UNG_3R (SEQ ID 377) | NT_078089 | GCTCAGACCCTCTGGCCTCAAGCGATCCTCCAGCCTGGGCCTCCC | TCAAACCCTCTAACCTCAAACG | TCCTCCAACCTAAACCTCCC | ACTCAAACCCTCTAACCTCAAACA |

TABLE 2

Methylation Markers for Squamous Cell Carcinoma
METHYLATION MARKERS FOR SQUAMOUS CELL CARCINOMA

| Panel_I | | Panel_II | | Panel_III | | Panel_IV | |
|---|---|---|---|---|---|---|---|
| Marker Name | p-value | Marker Name | p-value | Marker Name | p-value | Marker Name | p-value |
| HTR1B_2r | 2.559E-06 | MTHFR_1r | 0.00004 | HTR1B_2r | 0.00043 | HTR1B_2r | 0.00043 |
| GDF10_3r | 1.065E-05 | TSLL2_2r | 0.00053 | MTHFR_1r | 0.00080 | MTHFR_1r | 0.00080 |
| ARHI_2r | 2.616E-05 | HTR1B_2r | 0.00056 | MLH1_2r | 0.00099 | MLH1_2r | 0.00099 |
| SFN_1r | 4.169E-05 | ABCC5_2r | 0.00206 | GDF10_3r | 0.00183 | GDF10_3r | 0.00183 |
| CALCA_1r | 4.187E-05 | GDF10_3r | 0.00244 | APC_1r | 0.00228 | APC_1r | 0.00228 |
| ADCYAP1_2r | 4.533E-05 | MLH1_2r | 0.00290 | TP53_3r | 0.00279 | TP53_3r | 0.00279 |
| TERT_1r | 1.094E-04 | VHL_1r | 0.00350 | ARHI_2r | 0.00339 | ARHI_2r | 0.00339 |
| RASSF1_3r | 1.384E-04 | UBB_2r | 0.00400 | BRCA1_3r | 0.00397 | BRCA1_3r | 0.00397 |
| MOS_1r | 1.497E-04 | CALCA_1r | 0.00474 | CALCA_1r | 0.00468 | CALCA_1r | 0.00468 |
| SFTPC_3r | 4.626E-04 | SNCG_3r | 0.00522 | ADCYAP1_2r | 0.00505 | ADCYAP1_2r | 0.00505 |
| TERT_3r | 4.681E-04 | S100A2_1r | 0.00532 | SFTPC_3r | 0.00555 | SFTPC_3r | 0.00555 |
| MYOD1_2r | 6.924E-04 | SFN_2r | 0.00639 | TSLL2_2r | 0.00676 | TSLL2_2r | 0.00676 |
| C4B_2r | 7.712E-04 | SFTPC_3r | 0.00817 | TERT_1r | 0.00713 | TERT_1r | 0.00713 |
| CALCA_2r | 7.857E-04 | ADCYAP1_2r | 0.00910 | MYC_2r | 0.00745 | MYC_2r | 0.00745 |
| | | SFN_3r | 0.00923 | RASSF1_3r | 0.00825 | RASSF1_3r | 0.00825 |
| | | | | MOS_1r | 0.00872 | MOS_1r | 0.00872 |
| | | | | SNCG_3r | 0.00876 | SNCG_3r | 0.00876 |
| | | | | TGFBR2_3r | 0.00957 | TGFBR2_3r | 0.00957 |
| | | | | | | APC_2r | 0.01187 |
| | | | | | | HOXA5_3r | 0.01204 |
| | | | | | | TYMS_2r | 0.01442 |
| | | | | | | CDKN2B_3r | 0.01455 |
| | | | | | | CALCA_2r | 0.01579 |
| | | | | | | MYOD1_2r | 0.01594 |
| | | | | | | TERT_3r | 0.01734 |
| | | | | | | PTEN_1r | 0.01896 |
| | | | | | | C4B_2r | 0.01927 |
| | | | | | | GSTP1_3r | 0.01964 |

TABLE 3

Methylation Markers for Adenocarcinoma

| Panel_I | | Panel_II | |
|---|---|---|---|
| Marker Name | p-value | Marker Name | p-value |
| SFN__2r | 0.00000000007 | SFN__2r | 0.000009 |
| TWIST1__3r | 0.00000093146 | CD1A__1r | 0.000511 |
| SERPINB5__1r | 0.00000098742 | TNF__2r | 0.000526 |
| GDF10__3r | 0.00000130650 | SERPINB5__1r | 0.000638 |
| PGR__1r | 0.00000188610 | PGR__1r | 0.001117 |
| SFTPD__1r | 0.00000420738 | TWIST1__3r | 0.001288 |
| ARHI__3r | 0.00000598158 | GDF10__3r | 0.001469 |
| CALCA__1r | 0.00000933174 | SFTPD__1r | 0.002031 |
| SFTPB__1r | 0.00004835043 | ADCYAP1__2r | 0.002176 |
| CALCA__2r | 0.00008410116 | ARHI__3r | 0.002211 |
| WT1__1r | 0.00013356747 | IL13__3r | 0.002844 |
| PRDM2__3r | 0.00014989843 | HOXA5__2r | 0.002966 |
| TERT__1r | 0.00019412964 | CALCA__1r | 0.003758 |
| S100A2__2r | 0.00031181656 | HOXA5__1r | 0.004410 |
| ADCYAP1__3r | 0.00033644602 | SFTPB__1r | 0.004675 |
| RUNX3__2r | 0.00045917044 | MC2R__1r | 0.005590 |
| MYOD1__2r | 0.00061315386 | HOXA5__3r | 0.005836 |
| TWIST1__2r | 0.00077702738 | WT1__1r | 0.005920 |
| | | SERPINB5__3r | 0.008011 |
| | | CDH13__3r | 0.008365 |
| | | CALCA__2r | 0.008434 |
| | | RUNX3__1r | 0.008640 |

TABLE 4

Samples for Methylation Analysis

| Sample | Diagnosis | Age | Sex | Norm Match | Staging | Grading | R² correlation |
|---|---|---|---|---|---|---|---|
| D12152 | Adenocarcinoma | 73 | F | | no data | | 0.958 |
| D12155 | Adenocarcinoma | 60 | M | | no data | | 0.964 |
| D12157 | Normal | 79 | M | | | | 0.811 |
| D12158 | Adenocarcinoma | 87 | M | | no data | | 0.963 |
| D12160 | Adenocarcinoma | 79 | M | | no data | | 0.986 |
| D12162 | Adenocarcinoma | 47 | M | | no data | | 0.970 |
| D12163 | Adenocarcinoma | 54 | M | | no data | | 0.990 |
| D12164 | Normal | 21 | M | | | | 0.980 |
| D12165 | Adenocarcinoma | 76 | F | | no data | | 0.964 |
| D12170 | Adenocarcinoma | 62 | M | | no data | | 0.984 |
| D12173 | Normal | 77 | M | | | | 0.988 |
| D12180 | Normal | 69 | M | | | | 0.876 |
| D12181 | Adenocarcinoma | 64 | M | | no data | | 0.962 |
| D12182 | Normal | 64 | M | | | | 0.981 |
| D12184 | Normal | 75 | F | | | | 0.984 |
| D12188 | Normal | 66 | M | | | | 0.940 |
| D12190 | Adenocarcinoma | 49 | M | | no data | | 0.961 |
| D12195 | Normal | 62 | F | | | | 0.982 |
| D12197 | Adenocarcinoma | 50 | F | | no data | | 0.982 |
| D12198 | Normal | 74 | F | | | | 0.976 |
| D12202 | Normal | 71 | M | | | | 0.988 |
| D12203 | Adenocarcinoma | 71 | M | D12202 | no data | | 0.940 |
| D12205 | Normal | 68 | M | | | | 0.961 |
| D12207 | Adenocarcinoma | 62 | M | | no data | | 0.978 |
| D12209 | Normal | 6 | M | | | | 0.990 |
| G12001 | Squamous cell carcinoma | 74 | M | B12001 | pT1 N0 Mx | 1 | 0.995 |
| G12002 | Squamous cell carcinoma | 63 | M | B12002 | pT4 N2 Mx | 3 | 0.988 |
| G12003 | Squamous cell carcinoma | 67 | M | B12003 | pT1 N3 Mx | 2 | 0.981 |
| G12004 | Squamous cell carcinoma | 69 | M | B12004 | pT2 N1 Mx | 3 | 0.983 |
| G12005 | Squamous cell carcinoma | 59 | M | B12005 | pT2 N0 M0 | 2 | 0.994 |
| G12006 | Squamous cell carcinoma | 49 | M | B12006 | pT2 N1 Mx | 2 | 0.989 |
| G12007 | Squamous cell carcinoma | 71 | M | | pT2 N1 Mx | 2 | 0.988 |
| G12008 | Squamous cell carcinoma | 57 | F | B12008 | pT2 N0 Mx | 3 | 0.964 |
| G12009 | Squamous cell carcinoma | 62 | M | B12009 | pT2 N1 Mx | 3 | 0.986 |
| G12010 | Squamous cell carcinoma | 67 | M | B12010 | pT2 N1 Mx | 2 | 0.921 |
| G12011 | Squamous cell carcinoma | 73 | M | | pT2 N0 Mx | 2 | 0.977 |
| G12012 | Squamous cell carcinoma | 71 | M | B12012 | pT2 N0 Mx | 2 | 0.994 |
| G12013 | Squamous cell carcinoma | 73 | M | | pT2 N0 Mx | 1 | 0.938 |

TABLE 4-continued

Samples for Methylation Analysis

| Sample | Diagnosis | Age | Sex | Norm Match | Staging | Grading | $R^2$ correlation |
|---|---|---|---|---|---|---|---|
| G12014 | Squamous cell carcinoma | 64 | M |  | pT2 N2 Mx | 3 | 0.933 |
| G12018 | Adenocarcinoma | 60 | F | B12018 | pT1 N0 Mx | 2 | 0.996 |
| G12019 | Adenocarcinoma | 78 | M | B12019 | pT2 N1 M0 | 3 | 0.985 |
| G12020 | Adenocarcinoma | 64 | M | B12020 | pT2 N0 Mx | 3 | 0.990 |
| G12022 | Adenocarcinoma | 76 | M | B12022 | pT2 N0 Mx | 3 | 0.989 |
| G12023 | Adenocarcinoma | 55 | M | B12023 | pT2 N0 Mx | 2 | 0.832 |
| G12024 | Adenocarcinoma | 54 | M | B12024 | pT2 N3 Mx | 3 | 0.971 |
| G12025 | Adenocarcinoma | 52 | F | B12025 | pT2 N2 Mx | 2 | 0.987 |
| G12026 | Adenocarcinoma | 57 | F | B12026 | pT2 N2 Mx | 3 | 0.992 |
| G12027 | Adenocarcinoma | 65 | M | B12027 | pT2 N0 Mx | 1 | 0.990 |
| G12028 | Adenocarcinoma | 75 | M | B12028 | pT3 N3 Mx | 3 | 0.980 |
| G12029 | Adenocarcinoma | 71 | M | B12029 | pT2 N0 M0 | 3 | 0.992 |
| B12001 | Normal | 74 | M |  |  |  | 0.994 |
| B12002 | Normal | 63 | M |  |  |  | 0.977 |
| B12003 | Normal | 67 | M |  |  |  | 0.994 |
| B12004 | Normal | 69 | M |  |  |  | 0.982 |
| B12005 | Normal | 59 | M |  |  |  | 0.997 |
| B12006 | Normal | 49 | M |  |  |  | 0.985 |
| B12008 | Normal | 57 | F |  |  |  | 0.987 |
| B12009 | Normal | 62 | M |  |  |  | 0.994 |
| B12010 | Normal | 67 | M |  |  |  | 0.991 |
| B12012 | Normal | 71 | M |  |  |  | 0.995 |
| B12018 | Normal | 60 | F |  |  |  | 0.992 |
| B12019 | Normal | 78 | M |  |  |  | 0.978 |
| B12020 | Normal | 64 | M |  |  |  | 0.978 |
| B12022 | Normal | 76 | M |  |  |  | 0.993 |
| B12023 | Normal | 55 | M |  |  |  | 0.979 |
| B12024 | Normal | 54 | M |  |  |  | 0.964 |
| B12025 | Normal | 52 | F |  |  |  | 0.973 |
| B12026 | Normal | 57 | F |  |  |  | 0.931 |
| B12027 | Normal | 65 | M |  |  |  | 0.984 |
| B12028 | Normal | 75 | M |  |  |  | 0.995 |
| B12029 | Normal | 71 | M |  |  |  | 0.995 |

TABLE 5

Gene list.

| | | | | | | | |
|---|---|---|---|---|---|---|---|
| ABCB1 | CDH13 | EDNRB | HDAC11 | LAT | NNAT | RBP1 | TES |
| ABCB4 | CDH3 | EFNB1 | HFE | LIG4 | NPY | RDBP | TFPI2 |
| ABCC5 | CDK2 | EGFR | HIC1 | LMO2 | NUFIP1 | RET | TGFA |
| ABL1 | CDK4 | EGR4 | HIC2 | LOX | OAT | RNF139 | TGFB1 |
| ABO | CDKN1A | ELK1 | HLA-DPA1 | LRP2 | OPCML | RPS26 | TGFBR1 |
| ADAMTS12 | CDKN1B | EMR3 | HLA-DPB1 | LTB4R | PADI4 | RUNX3 | TGFBR2 |
| ADCYAP1 | CDKN1C | EP300 | HLA-DQA1 | LU | PAR-SN | S100A12 | THBS1 |
| AGXT | CDKN2A | EPHA3 | HLA-DQA2 | LY6G6E | PAX6 | S100A2 | THBS2 |
| APAF1 | CDKN2B | EPM2A | HLA-DRA | M6PR | PDGFRB | SCA7 | TIMP3 |
| APBA1 | CDKN2C | EPO | HLA-DRB1 | MAD2L1 | PEG10 | SCGB3A1 | TJP2 |
| APBA2 | CDKN2D | ERBB2 | HLA-F | MAGEA1 | PEG3 | SDBCAG84 | TM7SF3 |
| APC | CFTR | ERN1 | HOXA11 | MAGEC3 | PENK | SDHD | TMEFF1 |
| APOA1 | CHC1 | ESR1 | HOXA5 | MAGEL2 | PGR | SEMA3B | TMEFF2 |
| APOC1 | CHD2 | ESR2 | HOXB13 | MAP2K4 | PHLDA2 | SERPINB5 | TNF |
| APOC2 | CHEK2 | EYA4 | HOXC6 | MAS1 | PI3 | SEZ6L | TNFRSF10C |
| APP | CHFR | F2R | HRAS | MC2R | PLAGL1 | SFN | TNFRSF10D |
| AR | CHGA | FABP3 | HRASLS | MDM2 | PLAGL2 | SFRP1 | TP53 |
| ARHI | CHI3L2 | FANCF | HS3ST2 | MEG3 | PLAU | SFTPA1 | TP73 |
| ASB4 | COL1A2 | FEN1 | HSD17B12 | MEST | PLS3 | SFTPB | TRPM5 |
| ASC | COPG2 | FGFR2 | HSPA2 | MGMT | PMP22 | SFTPC | TSC1 |
| ASCL2 | CPA4 | FGFR3 | HTR1B | MKRN3 | PMS1 | SFTPD | TSC2 |
| ATM | CPNE1 | FLJ12455 | HTR2A | MKRN4 | PMS2 | SGCE | TSLL2 |

TABLE 5-continued

Gene list.

| | | | | | | | |
|---|---|---|---|---|---|---|---|
| ATP10A | CRIP1 | FLJ20712 | ICAM1 | MLH1 | POMC | SIAT1 | TSP50 |
| ATP5A1 | CSF1 | FMR1 | IGF2 | MLH3 | PPAT | SLC22A18 | TSSC4 |
| ATP5G1 | CSNK2B | FN1 | IGF2AS | MME | PPP2R1A | SLC22A2 | TUBB4 |
| BCAP31 | CSPG2 | FOS | IGF2R | MOS | PPP2R1B | SLC22A3 | TUSC3 |
| BCL2 | CSTB | G6PD | IGFBP1 | MRE11A | PRDM2 | SLC38A4 | TWIST1 |
| BCL6 | CTAG1 | GABRA5 | IGFBP3 | MSF | PRKAR1A | SLC5A5 | TYMS |
| BCR | CTAG2 | GABRB3 | IGFBP7 | MSH2 | PRKCDBP | SLC5A8 | UBB |
| BLM | CTBP1 | GABRG3 | IGSF4 | MSH3 | PROK2 | SLC6A8 | UBE3A |
| BRAF | CTLA4 | GAGE7B | IL13 | MSH6 | PRSS8 | SMARCA3 | UNG |
| BRCA1 | CTNNB1 | GALR1 | IL16 | MT1A | PTCH | SMARCB1 | USP29 |
| BRCA2 | CTSH | GDF10 | IL17RB | MTHFR | PTEN | SNCG | VAMP8 |
| C4B | CYLD | GJB2 | IL6 | MYC | PTGS2 | SNRPN | VEGF |
| CALCA | CYP1A1 | GLA | IMPACT | MYCL1 | PTHR1 | SNURF | VHL |
| CAPG | DAB21P | GNAS | INS | MYCN | PTPN6 | SOCS1 | WT1 |
| CASP8 | DAD1 | GNMT | IRF5 | MYOD1 | PTPNS1 | SOD1 | YWHAH |
| CAV1 | DAPK1 | GP1BB | IRF7 | NBL1 | PTPRO | SOD3 | ZIM3 |
| CCNA1 | DBC1 | GPC3 | ITGB1BP1 | NBS1 | PWCR1 | SPDEF | ZMYND10 |
| CCND2 | DCC | GPX3 | ITPR2 | NCL | RAB32 | ST7 | ZNF215 |
| CD1A | DDX17 | GRB10 | ITPR3 | NDN | RAD50 | STAT1 | ZNF264 |
| CD2 | DIO3 | GSTM2 | KAI1 | NEFL | RAD51 | STK11 | ZP3 |
| CD44 | DLC1 | GSTP1 | KCNK4 | NEU1 | RARB | STK23 | |
| CD63 | DLK1 | H19 | KCNQ1 | NF1 | RARRES1 | SYBL1 | |
| CD81 | DMP1 | H2AFX | KLF5 | NF2 | RASGRF1 | SYK | |
| CDC25A | DNAJD1 | HBII-13 | KLK10 | NKX3-1 | RASSF1 | TCEB3C | |
| CDH1 | EDN1 | HBII-52 | KRAS2 | NME1 | RB1 | TERT | |

TABLE 6

Sample information and array data reproducibility.

| Sample | Diagnosis | Age | Sex | R² correlation |
|---|---|---|---|---|
| D12152 | Adenocarcinoma | 73 | F | 0.981 |
| D12155 | Adenocarcinoma | 60 | M | 0.982 |
| nD12157 | Normal | 79 | M | 0.970 |
| D12158 | Adenocarcinoma | 87 | M | 0.992 |
| D12160 | Adenocarcinoma | 79 | M | 0.980 |
| D12162 | Adenocarcinoma | 47 | M | 0.989 |
| D12163 | Adenocarcinoma | 54 | M | 0.992 |
| nD12164 | Normal | 21 | M | 0.988 |
| D12165 | Adenocarcinoma | 76 | F | 0.979 |
| D12170 | Adenocarcinoma | 62 | M | 0.988 |
| nD12173 | Normal | 77 | M | 0.990 |
| nD12180 | Normal | 69 | M | 0.972 |
| D12181 | Adenocarcinoma | 64 | M | 0.990 |
| nD12182 | Normal | 64 | M | 0.980 |
| nD12184 | Normal | 75 | F | 0.979 |
| nD12188 | Normal | 66 | M | 0.974 |
| nD12195 | Normal | 62 | F | 0.989 |
| D12197 | Adenocarcinoma | 50 | F | 0.988 |
| nD12198 | Normal | 74 | F | 0.988 |
| nD12202 | Normal | 71 | M | 0.970 |
| D12203 | Adenocarcinoma | 71 | M | 0.983 |
| nD12205 | Normal | 68 | M | 0.970 |
| D12207 | Adenocarcinoma | 62 | M | 0.983 |
| nD12209 | Normal | 6 | M | 0.985 |
| G12018 | Adenocarcinoma | 60 | F | 0.996 |
| G12019 | Adenocarcinoma | 78 | M | 0.997 |
| G12020 | Adenocarcinoma | 64 | M | 0.996 |
| G12022 | Adenocarcinoma | 76 | M | 0.997 |
| G12023 | Adenocarcinoma | 55 | M | 0.997 |
| G12024 | Adenocarcinoma | 54 | M | 0.998 |
| G12025 | Adenocarcinoma | 52 | F | 0.998 |
| G12026 | Adenocarcinoma | 57 | F | 0.997 |
| G12027 | Adenocarcinoma | 65 | M | 0.997 |
| G12028 | Adenocarcinoma | 75 | M | 0.995 |
| G12029 | Adenocarcinoma | 71 | M | 0.996 |
| nB12018 | Normal | 60 | F | 0.997 |
| nB12019 | Normal | 78 | M | 0.995 |
| nB12020 | Normal | 64 | M | 0.997 |
| nB12022 | Normal | 76 | M | 0.998 |
| nB12023 | Normal | 55 | M | 0.995 |
| nB12024 | Normal | 54 | M | 0.997 |
| nB12025 | Normal | 52 | F | 0.998 |
| nB12026 | Normal | 57 | F | 0.871 |
| nB12027 | Normal | 65 | M | 0.998 |
| nB12028 | Normal | 75 | M | 0.998 |
| nB12029 | Normal | 71 | M | 0.998 |

TABLE 7

55 CpG sites differentially methylated in adenocarcinoma.

| Target ID | adj. p-value | Delta β |
|---|---|---|
| ASCL2-856 | 0.000112 | −0.1545 |
| DBC1-1053 | 0.000112 | −0.1724 |
| HS3ST2-311 | 0.000112 | −0.1909 |
| IGF2AS-1145 | 0.000112 | −0.1884 |
| NEFL-1367 | 0.000112 | −0.1943 |
| NEFL-524 | 0.000112 | −0.1690 |
| RET-1149 | 0.000112 | −0.2052 |
| RUNX3-368 | 0.000112 | −0.3127 |
| CD2-1433 | 0.000167 | 0.2286 |
| HTR2A-1387 | 0.000167 | 0.1518 |
| TNF-1343 | 0.000167 | 0.2784 |
| TNF-1371 | 0.000167 | 0.2310 |
| ASCL2-1038 | 0.000223 | −0.1921 |
| ASCL2-1048 | 0.000223 | −0.2236 |
| CCND2-604 | 0.000223 | −0.2003 |
| DIO3-1355 | 0.000223 | −0.3358 |
| DLK1-1226 | 0.000223 | −0.1780 |
| DLK1-1287 | 0.000223 | −0.2780 |
| HOXA11-558 | 0.000223 | −0.1906 |
| HOXA5-1247 | 0.000223 | −0.2068 |
| ASCL2-1339 | 0.000293 | −0.1837 |
| CDH13-1358 | 0.000293 | −0.1966 |
| HTR1B-1278 | 0.000293 | −0.1615 |
| NEFL-1341 | 0.000293 | −0.3134 |
| PENK-1293 | 0.000293 | −0.1785 |
| SEZ6L-1046 | 0.000293 | −0.1715 |
| TP73-358 | 0.000293 | −0.1973 |
| TWIST1-1348 | 0.000293 | −0.2190 |
| DLK1-1119 | 0.000396 | −0.1689 |
| GABRB3-1408 | 0.000396 | −0.1658 |
| IGF2-112 | 0.000396 | −0.1611 |

TABLE 7-continued

55 CpG sites differentially methylated in adenocarcinoma.

| Target ID | adj. p-value | Delta β |
|---|---|---|
| NPY-931 | 0.000396 | −0.2512 |
| OPCML-967 | 0.000396 | −0.3449 |
| PTPN6-1214 | 0.000396 | 0.2082 |
| PTPRO-1206 | 0.000396 | −0.1668 |
| DLC1-1012 | 0.00053 | 0.1928 |
| DLK1-1185 | 0.00053 | −0.2347 |
| HOXA11-802 | 0.00053 | −0.3419 |
| HOXA5-75 | 0.00053 | −0.2342 |
| NPY-793 | 0.00053 | −0.2576 |
| PAX6-1337 | 0.00053 | −0.1534 |
| PENK-1480 | 0.00053 | −0.2212 |
| POMC-1303 | 0.00053 | −0.2172 |
| TERT-900 | 0.00053 | −0.1561 |
| APBA2-1397 | 0.000747 | 0.1555 |
| CFTR-1051 | 0.000747 | −0.2994 |
| GDF10-1224 | 0.000747 | −0.2025 |
| NPY-1009 | 0.000747 | −0.2484 |
| ADCYAP1-1103 | 0.000947 | −0.2275 |
| CFTR-1191 | 0.000947 | −0.2710 |
| GALR1-1270 | 0.000947 | −0.1698 |
| HOXA5-1094 | 0.000947 | −0.2434 |
| HTR1B-315 | 0.000947 | −0.1932 |
| NEFL-600 | 0.000947 | −0.1868 |
| TWIST1-524 | 0.000947 | −0.1811 |

TABLE 8

Methylation-specific PCR primer sequence (SEQ ID NOS 1516-1537, respectively, in order of appearance) and amplicon size.

| Primer set | Forward primer, 5'→3' | Reverse primer, 5'→3' | Size, bp |
|---|---|---|---|
| ACTB | TGGTGATGGAGGAGGTTTAGTAAGT | AACCAATAAAACCTACTCCTCCCTTAA | 130 |
| CFTR-M | GTTTTGGGTTTGGCGGATTTTGACGC | CCCGCAAATAAACGACAATCGCGAC | 142 |
| CFTR-U | GGTTTTGGGTTTGGTGGATTTTGATGT | CATCCCACAAATAAACAACAATCACAAC | 146 |
| DBC1-M | ACGCGATCCCTTTAAATACTCGTACG | GAGGAGAGACGGGAGGTCGTTTCG | 131 |
| DBC1-U | ATATACACAATCCCTTTAAATACTCATACA | GGAGGAGAGATGGGAGGTTGTTTTG | 136 |
| DLK1-M | TCCGAAAAAATCTACGACCCAAATTCG | AGACGGGTATAGGTATTTCGCGAGC | 132 |
| DLK1-U | TCTCCAAAAAATCTACAACCCAAATTCA | GTTAGATGGGTATAGGTATTTTGTGAGT | 137 |
| EYA4-M | TACGGAGATTACGGCGGCGTTATTC | AACGCGAAAAACGACGACGCGCGA | 150 |
| EYA4-U | GGGTATGGAGATTATGGTGGTGTTATTT | CCAAAAACACAAAAAACAACAACACACAA | 158 |
| NPY-M | TTAAAACCCTCTAACCGAAAACTTCCG | ACGATTAGCGCGGTATTTTCGTCGG | 131 |
| NPY-U | CTTTAAAACCCTCTAACCAAAACTTCCA | TTTTTATGATTAGTGTGGTATTTTGTTGG | 138 |

TABLE 9

Bisulfite sequencing primer sequence (SEQ ID NOS 1538-1553, respectively, in order of appearance) and amplicon size.

| Primer set | Forward primer, 5'→3' | Reverse primer, 5'→3' | Size, bp |
|---|---|---|---|
| ASCL2 | GTAGTTTATTTTTATTTTAGTAGATTAA | AAAACCAAAATCTCAACCAATC | 260 |
| CDH13 | ATTTTTTGGAAAAGTGGAATTAGTT | CCAAATAAATCAACAACAACATCAC | 241 |
| HOXA11 | TAGTTTTTGTGTTTTTGTTTTTGT | ATAACTTAATTACACTCTCTCATTCATAAT | 272 |
| HOXA5 | GTTGTAGGGAGTTTGGGTTTATT | CCTAAAAAATCTTCATCACAAAATC | 102 |
| NPY | GAGAAGGGGTAGAAGTTTTTGAAAT | ATCTCCTACCAACAAAACTACCAAC | 267 |
| RUNX3 | TTTTGTAGTTATTGTTGTTTTTTTT | CAAATTTCAAAATCTTACAAACCTC | 187 |
| TERT | TTTGAGAATTTGTAAAGAGAAATGA | AATATAAAAACCCTAAAAACAAATAC | 290 |
| TP73 | AGTAAATAGTGGGTGAGTTATGAAGATG | TACACCAAACCCTAACTAAAAAACC | 287 |

TABLE 10

Methylation results generated from microarray analysis and bisulfite sequencing.

| CpG site | Sample ID | % methylation, Bisulfite sequencing | % methylation, Array analysis |
|---|---|---|---|
| ASCL2_1038 | nD12209 | 0.00 | 0.09 |
|  | D12155 | 0.67 | 0.79 |
| CDH13_1358 | nD12195 | 0.00 | 0.11 |
|  | D12170 | 0.40 | 0.71 |
| HOXA11_802 | nD12209 | 0.17 | 0.09 |
|  | D12155 | 0.92 | 0.92 |
| HOXA5_576 | nD12209 | 0.20 | 0.60 |
|  | D12163 | 0.75 | 0.75 |
| NPY_1009 | nD12209 | 0.00 | 0.12 |
|  | D12165 | 1.00 | 0.88 |
| RUNX3_368 | nD12195 | 0.90 | 0.27 |
|  | D12170 | 1.00 | 0.67 |
| TERT_900 | nD12209 | 0.00 | 0.60 |
|  | D12165 | 0.44 | 0.92 |
| TP73_377 | nD12195 | 0.09 | 0.05 |
|  | D12170 | 0.46 | 0.62 |

What is claimed is:

1. A method for identifying differentially methylated genomic CpG dinucleotide sequences associated with adenocarcinoma in an individual, said method comprising:
   (a) obtaining a biological sample comprising genomic DNA from said individual;
   (b) measuring the level of methylation in said biological sample at a CpG dinucleotide sequence in two or more genomic targets designated as SEQ ID NOS: 59, 293, 354, 373, 1556-1578, 1580-1604 or 1606-1609 in said sample, and
   (c) comparing the levels of methylation at said genomic CpG dinucleotide sequences in the biological sample to a reference level of methylation of said genomic CpG dinucleotide sequences, wherein said reference level comprises the level of methylation at said genomic CpG dinucleotide sequences in a normal sample,
   wherein an increase in the level of methylation of said genomic CpG dinucleotide sequences in the biological sample for the genomic targets designated as SEQ ID NOS: 293, 354, 1557-1561, 1563-1567, 1569-1578, 1580-1583, 1585-1598, 1600-1604 or 1607-1609, or a decrease in the level of methylation of said genomic CpG dinucleotide sequences in the biological sample for the genomic targets designated as SEQ ID NOS: 59, 373, 1556, 1562, 1568, 1584, 1599 or 1606, compared to the reference level identifies differentially methylated genomic CpG dinucleotide sequences associated with adenocarcinoma in said individual.

2. The method of claim 1, wherein the level of methylation of said differentially methylated genomic CpG dinucleotide sequences is used to diagnose adenocarcinoma in the individual.

3. The method of claim 1, wherein step (b) further comprises measuring the level of methylation in said sample at a CpG dinucleotide sequence in at least one of the genomic targets designated as SEQ ID NOS: 140, 174, 264, 265, 294, 305, 313, 314, 360, or 371, wherein an increase in the level of methylation of said genomic CpG dinucleotide sequences in the biological sample for the genomic targets designated as SEQ ID NOS: 140, 264, 265, 294, 313, 314 or 371, or a decrease in the level of methylation of said genomic CpG dinucleotide sequences in the biological sample for the genomic targets designated as SEQ ID NOS: 174, 305 or 360, compared to the reference level identifies differentially methylated genomic CpG dinucleotide sequences associated with adenocarcinoma.

4. A method for identifying differentially methylated genomic CpG dinucleotide sequences associated with squamous cell carcinoma in an individual, said method comprising:
   (a) obtaining a biological sample comprising genomic DNA from said individual;
   (b) measuring the level of methylation in said biological sample at a CpG dinucleotide sequence in two or more genomic targets designated as SEQ ID NOS: 57, 58, 72, 76, 139, 141, 266, 309, 315, 345 or 350 in said sample, and
   (c) comparing the levels of methylation at said genomic CpG dinucleotide sequences in the biological sample to a reference level of methylation of said genomic CpG dinucleotide sequences, wherein said reference level comprises the level of methylation at said genomic CpG dinucleotide sequences in a normal sample,
   wherein an increase in the level of methylation of said genomic CpG dinucleotide sequences in the biological sample for the genomic targets designated as SEQ ID NOS: 72, 76, 139, 141, 266, 309, 315 or 345, or a decrease in the level of methylation of said genomic CpG dinucleotide sequences in the biological sample for the genomic targets designated as SEQ ID NOS: 57, 58 or 350, compared to the reference level identifies differentially methylated genomic CpG dinucleotide sequences associated with squamous cell carcinoma in said individual.

5. The method of claim 4, wherein step (b) further comprises measuring the level of methylation in said sample at a CpG dinucleotide sequence in at least one of the genomic targets designated as SEQ ID NOS: 140, 174, 264, 265, 294, 305, 313, 314, 360 or 371, wherein an increase in the level of methylation of said genomic CpG dinucleotide sequences in the biological sample for the genomic targets designated as SEQ ID NOS: 140, 174, 264, 265, 294, 313, 314 or 371, or a decrease in the level of methylation of said genomic CpG dinucleotide sequences in the biological sample for the genomic targets designated as SEQ ID NOS: 305 or 360, compared to the reference level identifies differentially methylated genomic CpG dinucleotide sequences associated with squamous cell carcinoma.

6. The method of claim 4, wherein the level of methylation of said differentially methylated genomic CpG dinucleotide sequences is used to diagnose squamous cell carcinoma in the individual.

* * * * *